(12) United States Patent
Lee et al.

(10) Patent No.: US 10,217,944 B2
(45) Date of Patent: *Feb. 26, 2019

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si, Chungcheongnam-do (KR)

(72) Inventors: Bum Sung Lee, Cheonan-si (KR); Soung Yun Mun, Cheonan-si (KR); DaeSung Kim, Yongin-si (KR); Jung Cheol Park, Suwon-si (KR); Gyu Min Lee, Cheonan-si (KR); Sun-Hee Lee, Cheonan-si (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 252 days.

This patent is subject to a terminal disclaimer.

(21) Appl. No.: 15/113,505

(22) PCT Filed: Jan. 20, 2015

(86) PCT No.: PCT/KR2015/000551
§ 371 (c)(1),
(2) Date: Jul. 22, 2016

(87) PCT Pub. No.: WO2015/111888
PCT Pub. Date: Jul. 30, 2015

(65) Prior Publication Data
US 2017/0012212 A1   Jan. 12, 2017

(30) Foreign Application Priority Data
Jan. 22, 2014 (KR) .................... 10-2014-0007691
Jun. 17, 2014 (KR) .................... 10-2014-0073606

(51) Int. Cl.
| | |
|---|---|
| *H01L 51/50* | (2006.01) |
| *C07D 209/86* | (2006.01) |
| *C09K 11/06* | (2006.01) |
| *C07D 403/10* | (2006.01) |
| *C07D 409/12* | (2006.01) |
| *H01L 51/00* | (2006.01) |

(52) U.S. Cl.
CPC ........ *H01L 51/0061* (2013.01); *C07D 209/86* (2013.01); *C07D 403/10* (2013.01); *C07D 409/12* (2013.01); *C09K 11/06* (2013.01); *H01L 51/0072* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *C09K 2211/1044* (2013.01); *C09K 2211/1092* (2013.01); *H01L 51/5012* (2013.01); *H01L 51/5056* (2013.01); *Y02E 10/549* (2013.01)

(58) Field of Classification Search
CPC .. C07D 209/86; C07D 403/10; C07D 409/12; C09K 11/06; C09K 2211/1007; C09K 2211/1011; C09K 2211/1014; C09K 2211/1022; C09K 2211/1029; C09K 2211/1044; C09K 2211/1092; H01L 51/0061; H01L 51/0072; H01L 51/5012; H01L 51/5056; Y02E 10/549
See application file for complete search history.

(56) References Cited

U.S. PATENT DOCUMENTS

| | | | |
|---|---|---|---|
| 6,242,115 B1 | 6/2001 | Thomson et al. | |
| 9,917,257 B2* | 3/2018 | Lee | H01L 51/0061 |
| 2003/0052616 A1* | 3/2003 | Antoniadis | H01L 27/3211 315/169.3 |
| 2005/0221124 A1* | 10/2005 | Hwang | C07F 9/5728 428/690 |
| 2016/0190467 A1* | 6/2016 | Jang | H01L 51/0058 257/40 |

FOREIGN PATENT DOCUMENTS

| | | |
|---|---|---|
| JP | 10-316658 A | 12/1998 |
| JP | 2000-302756 A | 10/2000 |
| JP | 2004-103467 A | 4/2004 |
| KR | 10-1188280 B1 | 9/2012 |
| KR | 10-2013-0022232 A | 3/2013 |
| WO | WO 2015/041428 A1 * | 3/2015 |

OTHER PUBLICATIONS

Derwent abstract for WO 2015/041428 A1 (Mar. 2015 publication date).*
International Search Report for PCT Application No. PCT/KR2015/000551, dated Apr. 20, 2015, three pages; with English translation, two pages.
Korean Notice of Allowance for Korean Application No. 10-2014-0073606, dated May 26, 2016, two pages.

* cited by examiner

*Primary Examiner* — Dawn L Garrett
(74) *Attorney, Agent, or Firm* — Vorys, Sater, Seymour & Pease LLP; Mih Suhn Koh

(57) ABSTRACT

Provided are a compound of Formula 1 and an organic electric element including a first electrode, a second electrode, and an organic material layer between the first electrode and the second electrode and comprising the compound, the element showing improved luminous efficiency, stability, and life span.

14 Claims, 1 Drawing Sheet

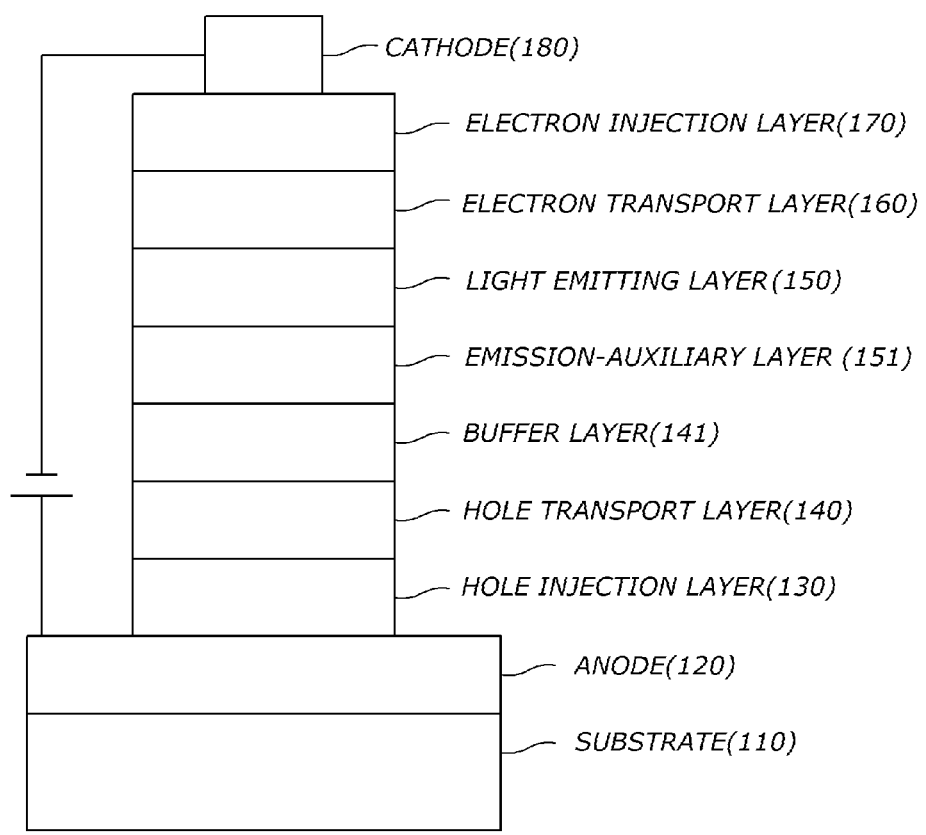

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATION

This application claims priority from and the benefit under 35 U.S.C. § 119(a) of Korean Patent Application No. 10-2014-0007691 filed on Jan. 22, 2014, and Korean Patent Application No. 10-2014-0073606 filed on Jun. 17, 2014, the contents of which are hereby incorporated by reference for all purposes as if fully set forth herein.

BACKGROUND

Technical Field

The present invention relates to compounds for organic electric elements, organic electric elements using the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer may have a multilayered structure including multiple layers made of different materials in order to improve the efficiency and stability of an organic electric element, and for example, may include a hole injection layer, a hole transport layer, a light emitting layer, an electron transport layer, an electron injection layer, or the like.

A material used as an organic material layer in an organic electric element may be classified into a light emitting material and a charge transport material, for example, a hole injection material, a hole transport material, an electron transport material, an electron injection material, and the like according to its function.

Currently, the power consumption is required more and more as the size of display becomes larger and larger in the portable display market. Therefore, the power consumption became a very important factor in the portable display with a limited power source of the battery, and efficiency and life span also became issues to be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given. Therefore it is required to develop a light emitting material that has high thermal stability and can achieve efficiently a charge balance in the light-emitting layer.

Further, in order to solve the emission problem with a hole transport layer in a recent organic electric element, an emission-auxiliary layer is present between the hole transport layer and a light emitting layer, and it is time to develop different emission-auxiliary layers according to respective light emitting layers (R, G, B).

In general, an electron transferred from an electron transport layer to a light emitting layer and a hole transferred from a hole transport layer to the light emitting layer are recombined to form an exciton.

However, since a material used in a hole transporting layer should have a low HOMO value, it mainly has a low T1 value. Due to this, excitons generated from a light emitting layer are transported to the hole transporting layer, resulting in a charge unbalance in the light emitting layer. Thus, light emission occurs in the hole transporting layer or at an interface of the hole transporting layer so that the organic electroluminescent device is reduced in color purity, efficiency, and lifespan.

Also, when using a material having rapid hole mobility for reducing a driving voltage, this is tend to decrease the efficiency. In an OLEDs, a charge unbalance in the light emitting layer is caused because of that hole mobility is faster than electron mobility, and reduced efficiency and lifespan is happened.

Therefore, an emitting auxiliary layer must be formed by a material what can solve the problems of an hole transport layer, having hole mobility (within the driving voltage range of the blue element of full device) to give the suitable driving voltage, high T1 energy value (electron block) and wide band gap. These requirements are not satisfied only by structural characteristics about a core of the emitting auxiliary layer's material. Therefore, it is necessary to develop of the material for the emitting auxiliary layer having high T1 energy value and wide band gap, to improve efficiency and lifespan of the organic electric element as combined core of material and characteristics of sub substituents appropriately.

In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed. Accordingly, there is a continuous need to develop new materials for an organic material layer.

SUMMARY

In order to solve one or more of the above-mentioned problems occurring in the prior art, an aspect of the present invention is to provide a compound which allows an organic electric element to improve in luminous efficiency, stability and lifespan, an organic electric element containing the same, and an electronic device including the organic electric element.

In accordance with an aspect of the present invention, the compound represented by the following Formula is provided.

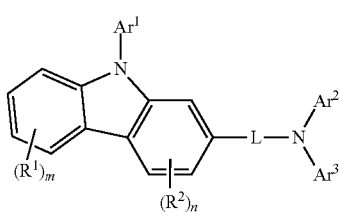

In another aspect of the present invention, organic electric elements containing the compound represented by the formula above and electronic devices including the organic electric element are provided.

By employing the compound of the present invention that has wide band gap and high T1 energy value due to the non-linear linker (L) attached to the carbazole core, the organic electric element according to one or more embodiments of the present invention can have not only high luminous efficiency and high heat-resistance, but also significantly improved color purity and lifespan.

BRIEF DESCRIPTION OF THE DRAWING

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "haloalkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below. Also, "substituted fluorenyl group" or "substituted fluorenylene group" means, functional group which at least any one of R, R' and R" is a functional group other than hydrogen and spiro compound which R and R' can be linked together with the carbon to which they are attached to form spiro compound.

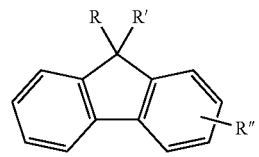

Unless otherwise stated, the term "aryl group" or "arylene group" as used herein has, but not limited to, 6 to 60 carbon atoms. Herein, the aryl group or arylene group means a monocyclic, ring assemblies, fused polycyclic system or spiro compound.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents at least one of N, O, S, P, and Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes compound below.

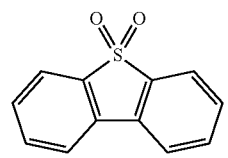 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Otherwise specified, the Formulas used in the present invention are as defined in the index definition of the substituent of the following Formula.

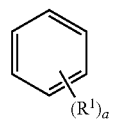

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different, and are linked to the benzene ring as follows. when a is an integer of 4 to 6, the substituents $R^1$s may be the same and different, and are linked to the benzene ring in a similar manner to that when a is an integer of 2 or 3, hydrogen atoms linked to carbon constituents of the benzene ring being not represented as usual.

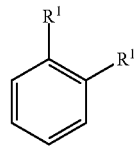

(a=2)

(a=3)

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer between the first electrode 110 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150. For example, the inventive compound may be used as the light emitting layer 150, the hole transport layer 140, and/or the emission-auxiliary layer 151.

Since depending on the type and position of a substituent to be attached, a band gap, electrical properties, interfacial properties, and the like may vary even in the same core, it is very important what the types of core and a combination of substituent attached to the core are. Specially, long life span and high efficiency can be simultaneously achieved when an optimal combination of energy levels and T1 values, inherent material properties (mobility, interfacial properties, etc.), and the like among the respective layers included in the organic material layer is given.

As already described above, in order to solve the emission problem with a hole transport layer in a conventional organic electric element, an emission-auxiliary layer is preferably formed between the hole transport layer and a light emitting layer, and it is time to develop different emission-auxiliary layers according to respective light emitting layers (R, G, B). However, even when a similar core is used, it is very difficult to infer the characteristics of an emission-auxiliary layer if a used organic material layer varies because the correlation between the emission-auxiliary layer and a hole transport layer and the correlation between the emission-auxiliary layer and a light emitting layer (host) mused be discovered.

Accordingly, in the present invention, a combination of energy levels and T1 values, inherent material properties (mobility, interfacial properties, etc.), and the like among the respective layers included in the organic material layer is optimized by forming a light emitting layer and/or an emission-auxiliary layer by using the compound represented by Formula 1, and thus the life span and efficiency of the organic electric element can be improved at the same time.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be comprised between the hole transport layer 140 and the light emitting layer 150.

And also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R (Red), G (Green), B (Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

The compound according to an aspect of the present invention is represented by the following Formula 1.

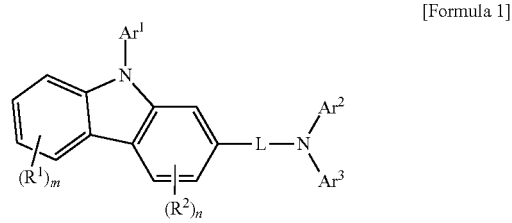

[Formula 1]

In Formula 1 above, L may be

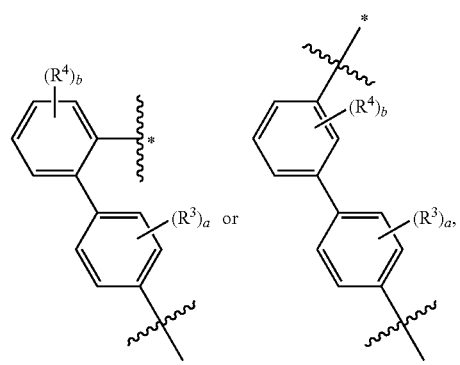

wherein * indicates the position to which N (nitrogen) of the amine group in Formula 1 is bonded.

Each of a, b and m may be an integer of 0 to 4. Also, $R^3$ and $R^4$ may be each independently selected form the group consisting of i) deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; -L'-N($R^a$)($R^b$); and combinations thereof, or ii) at least one of any two adjacent groups, namely, adjacent $R^3$s, $R^4$s and/or $R^3$ and $R^4$, may be linked together to form at least one fused ring, with the proviso that the group(s) not forming a ring among $R^3$ and $R^4$ may be the same as defined in i) above.

The fused ring may be a mono or poly cyclic ring, including a $C_6$-$C_{60}$ aromatic ring, a $C_2$-$C_{60}$ hetero cyclic ring, a $C_3$-$C_{60}$ alicyclic ring, or a fused ring formed by combination thereof. The fused ring may be a saturated or unsaturated ring.

R³s may be same or different each other when a is 2 or more, R⁴s may be same or different each other when b is 2 or more.

Preferably, both $R^3$ and $R^4$ are hydrogen, or $R^3$ and $R^4$ may be a $C_6$-$C_{16}$ aryl group, a $C_5$-$C_9$ heterocyclic group, more preferably a $C_6$, $C_{10}$, $C_{12}$ or $C_{16}$ aryl group, or a $C_5$, $C_8$ or $C_9$ heterocyclic group.

Furthermore, preferably, $R^3$ and $R^4$ may be each independently selected from the following structures:

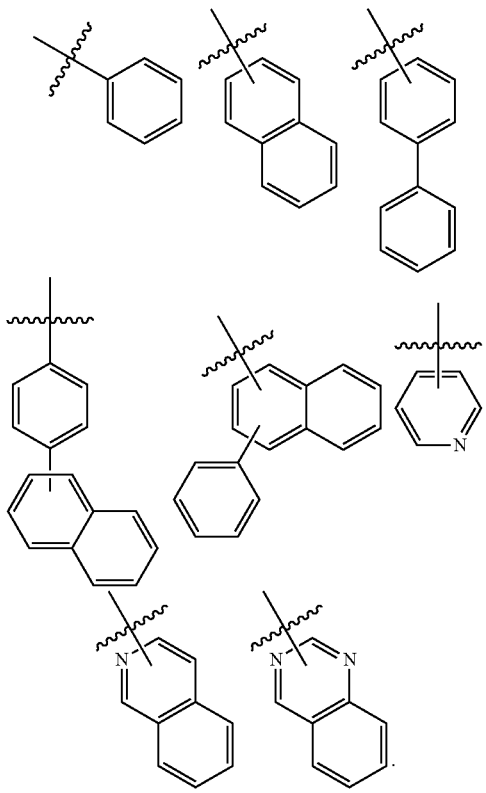

Meanwhile, the fused ring of R³s, R⁴s and/or any adjacent groups may be optionally substituted with one or more substituents selected from the group consisting of deuterium, halogen, a silane group, a siloxane group, a boron group, a germanium group; a cyano group; a nitro group; C, a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si, and P; a $C_3$-$C_{20}$ cycloalkyl group; a $C_7$-$C_{20}$ arylalkyl group; and a $C_8$-$C_{20}$ arylalkenyl group.

In Formula 1 above, Ar¹ to Ar³ may be each independently selected from the group consisting of a $C_6$-$C_{60}$ aryl group; a fluorenylene group; a $C_2$-$C_{60}$ heterocyclic group containing at least one heteroatom selected from the group consisting of O, N, S, Si, and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; or combinations thereof.

Preferably, Ar¹ may be any one of the following structures:

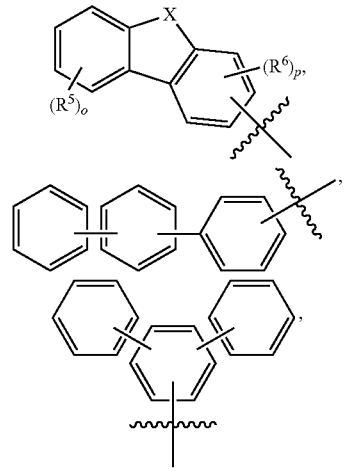

wherein X may be O, S or C(R')(R"), R' and R" may be each independently selected from the group consisting of hydrogen; deuterium; tritium; a $C_6$-$C_{20}$ aryl group; a $C_1$-$C_{20}$ alkyl group; and a $C_2$-$C_{20}$ alkenyl group; and R' and R" may be linked together to form a spiro compound with the carbon to which they are attached.

Preferably, Ar¹ may be

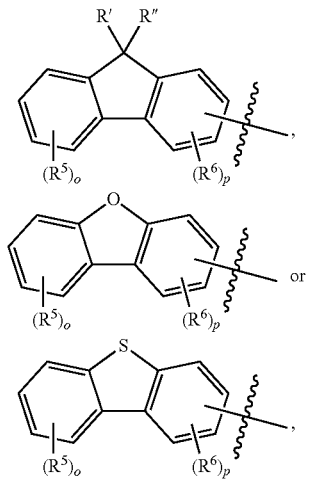

wherein the symbols of R', R", o, and p are the same as defined above.

R⁵ and R⁶ in the above structures may be each independently selected from the group consisting of i) deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and combinations thereof, or ii) any two adjacent groups may be independently linked together to form at least one fused ring, and the group(s) not forming a ring among R⁵ and R⁶ may be the same as defined in the above i).

For example, when both o and p are 2, any two adjacent R⁵s may be linked together to form a ring, but even if R⁶s are adjacent group, they may be each independently an aryl group or a heterocyclic group. Where o is 2 or more, plural $R^5$s are same or different each other, and some of the adjacent groups may be linked together to form a ring, and the other groups not forming a ring may be selected from the substituent group defined above. The same applies to plural $R^6$s where p is 2 or more.

Preferably, $Ar^1$ may be a $C_6$-$C_{25}$ aryl group, more preferably a $C_6$-$C_{18}$ aryl group, more preferably a $C_6$, $C_{10}$, $C_{12}$, $C_{18}$ aryl group, each of which may be substituted by at least one deuterium. For example, $Ar^1$ may be phenyl, naphthyl, biphenyl, terphenyl, phenyl substituted with biphenyl and these may be substituted by at least one deuterium.

Also, preferably $Ar^1$ may be a fluorenyl group, 9,9-diphenyl-9H-fluorenyl group or 7,7-dimethyl-7H-benzo[c] fluorenyl group.

Also, $Ar^1$ may be preferably a $C_3$-$C_{12}$ heterocyclic group, more preferably a $C_{12}$ heterocyclic group, also preferably dibenzothienyl or dibenzofuryl.

Preferably, $Ar^2$ and $Ar^3$ may be each independently a $C_6$-$C_{25}$ aryl, also preferably a $C_6$-$C_8$ aryl group, more preferably a $C_6$, $C_{10}$, $C_{12}$, $C_{18}$ aryl group. Specifically, $Ar^2$ and $Ar^3$ may be each independently phenyl, naphthyl, biphenyl or terphenyl (including p-terphenyl, m-terphenyl), and phenyl may be further substituted by deuterium, methoxyl, or t-butyl.

Also, preferably $Ar^2$ and $Ar^3$ may be each independently, 9,9-dimethyl-9H-fluorenyl, 9,9-diphenyl-9H-fluorenyl or 9,9'-spirobifluorenyl.

Also, preferably $Ar^2$ and $Ar^3$ may be each independently a $C_3$-$C_{12}$ heterocyclic group, specifically pyrimidyl substituted or unsubstituted with phenyl, dibenzothienyl, dibenzofuryl.

Also, preferably, $Ar^2$ and $Ar^3$ may be each independently selected from the following structures:

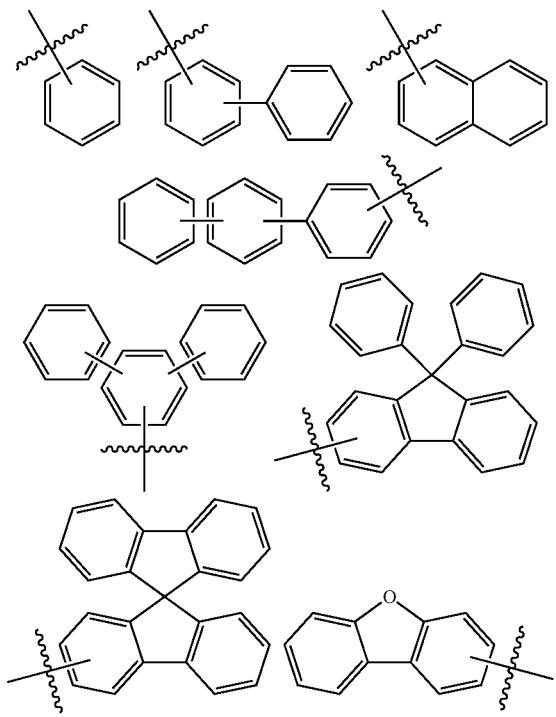

Preferably, $Ar^1$ to $Ar^3$ may be optionally substituted with one or more substituents selected from the group consisting of deuterium, halogen, a silane group, a siloxane group, a boron group, a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si, and P; a $C_3$-$C_{20}$ cycloalkyl group; a $C_7$-$C_{20}$ arylalkyl group; and a $C_8$-$C_{20}$ arylalkenyl group.

In Formula 1 above, $R^1$ and $R^2$ may be each independently selected from the group consisting of i) deuterium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; -L'-N($R^{a)}$) ($R^b$); and combinations thereof, or ii) adjacent groups, that is, adjacent $R^1$s, adjacent $R^2$s and/or adjacent R and $R^2$ may be optionally linked together to form at least one fused ring, and the group(s) of $R^1$ and $R^2$ not forming a ring may be the same as defined in the above i). The fused ring formed between the adjacent groups may be a $C_6$-$C_{60}$ aromatic ring, a $C_2$-$C_{60}$ heterocyclic ring, a $C_3$-$C_{60}$ alicyclic ring, or a fused ring formed by combination thereof, and it may be a mono-cyclic or poly cyclic ring, and/or a saturated or unsaturated ring.

Also, in Formula 1, m may be an integer of 0 to 4, n is an integer of 0 to 3, wherein plural $R^1$s may be same or different each other when m is an integer of 2 or more, and plural $R^2$s may be same or different each other when n is 2 or more.

Preferably, m=n=O, or $R^1$ may be a $C_6$-$C_{18}$ aryl group, a $C_3$-$C_{10}$ heterocyclic group, or a $C_2$-$C_5$ alkenyl group, preferably a $C_6$ aryl, $C_3$, $C_8$, $C_9$, $C_{10}$ heterocyclic group or a $C_3$ alkenyl group, specifically, phenyl, dibenzothienyl, triazinyl, quinolyl, qunazolyl substituted or unsubstituted with phenyl, propenyl.

Also, preferably adjacent $R^1$s may be linked together to form one or two benzene ring, and it may form naphthalene or phenanthrene, and so on, with the benzene ring to which they are attached.

Also, preferably adjacent $R^2$s may be linked together to form one or two benzene ring, and it may form naphthalene or phenanthrene, and so on, with the benzene ring to which they are attached.

Meanwhile, $R^1$ and $R^2$ may be optionally substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si, and P; a $C_3$-$C_{20}$ cycloalkyl group; a $C_7$-$C_{20}$ arylalkyl group; and a $C_8$-$C_{20}$ arylalkenyl group.

In -L'-N($R^a$)($R^b$) of $R^1$ to $R^4$ above, L' may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group containing at least one heteroatom selected from the group consisting of O, N, S, Si, and P.

In Formula 1 above, when adjacent $R^1$ and/or $R^2$ may be linked together to form a ring, it may represent any one of Formula 2 to Formula 10. Formula 2 to Formula 5 below may be examples of when adjacent $R^1$s may be linked together to form a benzene ring, Formula 6 to Formula 9 below may be examples of when adjacent all of $R^1$s and $R^2$s may be linked together to form benzene rings, Formula 10 may be an example of when adjacent $R^2$s may be linked together to form a benzene ring.

[Formula 2]

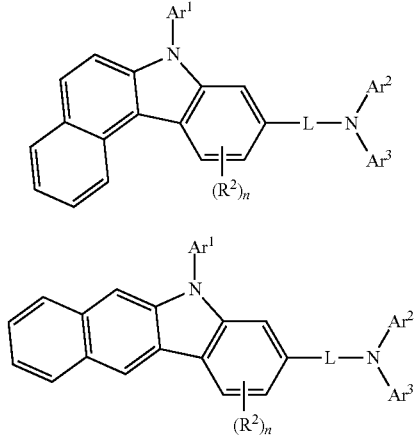

[Formula 3]

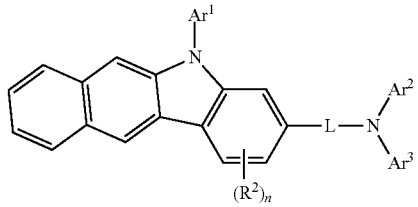

[Formula 4]

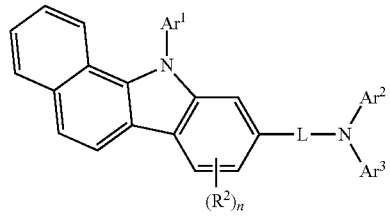

[Formula 5]

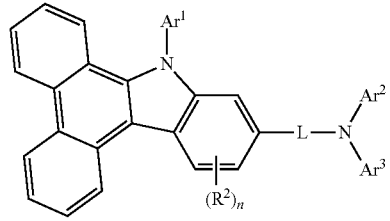

[Formula 6]

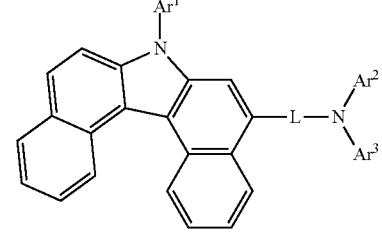

[Formula 7]

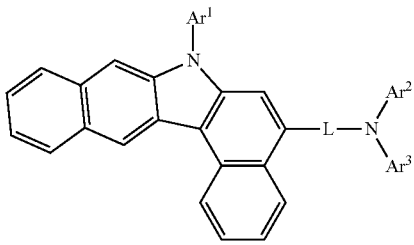

[Formula 8]

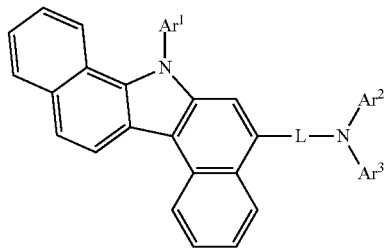

[Formula 9]

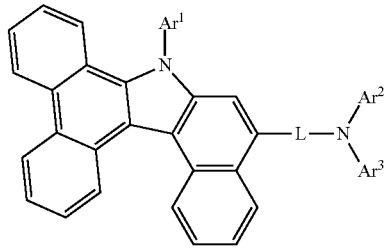

[Formula 10]

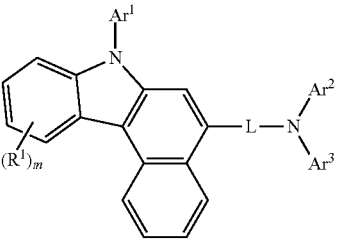

In the Formula 2 to Formula 10 above, $Ar^1$ to $Ar^3$, L, $R^1$, $R^2$, m and n are the same as defined in Formula 1 above.

Preferably, in Formula 1 above, when $Ar^1$ is

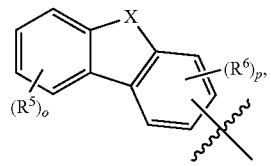

Formula 1 may be represented by any one of Formula 11 to Formula 20 below.

Formula 12 to Formula 15 below may be examples of when adjacent R1s may be linked together to form a benzene ring, Formula 16 to Formula 19 below may be examples of when adjacent all of $R^1$s and $R^2$s may be linked together to form benzene rings, Formula 20 below may be an example of when adjacent $R^2$s may be linked together to form benzene rings.

[Formula 11]
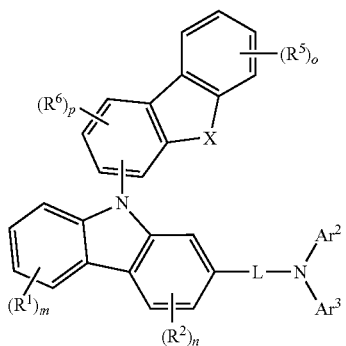
[Formula 12]
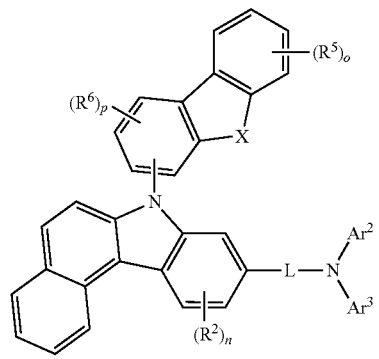
[Formula 13]
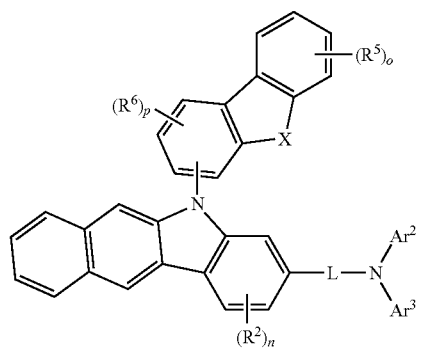
[Formula 14]
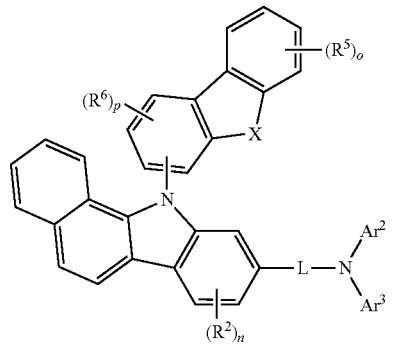
[Formula 15]
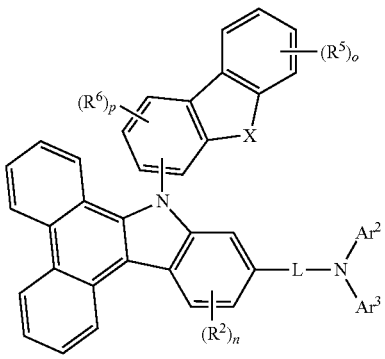
[Formula 16]
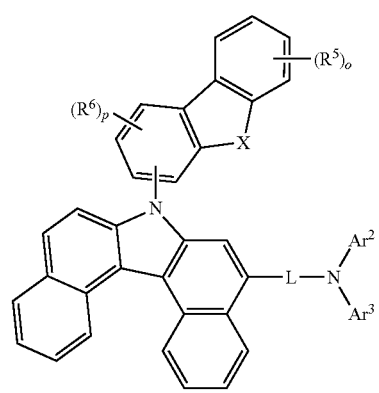
[Formula 17]
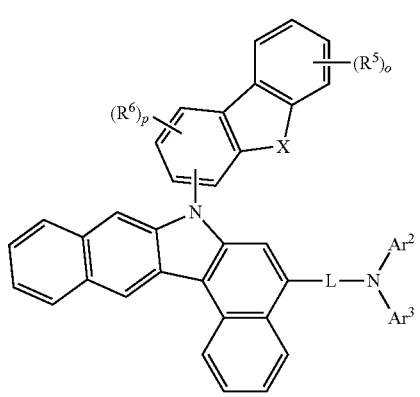
[Formula 18]
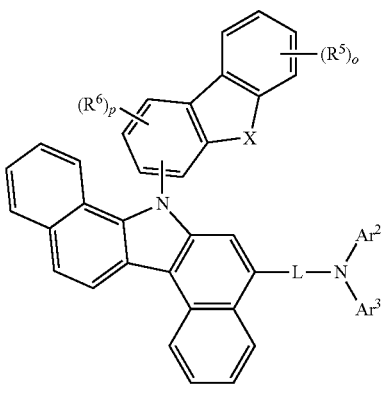

-continued

[Formula 18]

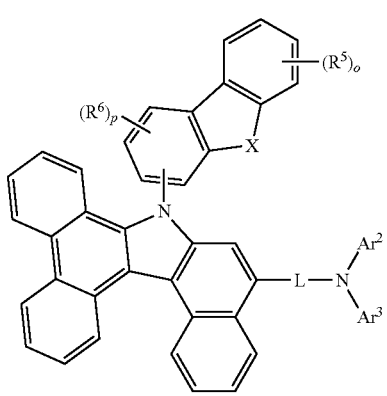

[Formula 20]

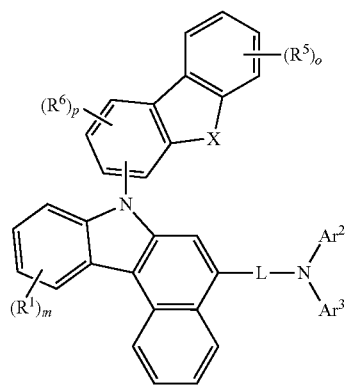

In Formula 11 to Formula 20 above, wherein $Ar^2$, $Ar^3$, L, $R^1$, $R^2$, m and n may be the same as defined in Formula 1.

Also, X may be O, S or C(R')(R''), wherein R' and R'' may be each independently selected from the group consisting of hydrogen; deuterium; tritium; a $C_6$-$C_{20}$ aryl group; a $C_1$-$C_{20}$ alkyl group; and a $C_2$-$C_{20}$ alkenyl group; R' and R'' may be linked together to form a spiro compound with the carbon to which they are attached.

Also, in Formula 11 to Formula 20, o may be an integer of 0 to 4, p may be an integer of 0 to 3. $R^5$ and $R^6$ may be each independently selected from the group consisting of i) deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and combinations thereof, or ii) at least one of any two adjacent groups may be optionally linked together to form a ring, with the proviso that the group(s) not forming a ring among $R^5$ to $R^6$ are the same as defined in i) above More specifically, the compound represented by Formula 1 to Formula 20 above may be any one of the following compounds.

P1-1

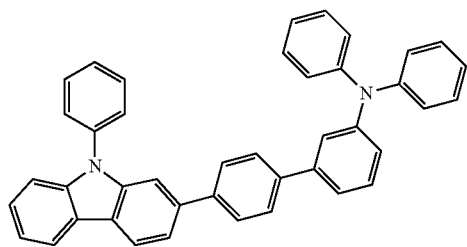

P1-2

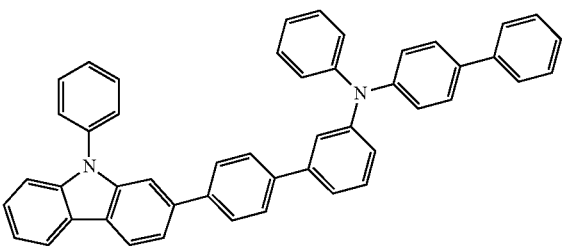

P1-3

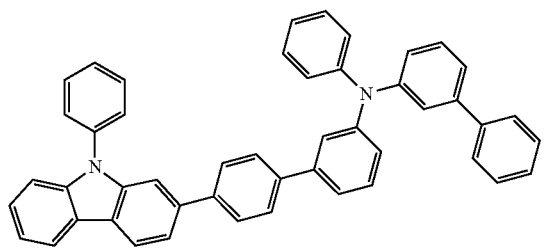

P1-4

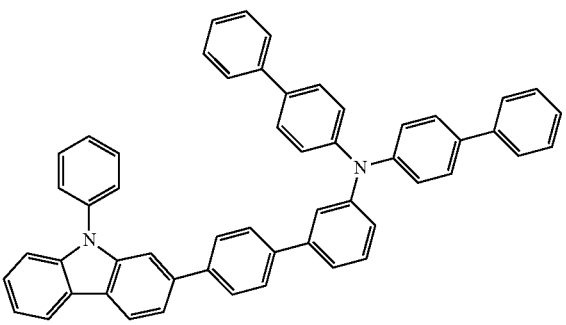

-continued
P1-5
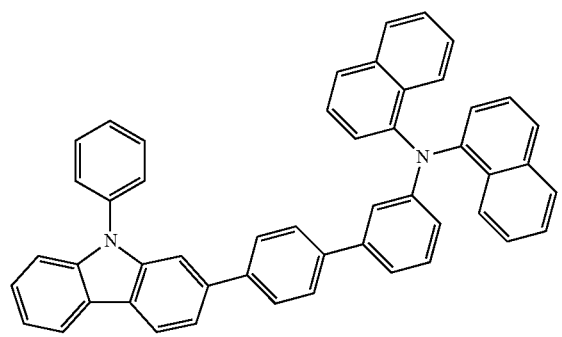
P1-6
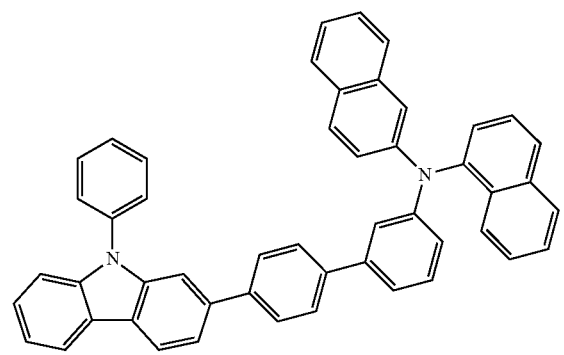
P1-7
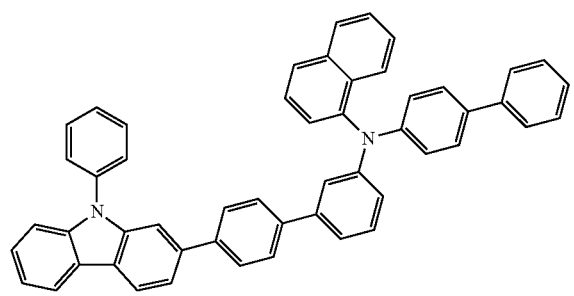
P1-8
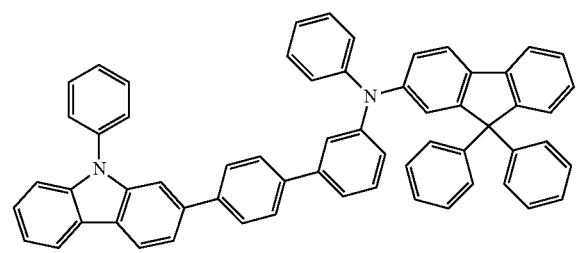
P1-9
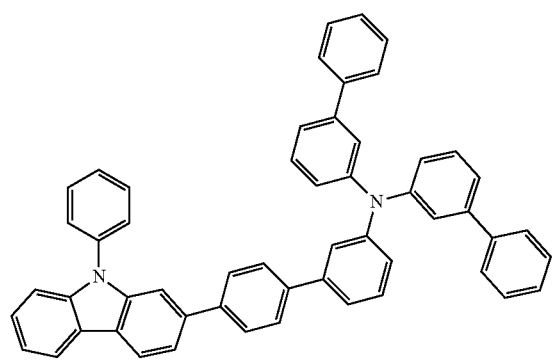
P1-10
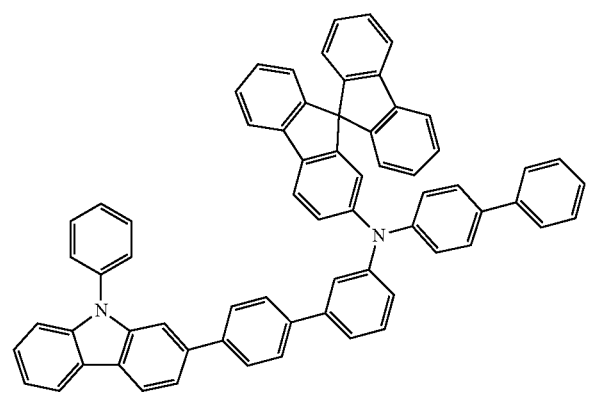
P1-11
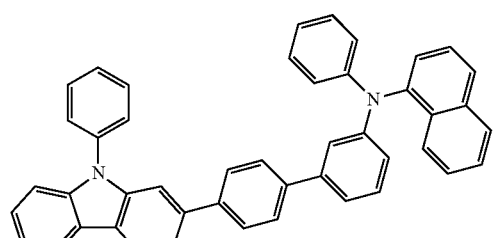
P1-12
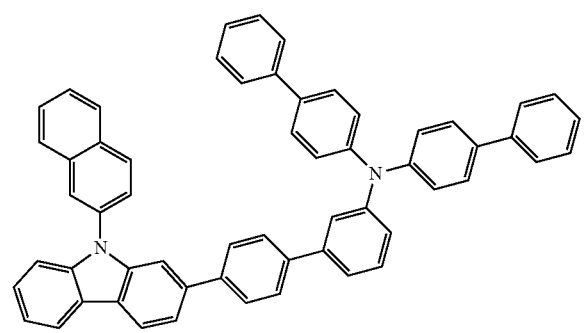

-continued
P1-13
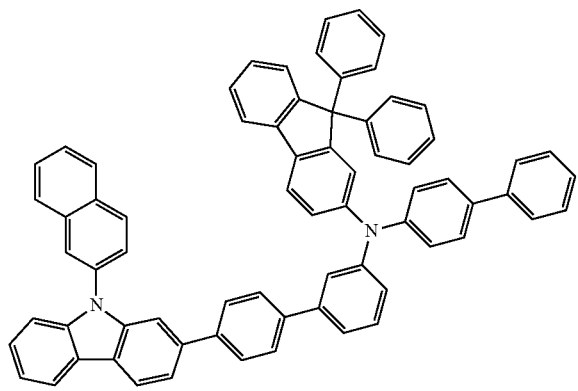
P1-14
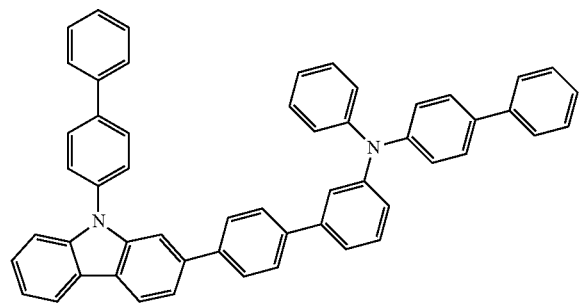
P1-15
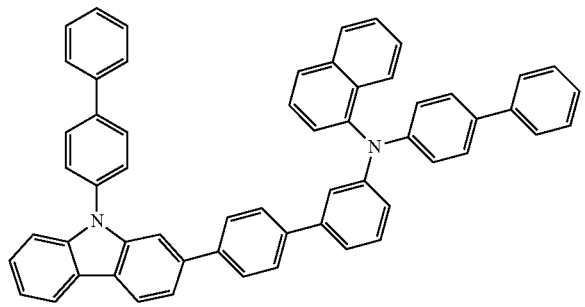
P1-16
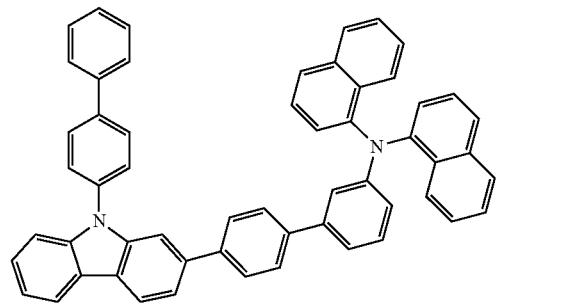
P1-17
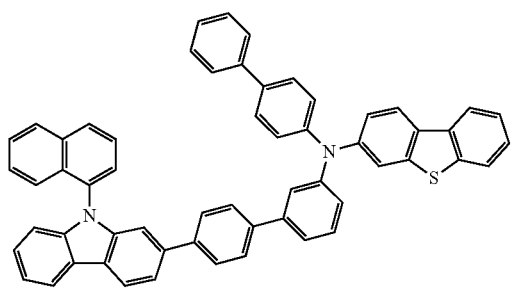
P1-18
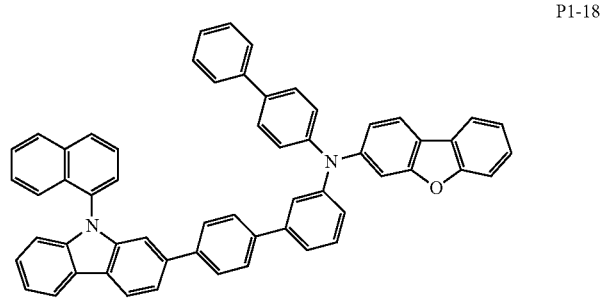
P1-19
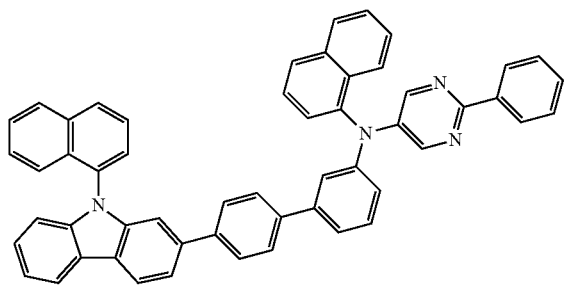
P1-20
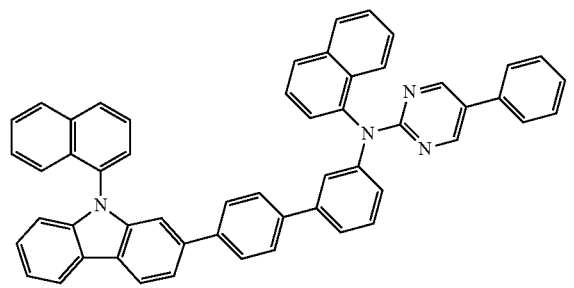

-continued
P1-21
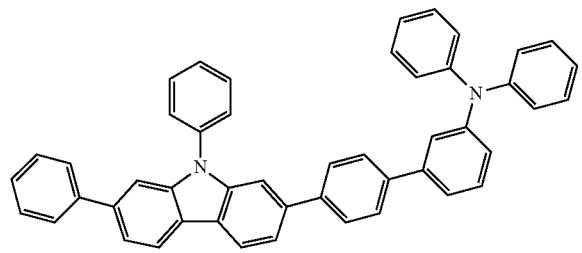
P1-22
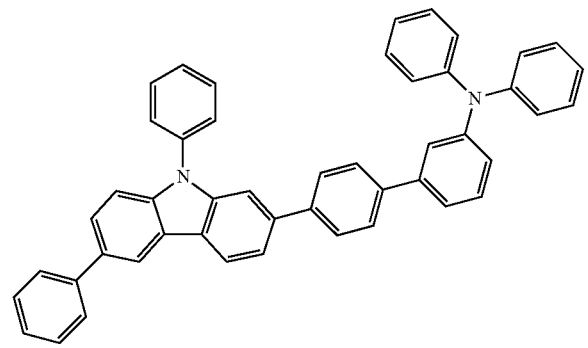
P1-23
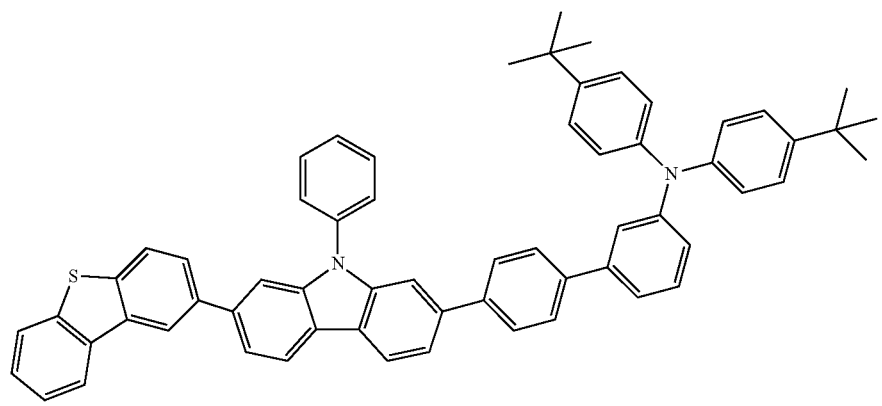
P1-24
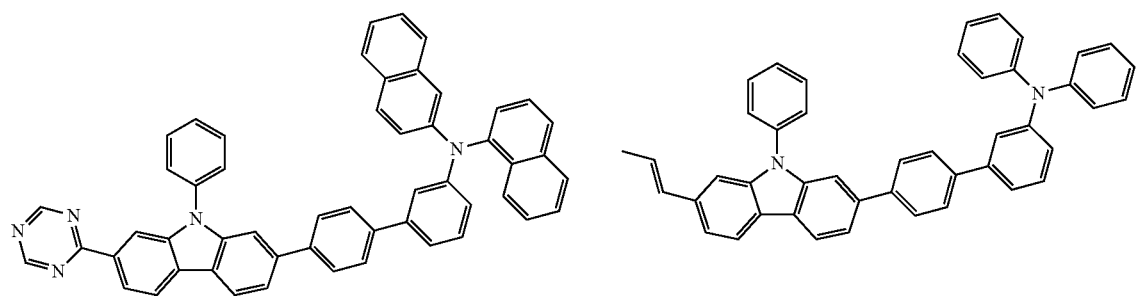
P1-25
P1-26
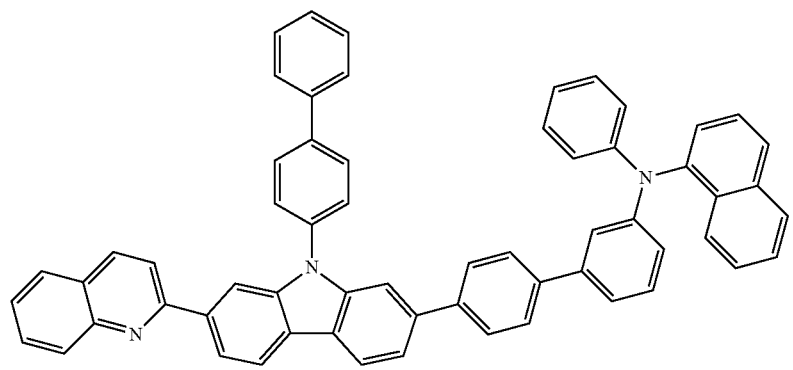

-continued
P1-27
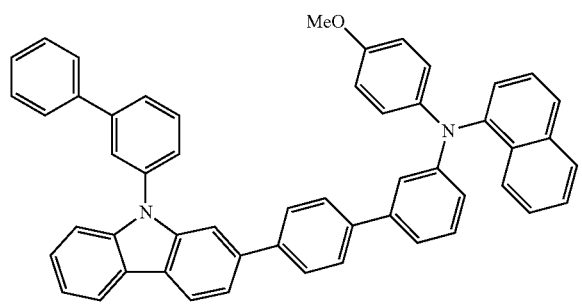
P1-28
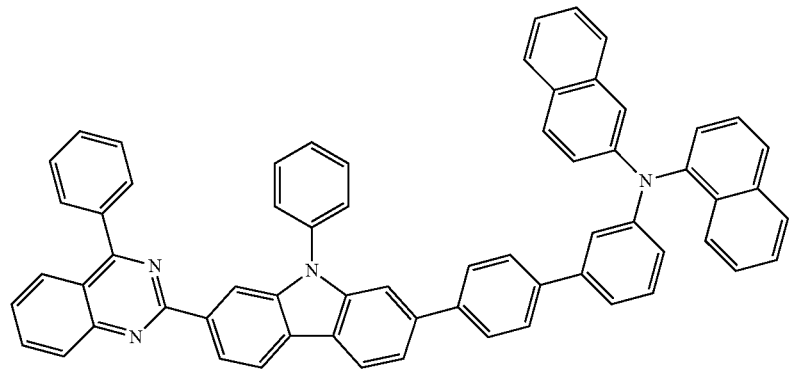
P1-29
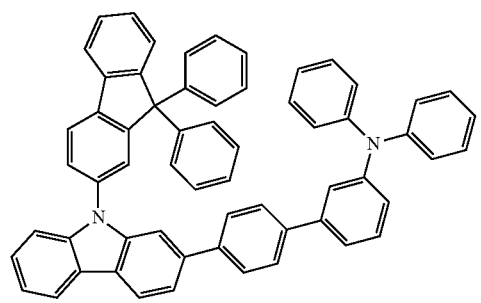
P1-30
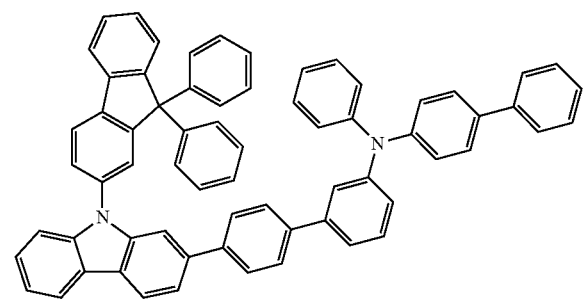
P1-31
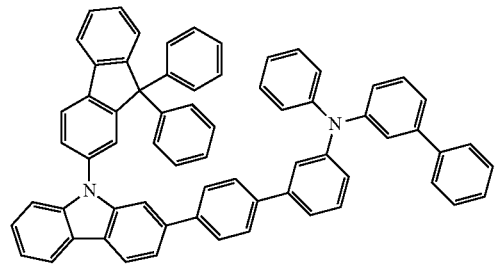
P1-32
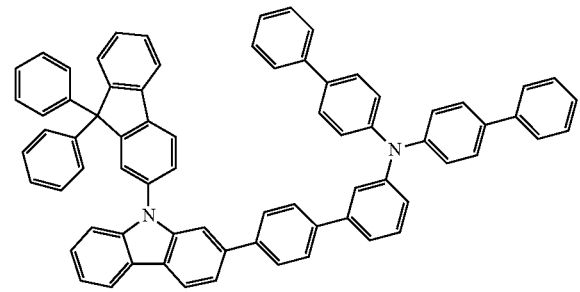

-continued
P1-33
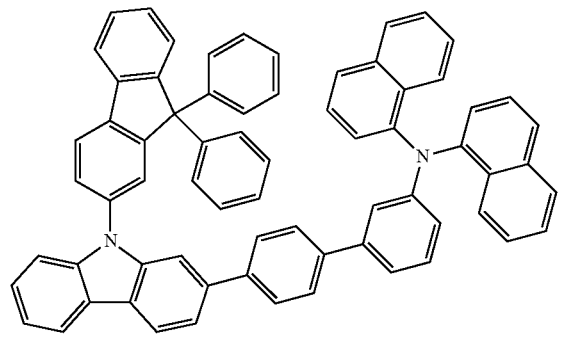
P1-34
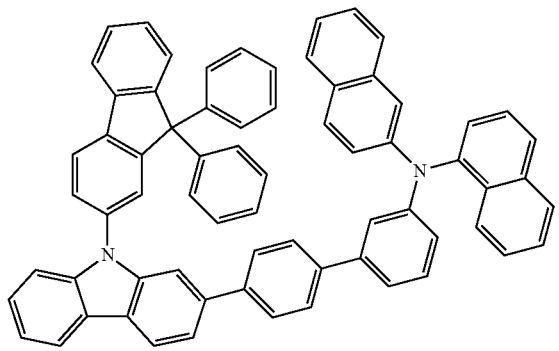
P1-35
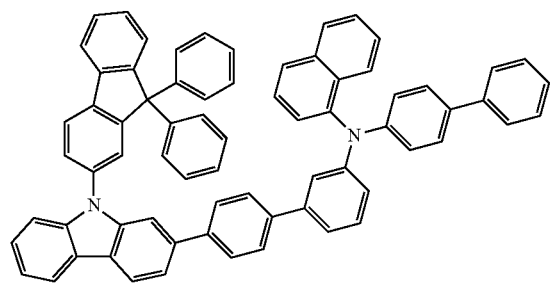
P1-36
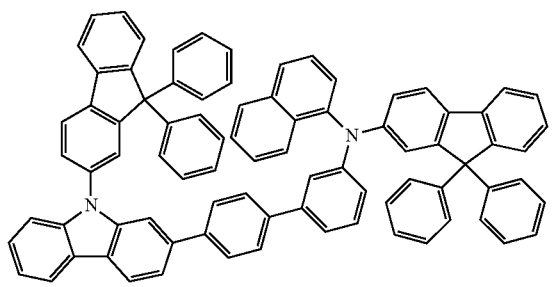
P1-37
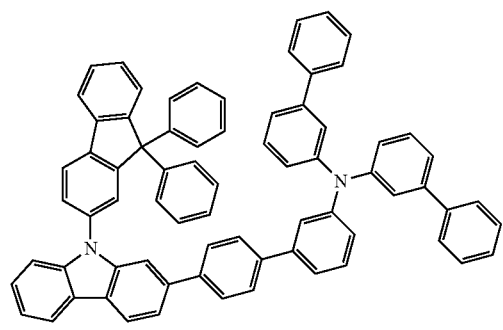
P1-38
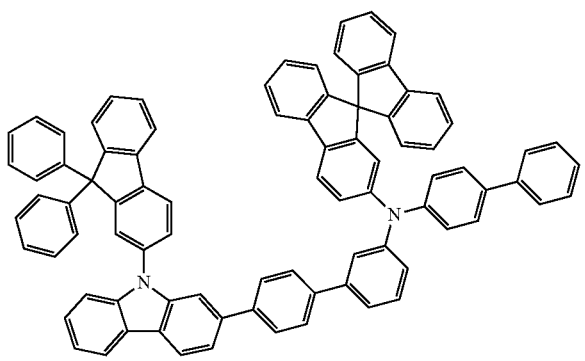
P1-39
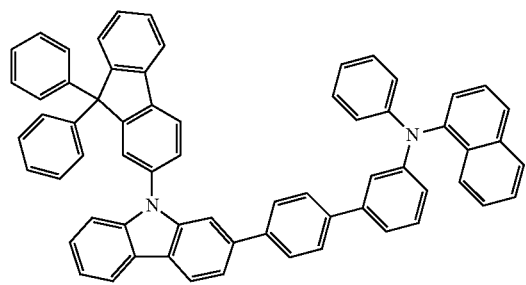
P1-40
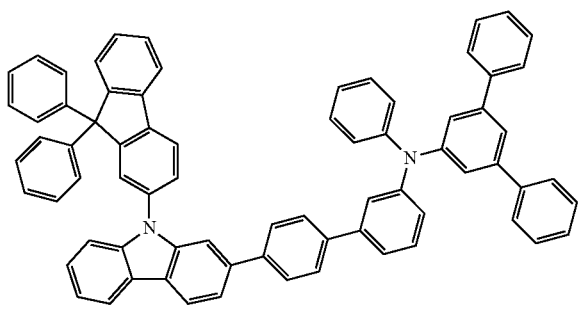

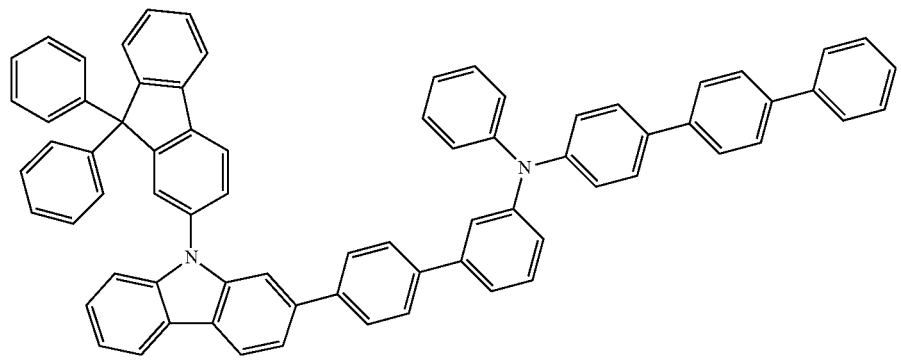
P1-41
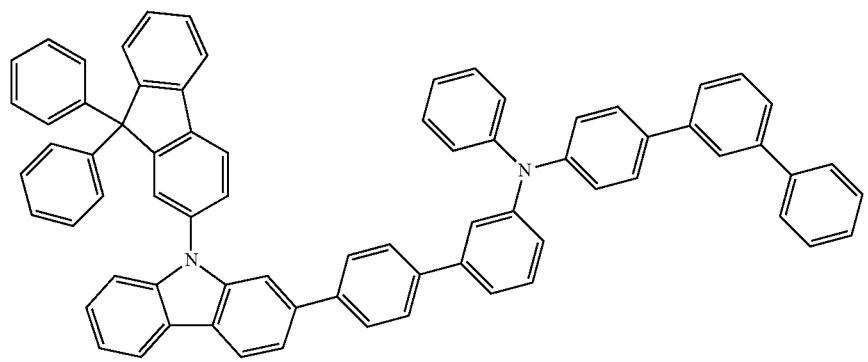
P1-42
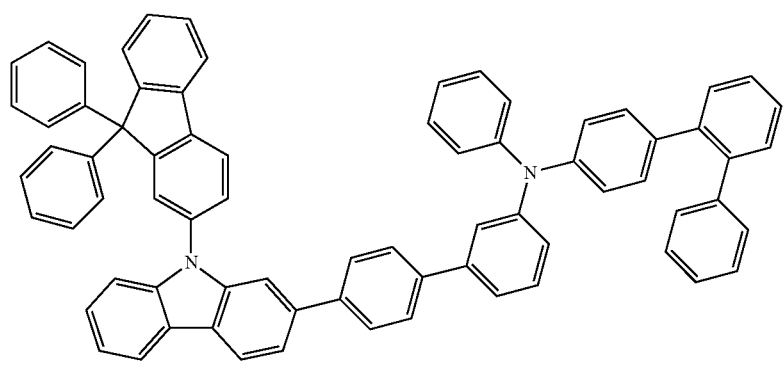
P1-43
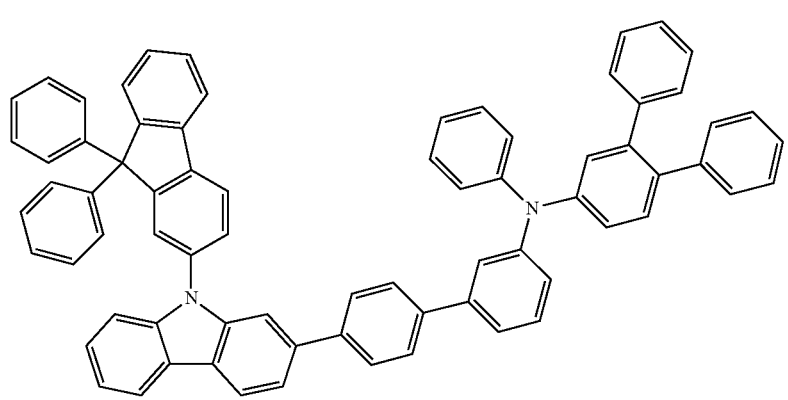
P1-44

-continued
P1-45
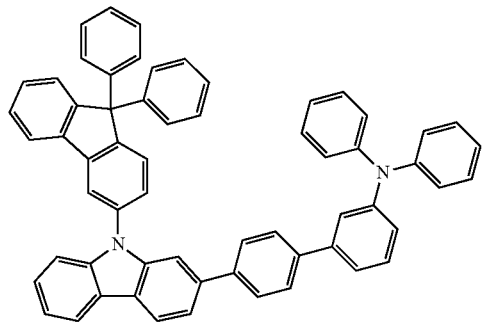
P1-46
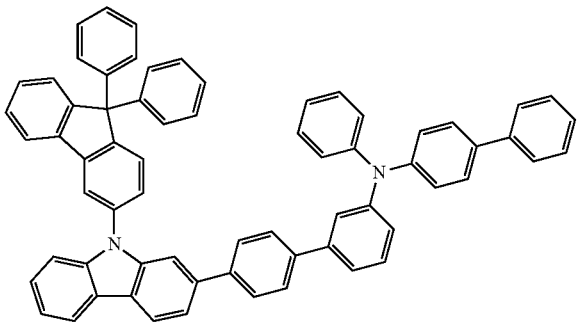
P1-47
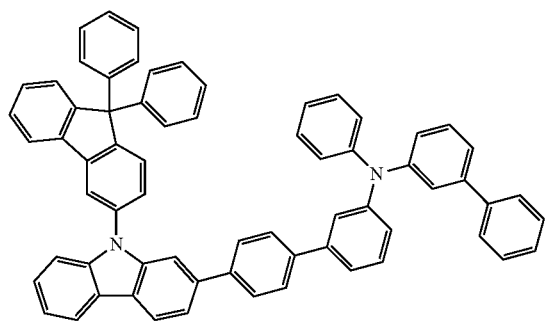
P1-48
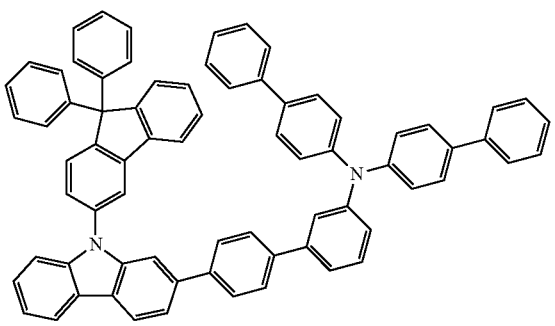
P1-49
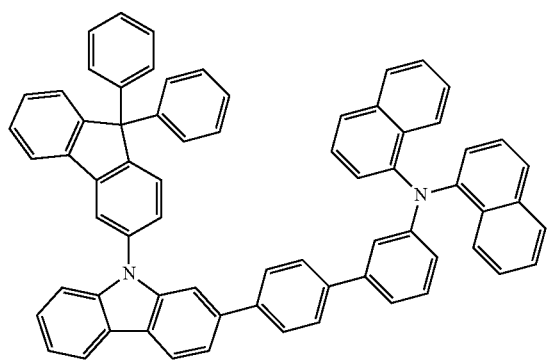
P1-50
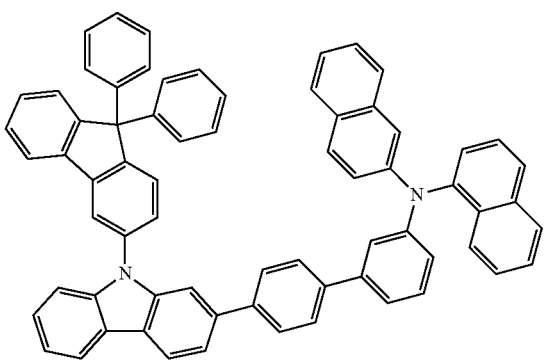
P1-51
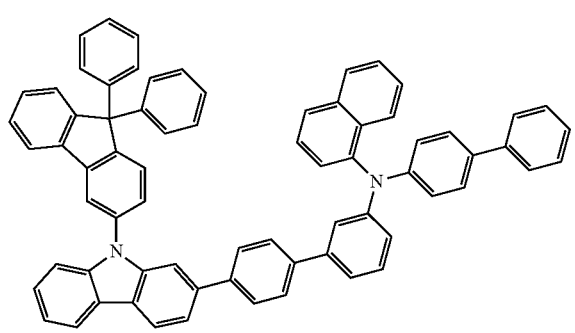
P1-52
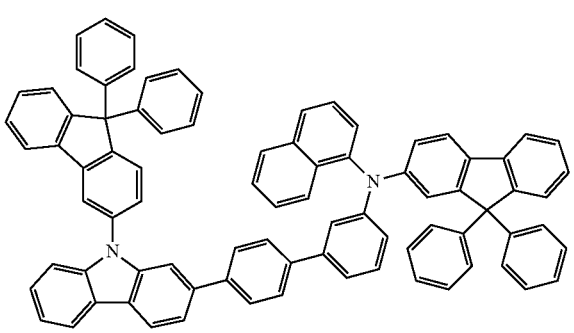

-continued
P1-53
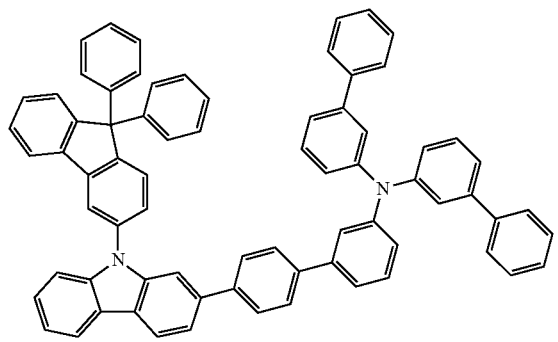
P1-54
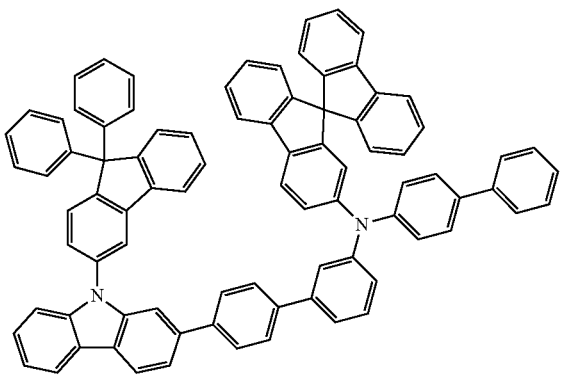
P1-55
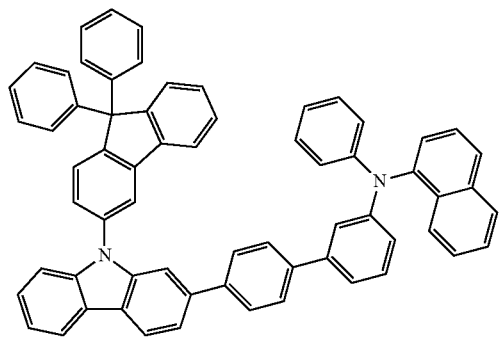
P-56
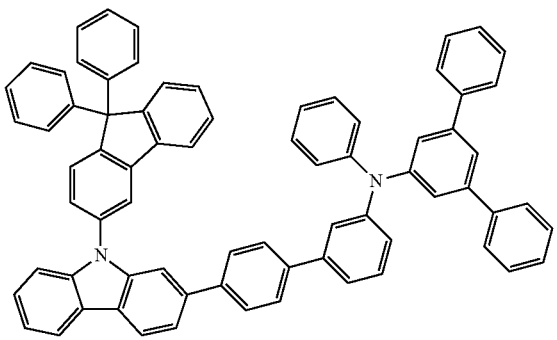
P1-57
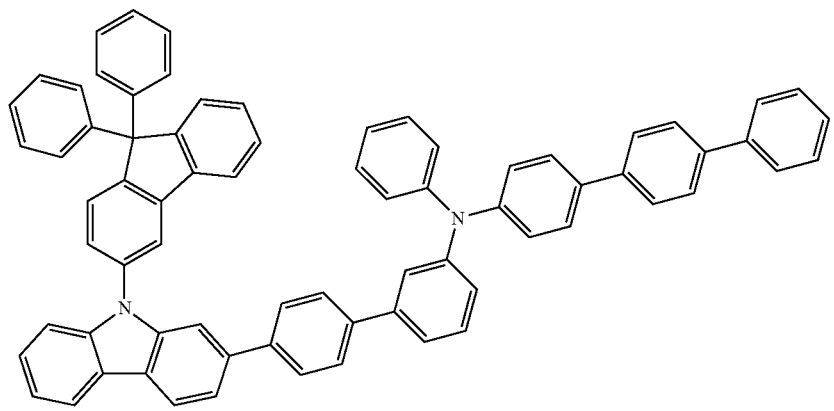
P1-58
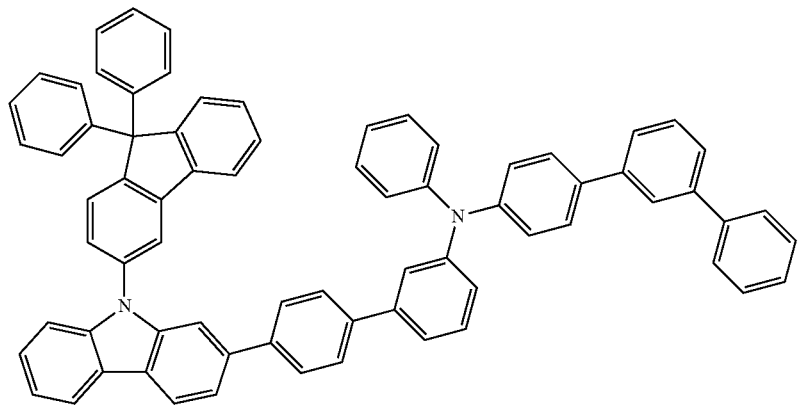

-continued
P1-59
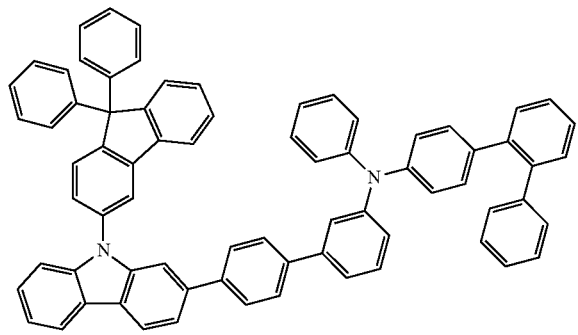
P1-60
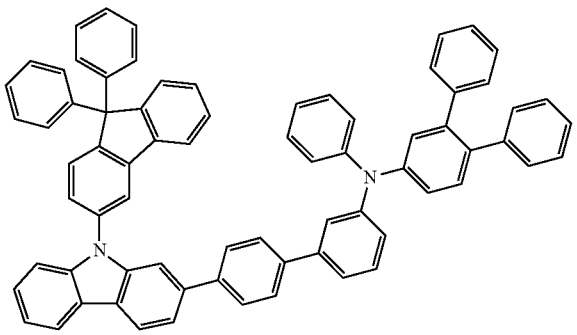
P1-61
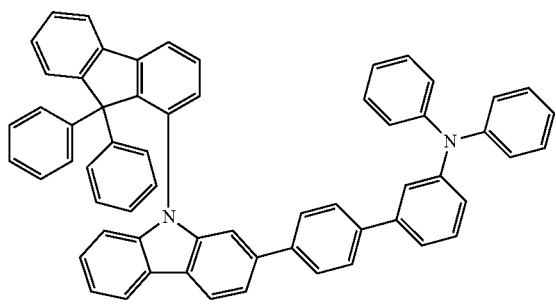
P1-62
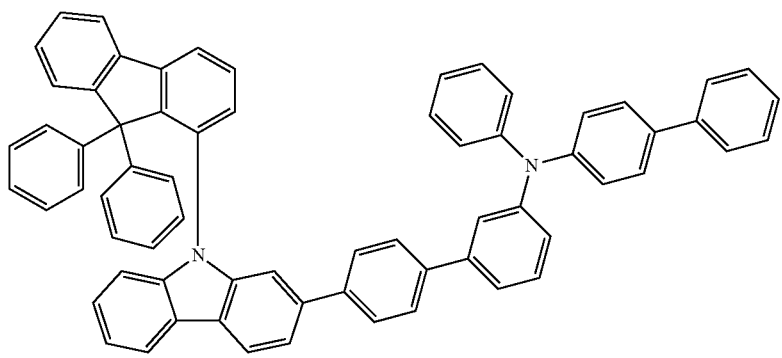
P1-63
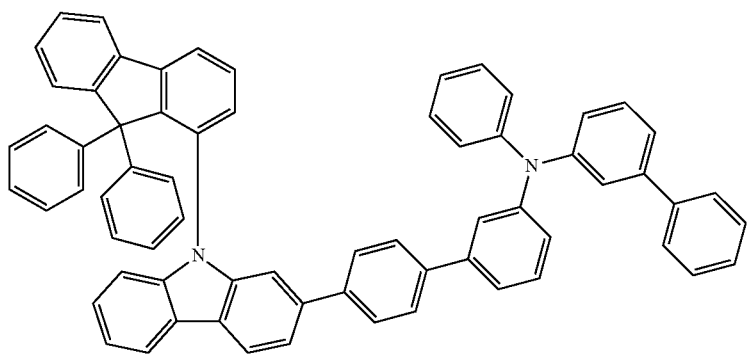

-continued
P1-64
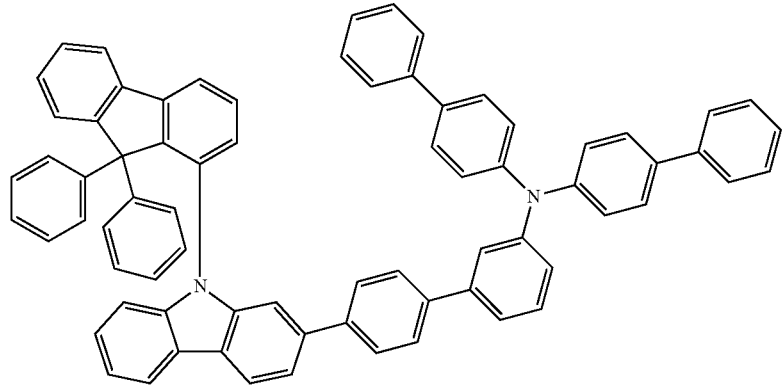
P1-65
P66
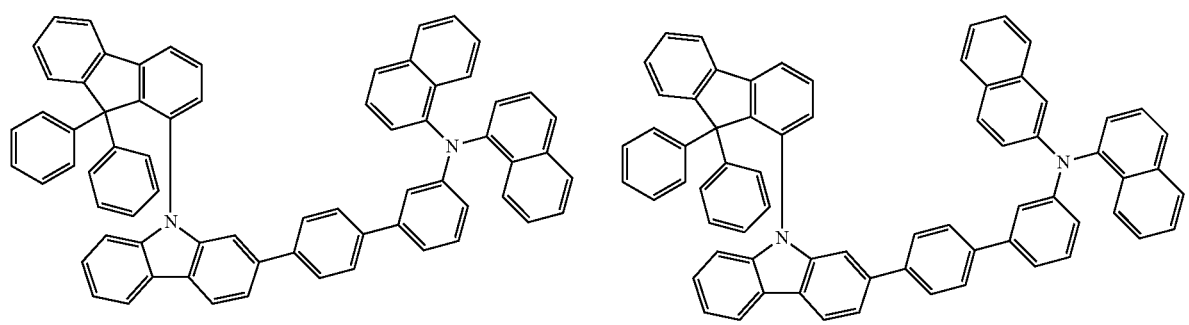
P1-67
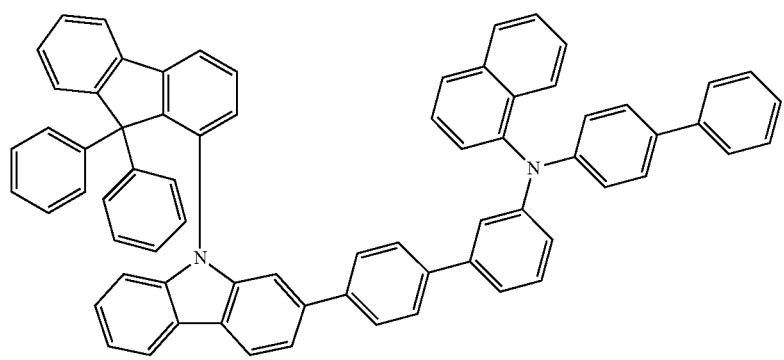
P1-68
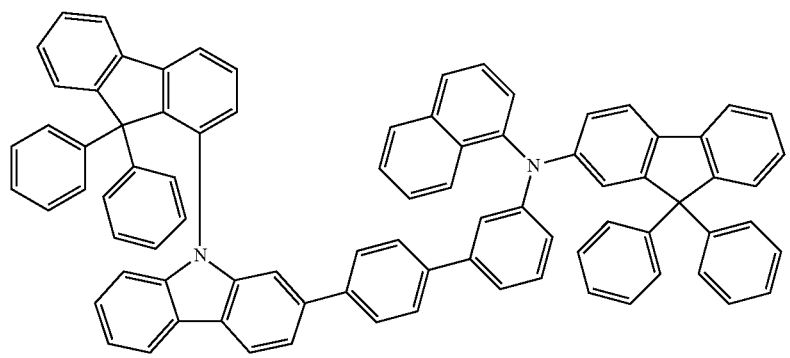

-continued
P1-69
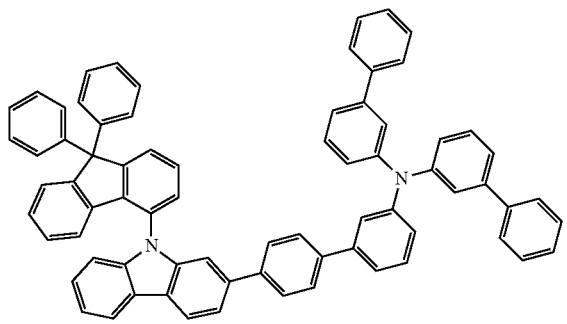
P1-70
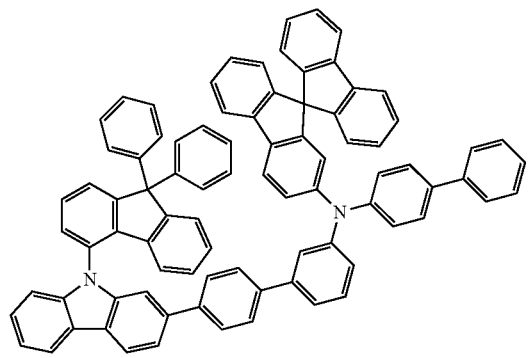
P1-71
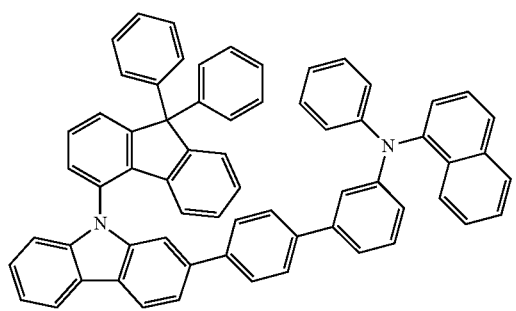
P1-72
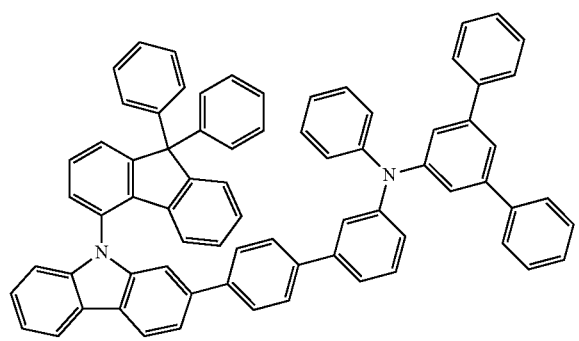
P1-73
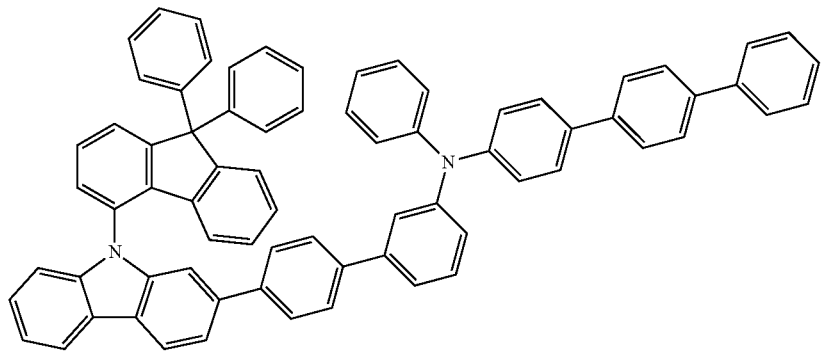
P1-74
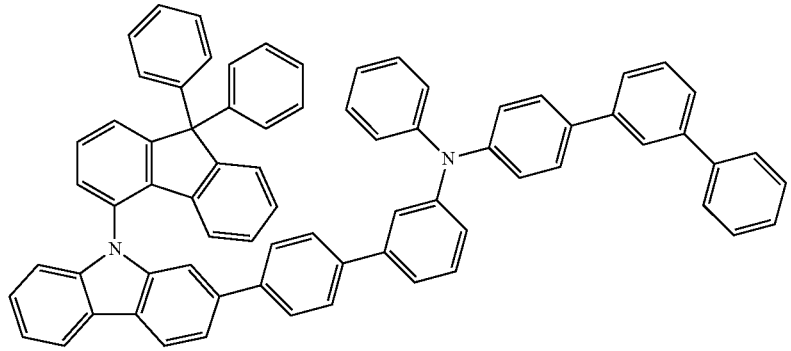

-continued
P1-75
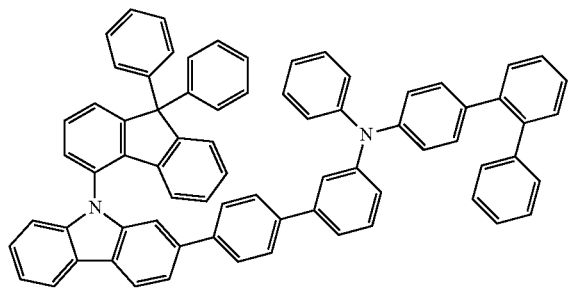
P1-76
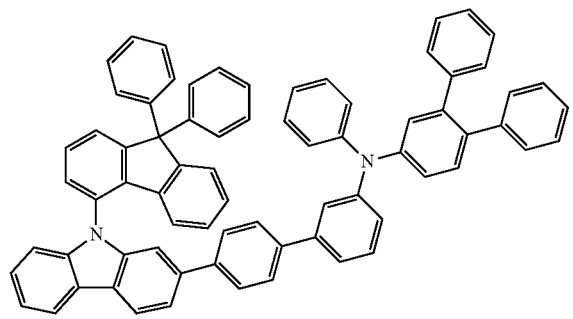
P1-77
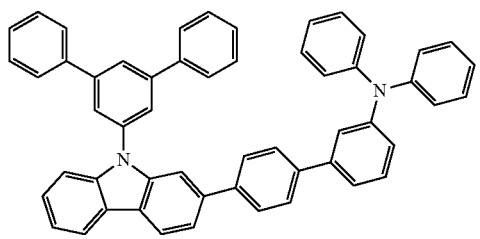
P1-78
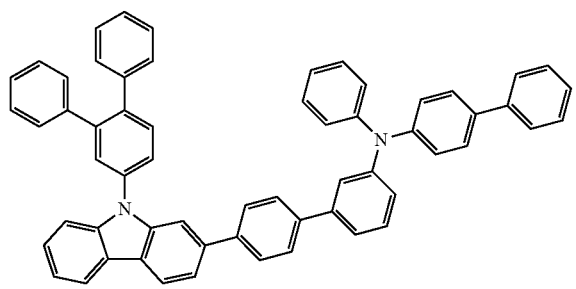
P1-79
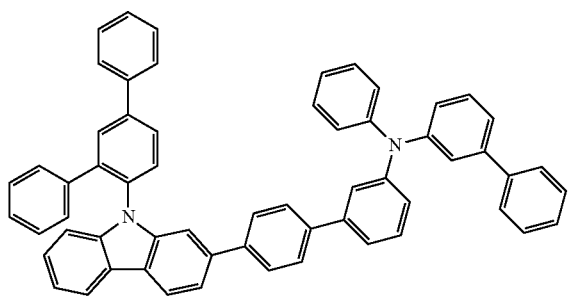
P1-80
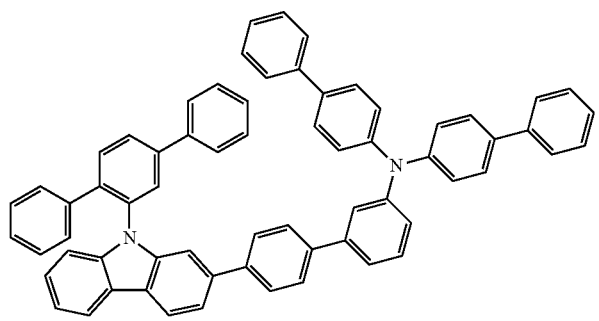
P1-81
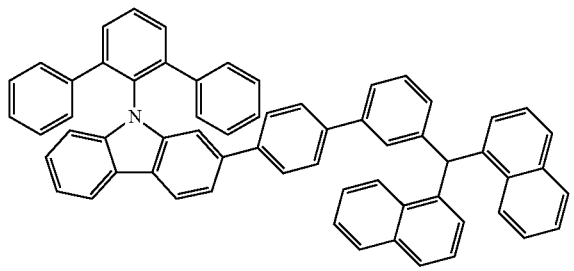
P1-82
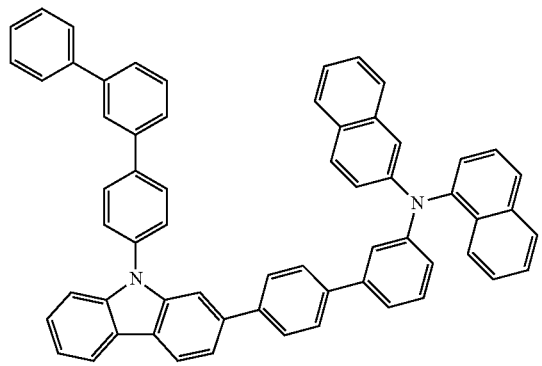

-continued
P1-83
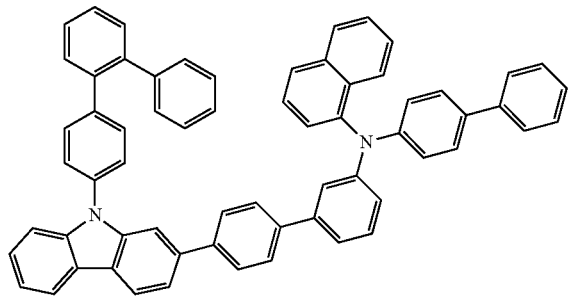
P1-84
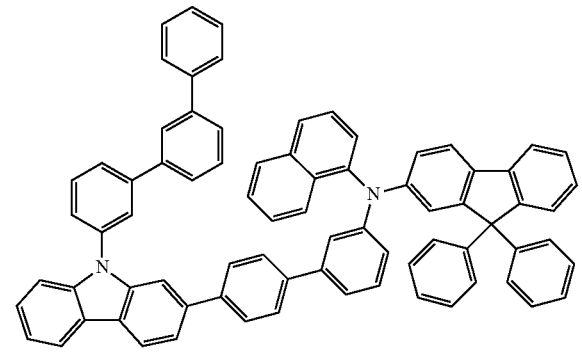
P1-85
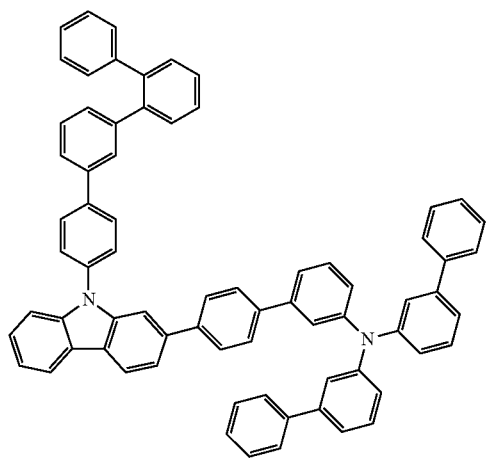
P1-86
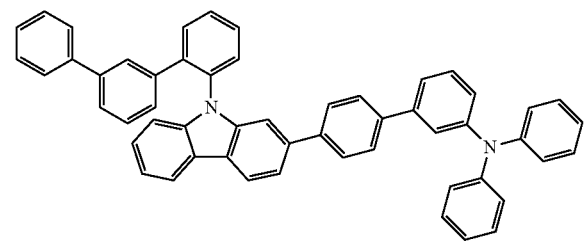
P1-87
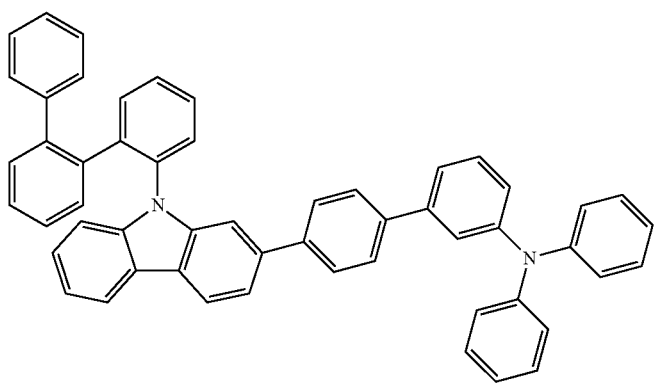
P1-88
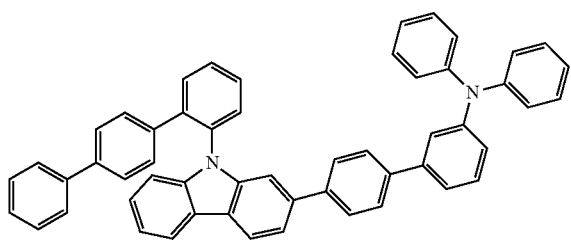
P1-89
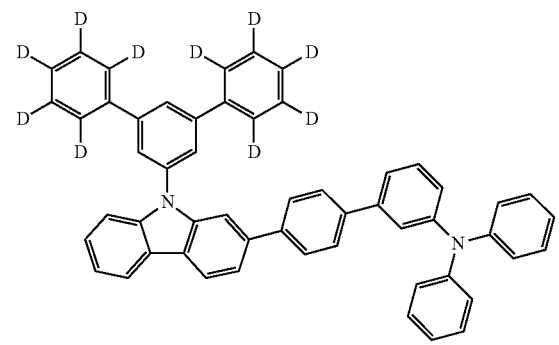

-continued
P1-90
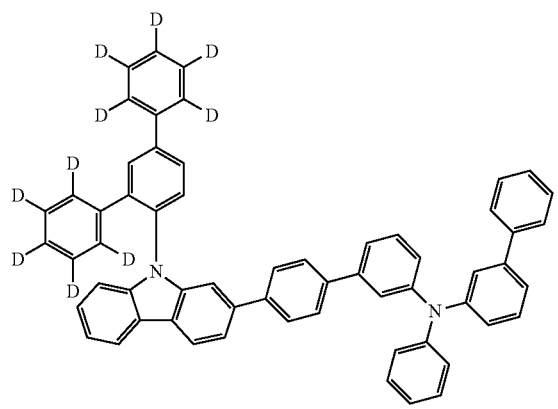
P1-91
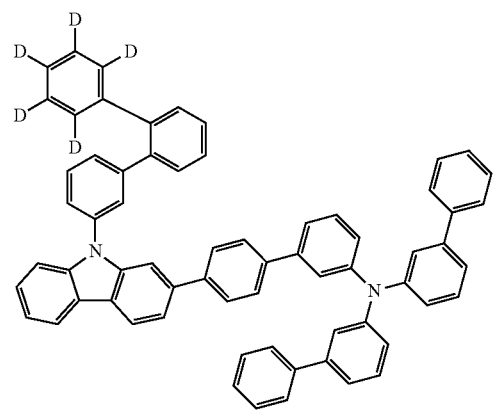
P-92
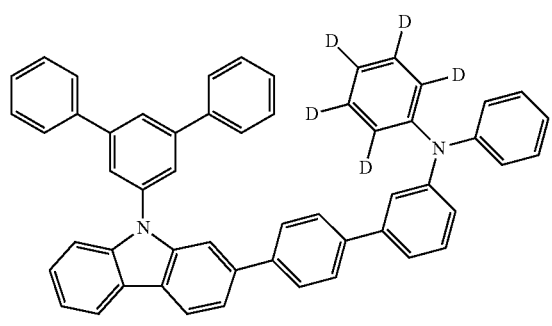
P1-93
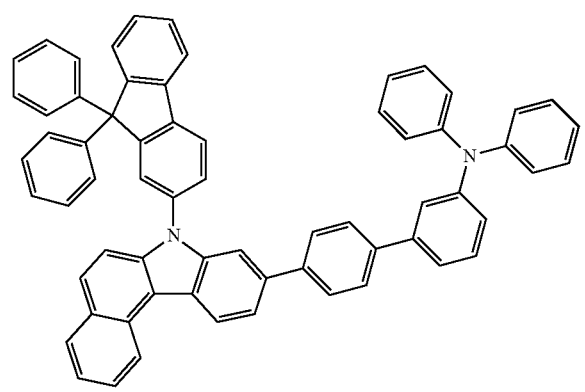
P1-94
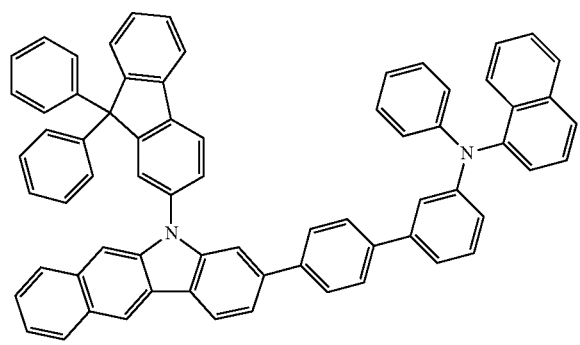
P1-95
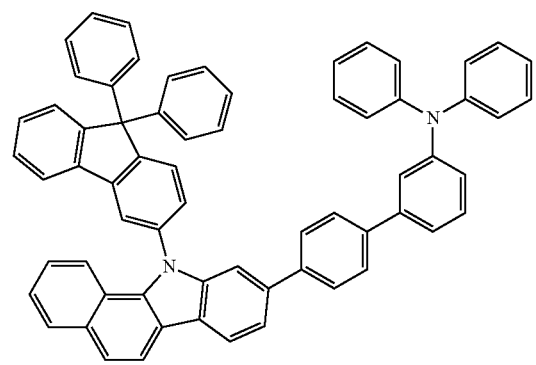
P1-96
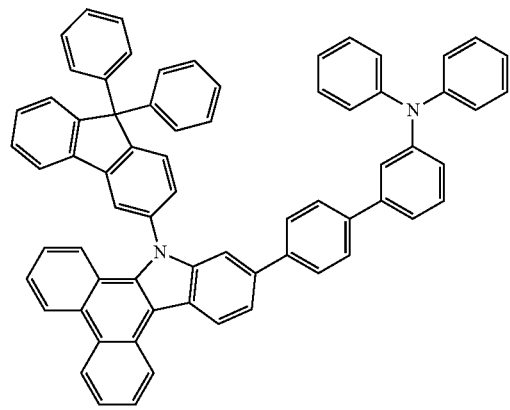
P1-97
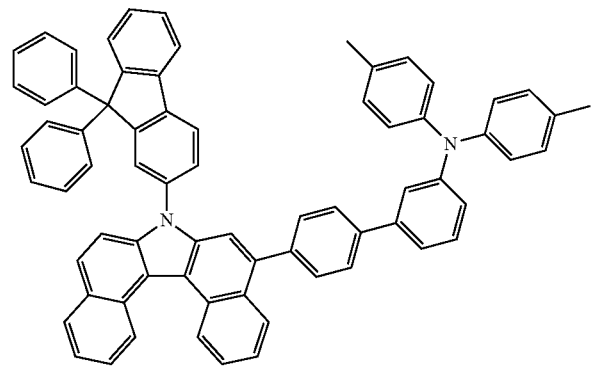

-continued
P1-98
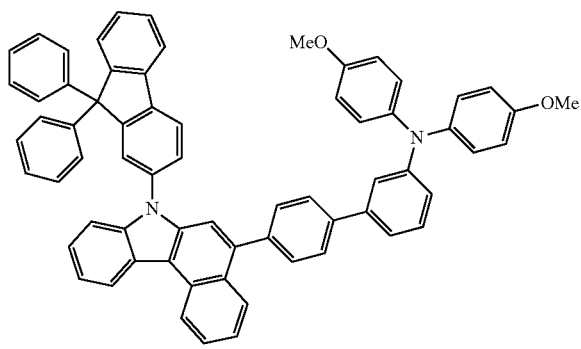
P1-99
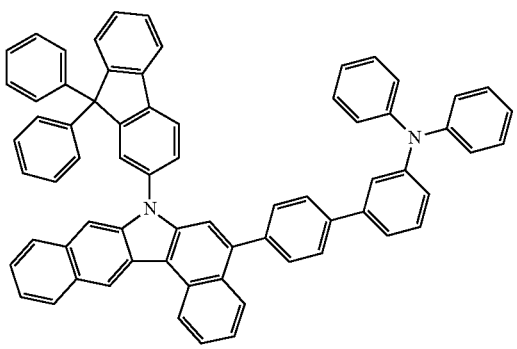
P1-100
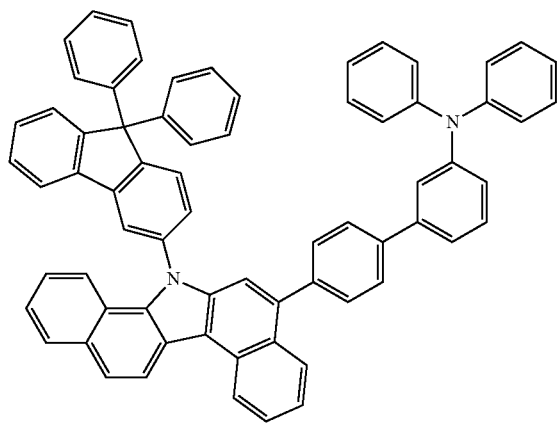
P1-101
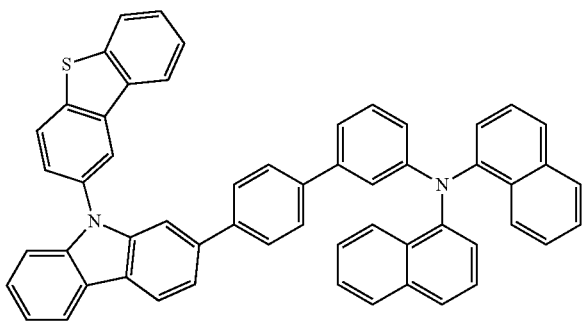
P1-102
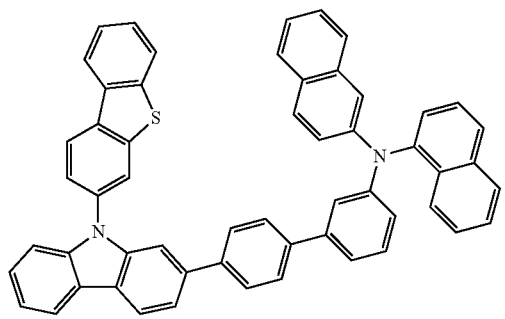
P1-103
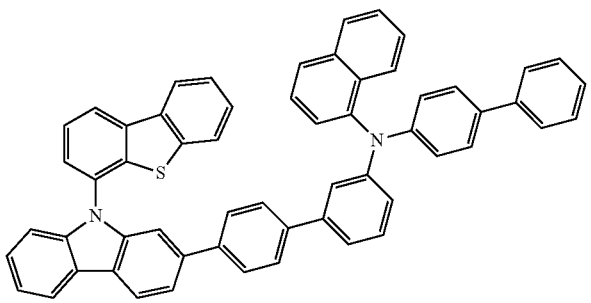
P1-104
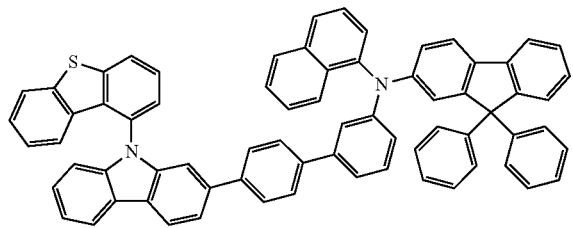
P1-105
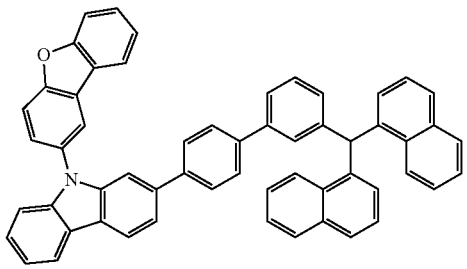

-continued
P1-106
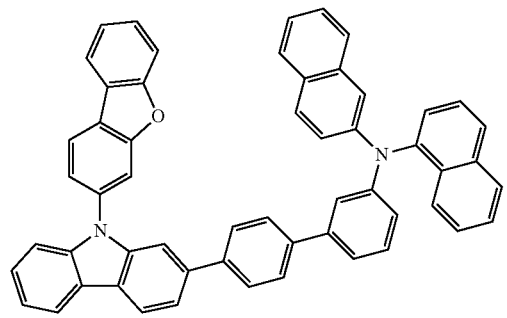
P1-107
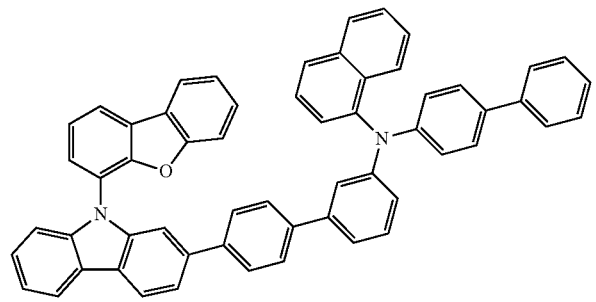
P1-108
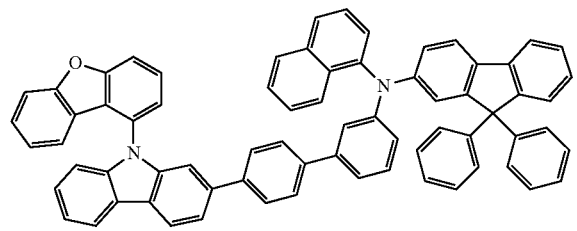
P1-109
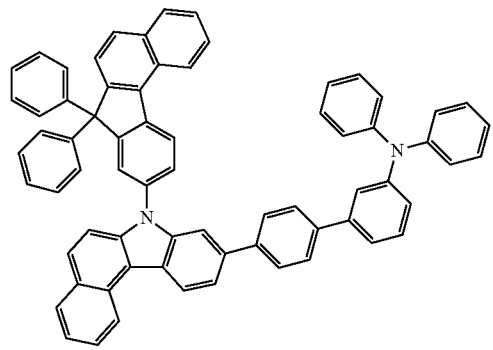
P1-110
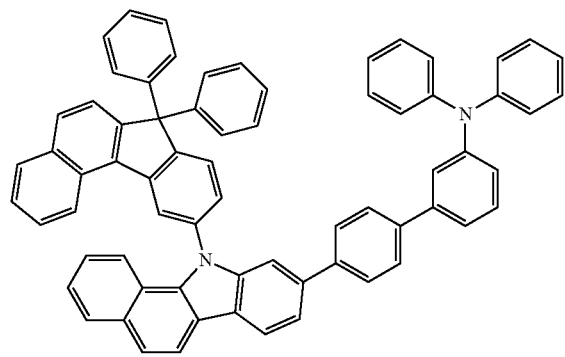
P1-111
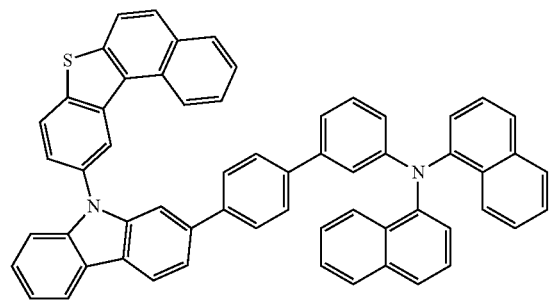
P1-112
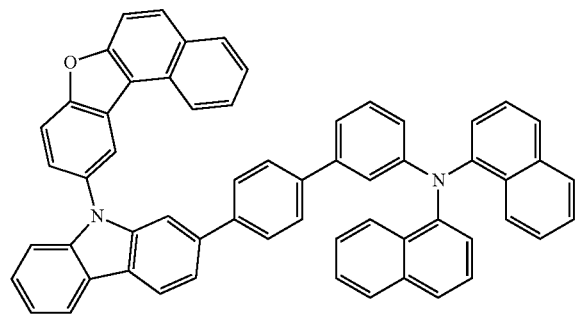
P2-1
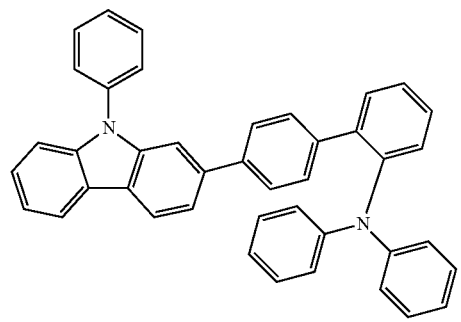

-continued
P2-2
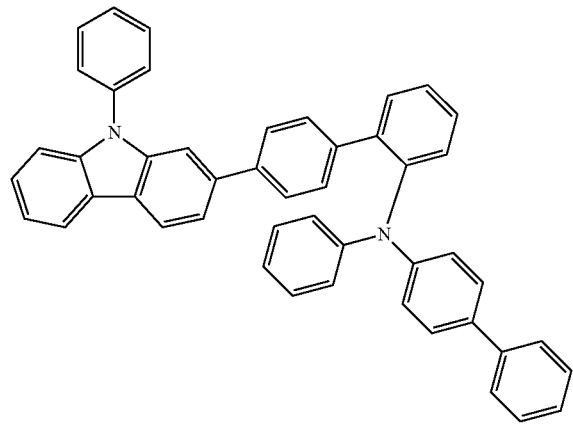
P2-3
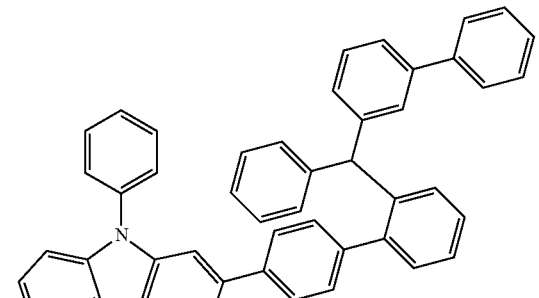
P2-4
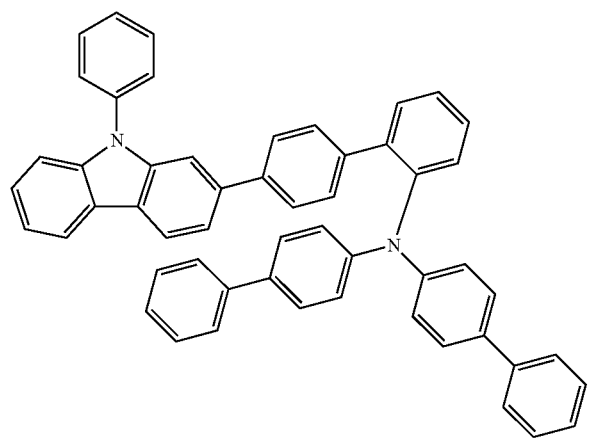
P2-5
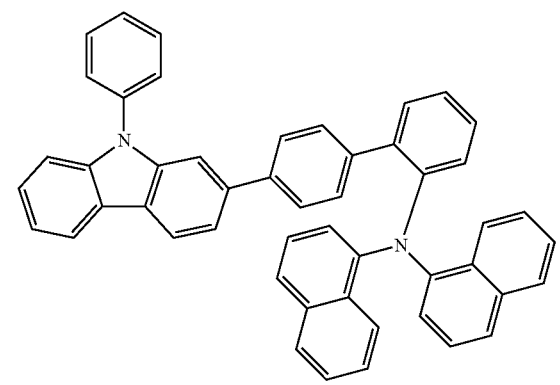
P2-6
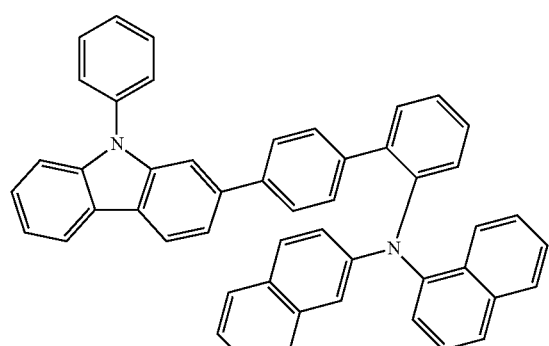
P2-7
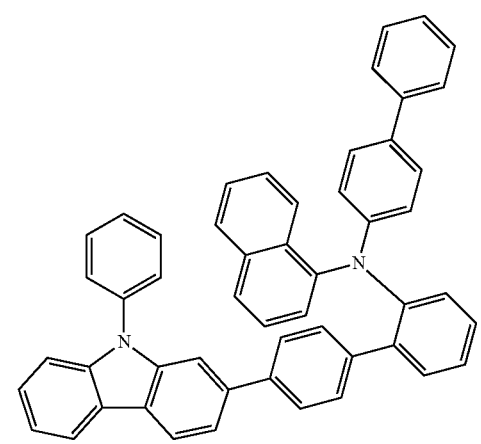

-continued
P2-8
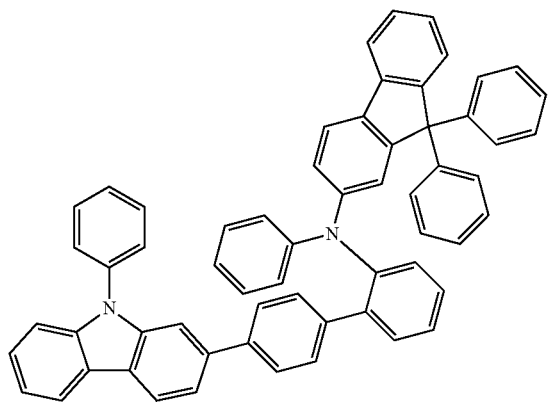
P2-9
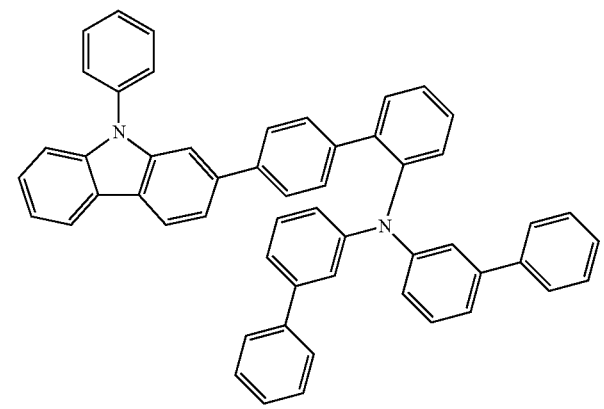
P2-10
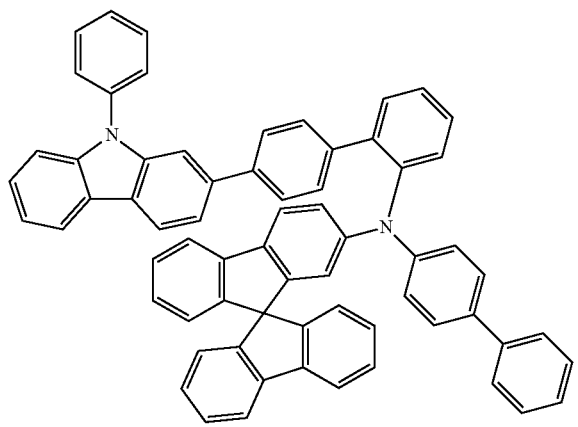
P2-11
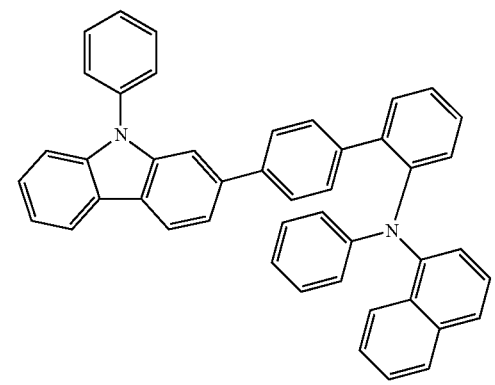
P2-12
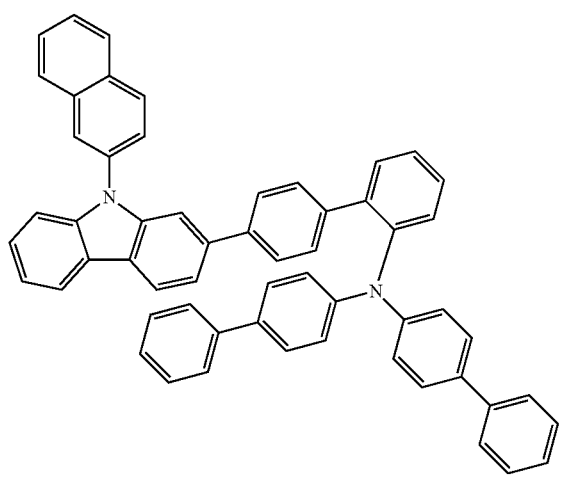
P2-13
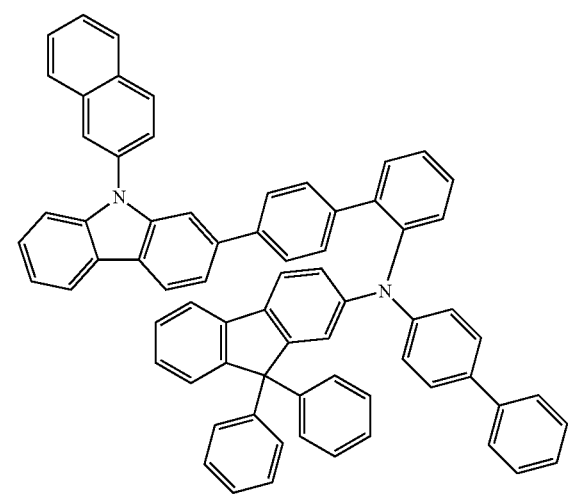

-continued
P2-14
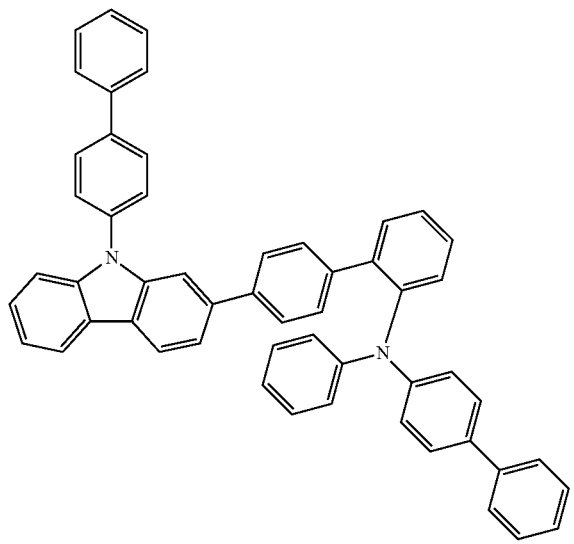
P2-15
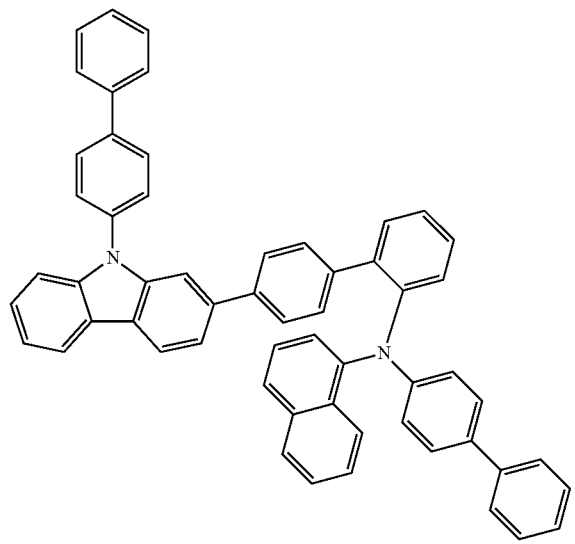
P2-16
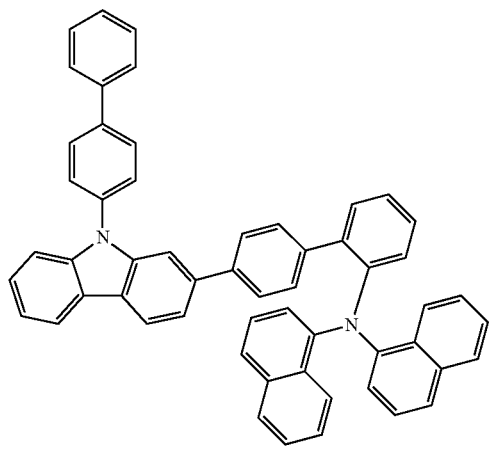
P2-17
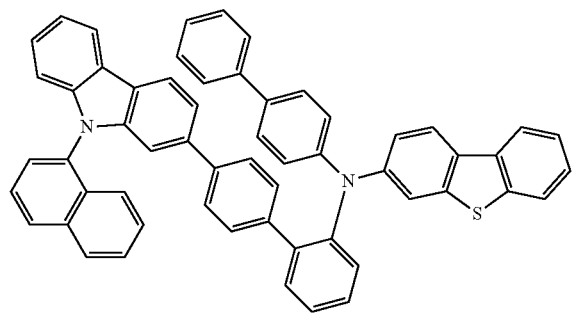
P2-18
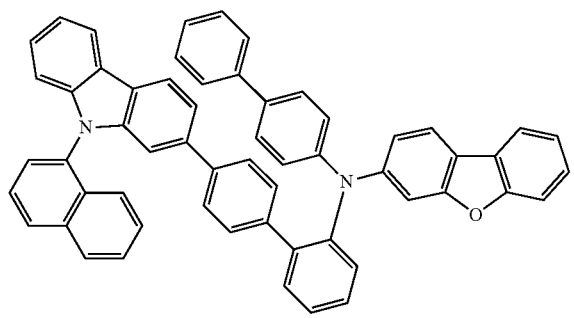
P2-19
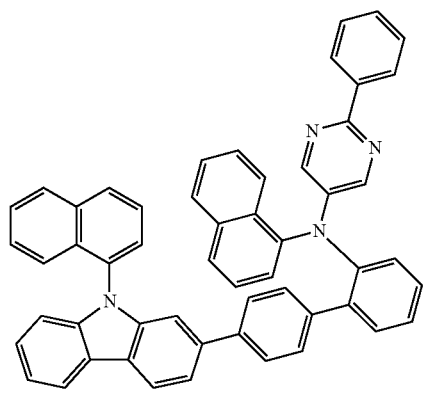

-continued
P2-20
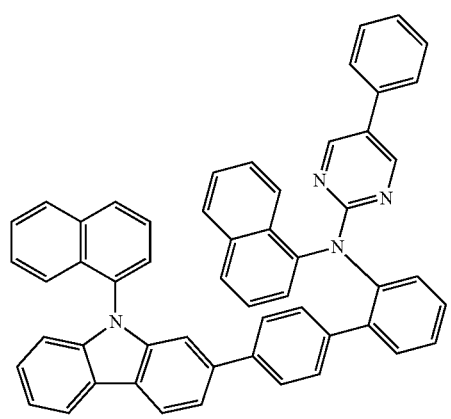
P2-21
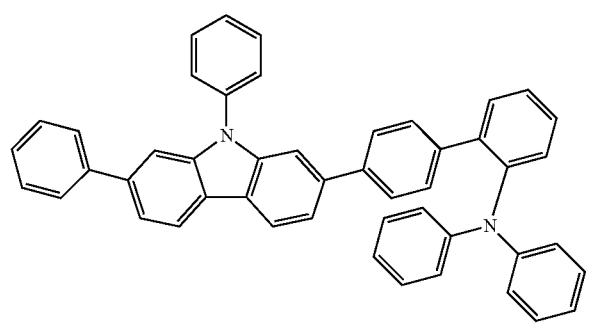
P2-22
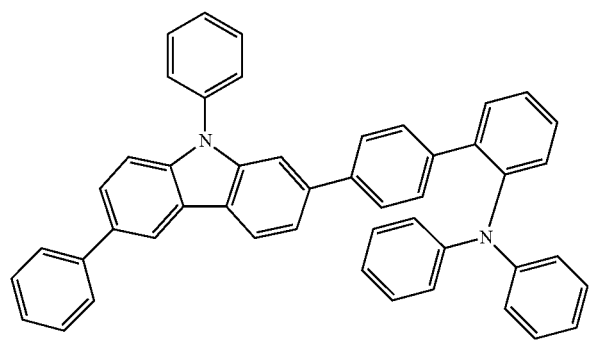
P2-23
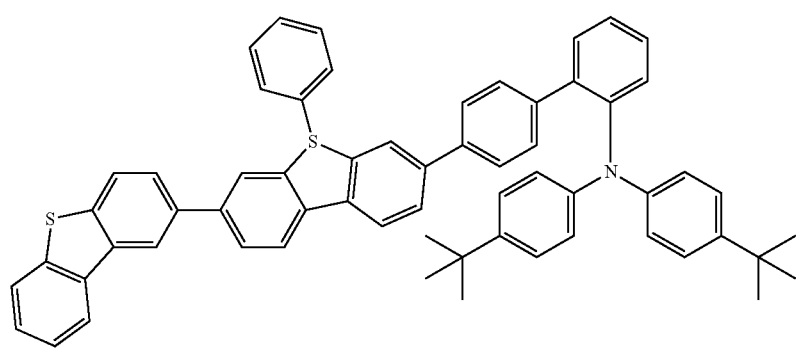
P2-24
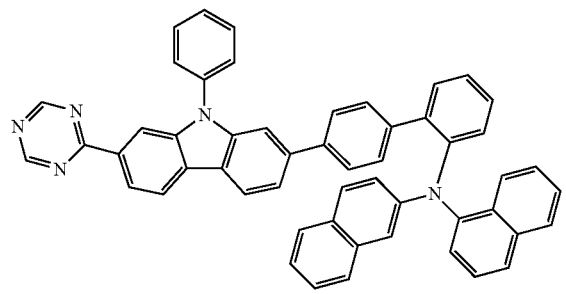
P2-25
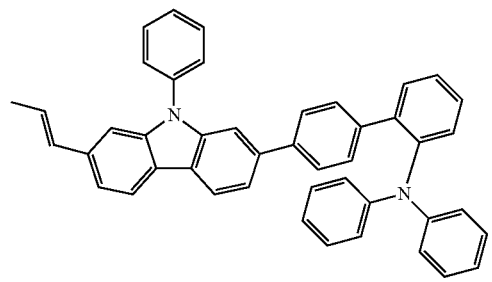

-continued
P2-26
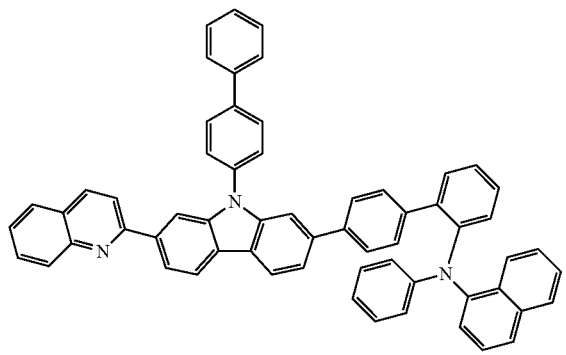
P2-27
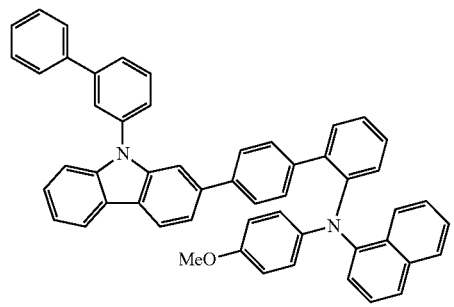
P2-28
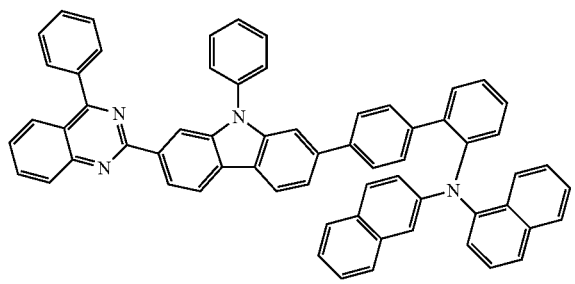
P2-29
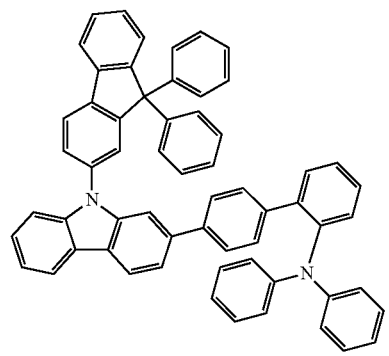
P2-30
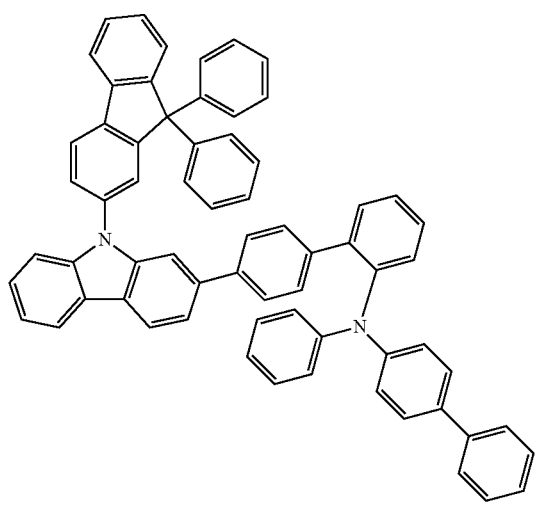
P2-31
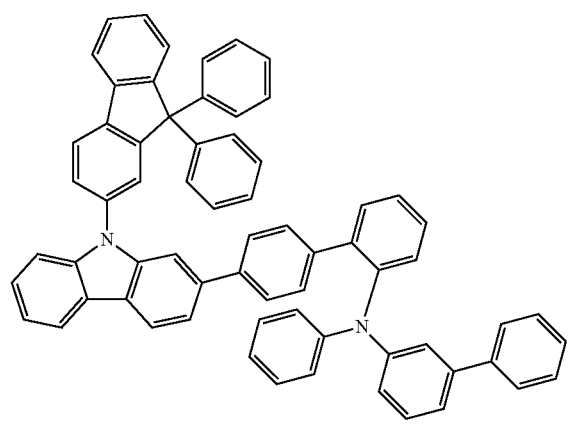

-continued
P2-32
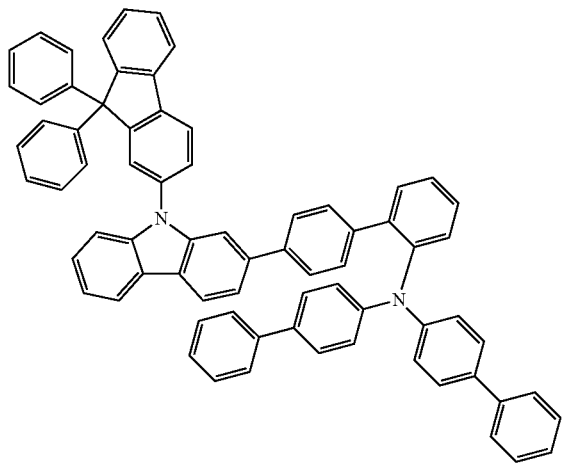
P2-33
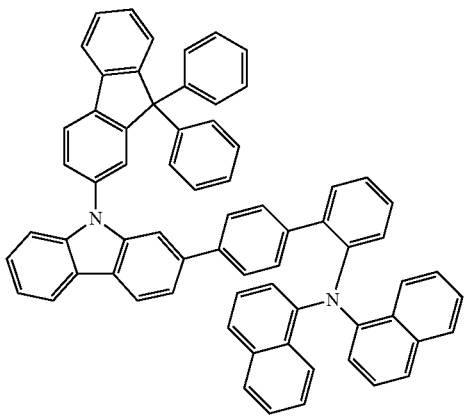
P2-34
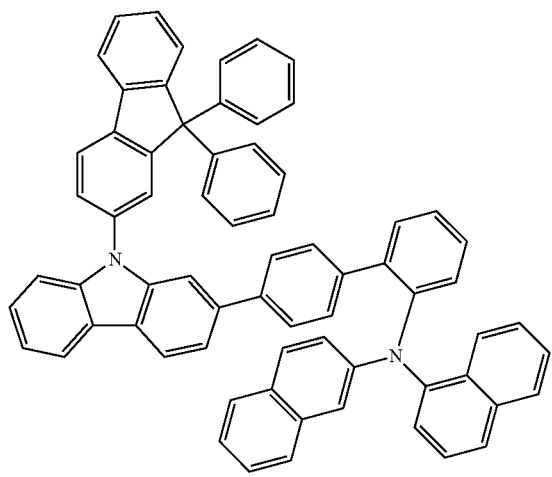
P2-35
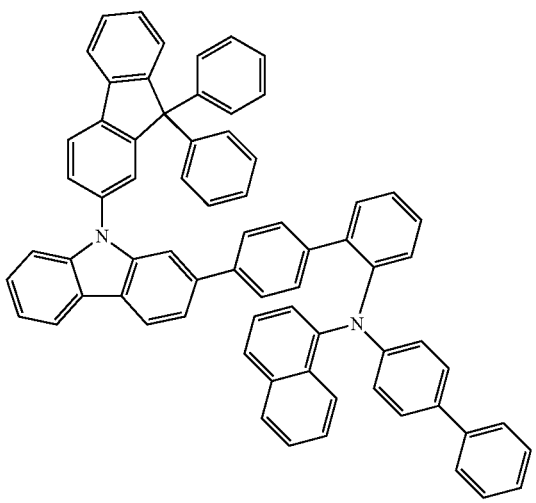
P2-36
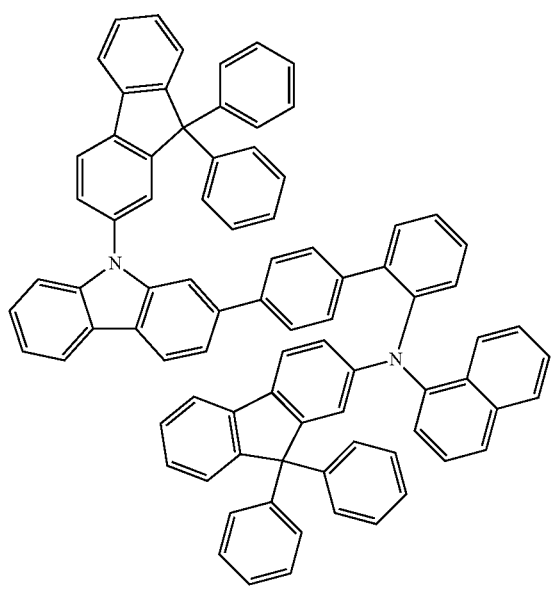

P2-37
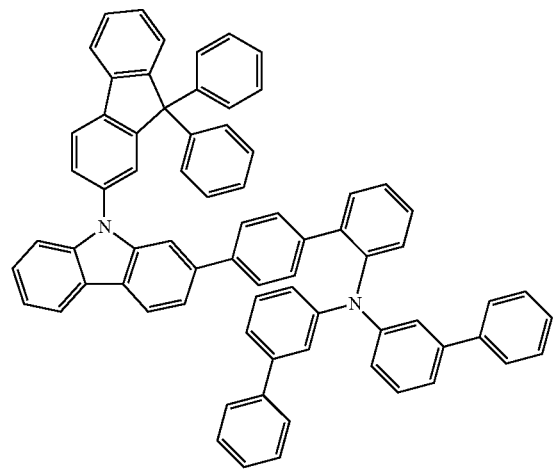
P2-38
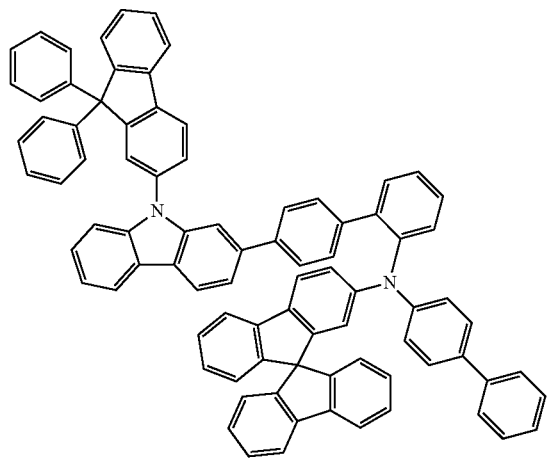
P2-39
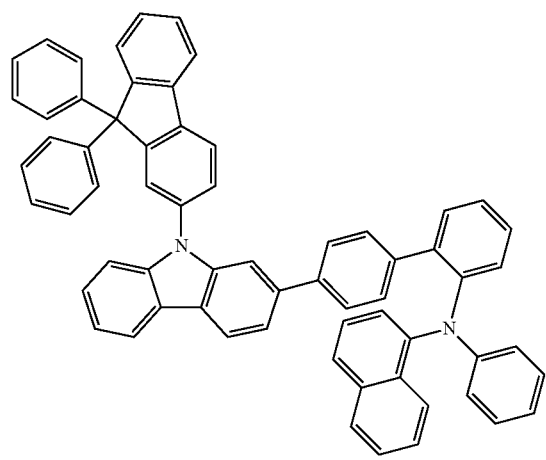
P2-40
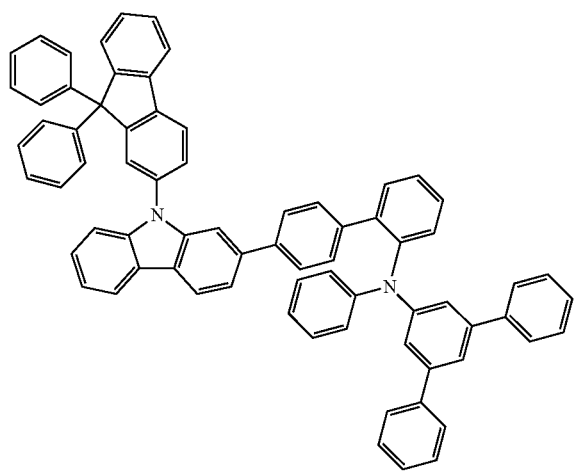
P2-41
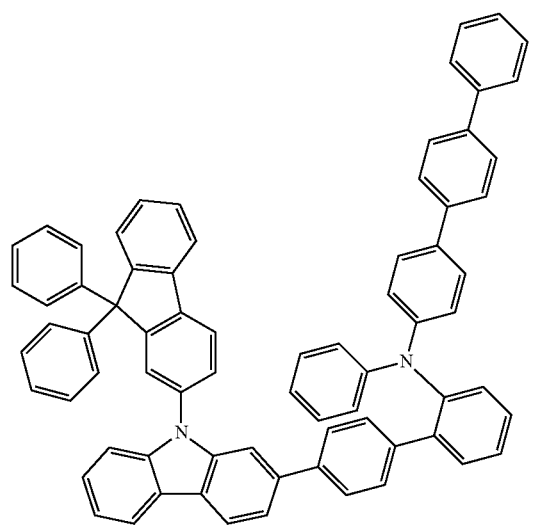
P2-42
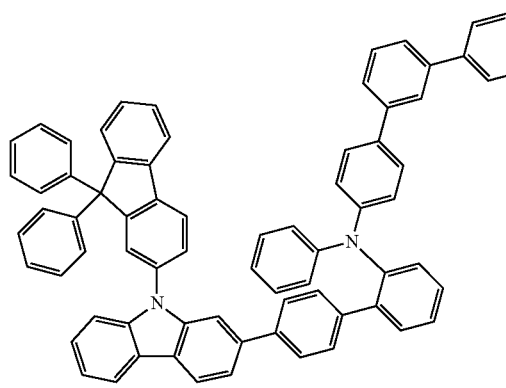

-continued
P2-43
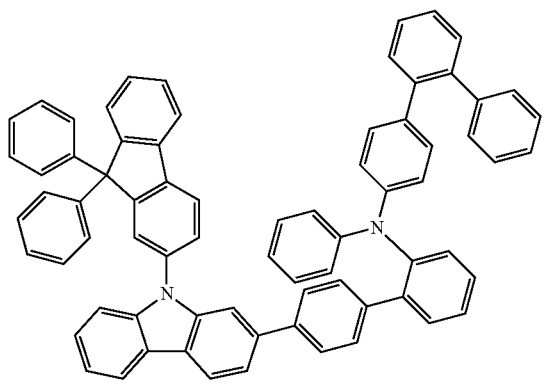
P2-44
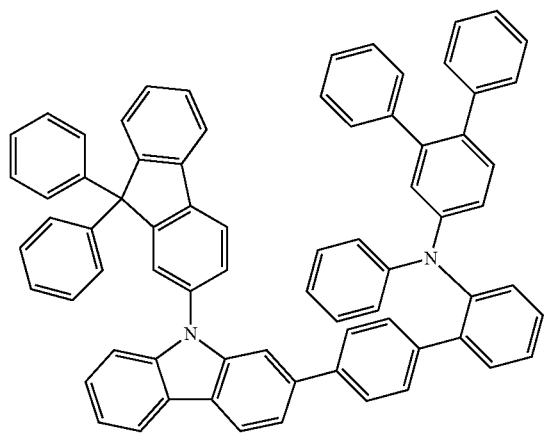
P2-45
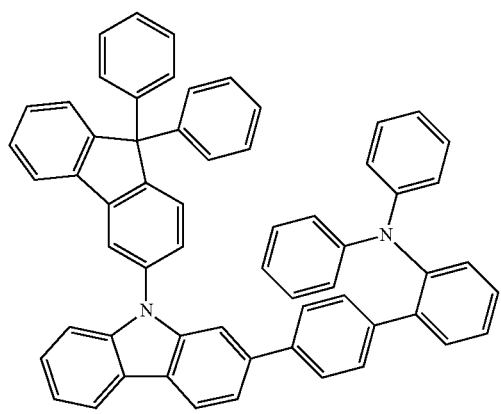
P2-46
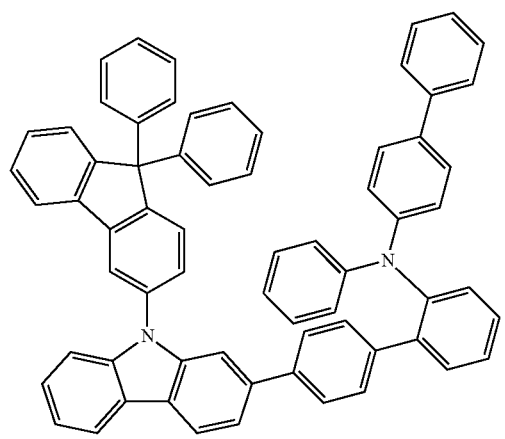
P2-47
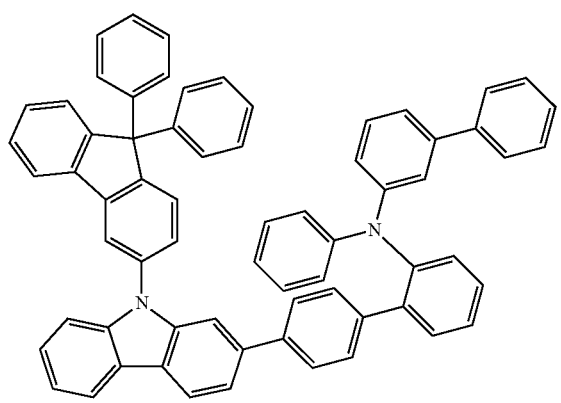
P2-48
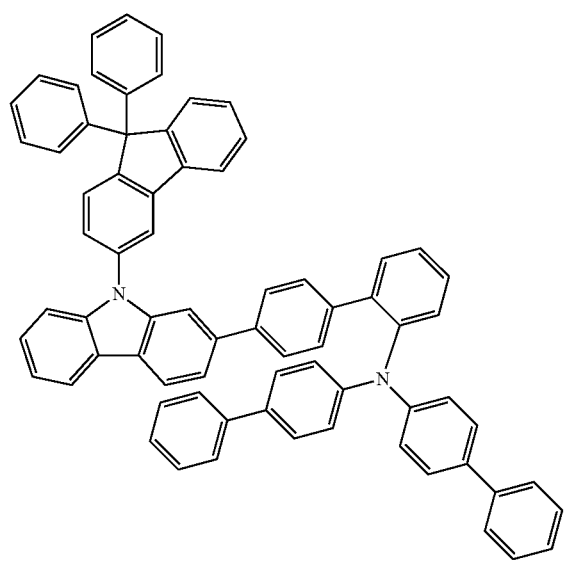

-continued
P2-49
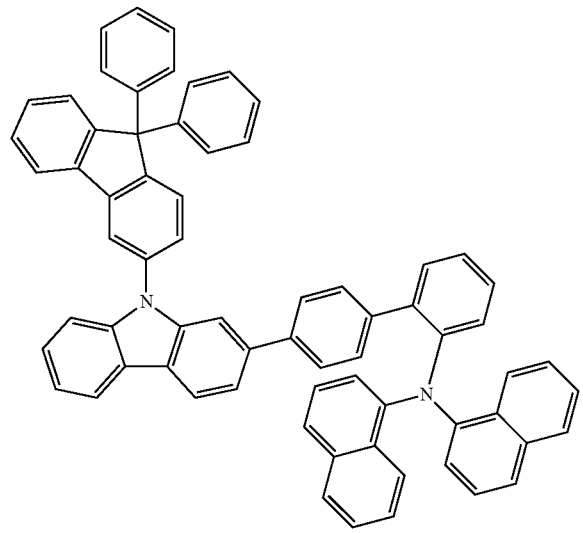
P2-50
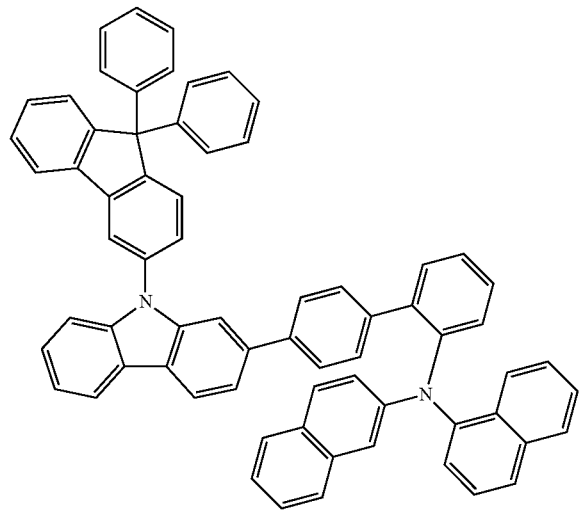
P2-51
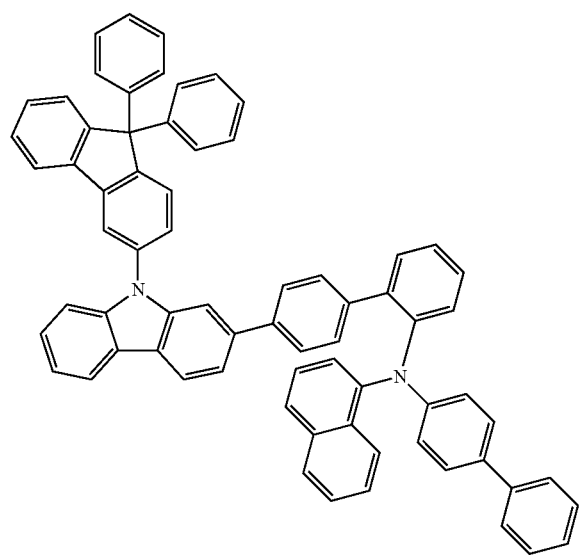
P2-52
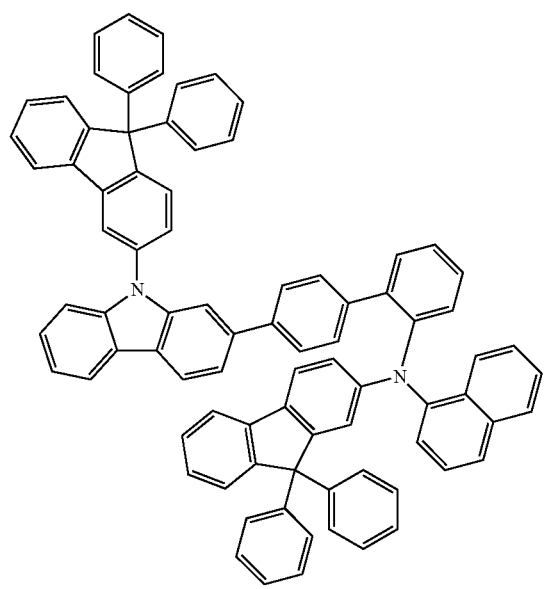

-continued
P2-53
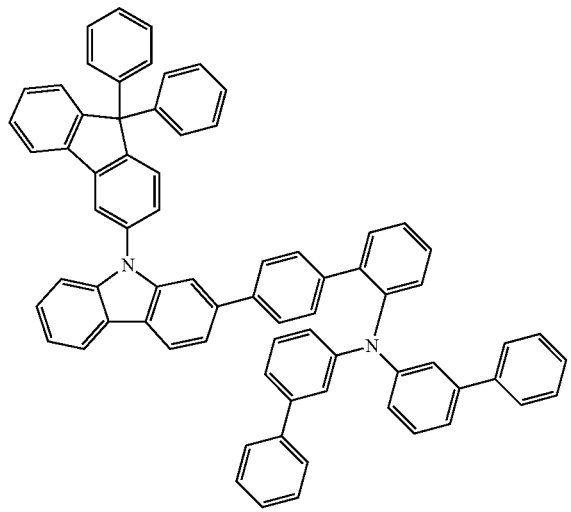
P2-54
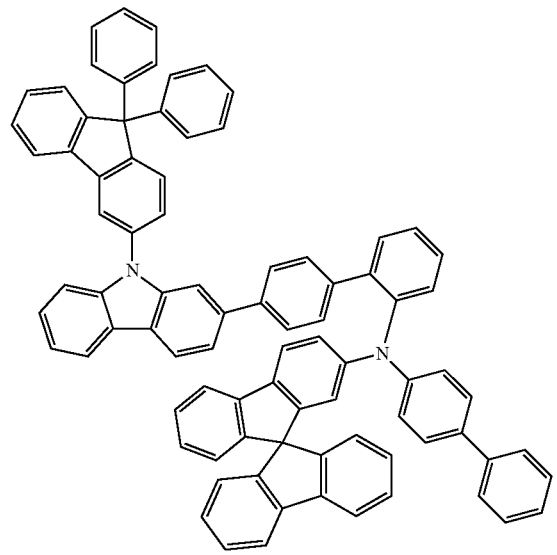
P2-55
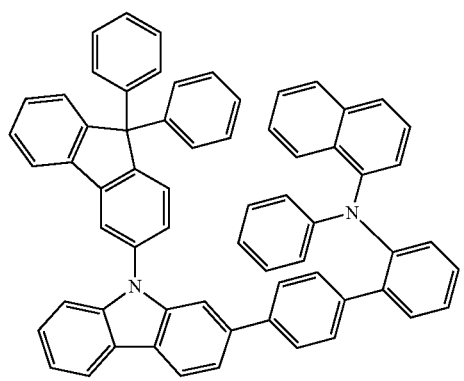
P2-56
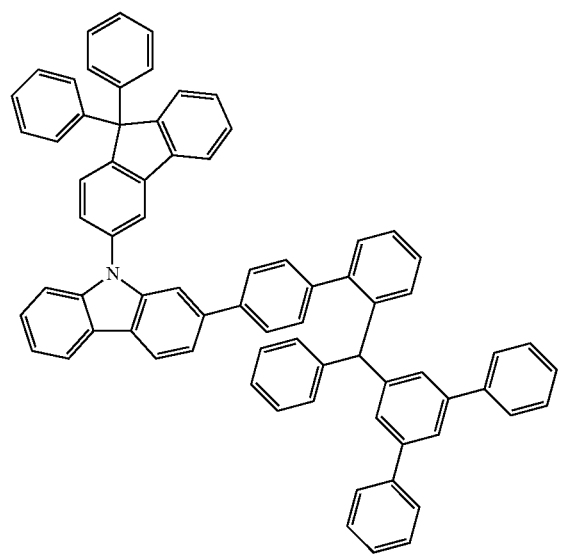

-continued
P2-57
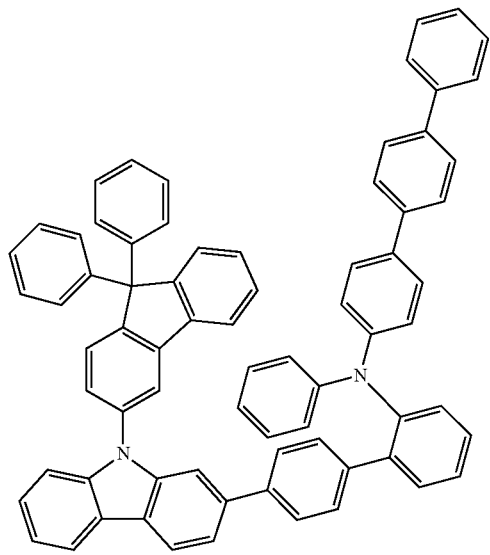
P2-58
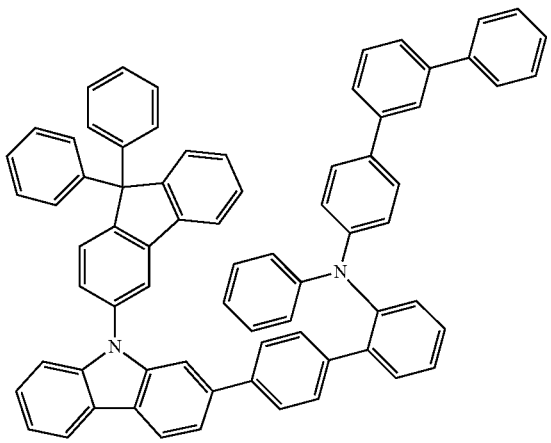
P2-59
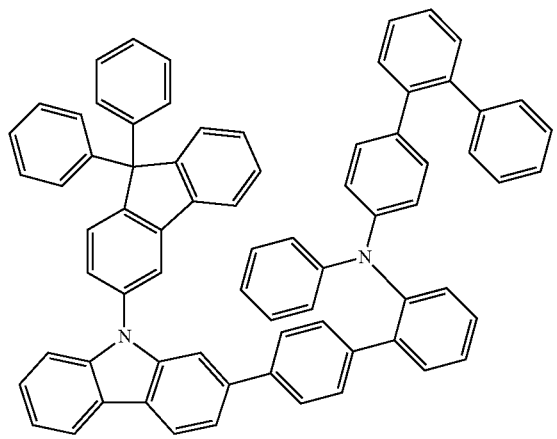
P2-60
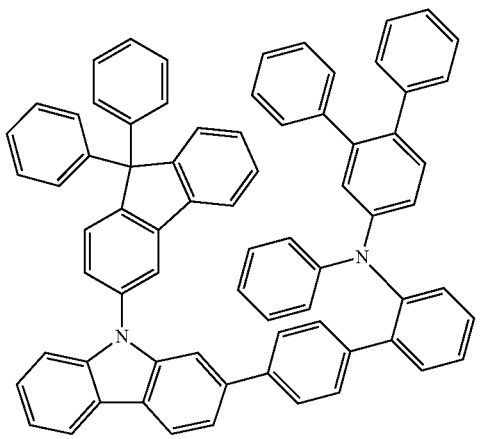
P2-61
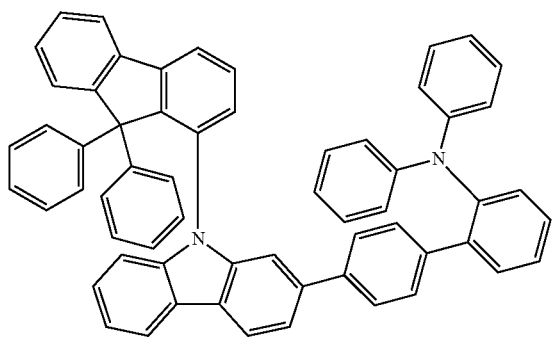
P2-62
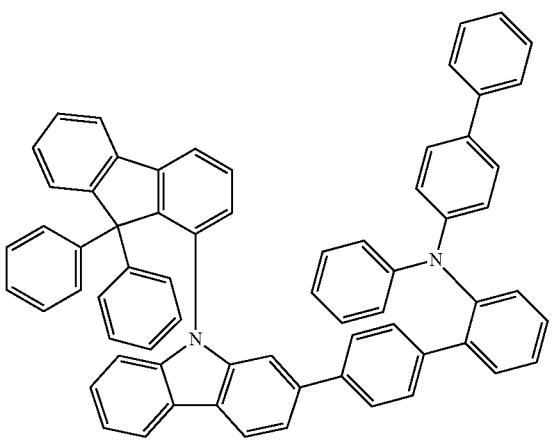

-continued
P2-63
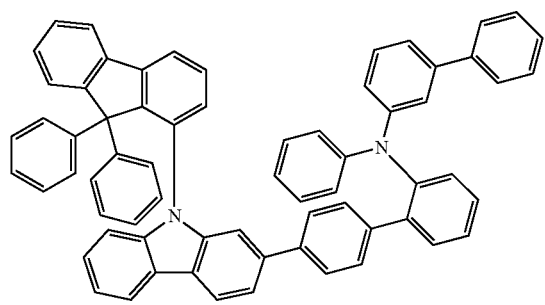
P2-64
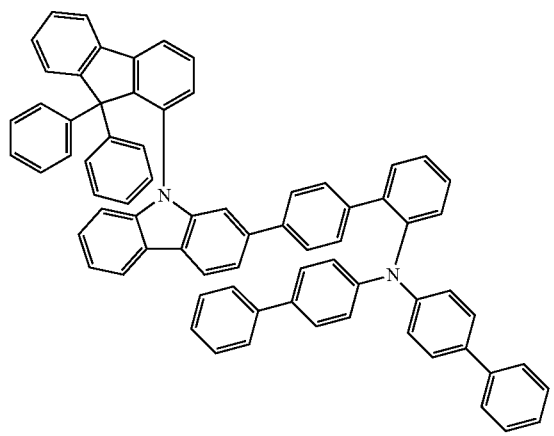
P2-65
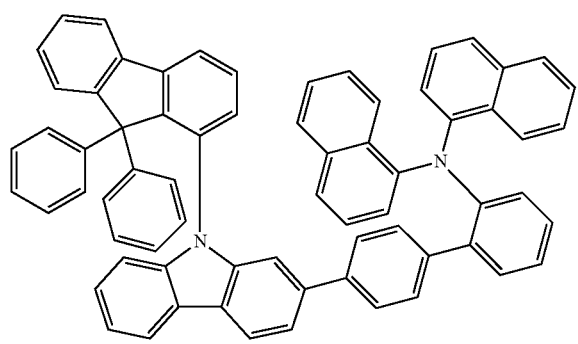
P2-66
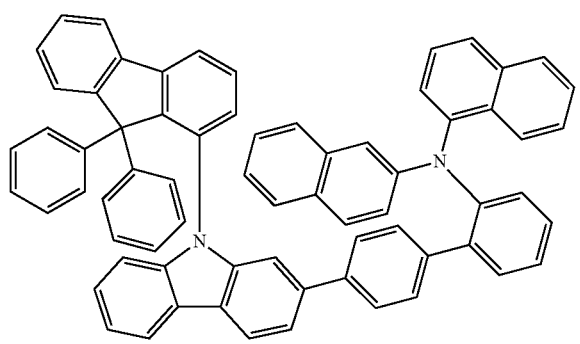
P2-67
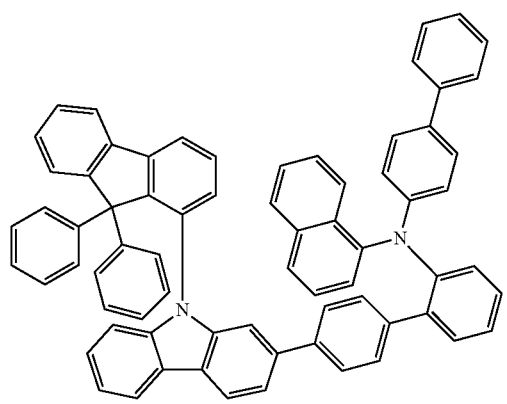
P2-68
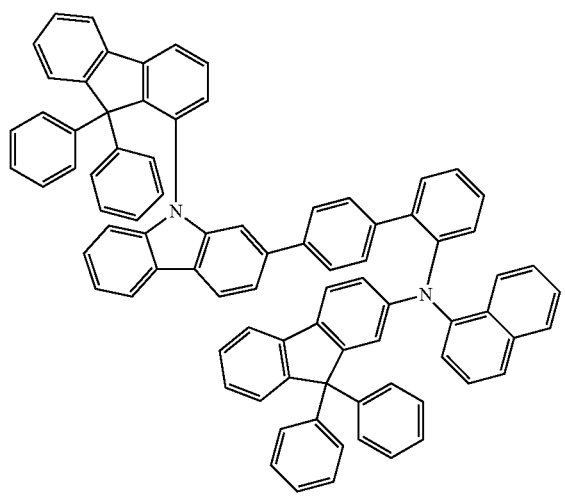

-continued
P2-69
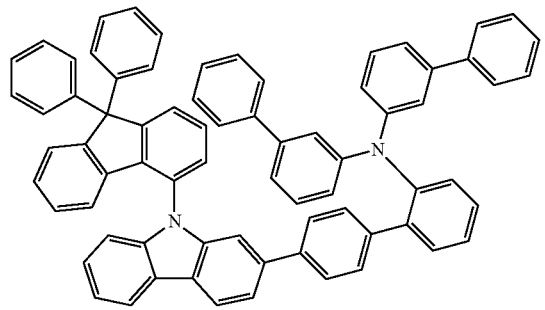
P2-70
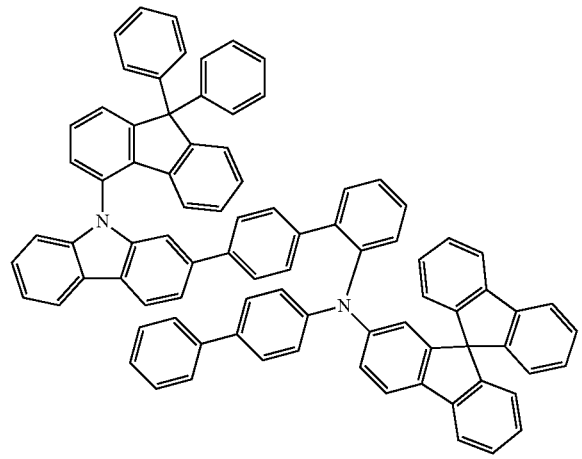
P2-71
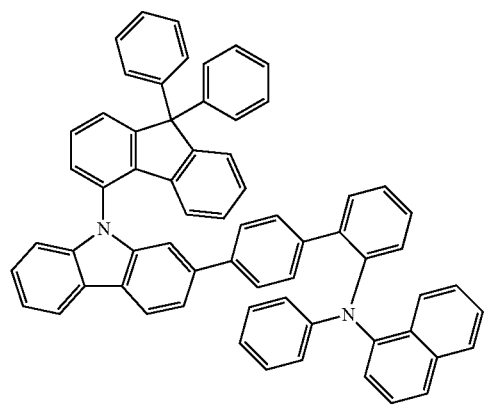
P2-72
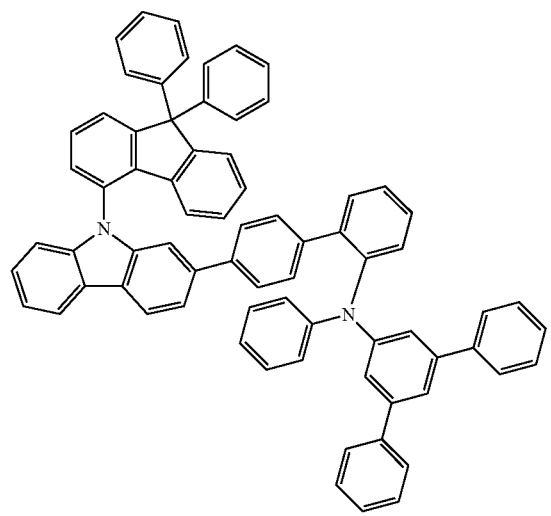
P2-73
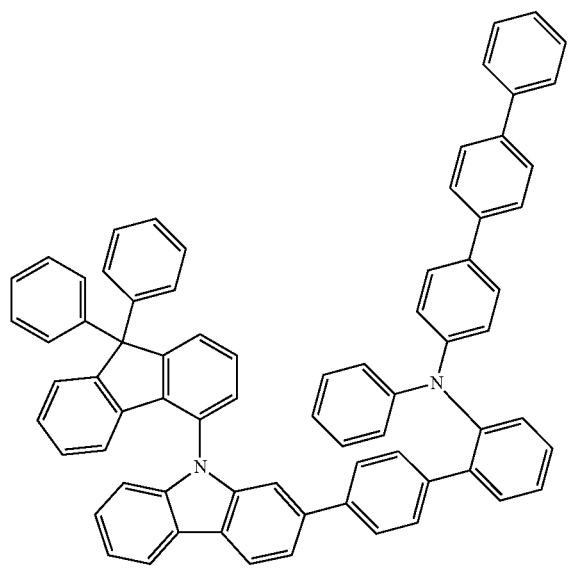
P2-74
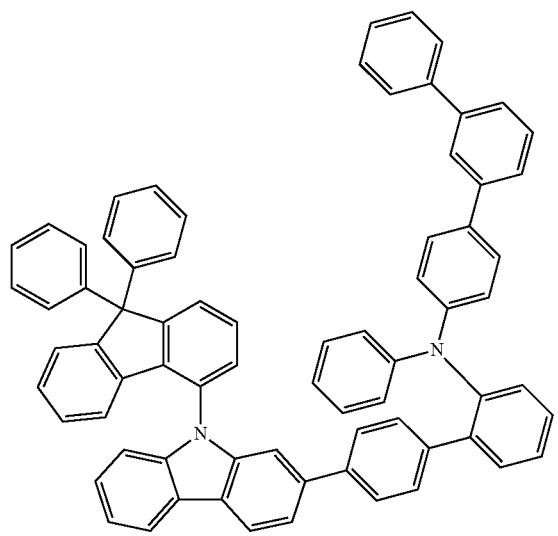

-continued
P2-75
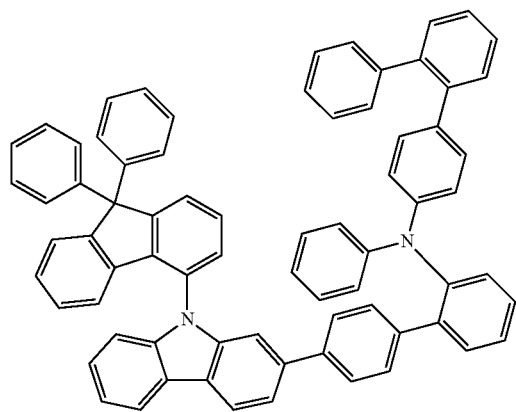
P2-76
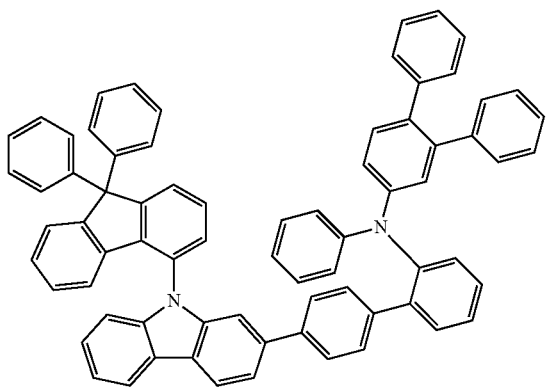
P2-77
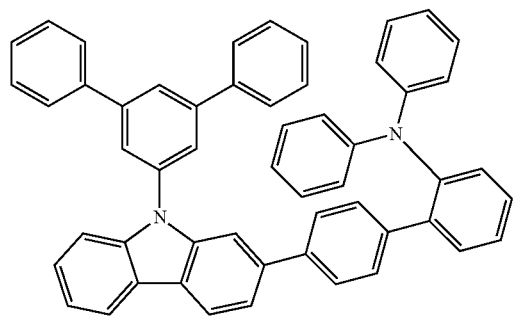
P2-78
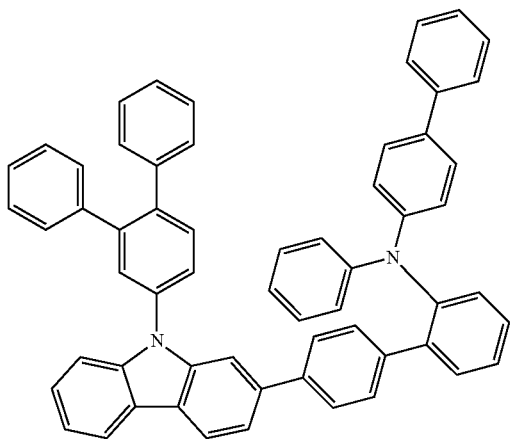
P2-79
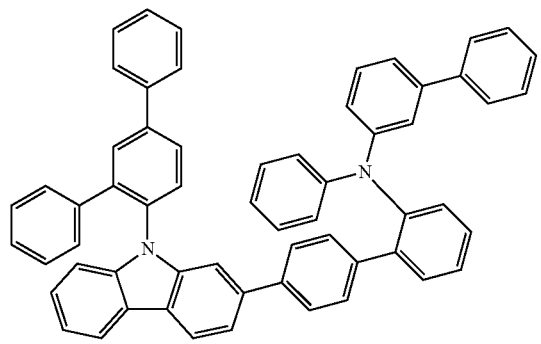
P2-80
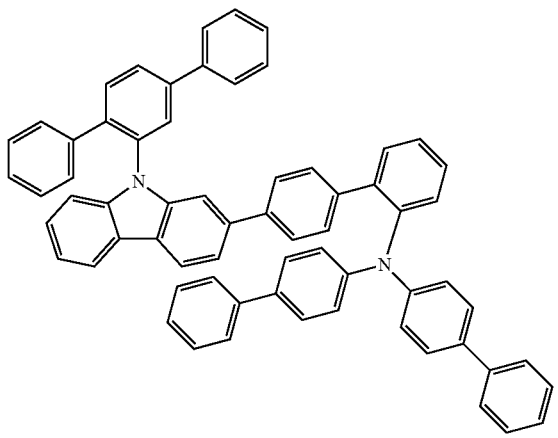

-continued
P2-81
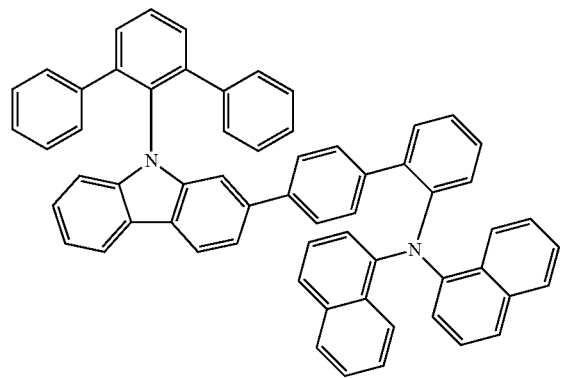
P2-82
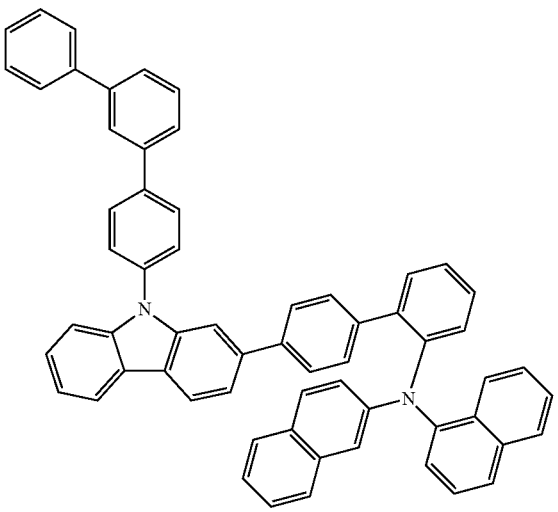
P2-83
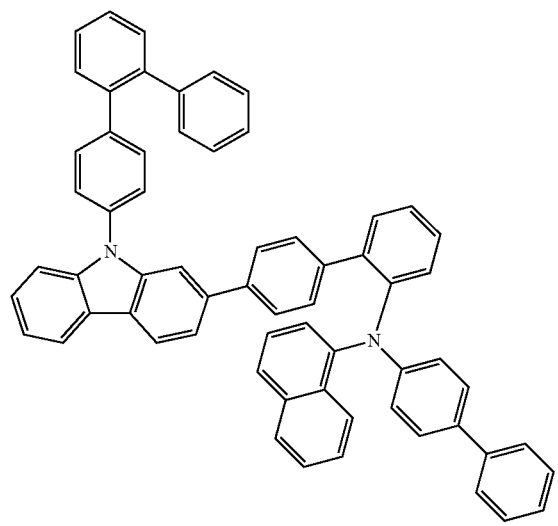
P2-84
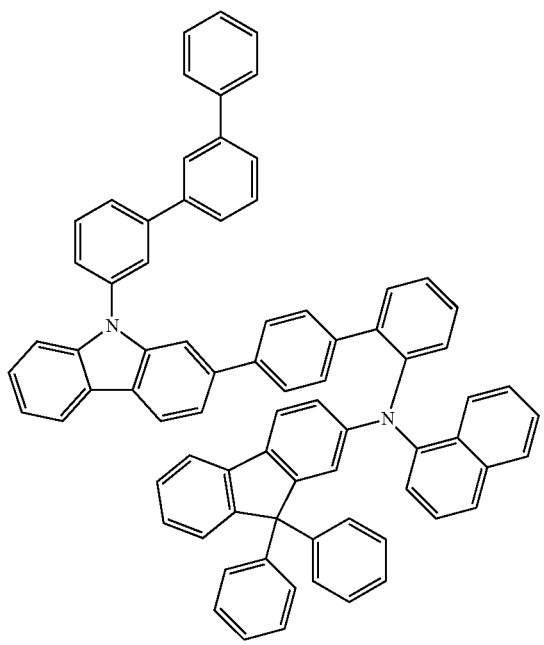

-continued
P2-85
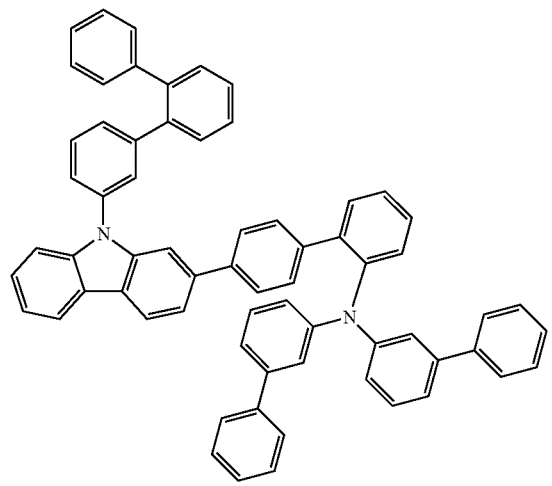
P2-86
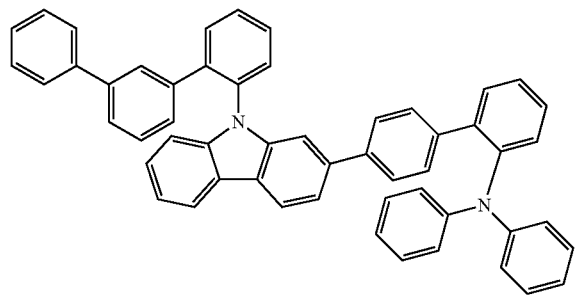
P2-87
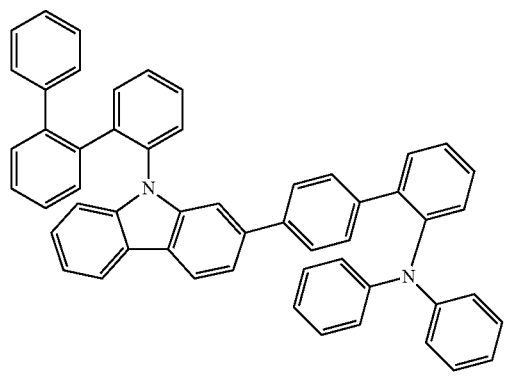
P2-88
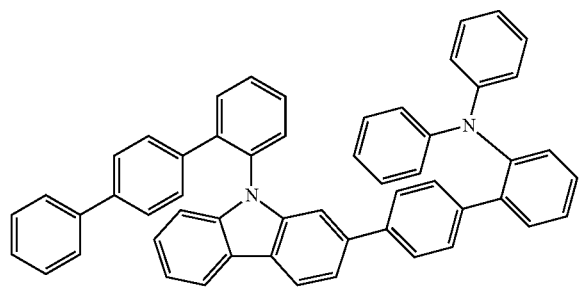
P2-89
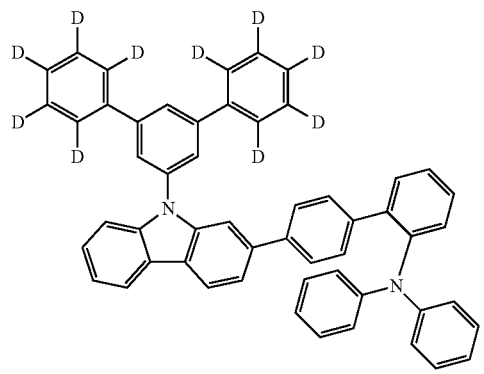
P2-90
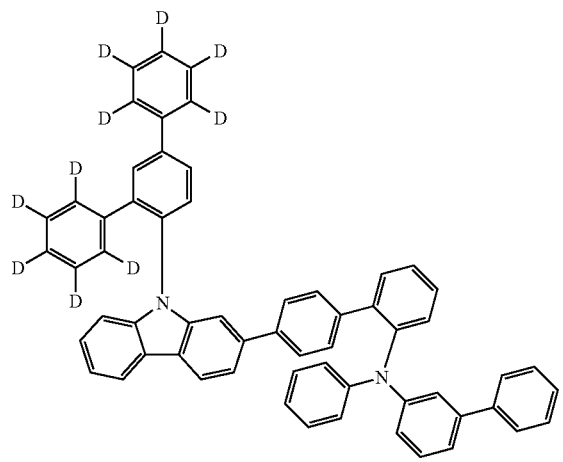

-continued
P2-91
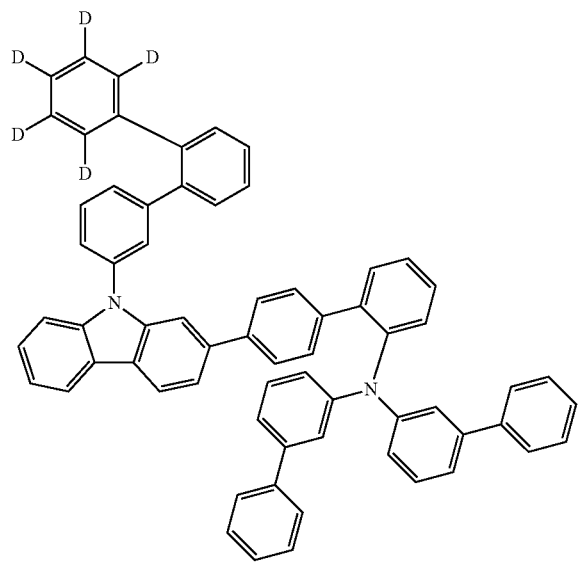
P2-92
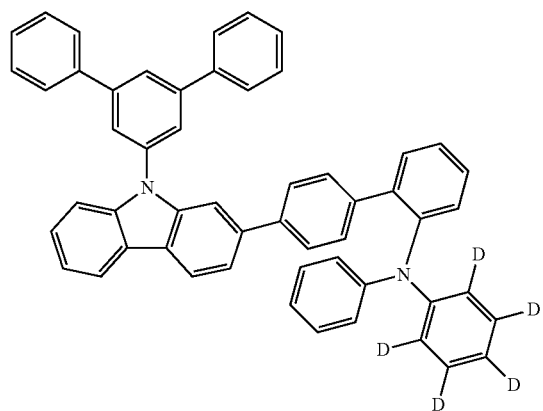
P2-93
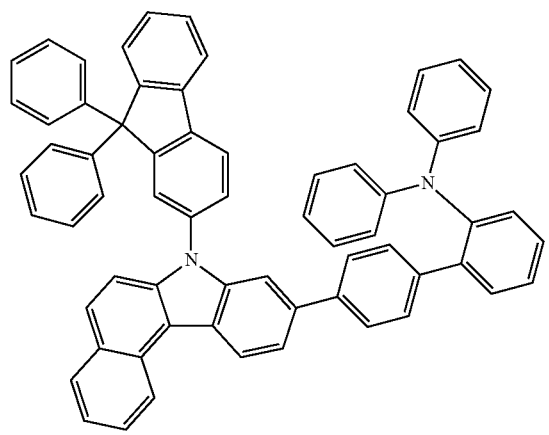
P2-94
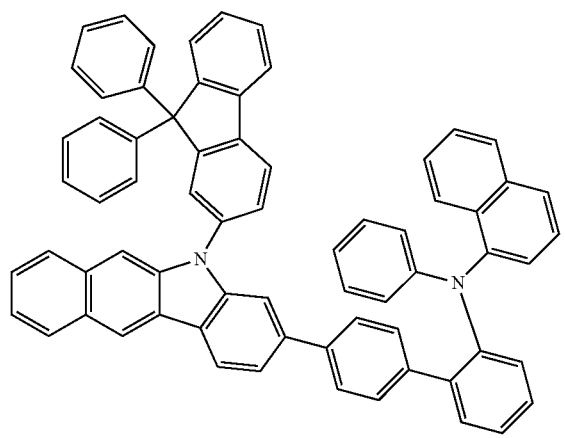
P2-95
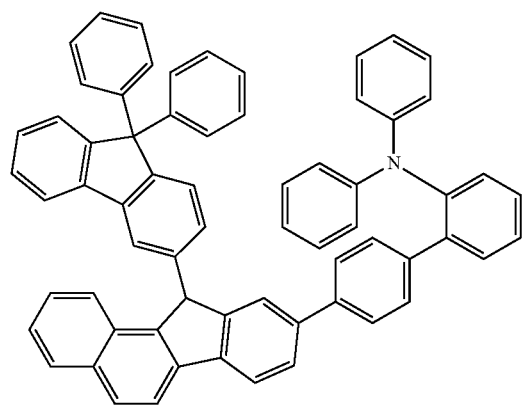
P2-96
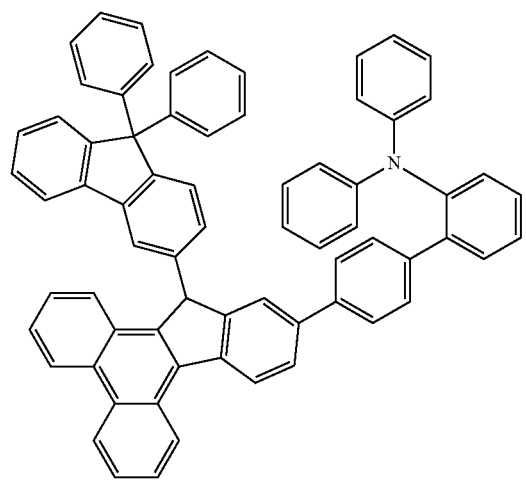

-continued
P2-97
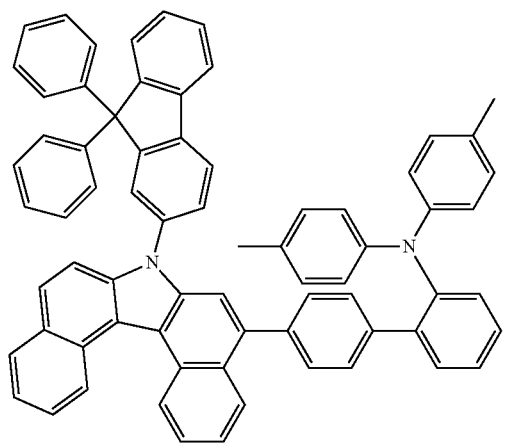
P2-98
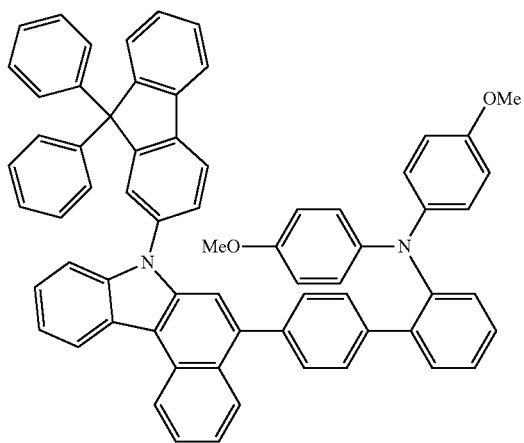
P2-99
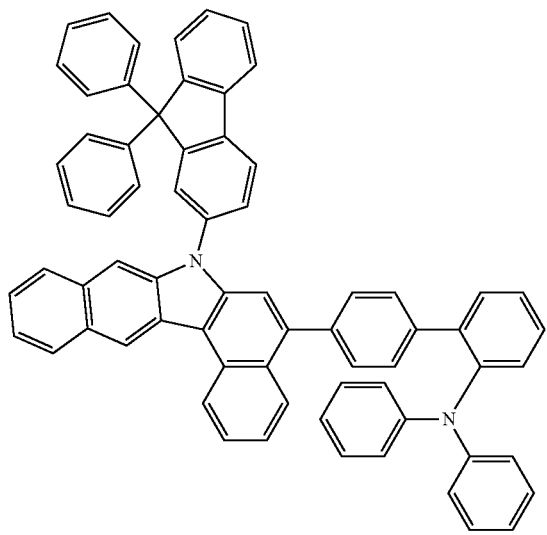
P2-100
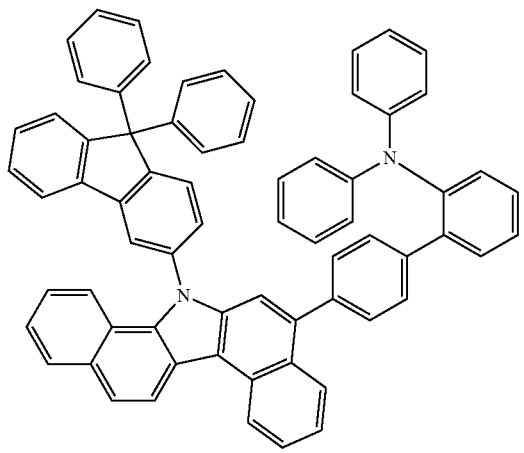
P2-101
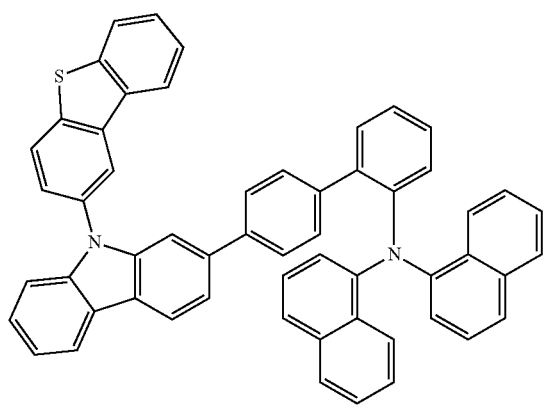
P2-102
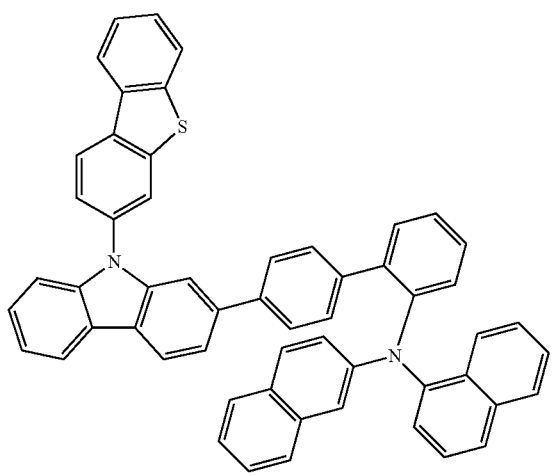

-continued
P2-103
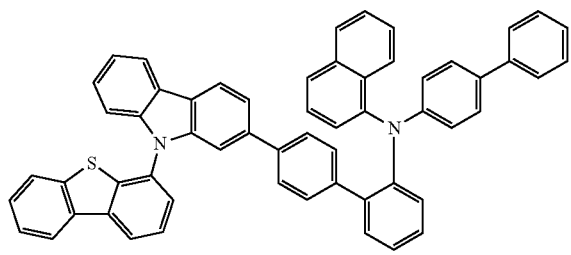
P2-104
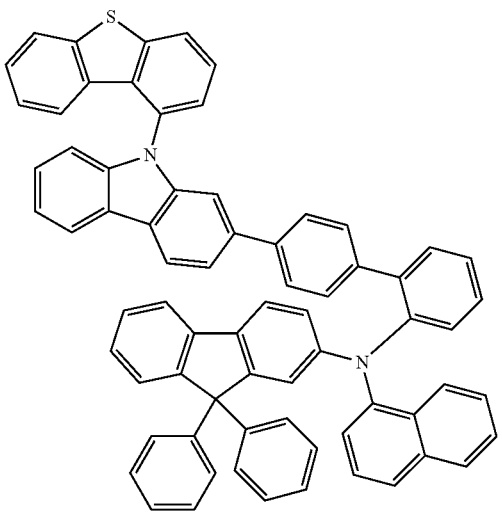
P2-105
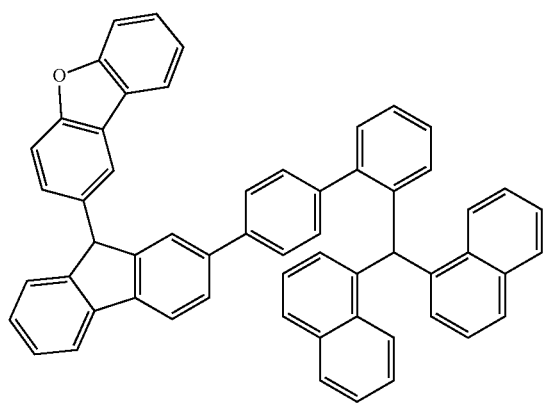
P2-106
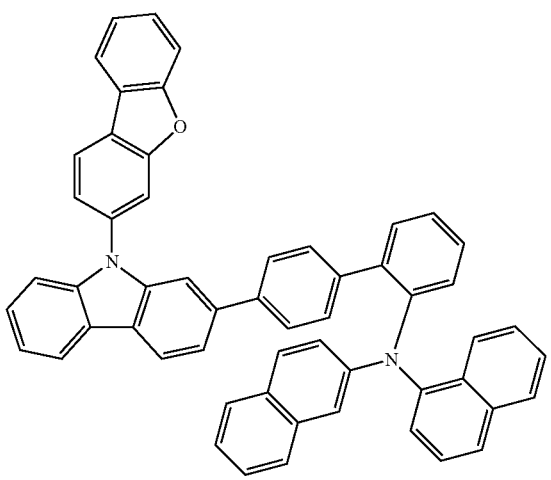
P2-107
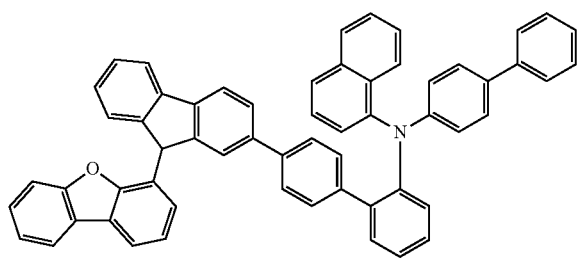
P2-108
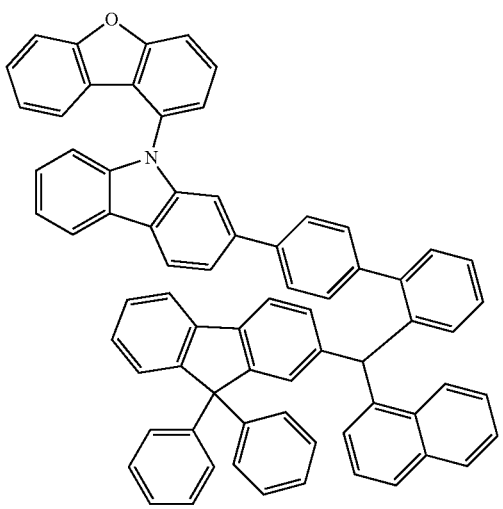

-continued
P2-109
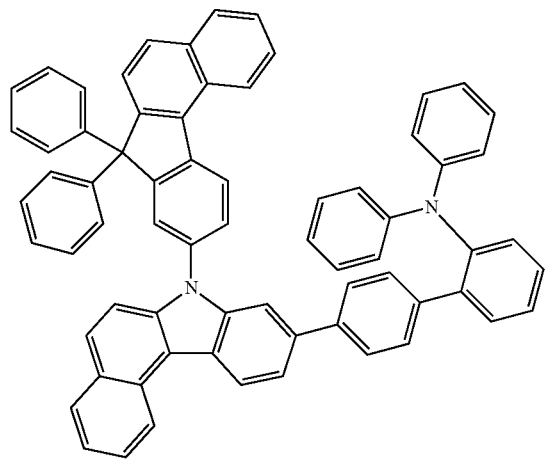
P2-110
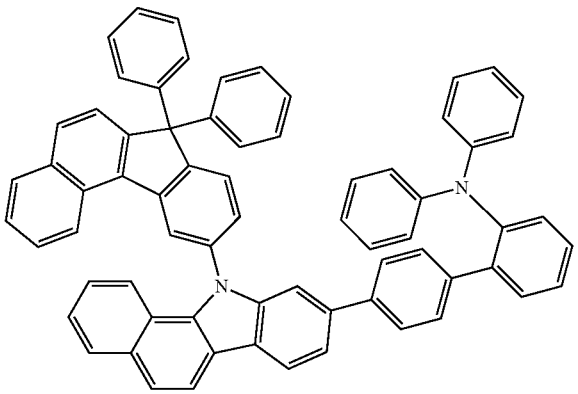
P2-111
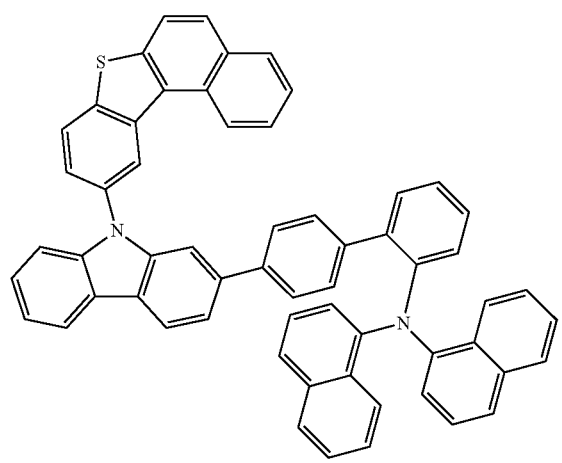
P2-112
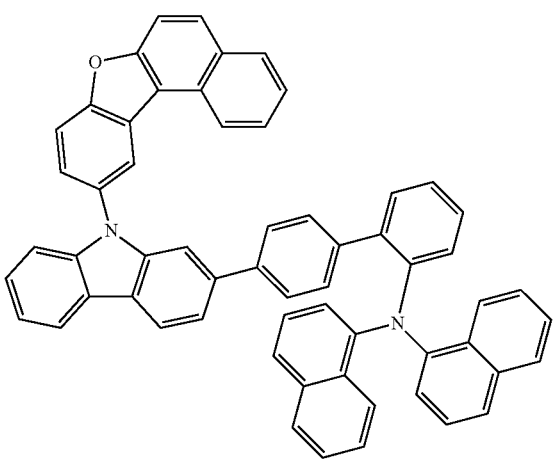
P3-1
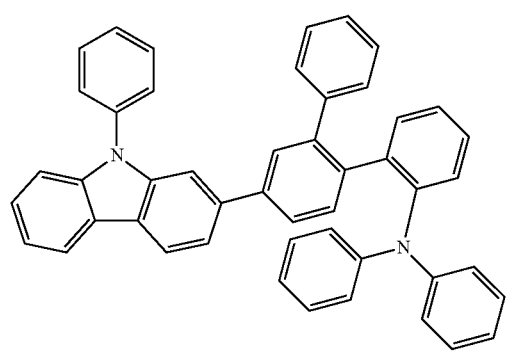
P3-2
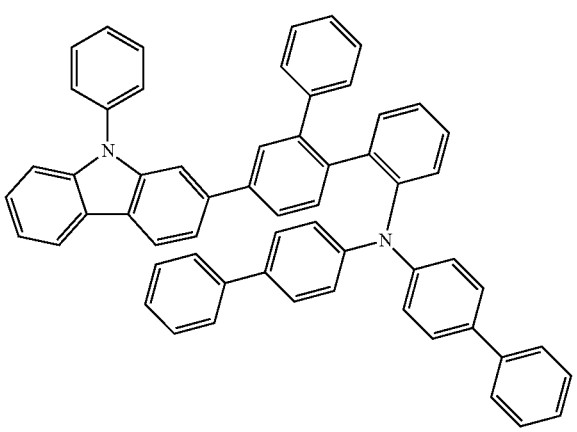

-continued
P3-3
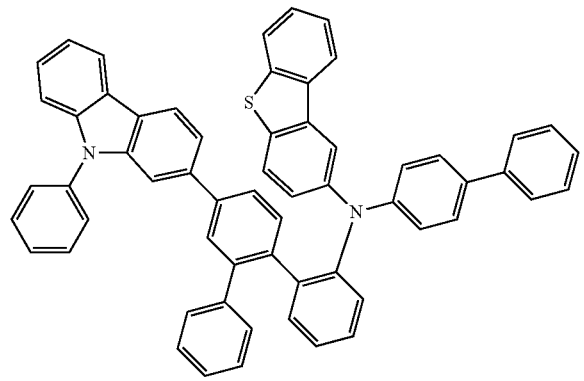
P3-4
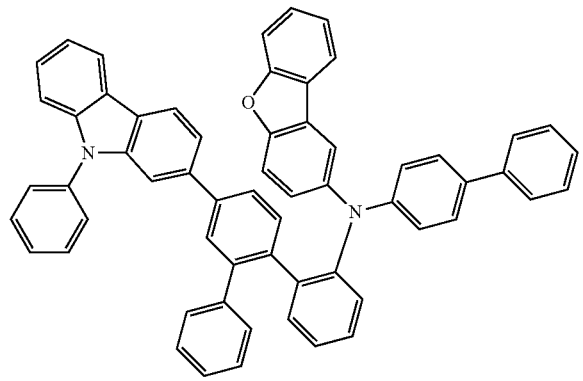
P3-5
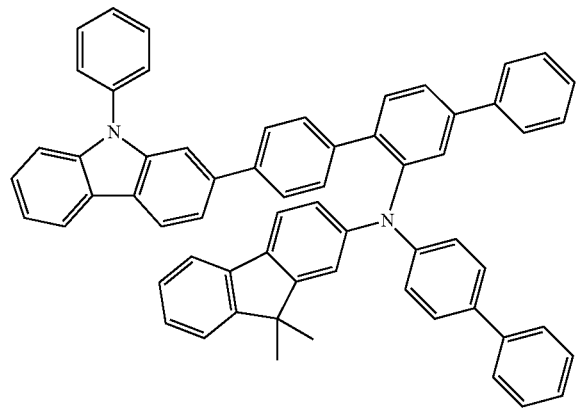
P3-6
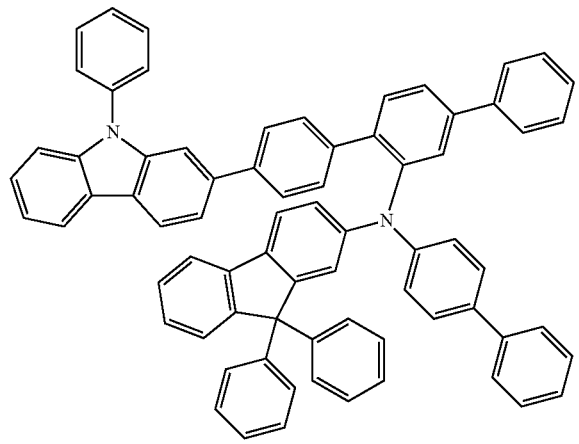
P3-7
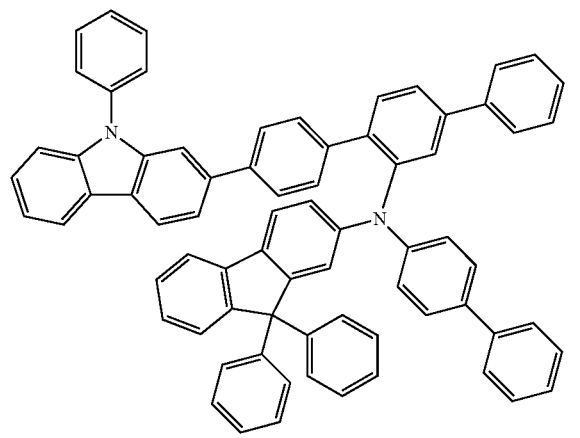
P3-8
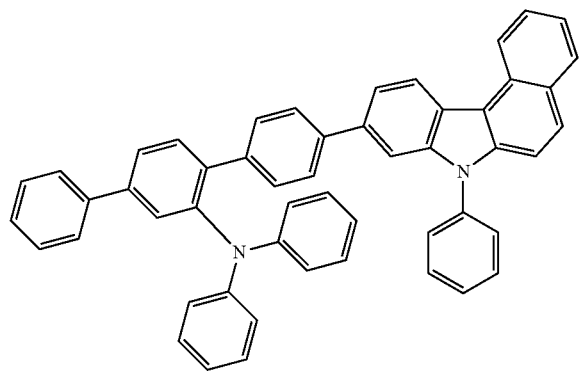

-continued
P3-9
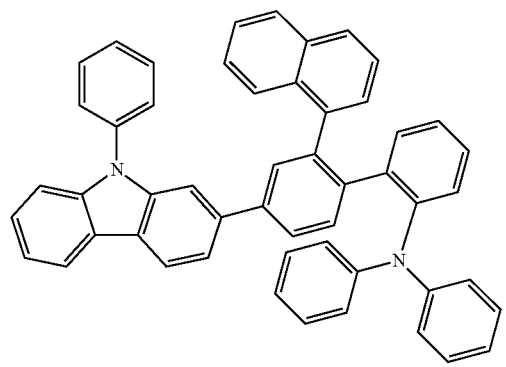
P3-10
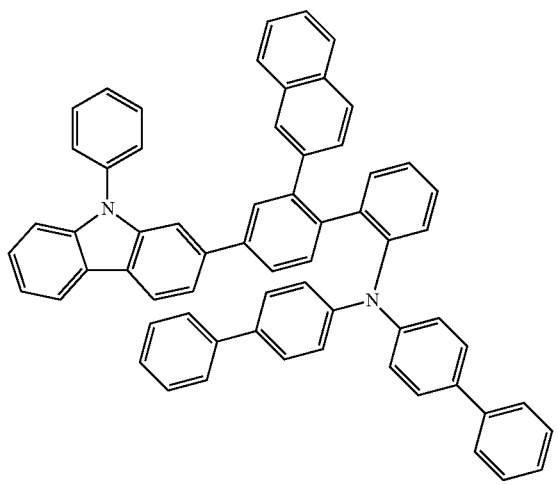
P3-11
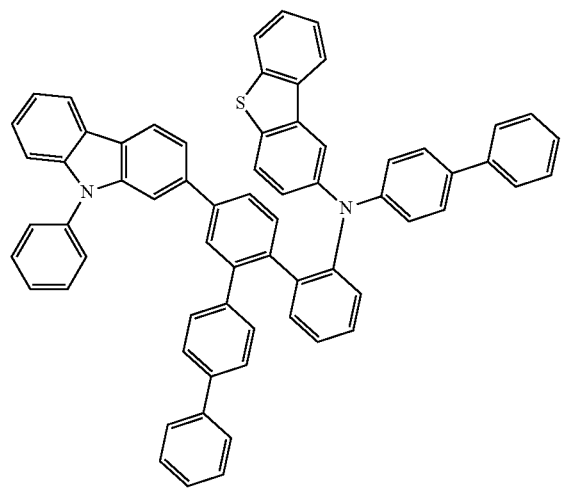
P3-12
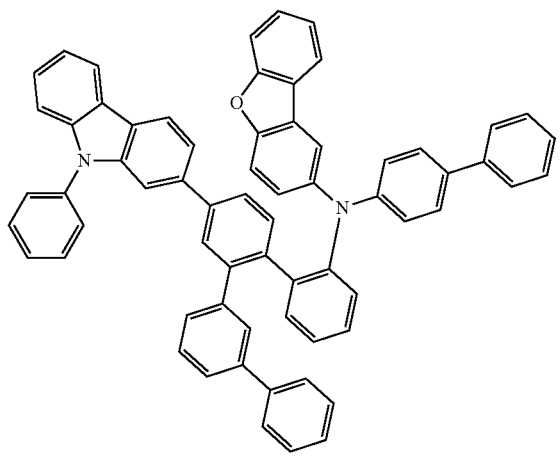
P3-13
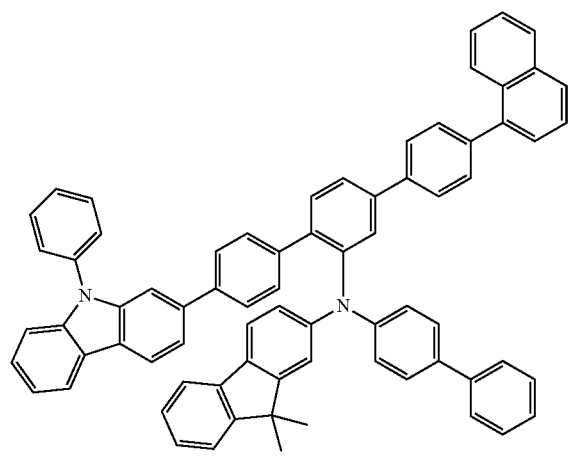
P3-14
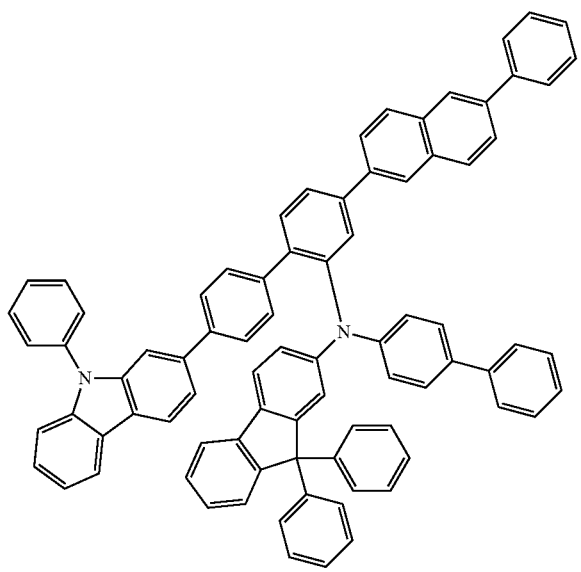

-continued
P3-15
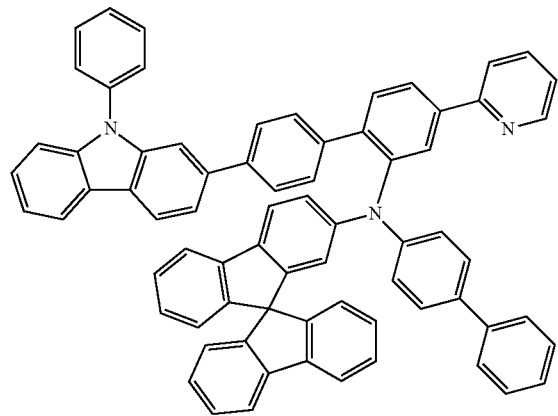
P3-16
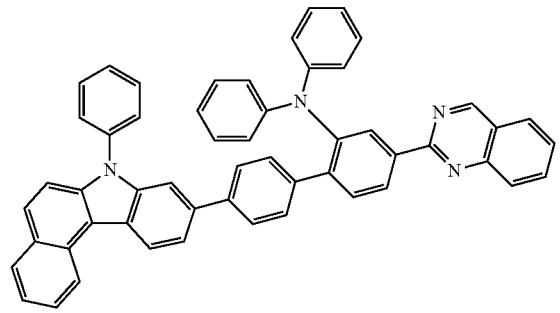
P3-17
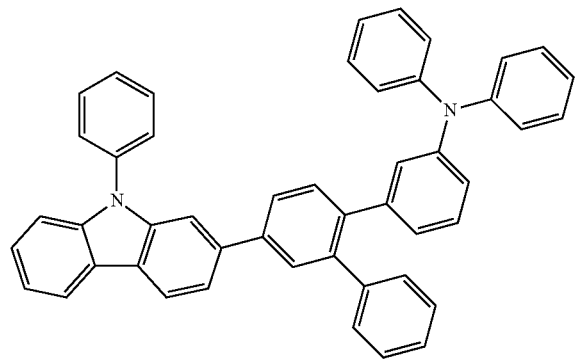
P3-18
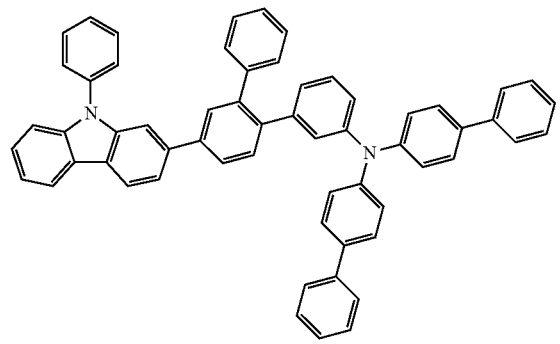
P3-19
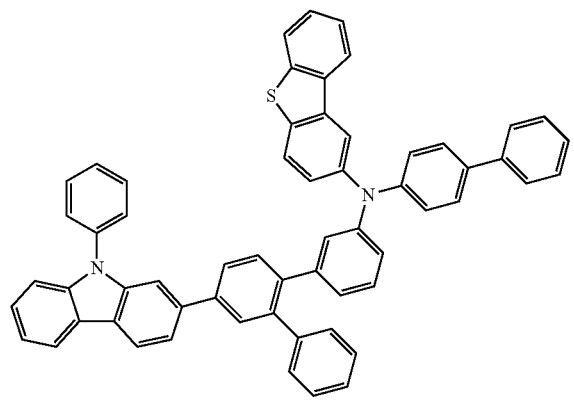
P3-20
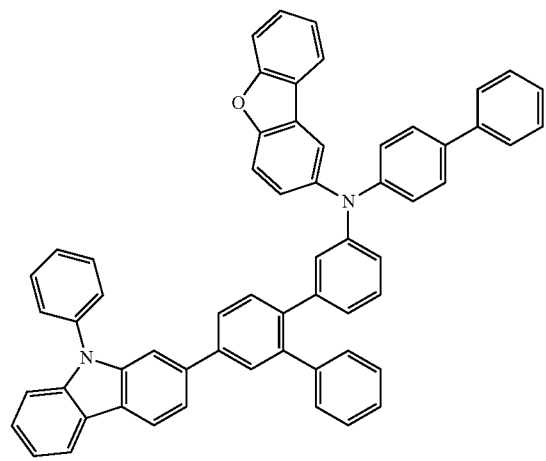

-continued
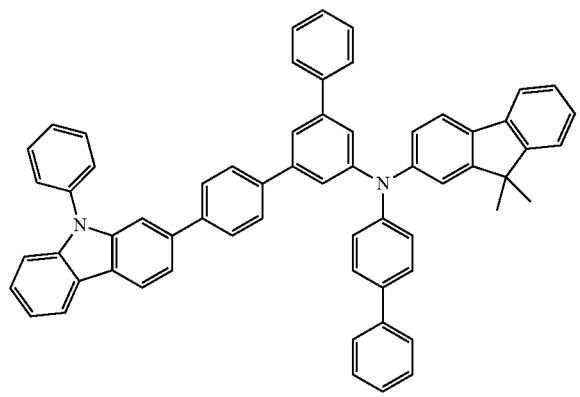
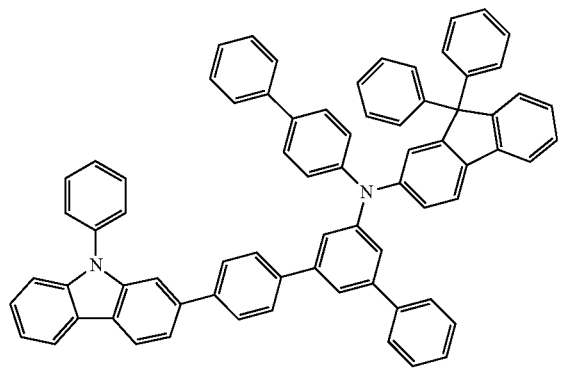
P3-22
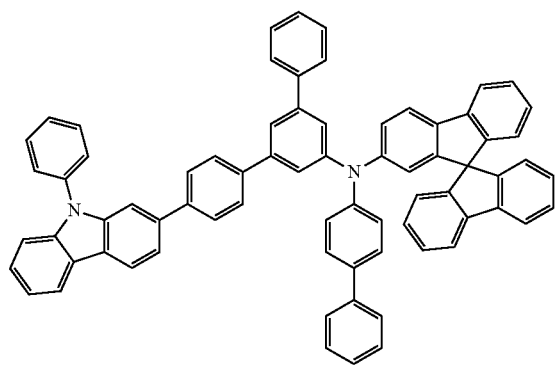
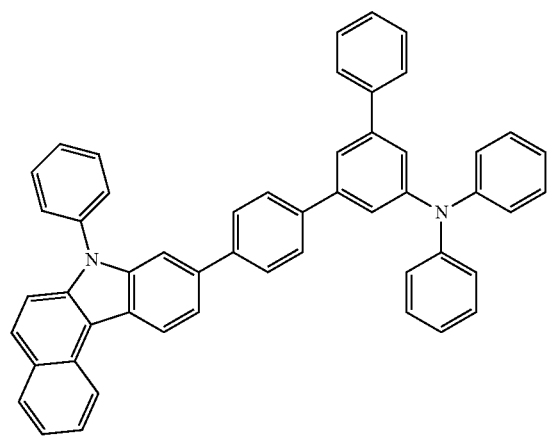
P3-24
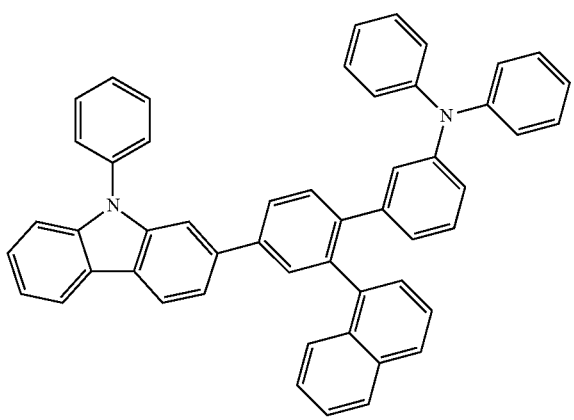
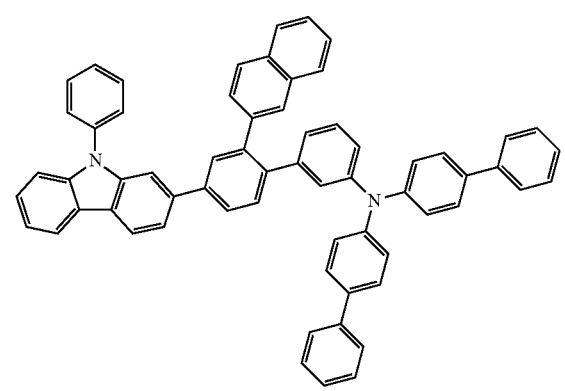
P3-26

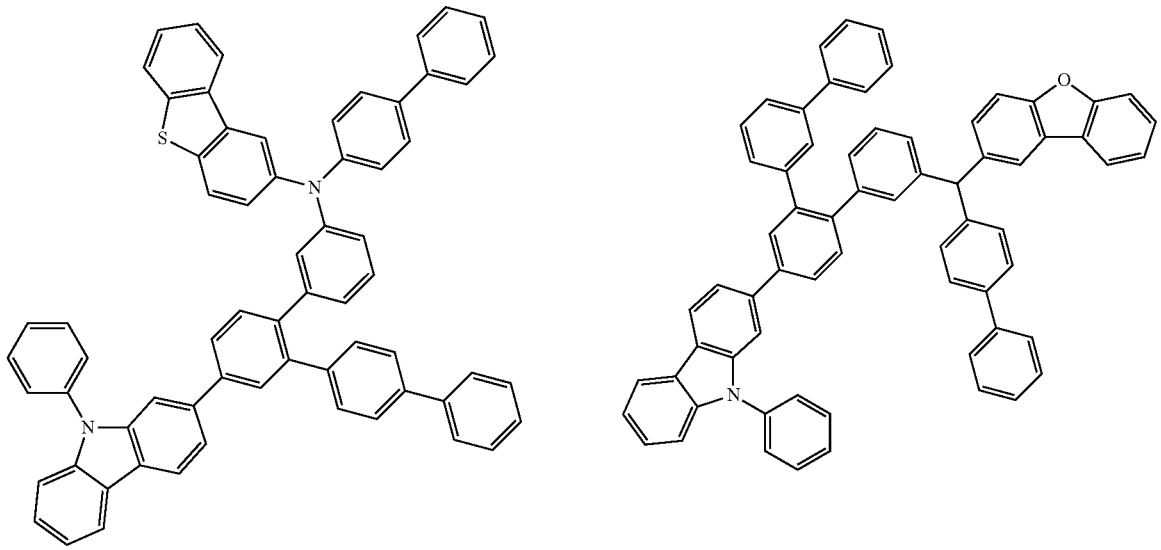
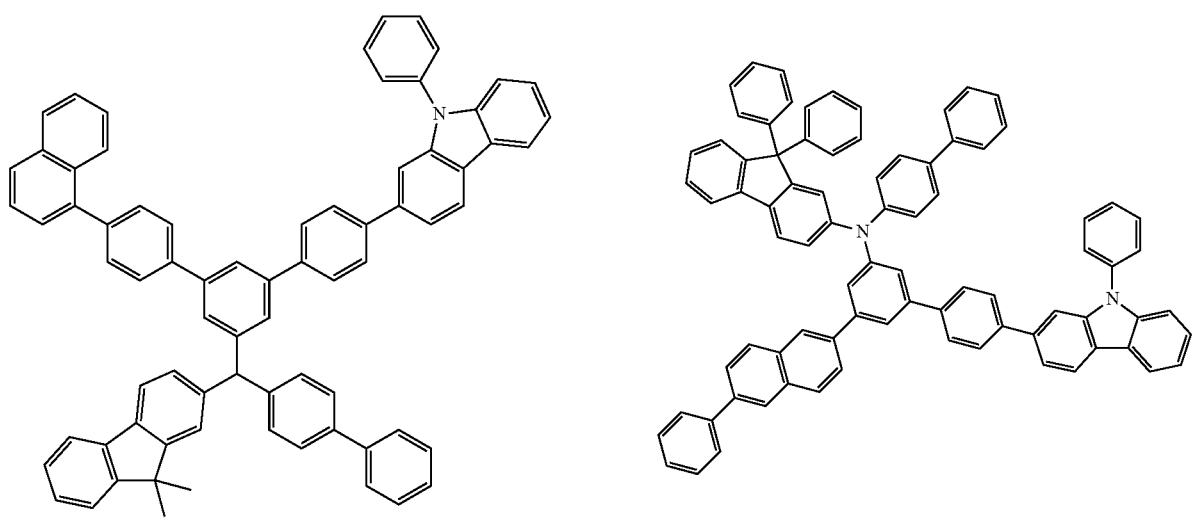
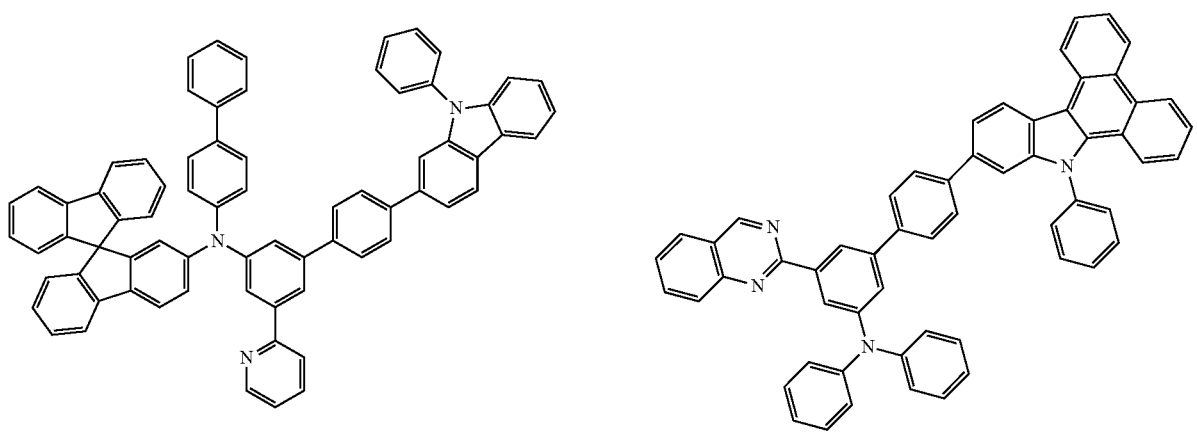
In another aspect of the present invention, a compound for an organic electric element represented by Formula 1 above is provided.
In another aspect of the present invention, an organic electric element comprising the compound represented by Formula 1 above is provided.

The organic electric element can comprise a first electrode, a second electrode, and an organic material layer disposed between the first electrode and the second electrode. The organic material layer can comprise the compound represented by Formula 1. The compound represented Formula 1 can be contained in at least one layer of a hole injection layer, a hole transport layer, an emission-auxiliary layer, or a light emitting layer of the organic material layer. The compound represented by Formula 1 may be used a material in the hole injection layer, a material in the hole transport layer, a material in the emission-auxiliary layer, or a material in the light emitting layer.

Specifically, the organic electric element comprising the organic material layer comprising at least one of the compounds represented by Formula 2 to 10 is provided, and more specifically the organic electric element comprising the organic material layer comprising at least one of the compounds represented by Formula 11 to 20 is provided, more specially, the organic electric element comprising the organic material layer comprising at least one of the compounds represented by individual Formula P1-1 to P1-112, P2-1 to P2-112, and P3-1 to P3-32 is provided.

Furthermore, the compounds comprising of an organic material layer can be one kind or two or more different kinds of the compounds represented by Formula 1 above. As an example, an emission-auxiliary layer or a light emitting layer of an organic material layer may be formed of a compound P1-1 or comprised a mixture of the compound P1-1 and P1-3.

In another aspect of the present invention, the present invention provides an organic electric element further including at least a layer to improve luminous efficiency which is formed on at least one of the sides the first and second electrodes, which is opposite to the organic material layer.

Hereinafter, Synthesis Examples of the inventive compound represented by Formula 1 above and Preparation Examples of an organic electric element will be described in detail by way of example. However, the following examples are only for illustrative purposes and are not intended to limit the scope of the invention.

Synthesis Example

The final product of the present invention represented by Formula 1 can be synthesized by reaction of Sub 1 and Sub 2 as illustrated in, but not limited to, the following Reaction Scheme 1.

<Reaction Scheme 1>

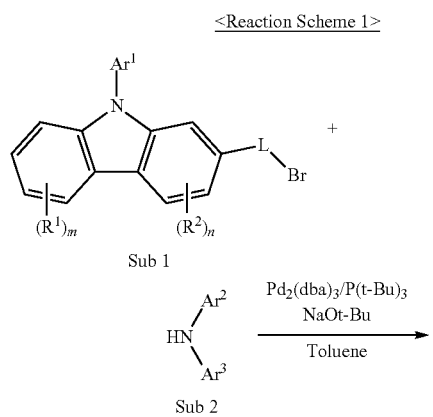

-continued

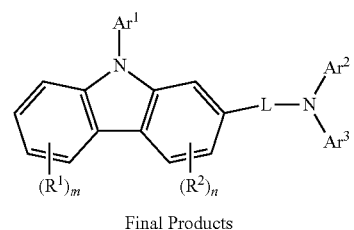

Final Products

I. Synthesis Example of Sub 1

Sub 1 of the Reaction Scheme 1 can be synthesized according to, but not limited to, the following Reaction Scheme 2.

<Reaction Scheme 2>

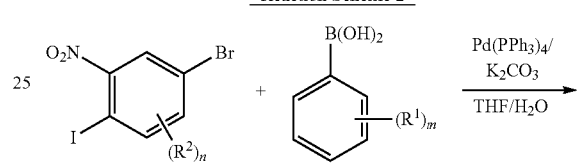

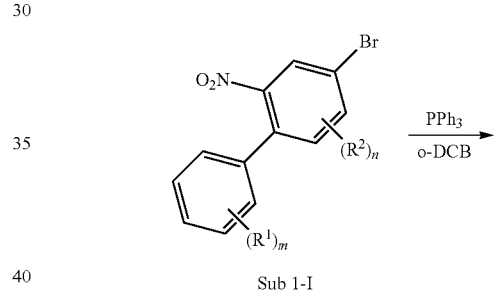

Sub 1-I

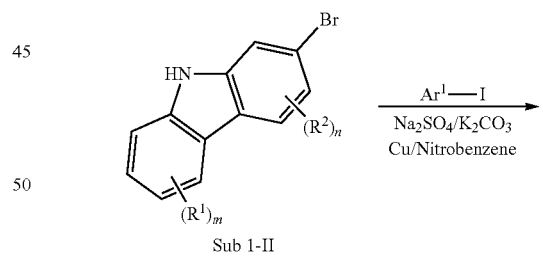

Sub 1-II

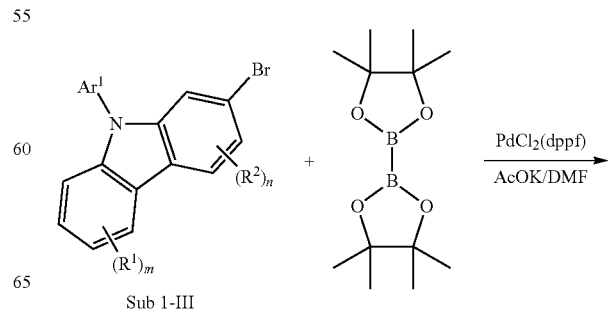

Sub 1-III

-continued

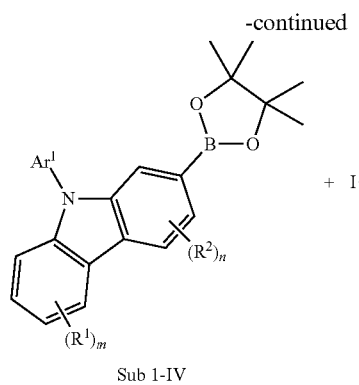

Sub 1-IV

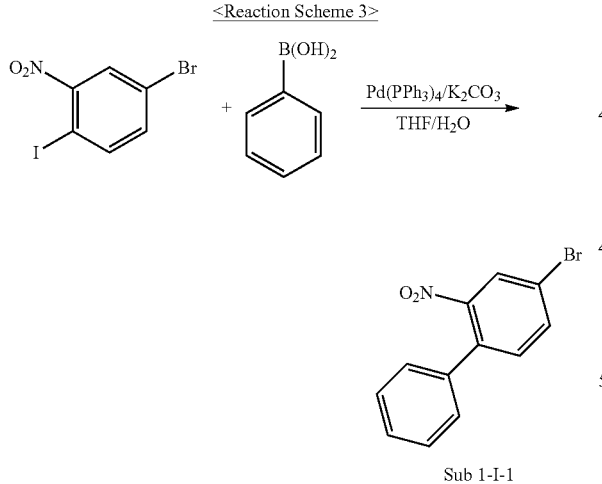

Sub 1

1. Synthesis Example of Sub 1-1

(1) Synthesis of Sub 1-I-1

<Reaction Scheme 3>

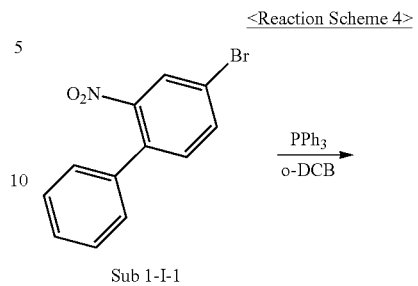

Sub 1-I-1

To a solution of phenylboronic acid (76.84 g, 630.2 mmol) as a starting material in THF (2780 ml) in a round bottom flask was added 4-bromo-1-iodo-2-nitrobenzene (309.96 g, 945.3 mmol), Pd(PPh$_3$)$_4$ (36.41 g, 31.5 mmol), K$_2$CO$_3$ (261.3 g, 1890.6 mmol), water (1390 ml) and stirred at 80° C. After completion of the reaction, the reaction solution was extracted with CH$_2$Cl$_2$ and water and then, the organic layer was dried over MgSO$_4$ and concentrated under pressure. The residue was separated by silica gel column chromatography and recrystallization to obtain target material (122.68 g, 70%).

(2) Synthesis of Sub 1-II-1

<Reaction Scheme 4>

Sub 1-I-1

Sub 1-II-1

To a solution of Sub 1-I-1 (122.68 g, 441.1 mmol) obtained above in o-dichlorobenzene (1810 ml) in a round bottom flask was added triphenylphosphine (289.26 g, 1102.8 mmol) and stirred at 200° C. After completion of the reaction, o-dichlorobenzene was removed by vacuum distillation and the residue was extracted with CH$_2$Cl$_2$ and water. The organic layer was dried over MgSO$_4$ and concentrated under pressure. The residue was separated by silica gel column and recrystallization to obtain target material (80.34 g, 74%).

(3) Synthesis of Sub 1-III-1

<Reaction Scheme 5>

Sub 1-II-1

Sub 1-III-1

To a solution of Sub 1-II-1 (80.34 g, 326.5 mmol) obtained above in nitrobenzene (653 ml) in a round bottom flask was added iodobenzene (99.9 g, 489.7 mmol), Na$_2$SO$_4$ (46.37 g, 326.5 mmol), K$_2$CO$_3$ (45.12 g, 326.5 mmol), Cu (6.22 g, 97.9 mmol) and stirred at 200° C. After completion of the reaction, nitrobenzene was removed by vacuum distillation and the residue was extracted with CH$_2$Cl$_2$ and water. The organic layer was dried over MgSO$_4$ and concentrated under pressure. The residue was separated by silica gel column chromatography and recrystallization to obtain target material (76.78 g, 73%).

(4) Synthesis of Sub 1-IV-1

<Reaction Scheme 6>

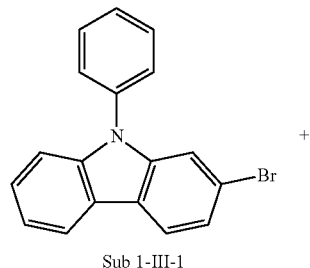

Sub 1-III-1

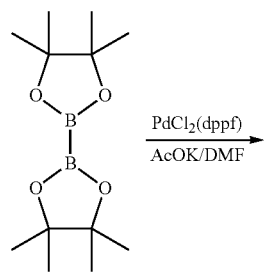

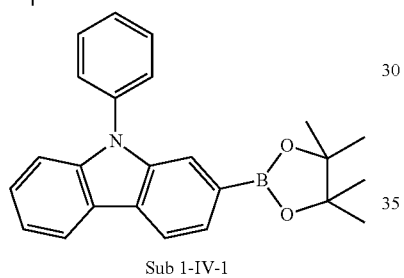

Sub 1-IV-1

To a solution of Sub 1-III-1 (76.78 g, 238.3 mmol) obtained above in DMF in a round bottom flask was added Bis(pinacolato)diboron (66.57 g, 262.1 mmol), Pd(dppf)C12 (5.84 g, 7.1 mmol), KOAc (70.16 g, 714.9 mmol) and stirred at 90° C. After completion of the reaction, DMF was removed by vacuum distillation and the residue was extracted with CH₂Cl₂ and water. The organic layer was dried over MgSO₄ and concentrated under pressure. The residue was separated by silica gel column chromatography and recrystallization to obtain target material (73.92 g, 84%).

(5) Synthesis of Sub 1-1

<Reaction Scheme 7>

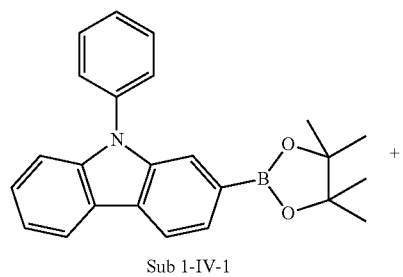

Sub 1-IV-1

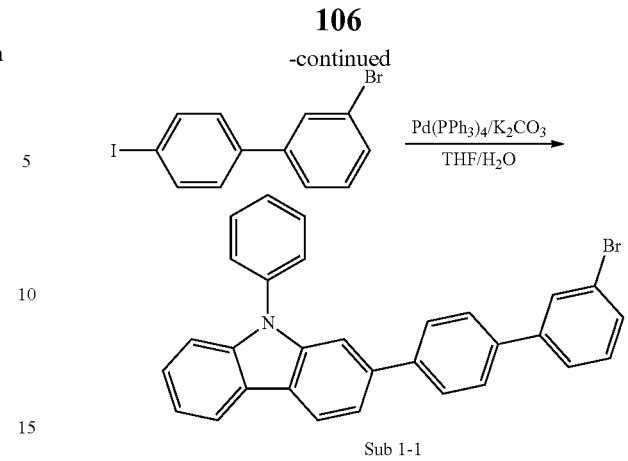

Sub 1-1

To a solution of Sub 1-IV-1 (73.92 g, 200.2 mmol) obtained above in THF (880 ml) in a round bottom flask was added 3-bromo-4'-iodo-1,1'-biphenyl (108 g, 300.3 mmol), Pd(PPh₃)₄ (11.6 g, 10 mmol), K₂CO₃ (83 g, 600.6 mmol), water (440 mL) and stirred at 80° C. After completion of the reaction, the reactant was extracted with CH₂Cl₂ and water. The organic layer was dried over MgSO₄ and concentrated under pressure. The residue was separated by silica gel column chromatography and recrystallization to obtain target material (63.6 g, 67%).

2. Synthesis Examples of Sub 1-7

(1) Synthesis of Sub 1-I-7

<Reaction Scheme 8>

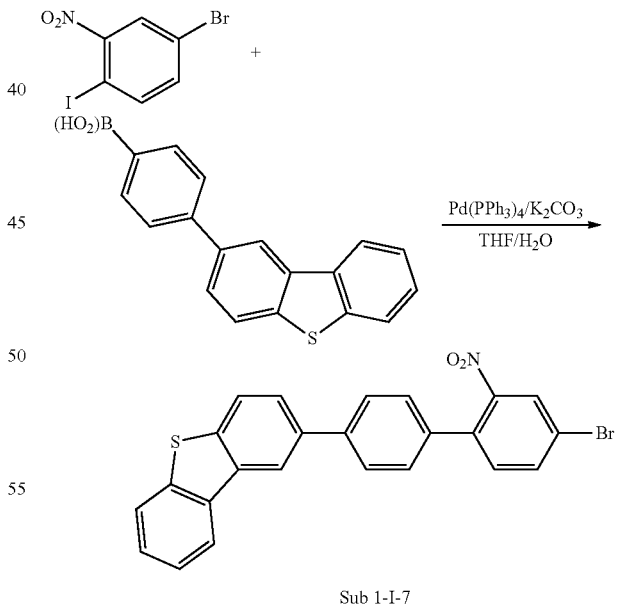

Sub 1-I-7

Using (4-(dibenzo[b,d]thiophen-2-yl)phenyl)boronic acid (95.8 g, 315.1 mmol), THF (1390 ml), 4-bromo-1-iodo-2-nitrobenzene (155 g, 472.7 mmol), Pd(PPh₃)₄ (18.2 g, 15.8 mmol), K₂CO₃ (130.7 g, 945.3 mmol), water (695 ml), the same procedure as described in the synthesis method of Sub 1-I-1 was carried out to obtain target material (103 g, 68%).

(2) Synthesis of Sub 1-II-7

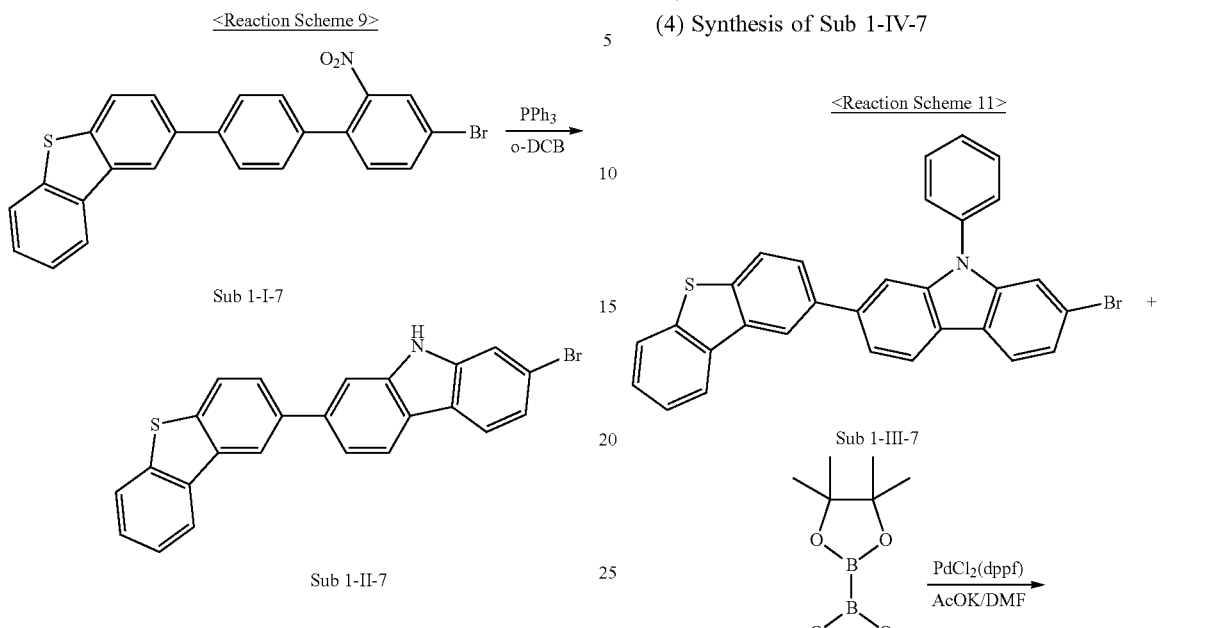

Sub 1-I-7

Sub 1-II-7

Using Sub 1-I-7 (103 g, 223.7 mmol), o-dichlorobenzene (917 ml), triphenylphosphine (146.7 g, 559.3 mmol), the same procedure as described in the synthesis method of Sub 1-II-1 was carried out to obtain target material (69 g, 72%).

(3) Synthesis of Sub 1-III-7

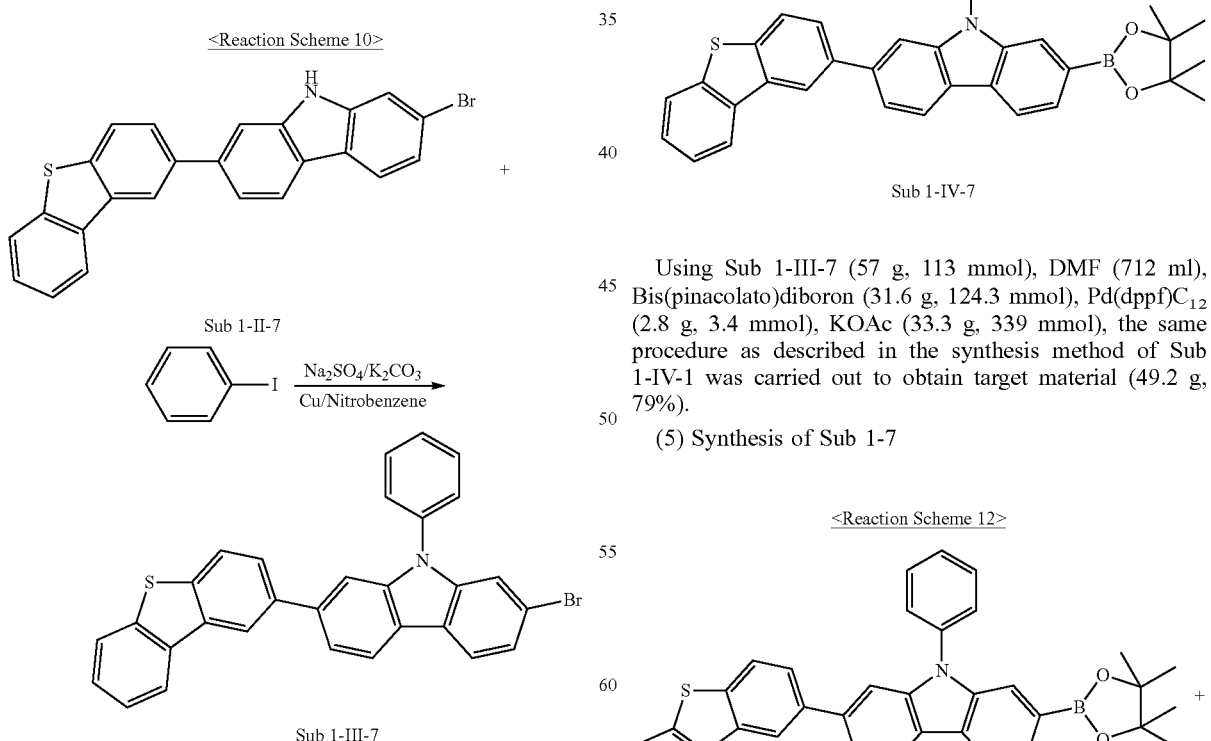

Sub 1-II-7

Sub 1-III-7

Using Sub 1-II-7 (69 g, 161.1 mmol), nitrobenzene (322 ml), iodobenzene (49.4 g, 242 mmol), Na$_2$SO$_4$ (22.9 g, 161.1 mmol), K$_2$CO$_3$ (22.3 g, 161.1 mmol), Cu (3.1 g, 48.3 mmol), the same procedure as described in the synthesis method of Sub 1-III-1 was carried out to obtain target material (57 g, 70%).

(4) Synthesis of Sub 1-IV-7

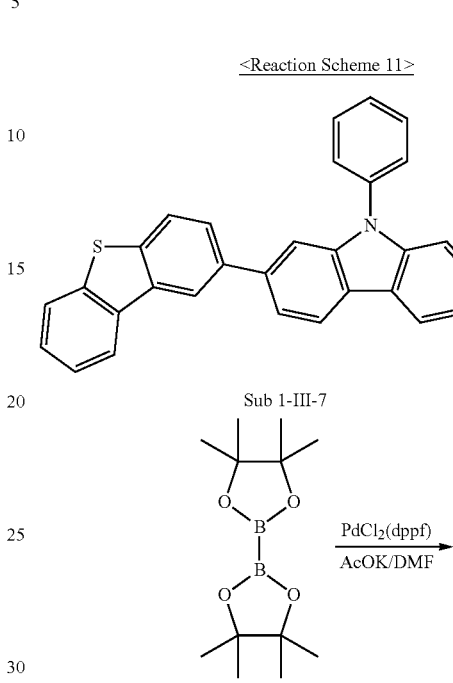

Sub 1-III-7

Sub 1-IV-7

Using Sub 1-III-7 (57 g, 113 mmol), DMF (712 ml), Bis(pinacolato)diboron (31.6 g, 124.3 mmol), Pd(dppf)C$_{12}$ (2.8 g, 3.4 mmol), KOAc (33.3 g, 339 mmol), the same procedure as described in the synthesis method of Sub 1-IV-1 was carried out to obtain target material (49.2 g, 79%).

(5) Synthesis of Sub 1-7

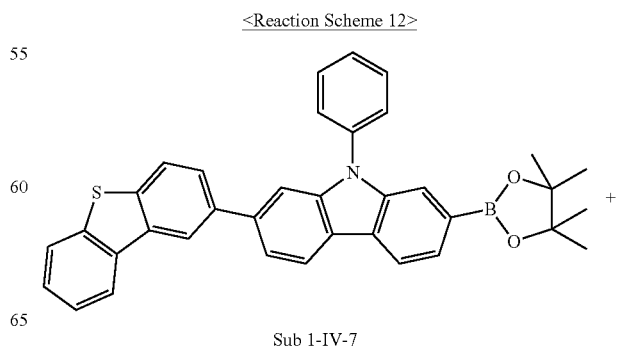

Sub 1-IV-7

(2) Synthesis of Sub 1-IV-13

<Reaction Scheme 14>

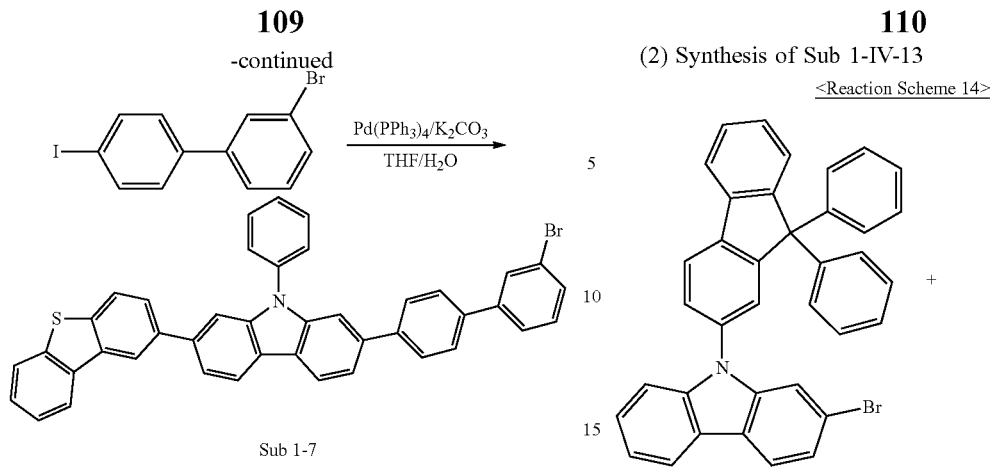

Sub 1-7

Using Sub 1-IV-7 (49.2 g, 89.2 mmol), 3-bromo-4'-iodo-1,1'-biphenyl (48.1 g, 134 mmol), Pd(PPh$_3$)$_4$ (5.2 g, 4.5 mmol), K$_2$CO$_3$ (37 g, 268 mmol), THF (392 ml), water (196 ml), the same procedure as described in the synthesis method of Sub 1-1 was carried out to obtain target material (40.4 g, 69%).

3. Synthesis Examples of Sub 1-13

(1) Synthesis of Sub 1-III-13

<Reaction Scheme 13>

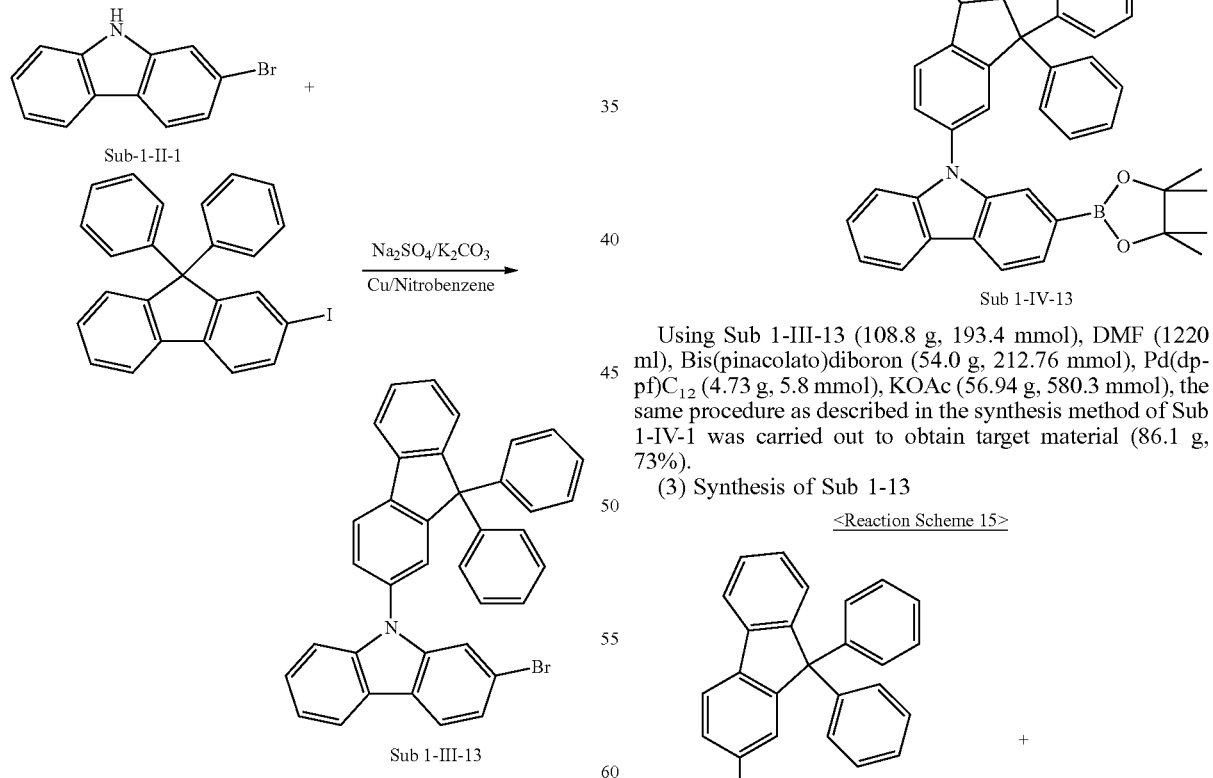

Sub 1-III-13

Using Sub 1-II-1 (70 g, 284.4 mmol), nitrobenzene (570 ml), 2-iodo-9,9-diphenyl-9H-fluorene (189.6 g, 426.7 mmol), Na$_2$SO$_4$ (40.4 g, 284.4 mmol), K$_2$CO$_3$ (39.3 g, 284.4 mmol), Cu (5.42 g, 85.3 mmol), the same procedure as described in the synthesis method of Sub 1-III-1 was carried out to obtain target material (108.8 g, 68%).

Using Sub 1-III-13 (108.8 g, 193.4 mmol), DMF (1220 ml), Bis(pinacolato)diboron (54.0 g, 212.76 mmol), Pd(dppf)C$_{12}$ (4.73 g, 5.8 mmol), KOAc (56.94 g, 580.3 mmol), the same procedure as described in the synthesis method of Sub 1-IV-1 was carried out to obtain target material (86.1 g, 73%).

(3) Synthesis of Sub 1-13

<Reaction Scheme 15>

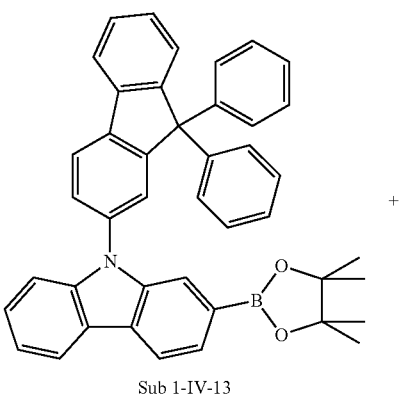

Sub 1-IV-13

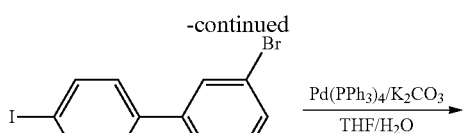

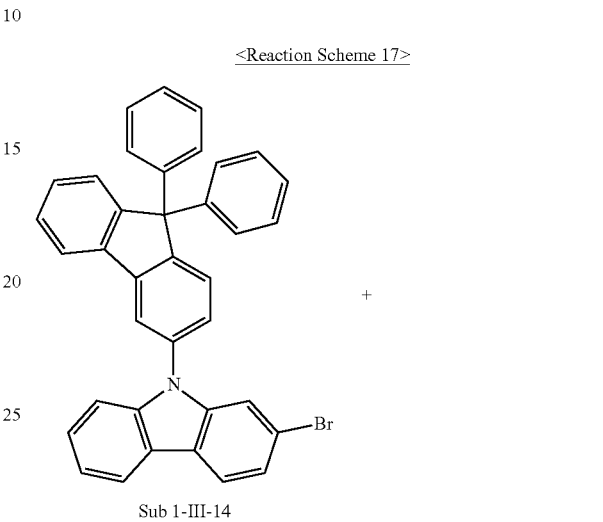

Using Sub 1-II-1 (63 g, 255.9 mmol), nitrobenzene (512 ml), 3-iodo-9,9-diphenyl-9H-fluorene (170.6 g, 383.9 mmol), Na₂SO₄ (36.4 g, 256 mmol), K₂CO₃ (35.4 g, 256 mmol), Cu (4.88 g, 76.8 mmol), the same procedure as described in the synthesis method of Sub 1-III-1 was carried out to obtain target material (99.3 g, 69%).

(2) Synthesis of Sub 1-IV-14

Using Sub 1-IV-13 (86.1 g, 141.2 mmol), THF (620 ml), 3-bromo-4'-iodo-1,1'-biphenyl (76.1 g, 211.9 mmol), Pd(PPh₃)₄ (8.2 g, 7.06 mmol), K₂CO₃ (58.6 g, 423.7 mmol), water (310 ml), the same procedure as described in the synthesis method of Sub 1-1 was carried out to obtain target material (68.6 g, 68%).

4. Synthesis of Sub 1-14

(1) Synthesis of Sub 1-III-14

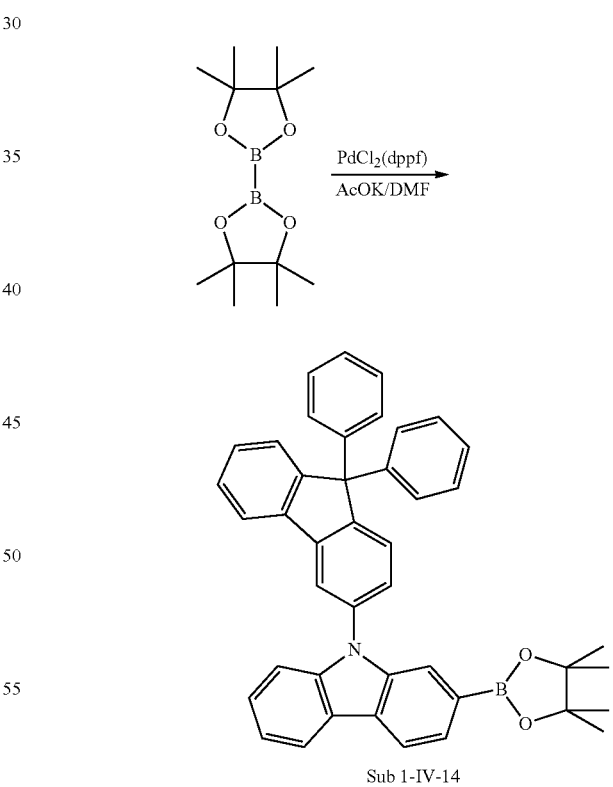

Using Sub 1-III-14 (99.3 g, 193.4 mmol), DMF (1110 ml), Bis(pinacolato)diboron (49.3 g, 194.2 mmol), Pd(dppf)C₁₂ (4.32 g, 5.3 mmol), KOAc (52 g, 529.6 mmol), the same procedure as described in the synthesis method of Sub 1-IV-1 was carried out to obtain target material (80.7 g, 75%).

(3) Synthesis of Sub 1-14

<Reaction Scheme 18>

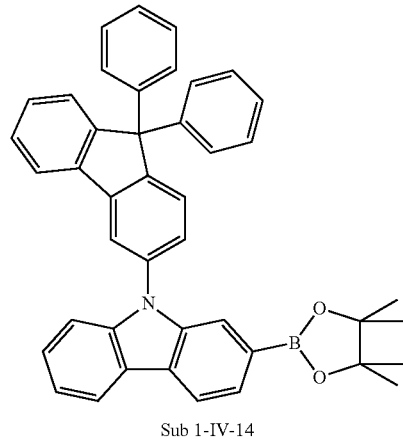

Sub 1-IV-14

+

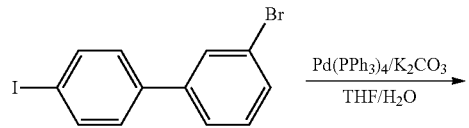

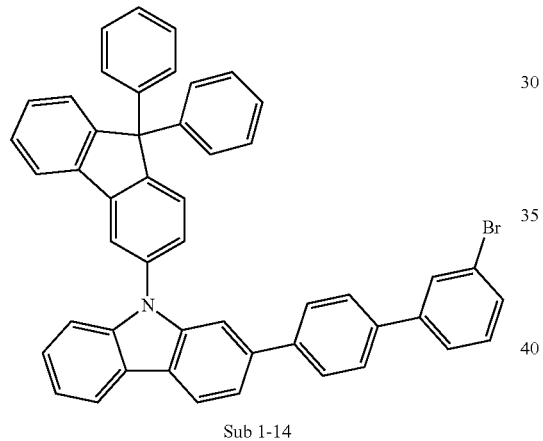

Sub 1-14

Using Sub 1-IV-14 (80.7 g, 132.3 mmol), THF (582 ml), 3-bromo-4'-iodo-1,1'-biphenyl (71.3 g, 198.6 mmol), Pd(PPh₃)₄ (7.65 g, 6.62 mmol), K₂CO₃ (54.9 g, 397.2 mmol), water (291 ml), the same procedure as described in the synthesis method of Sub 1-1 was carried out to obtain target material (62.4 g, 66%).

5. Synthesis of Sub 1-17

(1) Synthesis of Sub 1-III-17

<Reaction Scheme 19>

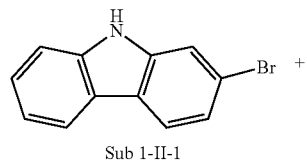

Sub 1-II-1

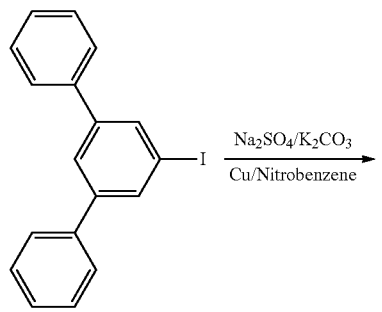

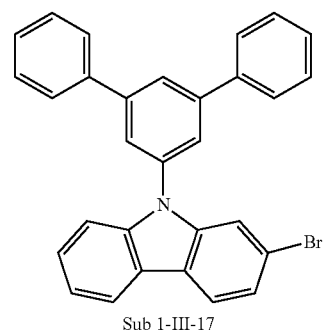

Sub 1-III-17

Using Sub 1-II-1 (60 g, 244 mmol), nitrobenzene (487 ml), 5'-iodo-1,1':3',1"-terphenyl (130.3 g, 365.7 mmol), Na₂SO₄ (34.6 g, 244 mmol), K₂CO₃ (33.7 g, 244 mmol), Cu (4.65 g, 73.1 mmol), the same procedure as described in the synthesis method of Sub 1-III-1 was carried out to obtain target material (82.1 g, 71%).

(2) Synthesis of Sub 1-IV-17

<Reaction Scheme 20>

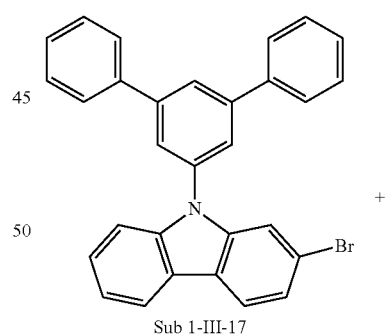

Sub 1-III-17

+

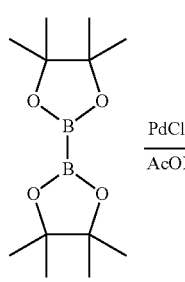

115

-continued

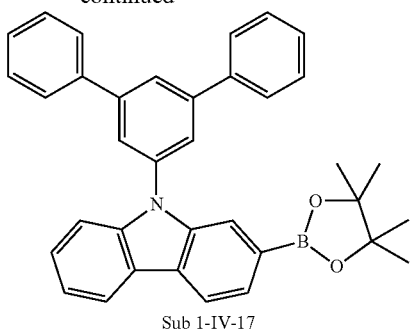
Sub 1-IV-17

Using Sub 1-III-17 (82.1 g, 173.1 mmol), DMF (1090 ml), Bis(pinacolato)diboron (48.3 g, 190.4 mmol), Pd(dppf)C$_{12}$ (4.24 g, 5.2 mmol), KOAc (51 g, 519.2 mmol), the same procedure as described in the synthesis method of Sub 1-IV-1 was carried out to obtain target material (65.9 g, 73%).

(3) Synthesis of Sub 1-17

<Reaction Scheme 21>

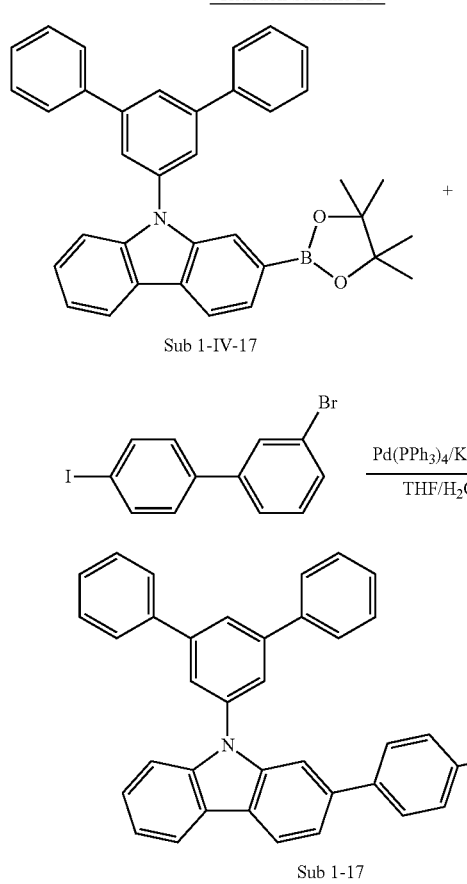
Sub 1-17

Using Sub 1-IV-17 (82.1 g, 173.1 mmol), DMF (1090 ml), Bis(pinacolato)diboron (48.3 g, 190.4 mmol), Pd(dppf)C$_{12}$ (4.24 g, 5.2 mmol), KOAc (51 g, 519.2 mmol), the same procedure as described in the synthesis method of Sub 1-1 was carried out to obtain target material (65.9 g, 69%).

116

6. Synthesis of Sub 1-32

(1) Synthesis of Sub 1-I-32

<Reaction Scheme 22>

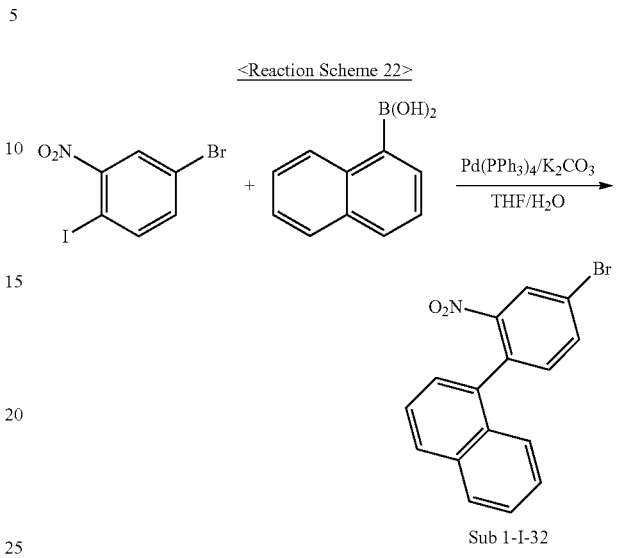
Sub 1-I-32

Using naphthalen-1-ylboronic acid (70 g, 407 mmol), THF (1790 ml), 4-bromo-1-iodo-2-nitrobenzene (200 g, 610.5 mmol), Pd(PPh$_3$)$_4$ (23.5 g, 20.35 mmol), K$_2$CO$_3$ (168.8 g, 1221 mmol), water (895 ml), the same procedure as described in the synthesis method of Sub 1-I-1 was carried out to obtain target material (94.8 g, 71%).

(2) Synthesis of Sub 1-II-32

<Reaction Scheme 23>

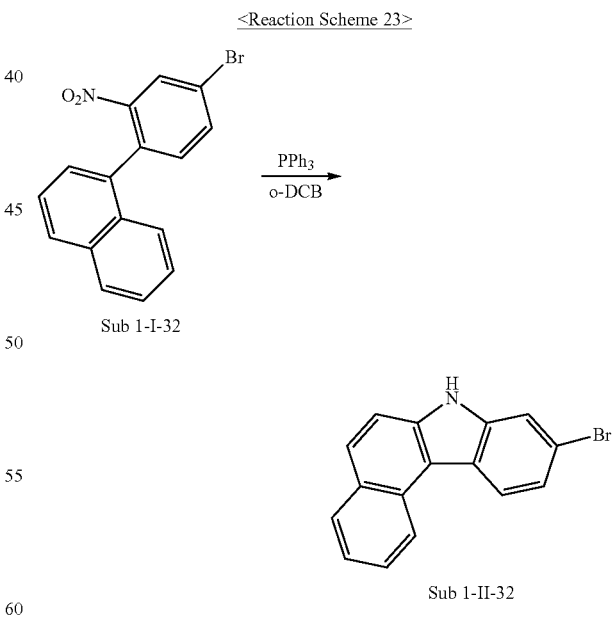
Sub 1-II-32

Using Sub 1-I-32 (94.8 g, 288.9 mmol), o-dichlorobenzene (1184 ml), triphenylphosphine (189.4 g, 722.2 mmol), the same procedure as described in the synthesis method of Sub 1-II-1 was carried out to obtain target material (61.2 g, 75%).

(3) Synthesis of Sub 1-III-32

<Reaction Scheme 24>

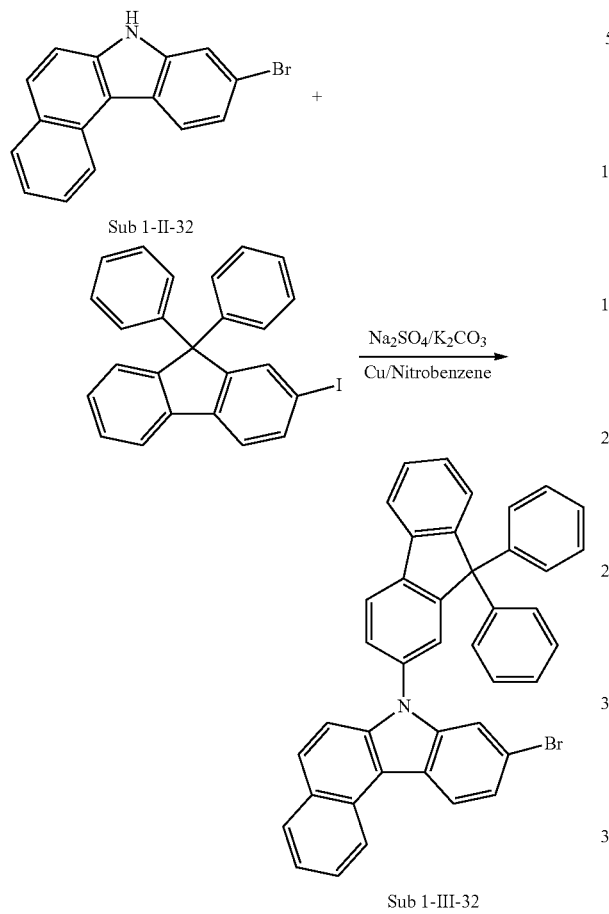

Sub 1-II-32

Sub 1-III-32

Using Sub 1-II-32 (61.2 g, 206.6 mmol), nitrobenzene (413 ml), 2-iodo-9,9-diphenyl-9H-fluorene (137.7 g, 310 mmol), Na$_2$SO$_4$ (29.35 g, 206.6 mmol), K$_2$CO$_3$ (28.6 g, 206.6 mmol), Cu (3.9 g, 62 mmol), the same procedure as described in the synthesis method of Sub 1-III-1 was carried out to obtain target material (89.86 g, 71%).

(4) Synthesis of Sub 1-IV-32

<Reaction Scheme 25>

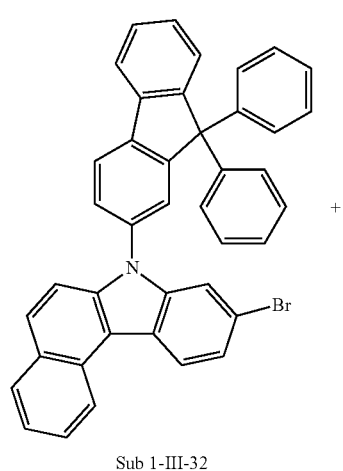

Sub 1-III-32

+

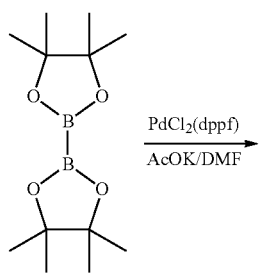

PdCl$_2$(dppf)
AcOK/DMF

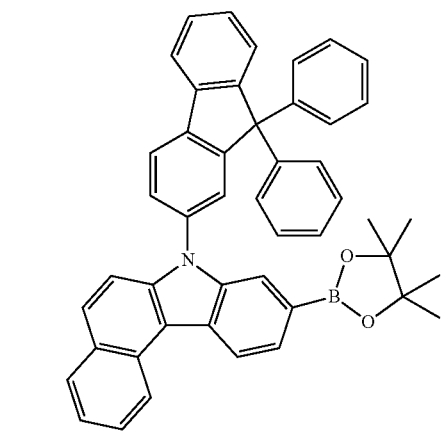

Sub 1-IV-32

Using Sub 1-III-32 (89.86 g, 146.7 mmol), DMF (924 ml), Bis (pinacolato)diboron (41 g, 161.4 mmol), Pd(dppf)C$_{12}$ (3.59 g, 4.4 mmol), KOAc (43.2 g, 440.1 mmol), the same procedure as described in the synthesis method of Sub 1-IV-1 was carried out to obtain target material (74.5 g, 77%).

(5) Synthesis of Sub 1-32

<Reaction Scheme 26>

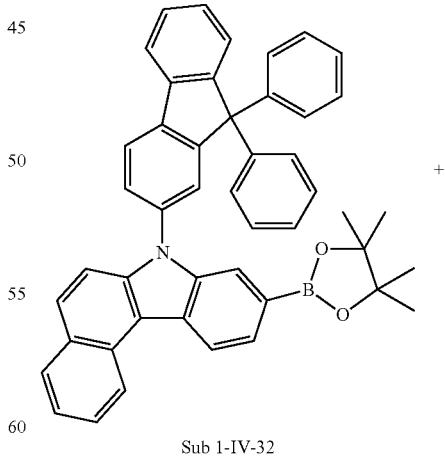

Sub 1-IV-32

+

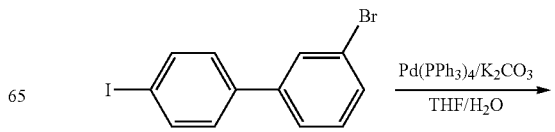

Pd(PPh$_3$)$_4$/K$_2$CO$_3$
THF/H$_2$O

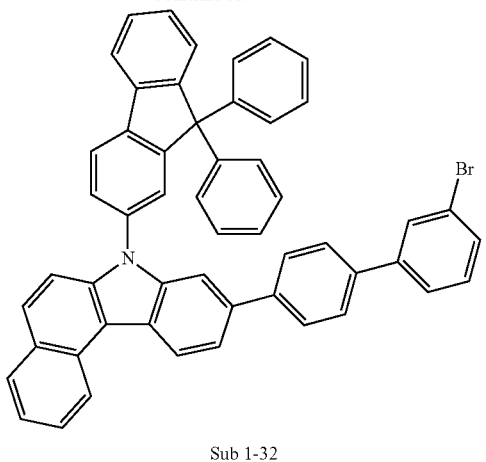

Sub 1-32

Using Sub 1-IV-32 (74.5 g, 112.9 mmol), THF (496 ml), 3-bromo-4'-iodo-1,1'-biphenyl (60.8 g, 169.4 mmol), Pd(PPh₃)₄ (6.53 g, 5.65 mmol), K₂CO₃ (46.8 g, 338.8 mmol), water (248 ml), the same procedure as described in the synthesis method of Sub 1-1 was carried out to obtain target material (59.6 g, 69%).

7. Synthesis of 1-34

(1) Synthesis of Sub 1-I-34

<Reaction Scheme 27>

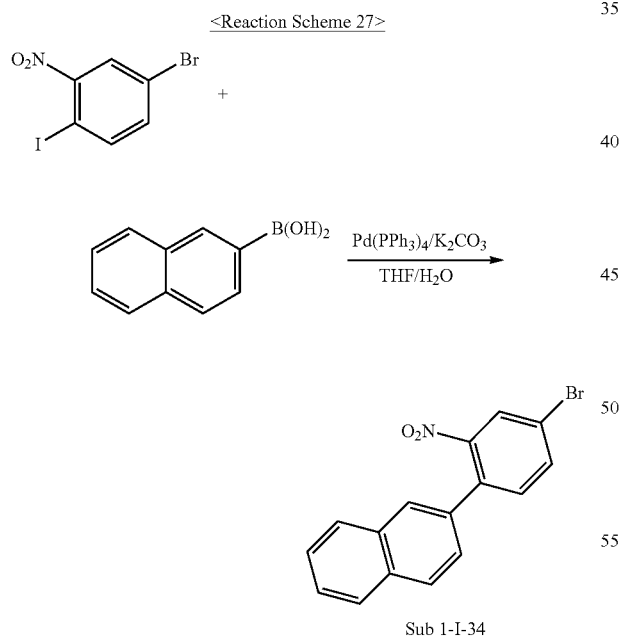

Sub 1-I-34

Using naphthalen-2-ylboronic acid (70 g, 407 mmol), THF (1790 ml), 4-bromo-1-iodo-2-nitrobenzene (200 g, 610.5 mmol), Pd(PPh₃)₄ (23.5 g, 20.35 mmol), K₂CO₃ (168.8 g, 1221 mmol), water (895 ml), the same procedure as described in the synthesis method of Sub 1-I-1 was carried out to obtain target material (97.5 g, 73%).

(2) Synthesis of Sub 1-II-34

<Reaction Scheme 28>

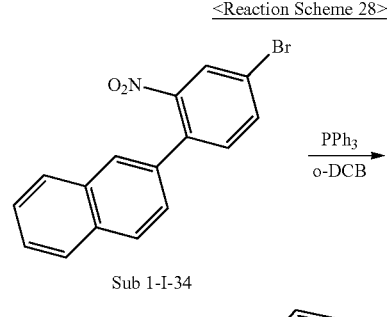

Sub 1-I-34

Sub 1-II-34

Using Sub 1-I-34 (97.5 g, 297.1 mmol), o-dichlorobenzene (1220 ml), triphenylphosphine (194.8 g, 742.8 mmol), the same procedure as described in the synthesis method of Sub 1-II-1 was carried out to obtain target material (65.1 g, 74%).

(3) Synthesis of Sub 1-III-34

<Reaction Scheme 29>

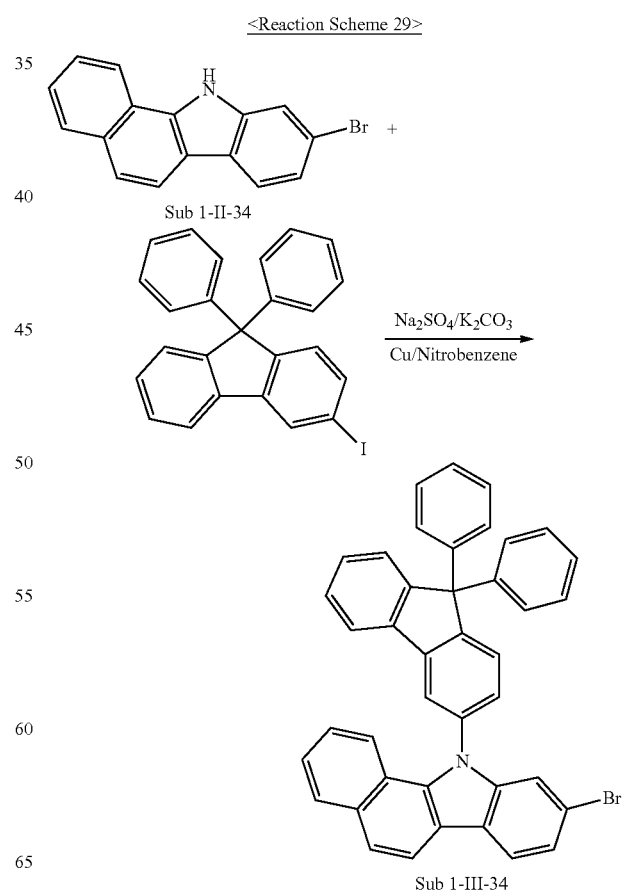

Sub 1-II-34

Sub 1-III-34

Using Sub 1-II-34 (65.1 g, 220 mmol), nitrobenzene (440 ml), 3-iodo-9,9-diphenyl-9H-fluorene (146.5 g, 330 mmol), Na$_2$SO$_4$ (31.2 g, 220 mmol), K$_2$CO$_3$ (30.4 g, 220 mmol), Cu (4.2 g, 66 mmol), the same procedure as described in the synthesis method of Sub 1-III-1 was carried out to obtain target material (95.6 g, 71%).

(4) Synthesis of Sub 1-IV-34

<Reaction Scheme 30>

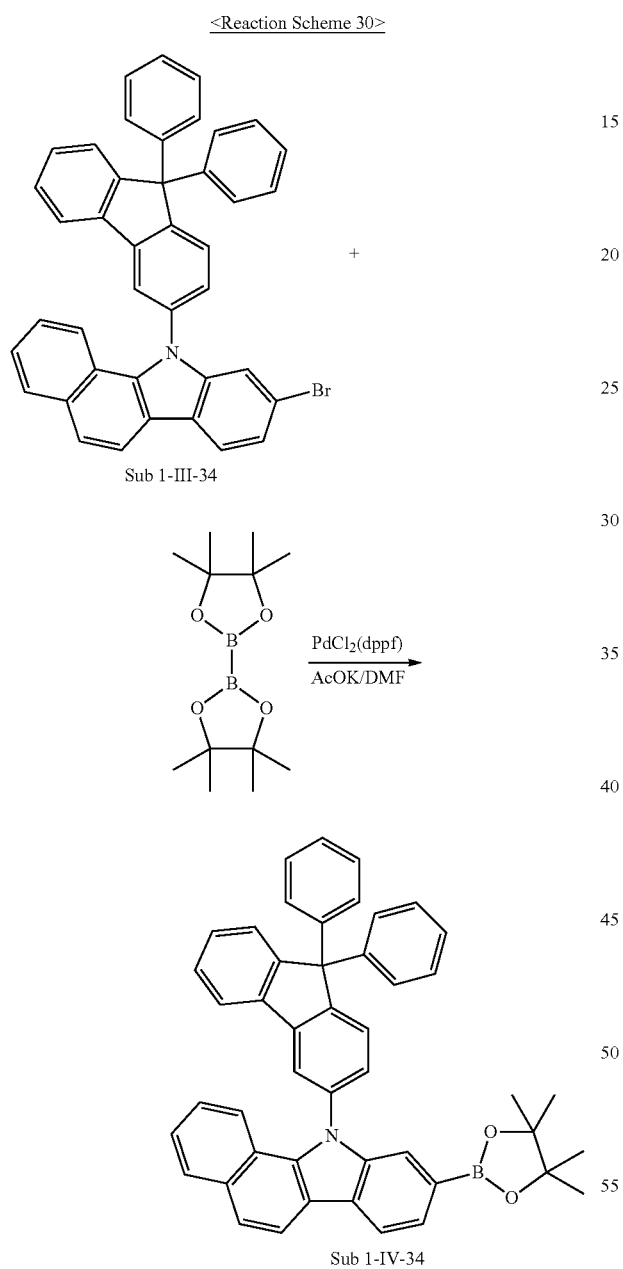

Using Sub 1-III-34 (95.6 g, 156.1 mmol), DMF (980 ml), Bis(pinacolato)diboron (43.6 g, 171.7 mmol), Pd(dppf)C$_{12}$ (3.82 g, 4.7 mmol), KOAc (46 g, 468.2 mmol), the same procedure as described in the synthesis method of Sub 1-IV-1 was carried out to obtain target material (77.2 g, 75%).

(5) Synthesis of Sub 1-34

<Reaction Scheme 31>

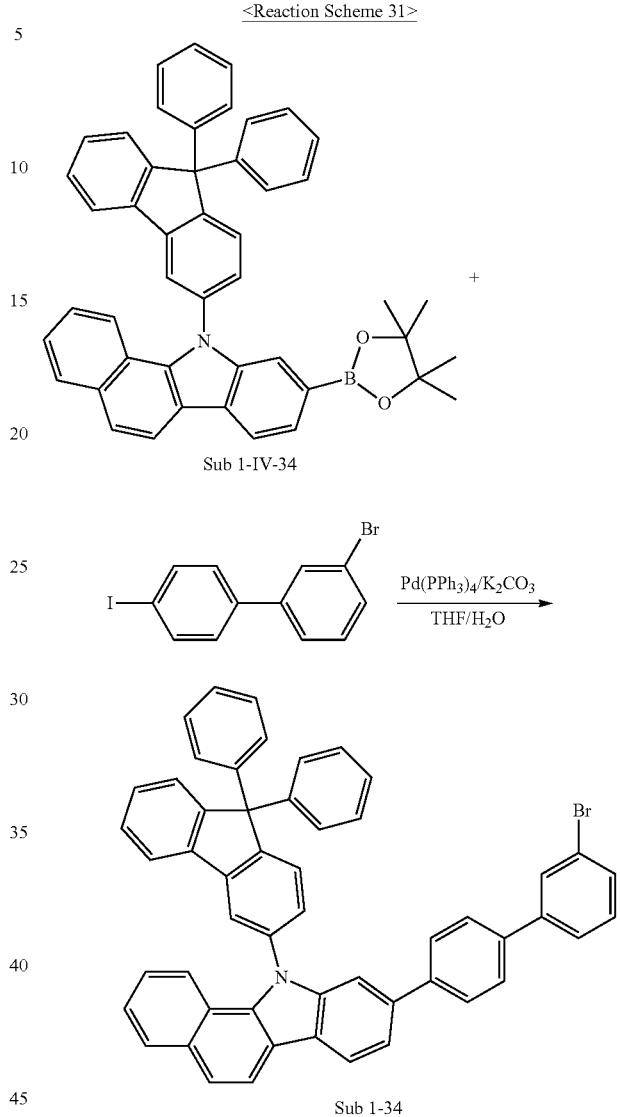

Using Sub 1-IV-34 (77.2 g, 117 mmol), THF (510 ml), 3-bromo-4'-iodo-1,1'-biphenyl (63 g, 175.6 mmol), Pd(PPh$_3$)$_4$ (6.76 g, 5.85 mmol), K$_2$CO$_3$ (48.5 g, 351 mmol), water (255 ml), the same procedure as described in the synthesis method of Sub 1-1 was carried out to obtain target material (58.2 g, 65%).

8. Synthesis of 1-35

(1) Synthesis of Sub 1-I-35

<Reaction Scheme 32>

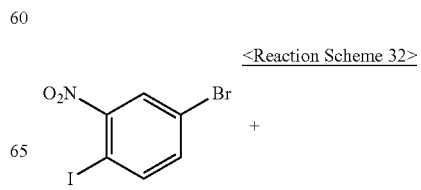

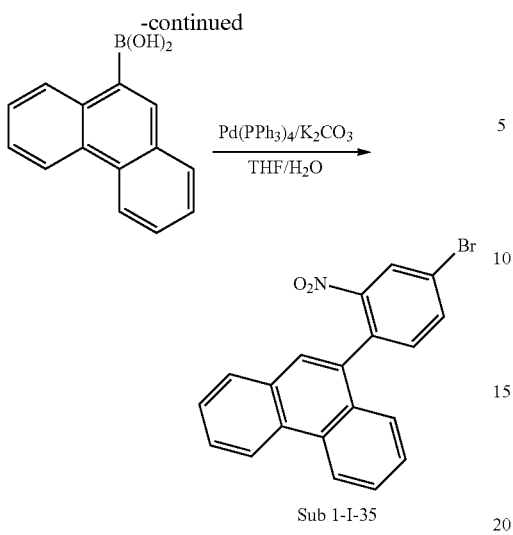

Sub 1-I-35

Using phenanthren-9-ylboronic acid (70 g, 315.2 mmol), THF (1388 ml), 4-bromo-1-iodo-2-nitrobenzene (155.1 g, 472.9 mmol), Pd(PPh$_3$)$_4$ (18.2 g, 15.8 mmol), K$_2$CO$_3$ (130.7 g, 945.7 mmol), water (694 ml), the same procedure as described in the synthesis method of Sub 1-I-1 was carried out to obtain target material (85.8 g, 72%).

(2) Synthesis of Sub 1-II-35

<Reaction Scheme 33>

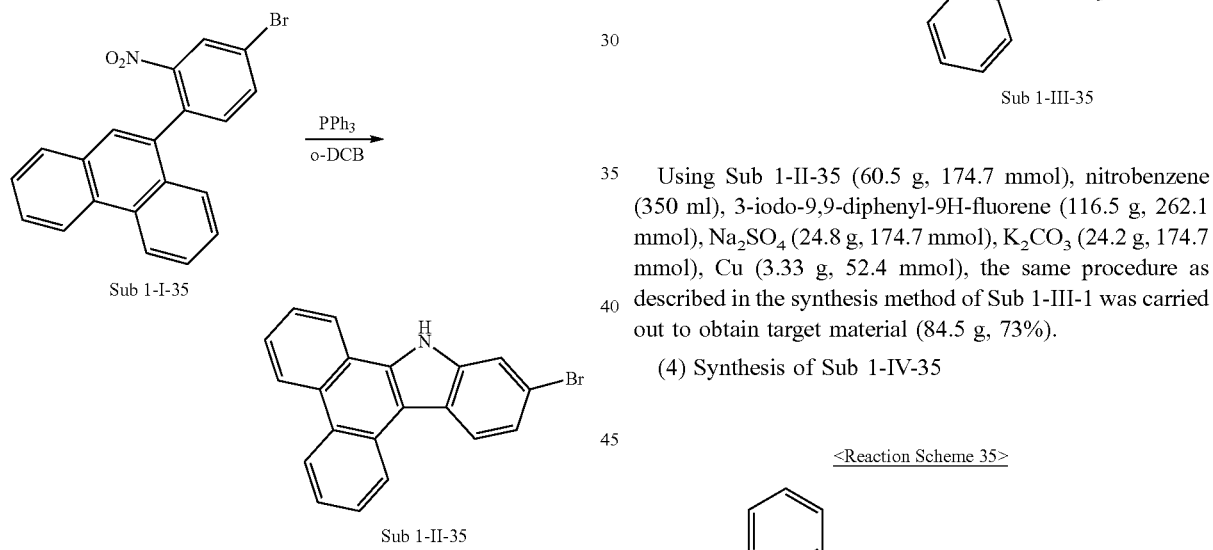

Using Sub 1-I-35 (85.8 g, 226.9 mmol), o-dichlorobenzene (930 ml), triphenylphosphine (148.8 g, 567.1 mmol), the same procedure as described in the synthesis method of Sub 1-II-1 was carried out to obtain target material (60.5 g, 77%).

(3) Synthesis of Sub 1-III-35

<Reaction Scheme 34>

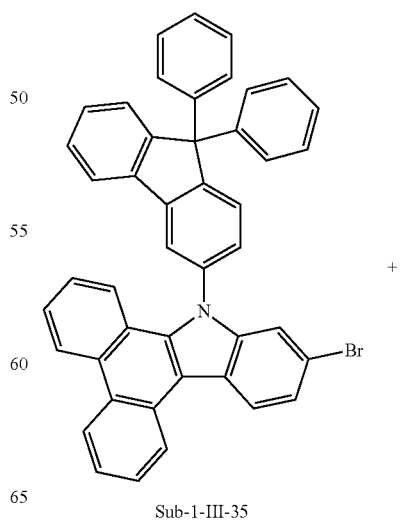

Using Sub 1-II-35 (60.5 g, 174.7 mmol), nitrobenzene (350 ml), 3-iodo-9,9-diphenyl-9H-fluorene (116.5 g, 262.1 mmol), Na$_2$SO$_4$ (24.8 g, 174.7 mmol), K$_2$CO$_3$ (24.2 g, 174.7 mmol), Cu (3.33 g, 52.4 mmol), the same procedure as described in the synthesis method of Sub 1-III-1 was carried out to obtain target material (84.5 g, 73%).

(4) Synthesis of Sub 1-IV-35

<Reaction Scheme 35>

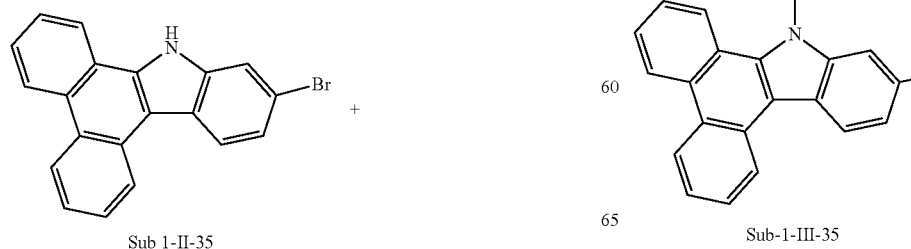

-continued

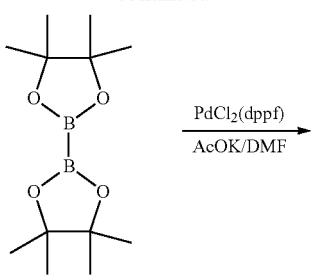

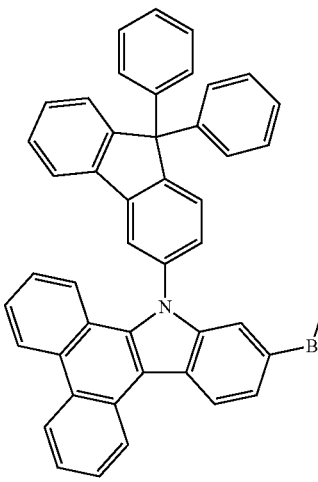

Sub-1-IV-35

Using Sub 1-III-35 (84.5 g, 127.5 mmol), DMF (854 ml), Bis(pinacolato)diboron (35.6 g, 140.3 mmol), Pd(dppf)C$_{12}$ (3.12 g, 3.82 mmol), KOAc (37.5 g, 382.5 mmol), the same procedure as described in the synthesis method of Sub 1-IV-1 was carried out to obtain target material (70.6 g, 78%).

(5) Synthesis of Sub 1-35

<Reaction Scheme 36>

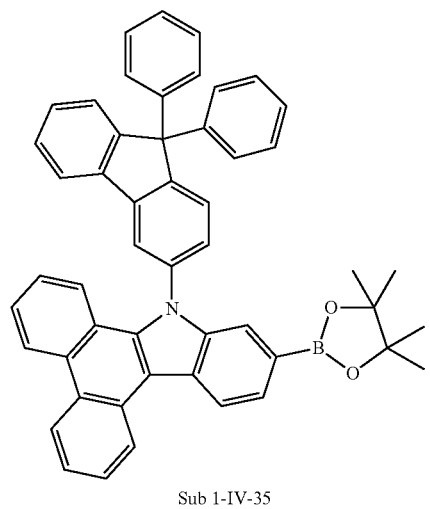

Sub 1-IV-35

-continued

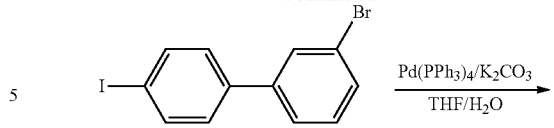

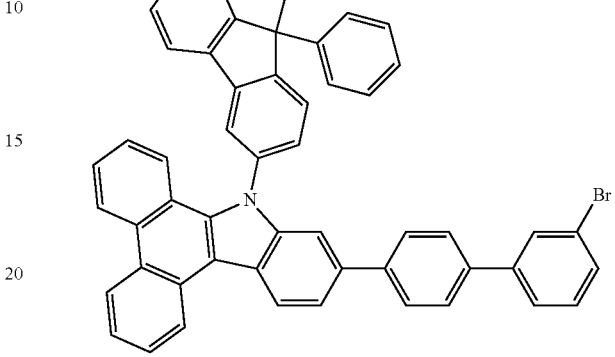

Sub 1-35

Using Sub 1-IV-35 (70.6 g, 99.5 mmol), THF (438 ml), 3-bromo-4'-iodo-1,1'-biphenyl (53.6 g, 149.2 mmol), Pd(PPh$_3$)$_4$ (5.75 g, 4.97 mmol), K$_2$CO$_3$ (41.2 g, 298.4 mmol), water (219 ml), the same procedure as described in the synthesis method of Sub 1-1 was carried out to obtain target material (55.1 g, 68%).

9. Synthesis of Sub 1-44

(1) Synthesis of Sub 1-III-44

<Reaction Scheme 37>

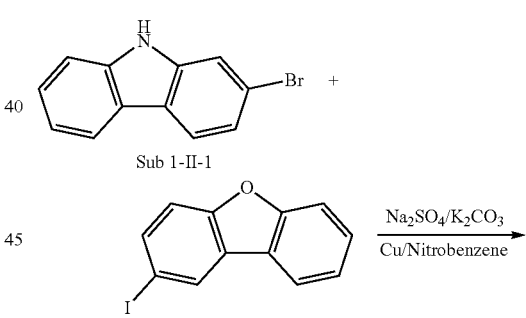

Sub 1-II-1

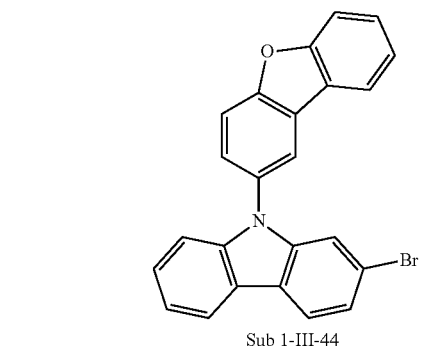

Sub 1-III-44

Using Sub 1-II-1 (60 g, 244 mmol), nitrobenzene (487 ml), 2-iododibenzo[b,d]furan (107.6 g, 365.7 mmol), Na$_2$SO$_4$ (34.6 g, 244 mmol), K$_2$CO$_3$ (33.7 g, 244 mmol), Cu (4.65 g, 73.1 mmol), the same procedure as described in the synthesis method of Sub 1-III-1 was carried out to obtain target material (68.4 g, 68%).

(2) Synthesis of Sub 1-IV-44

<Reaction Scheme 38>

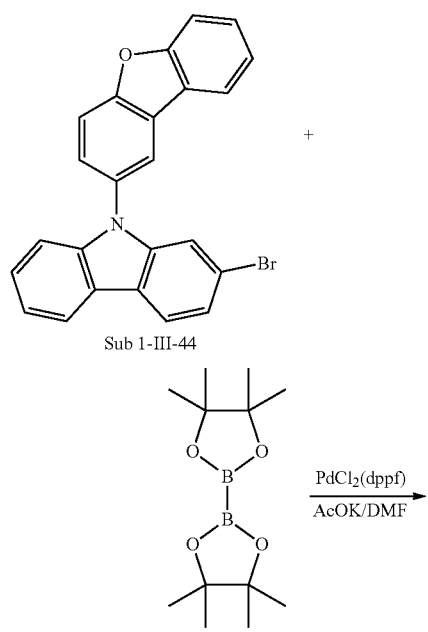

Using Sub 1-III-44 (68.4 g, 166 mmol), DMF (1045 ml), Bis(pinacolato)diboron (46.3 g, 182.5 mmol), Pd(dppf)C$_{12}$ (4.06 g, 5 mmol), KOAc (48.8 g, 497.7 mmol), the same procedure as described in the synthesis method of Sub 1-IV-1 was carried out to obtain target material (56.4 g, 74%).

(3) Synthesis of Sub 1-44

<Reaction Scheme 39>

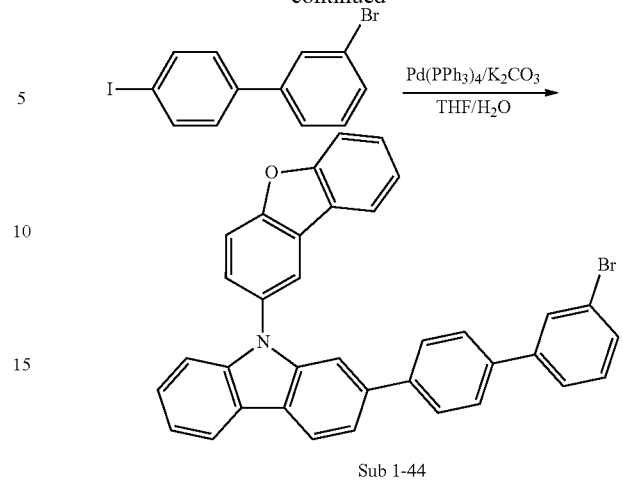

Using Sub 1-IV-44 (56.4 g, 122.8 mmol), THF (540 ml), 3-bromo-4'-iodo-1,1'-biphenyl (66.1 g, 184 mmol), Pd(PPh$_3$)$_4$ (7.1 g, 6.14 mmol), K$_2$CO$_3$ (50.9 g, 368.4 mmol), water (270 ml), the same procedure as described in the synthesis method of Sub 1-1 was carried out to obtain target material (47.8 g, 69%).

10. Synthesis of Sub 1-54

(1) Synthesis of Sub 1-III-54

<Reaction Scheme 40>

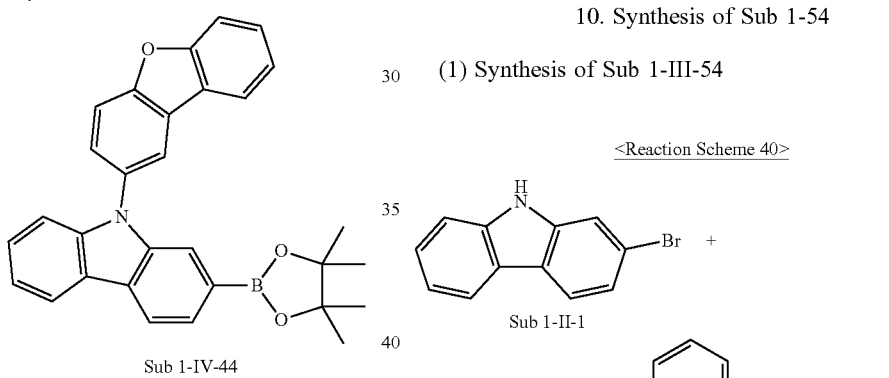

Using Sub 1-II-1 (50 g, 203.2 mmol), nitrobenzene (406 ml), 4-iodo-1,1'-biphenyl (85.4 g, 304.7 mmol), Na$_2$SO$_4$ (28.9 g, 203.2 mmol), K$_2$CO$_3$ (28.1 g, 203.2 mmol), Cu (3.87 g, 61 mmol), the same procedure as described in the synthesis method of Sub 1-III-1 was carried out to obtain target material (54.2 g, 68%).

(2) Synthesis of Sub 1-IV-54

<Reaction Scheme 41>

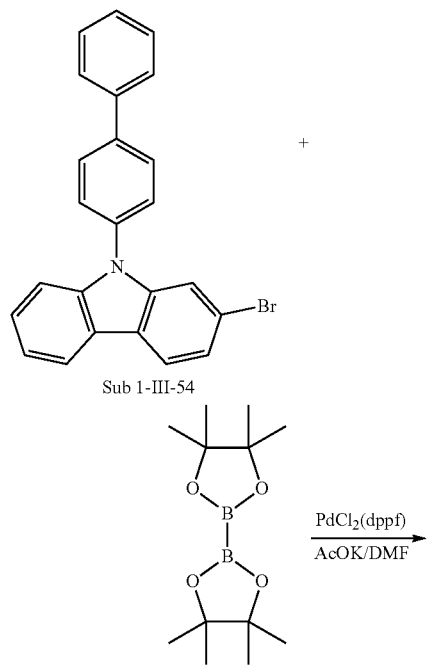

Sub 1-III-54

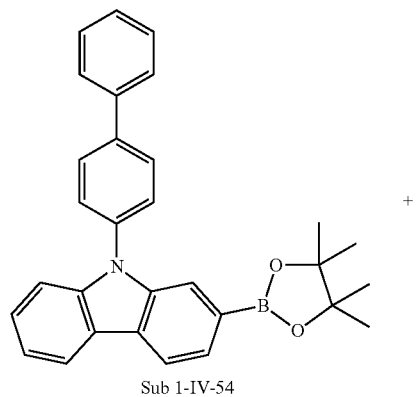

Sub 1-IV-54

Using Sub 1-III-54 (54.2 g, 136.1 mmol), DMF (857 ml), Bis (pinacolato)diboron (38.0 g, 150 mmol), Pd(dppf)C$_{12}$ (3.33 g, 4.1 mmol), KOAc (40.1 g, 408 mmol), the same procedure as described in the synthesis method of Sub 1-IV-1 was carried out to obtain target material (42.4 g, 70%).

(3) Synthesis of Sub 1-54

<Reaction Scheme 42>

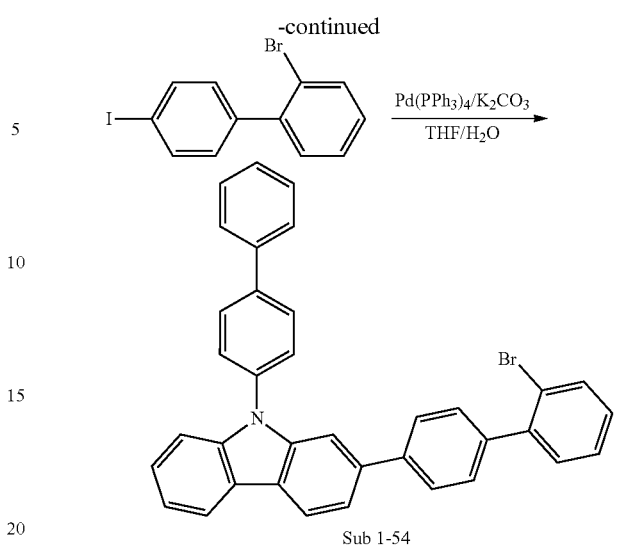

Sub 1-54

Using Sub 1-IV-54 (42.4 g, 95.2 mmol), THF (418 ml), 2-bromo-4'-iodo-1,1'-biphenyl (51.3 g, 142.8 mmol), Pd(PPh$_3$)$_4$ (5.5 g, 4.76 mmol), K$_2$CO$_3$ (39.5 g, 285.6 mmol), water (209 ml), the same procedure as described in the synthesis method of Sub 1-1 was carried out to obtain target material (34.1 g, 65%).

11. Synthesis of Sub 1-66

(1) Synthesis of Sub 1-III-66

<Reaction Scheme 43>

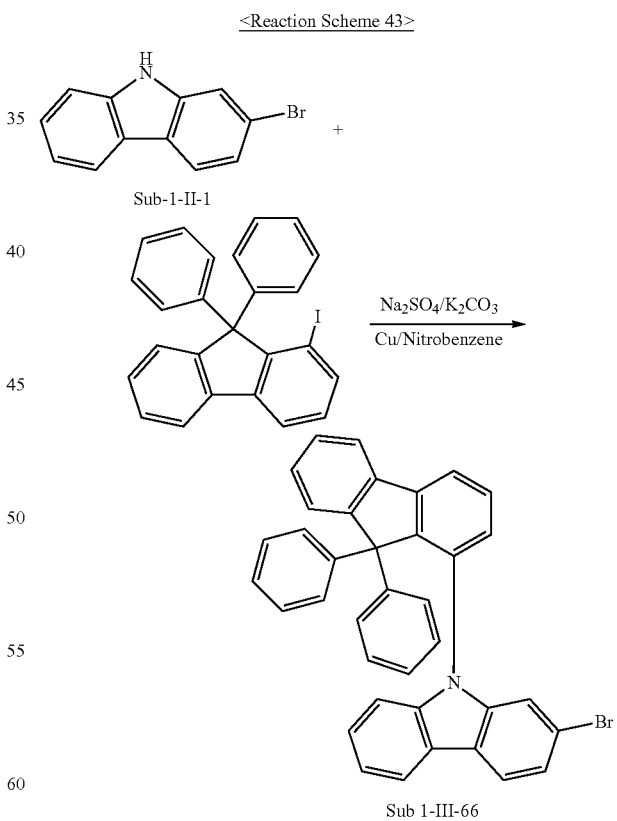

Sub 1-III-66

Using Sub 1-II-1 (50 g, 203.2 mmol), nitrobenzene (406 ml), 1-iodo-9,9-diphenyl-9H-fluorene (135.4 g, 305 mmol), Na$_2$SO$_4$ (28.9 g, 203.2 mmol), K$_2$CO$_3$ (28.1 g, 203.2 mmol), Cu (3.87 g, 61 mmol), the same procedure as described in the synthesis method of Sub 1-III-1 was carried out to obtain target material (70.9 g, 62%).

(2) Synthesis of Sub 1-IV-66

<Reaction Scheme 44>

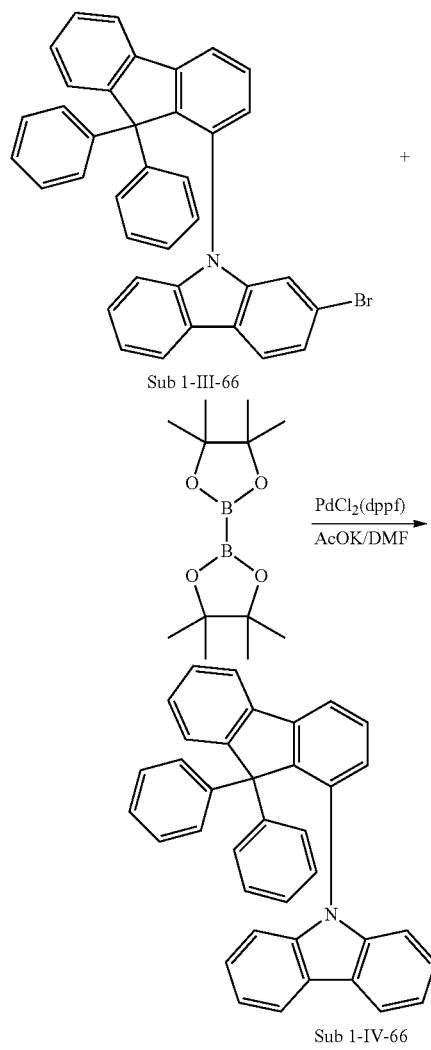

Using Sub 1-III-66 (70.9 g, 126 mmol), DMF (794 ml), Bis(pinacolato)diboron (35.2 g, 138.7 mmol), Pd(dppf)C₁₂ (3.09 g, 3.78 mmol), KOAc (37.11 g, 378.1 mmol), the same procedure as described in the synthesis method of Sub 1-IV-1 was carried out to obtain target material (51.5 g, 67%).

(3) Synthesis of Sub 1-66

<Reaction Scheme 45>

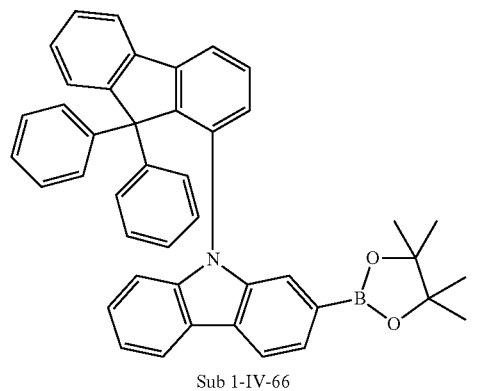

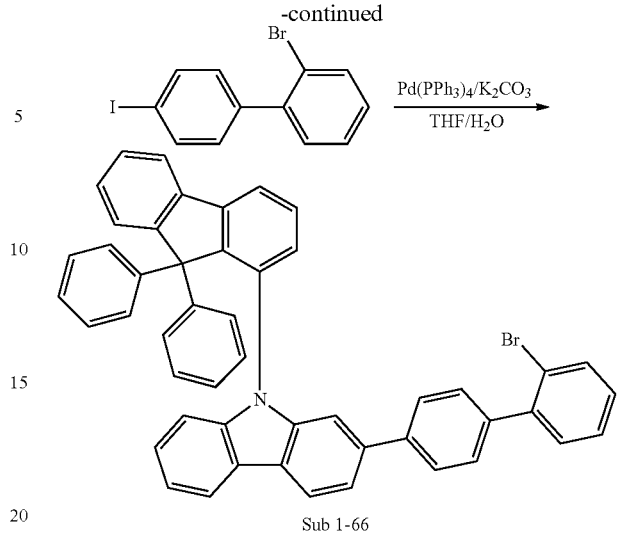

Using Sub 1-IV-66 (51.5 g, 84.5 mmol), THF (370 ml), 2-bromo-4'-iodo-1,1'-biphenyl (45.5 g, 126.7 mmol), Pd(PPh₃)₄ (4.88 g, 4.22 mmol), K₂CO₃ (35.03 g, 253.5 mmol), water (185 ml), the same procedure as described in the synthesis method of Sub 1-1 was carried out to obtain target material (36.2 g, 60%).

(4) Synthesis of Sub 1-104

<Reaction Scheme 46>

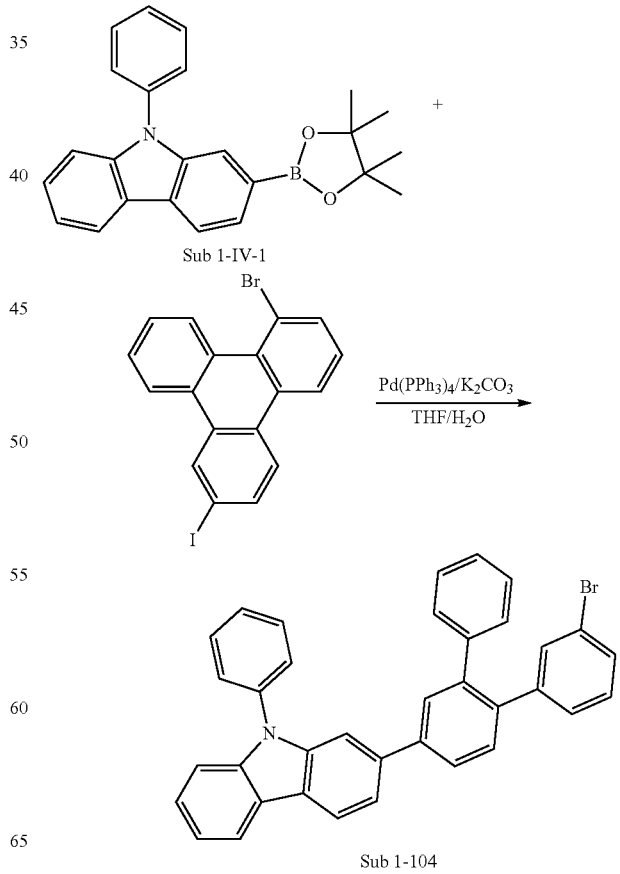

Using Sub 1-IV-11 (31.2 g, 84.5 mmol), THF 370 mL, 3-bromo-2'-iodo-1,1':4',1"-terphenyl (55.1 g, 126.7 mmol), Pd(PPh$_3$)$_4$ (4.88 g, 4.22 mmol), K$_2$CO$_3$ (35.03 g, 253.5 mmol), water (185 mL), the same procedure as described in the synthesis method of Sub 1-1 was carried out to obtain target material (31.6 g, 68%).

Examples of Sub 1 compounds include, but are not limited to, the following compounds, and FD-MS (Field Desorption-Mass Spectrometry) data of the compounds are given in Table 1 below.

Sub 1-1

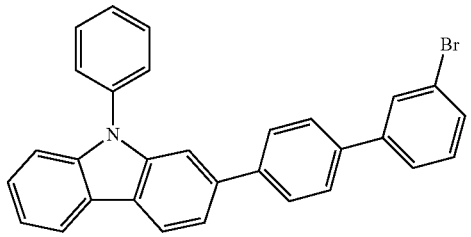

Sub 1-2

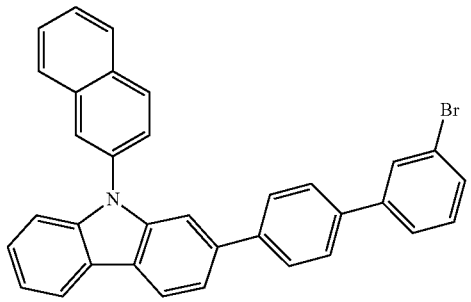

Sub 1-3

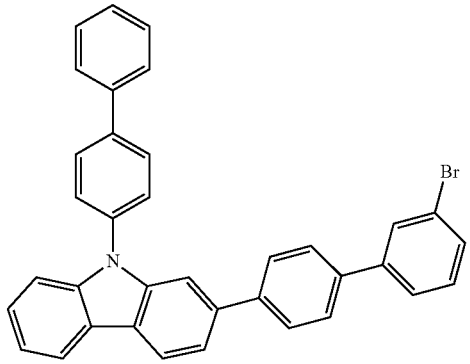

Sub 1-4

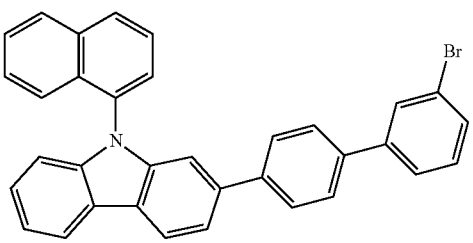

-continued

Sub 1-5

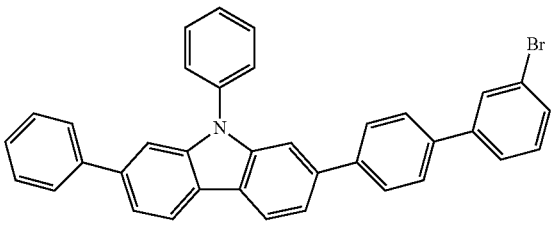

Sub 1-6

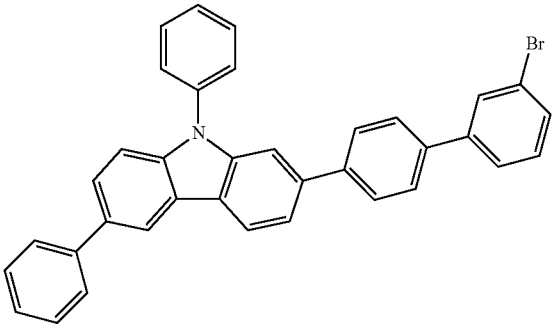

Sub 1-7

Sub 1-8

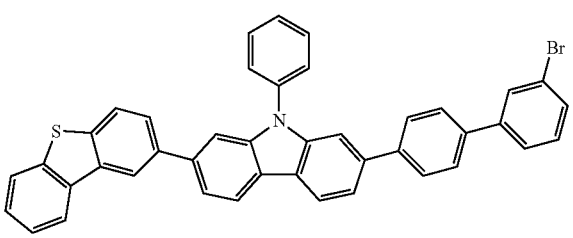

Sub 1-9

Sub 1-10
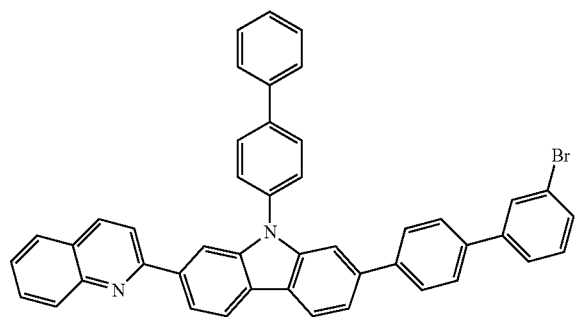
Sub 1-14
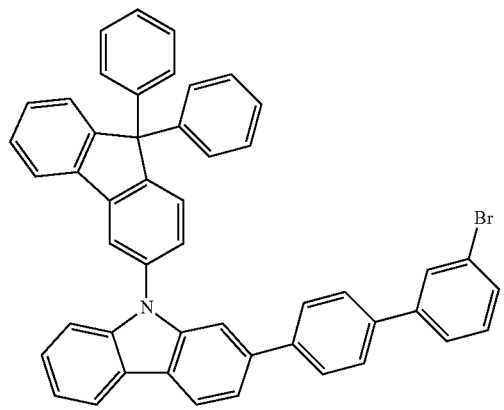
Sub 1-11
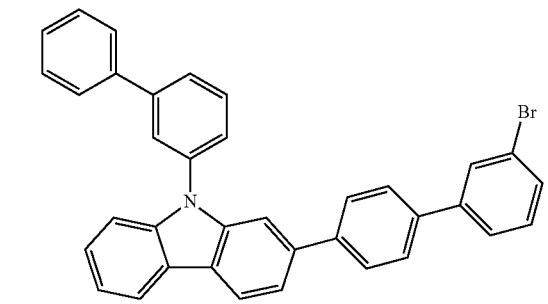
Sub 1-15
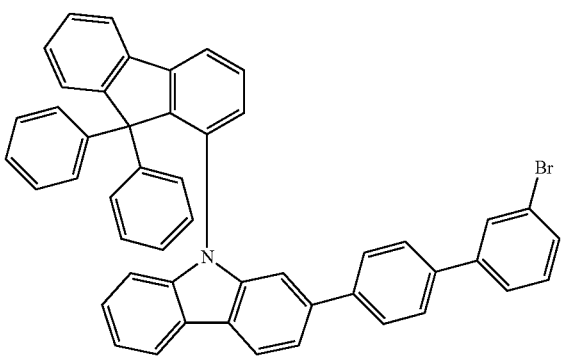
Sub 1-12
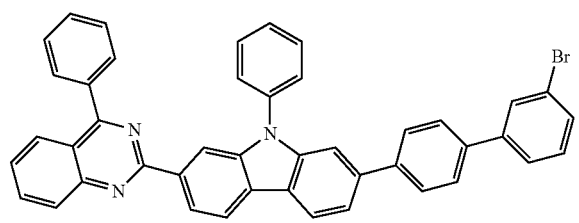
Sub 1-16
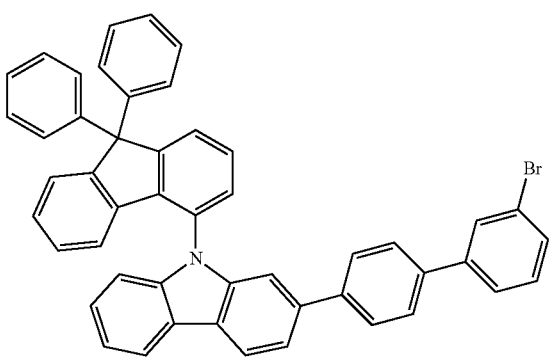
Sub 1-13
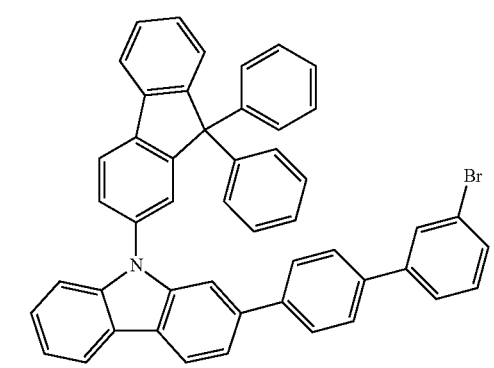
Sub 1-17
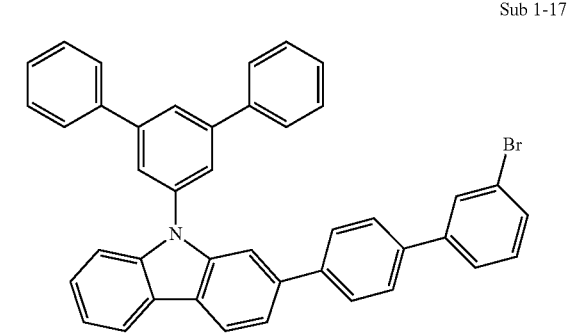

Sub 1-18
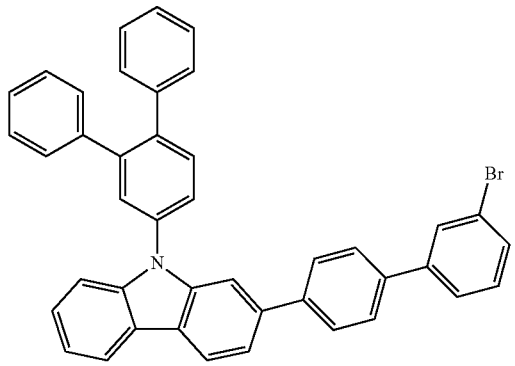
Sub 1-19
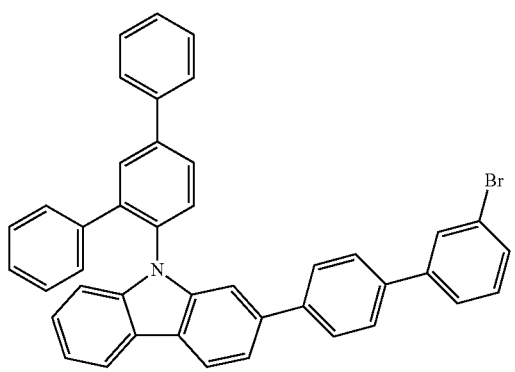
Sub 1-20
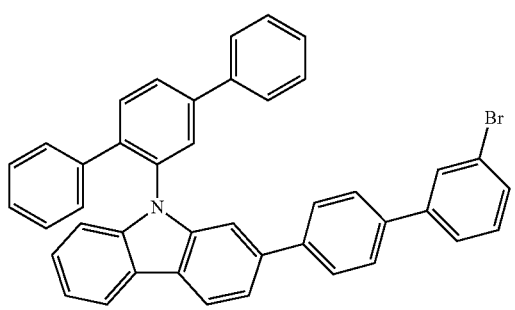
Sub 1-21
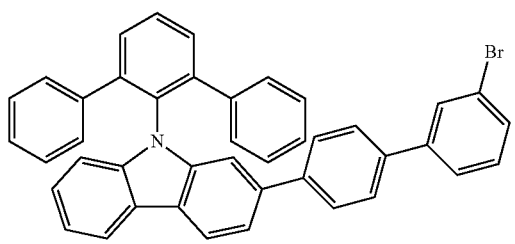
Sub 1-22
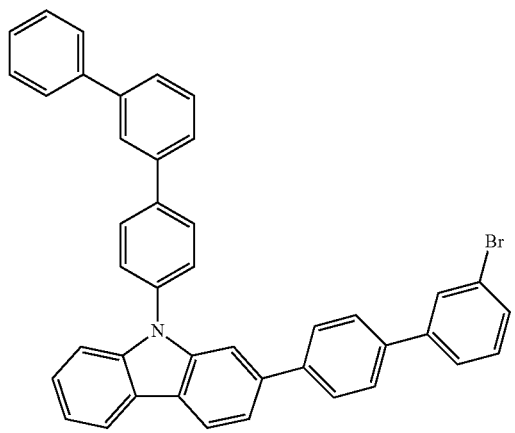
Sub 1-23
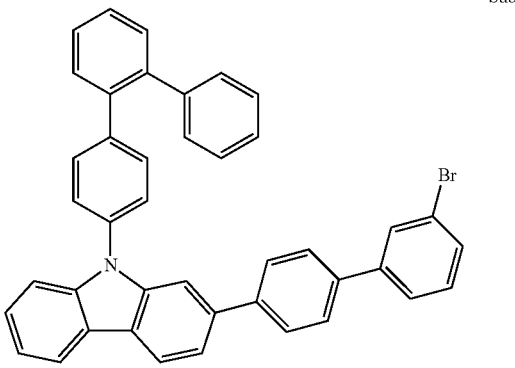
Sub 1-24
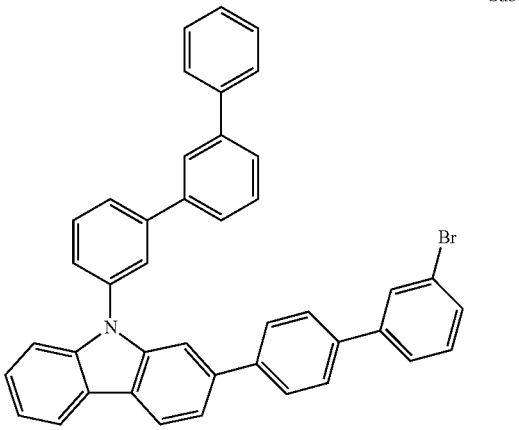
Sub 1-25
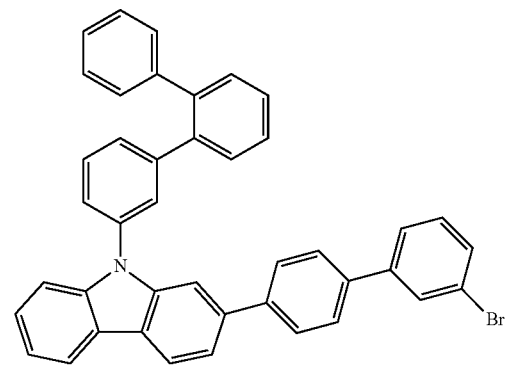

Sub 1-26
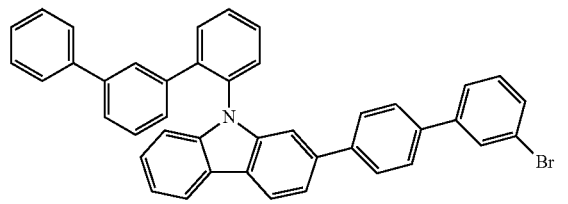
Sub 1-27
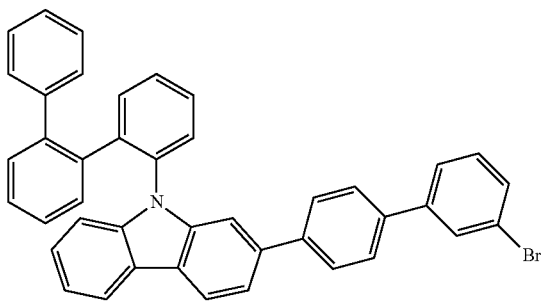
Sub 1-28
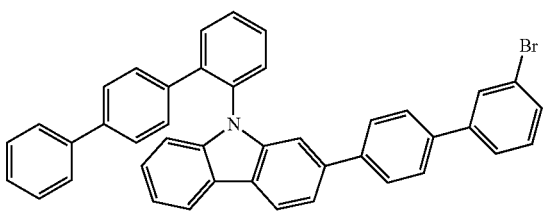
Sub 1-29
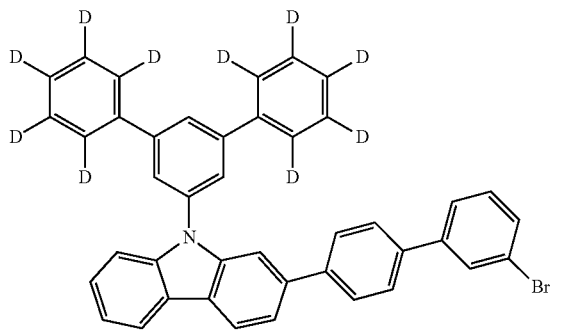
Sub 1-30
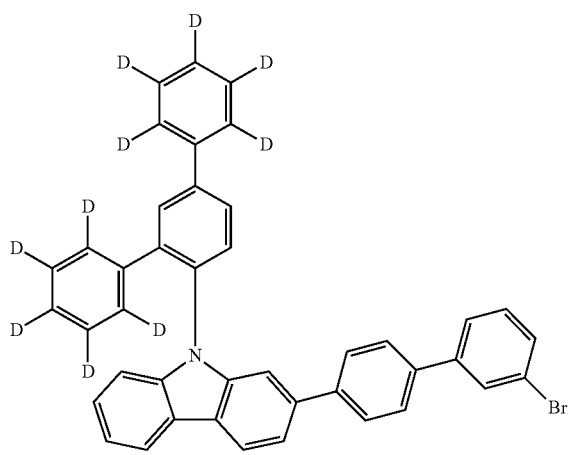
Sub 1-31
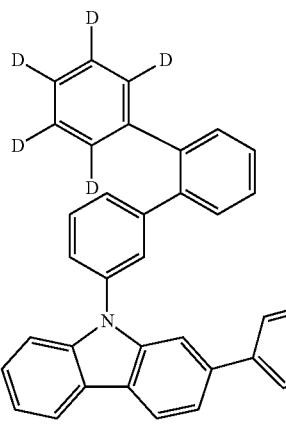
Sub 1-32
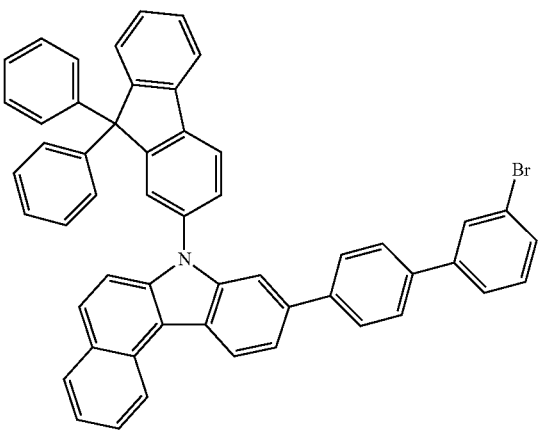
Sub 1-33
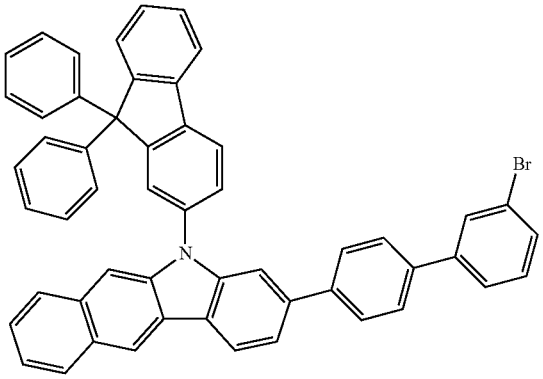

-continued
Sub 1-34
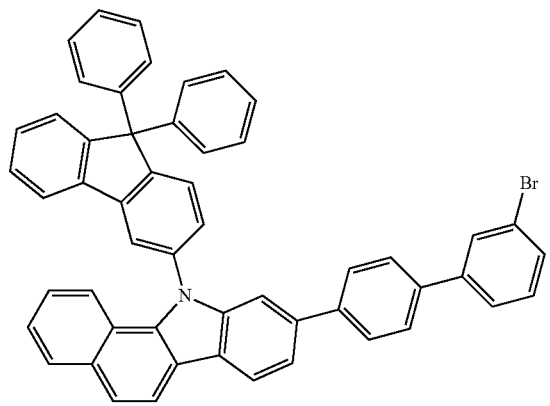
Sub 1-35
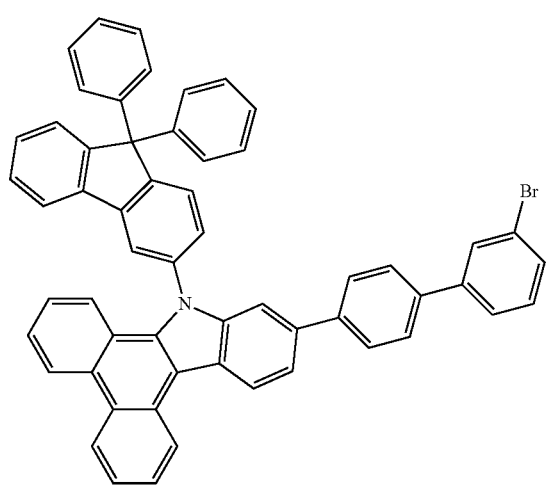
Sub 1-36
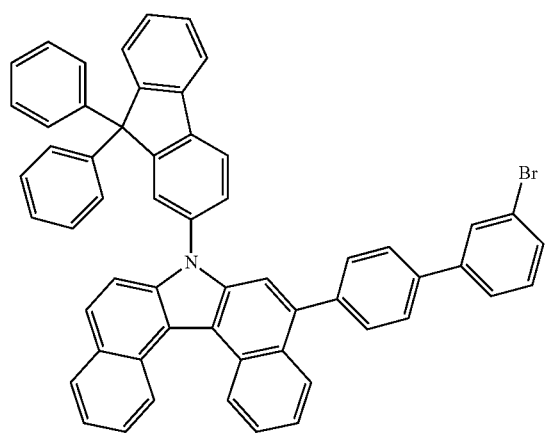
-continued
Sub 1-37
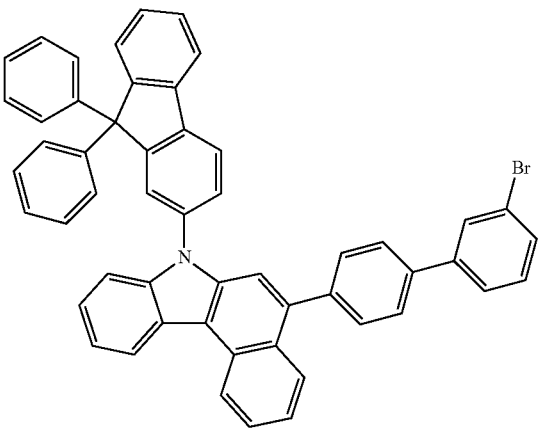
Sub 1-38
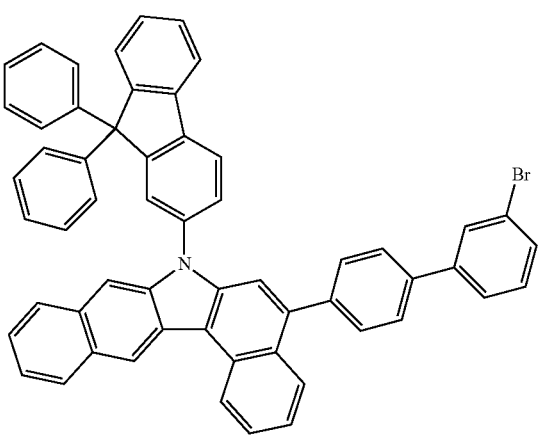
Sub 1-39
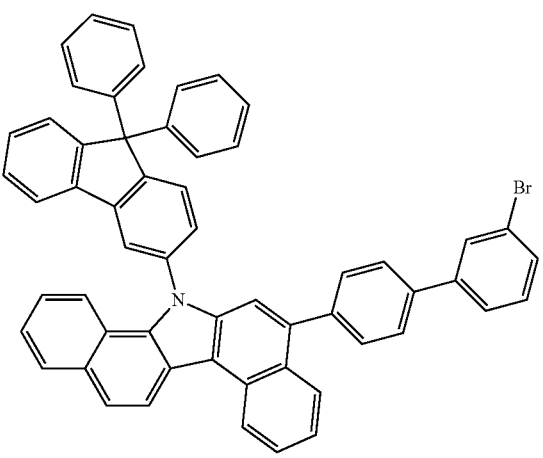

Sub 1-40
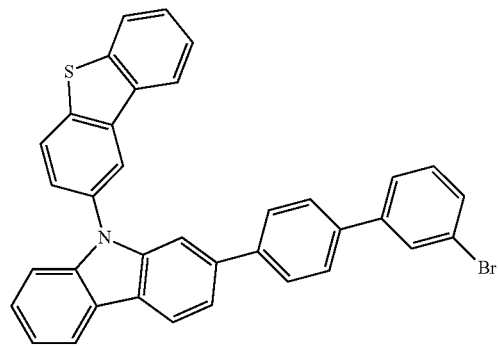
Sub 1-44
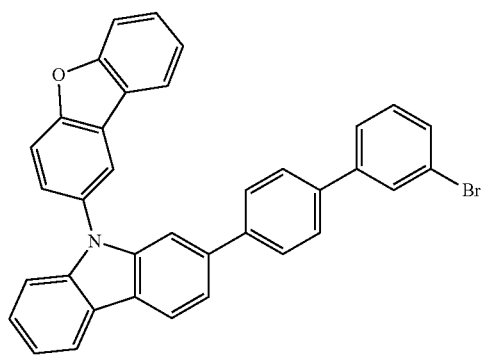
Sub 1-41
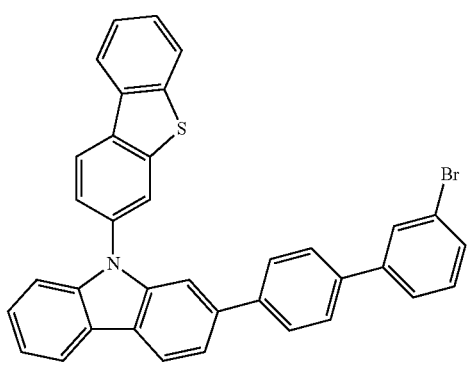
Sub 1-45
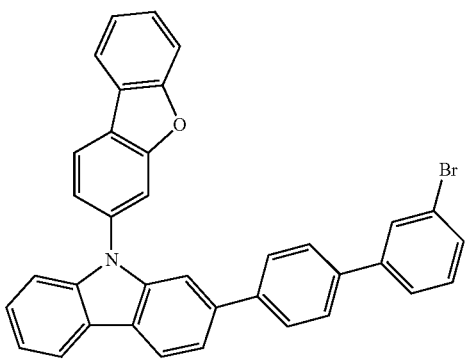
Sub 1-42
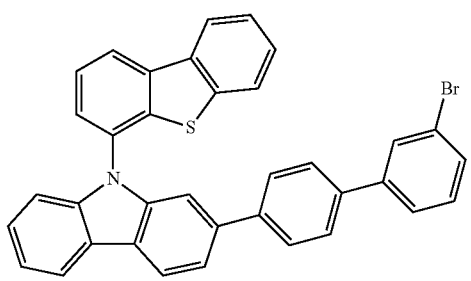
Sub 1-46
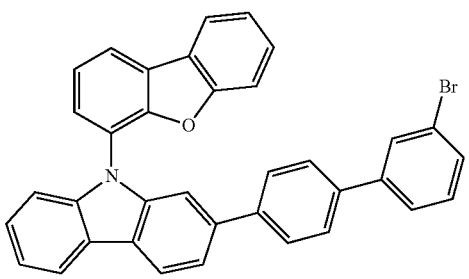
Sub 1-43
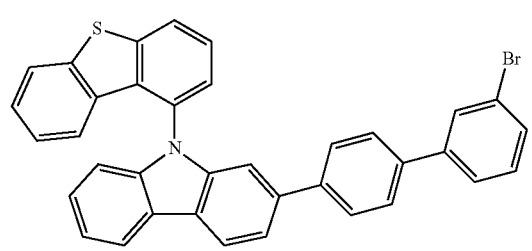
Sub 1-47
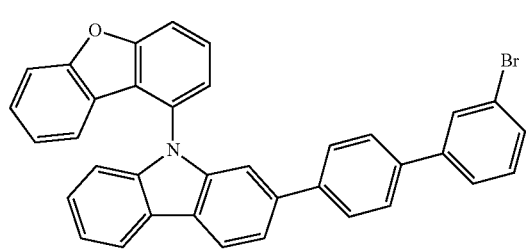

Sub 1-48
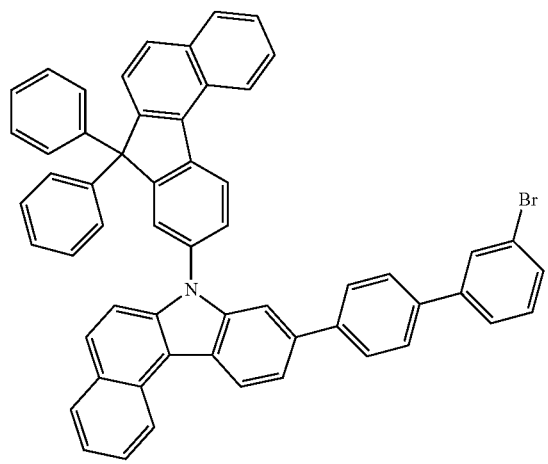
Sub 1-52
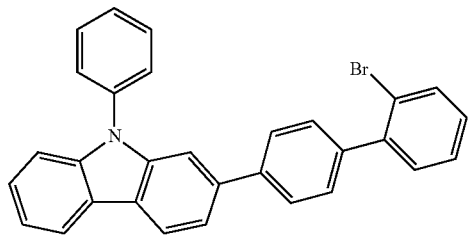
Sub 1-49
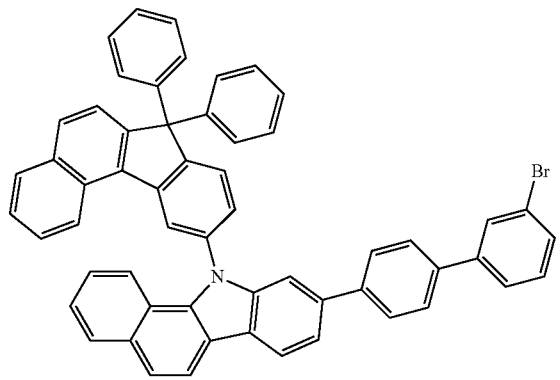
Sub 1-53
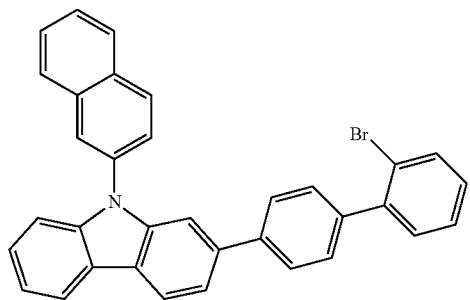
Sub 1-50
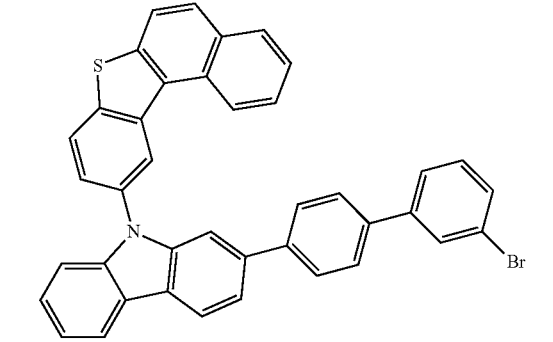
Sub 1-54
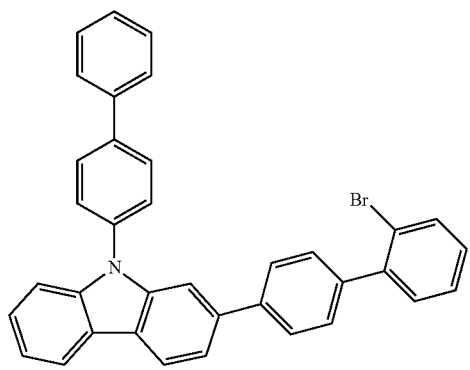
Sub 1-51
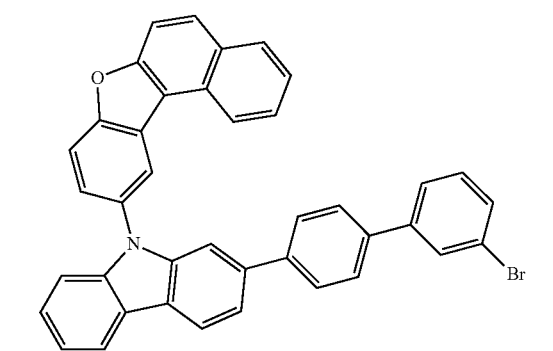
Sub 1-55
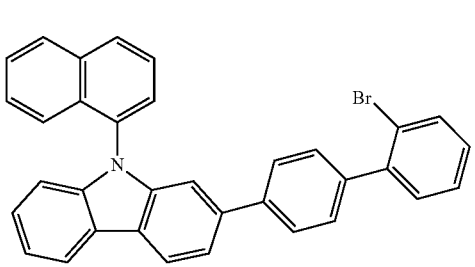
Sub 1-56
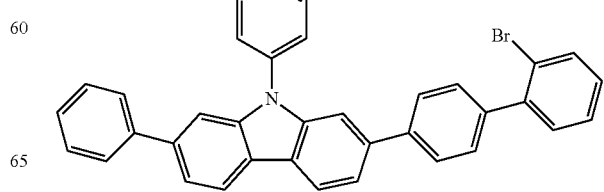

-continued
Sub 1-57
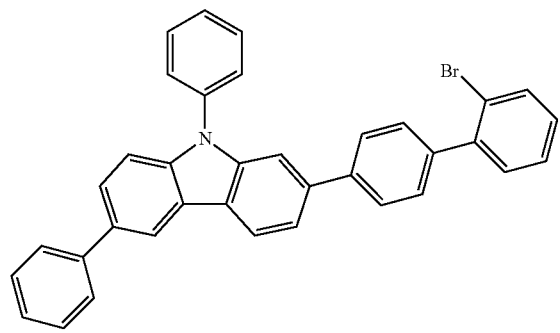
Sub 1-58
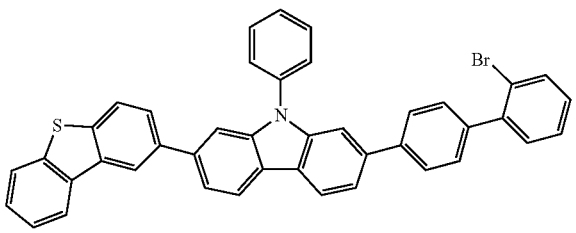
Sub 1-59
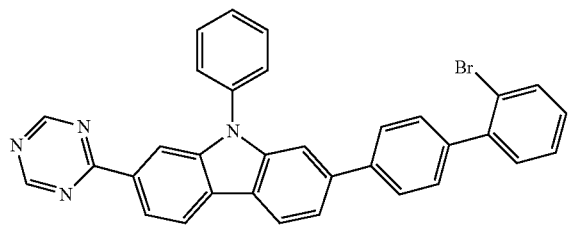
Sub 1-60
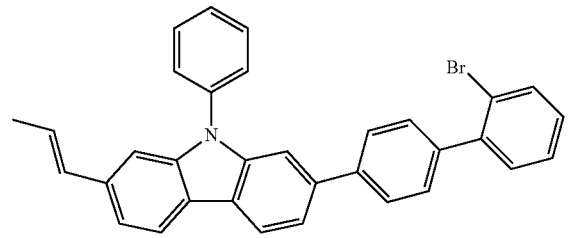
Sub 1-61
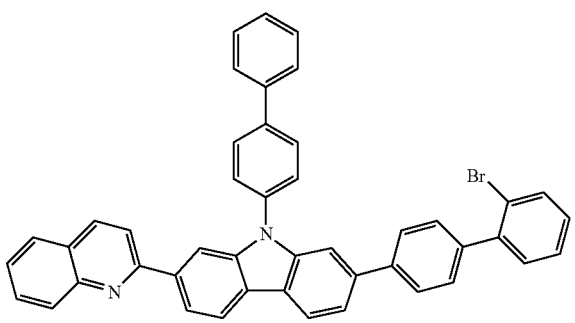
-continued
Sub 1-62
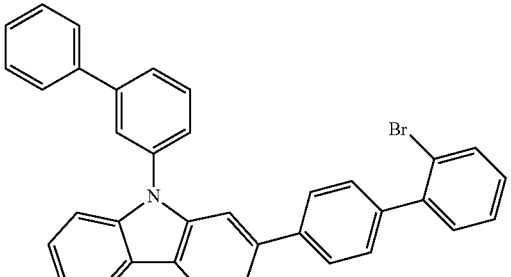
Sub 1-63
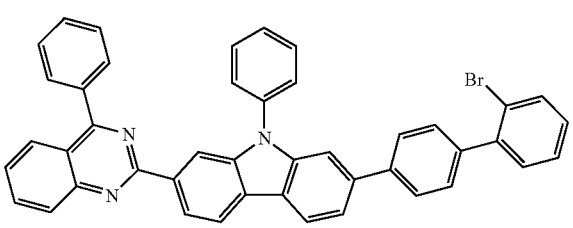
Sub 1-64
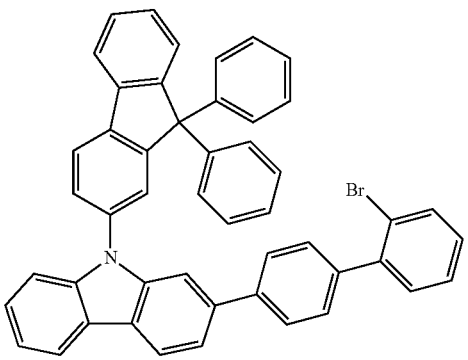
Sub 1-65
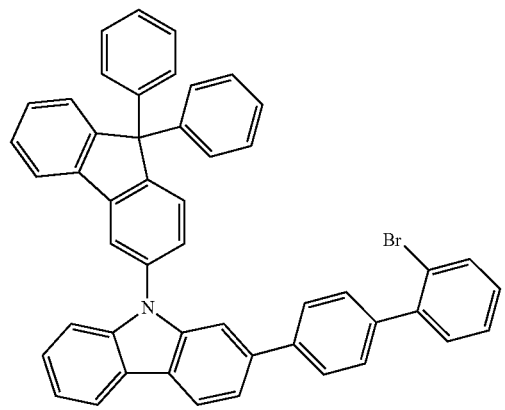

Sub 1-66
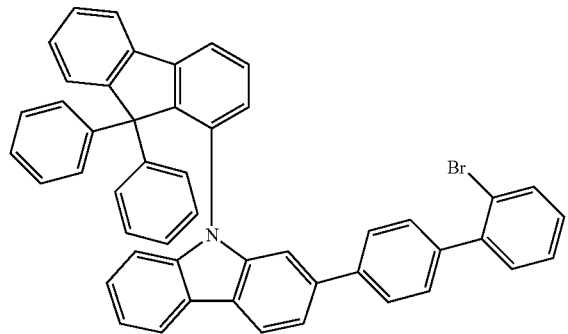
Sub 1-67
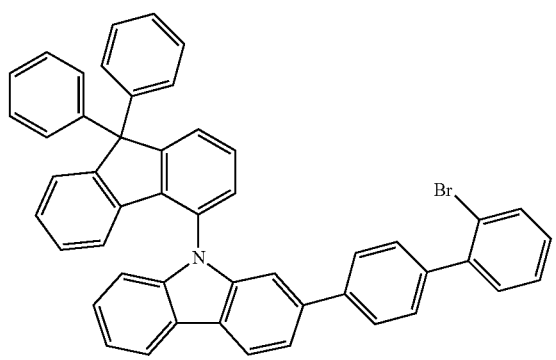
Sub 1-68
Sub 1-69
Sub 1-70
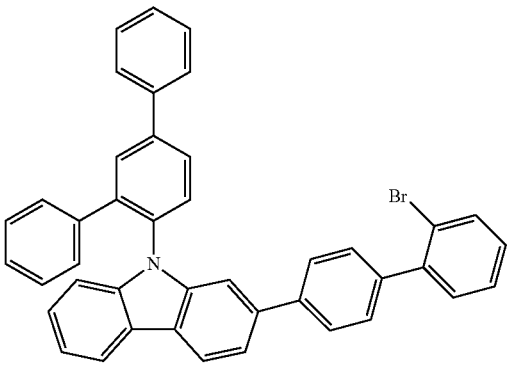
Sub 1-71
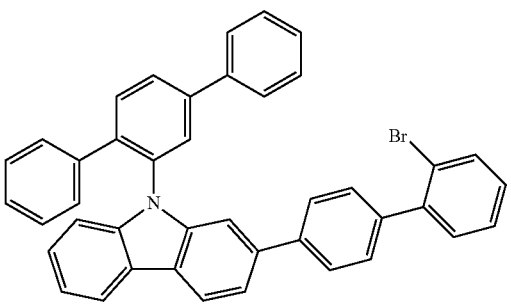
Sub 1-72
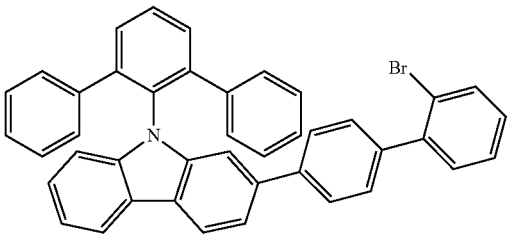
Sub 1-73
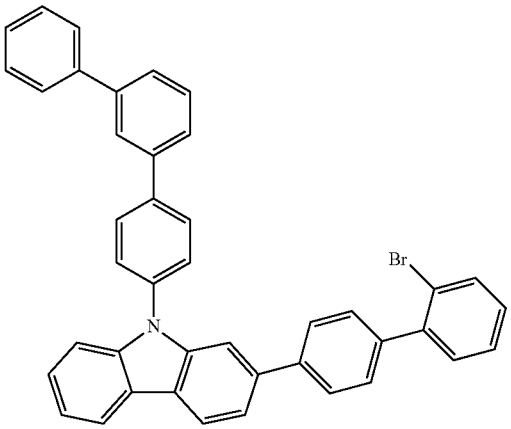

Sub 1-74
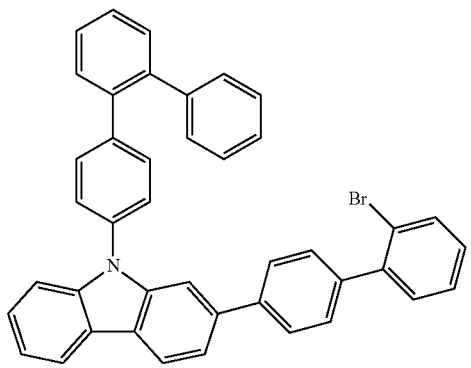
Sub 1-78
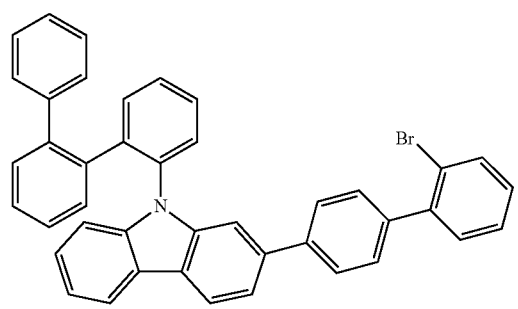
Sub 1-75
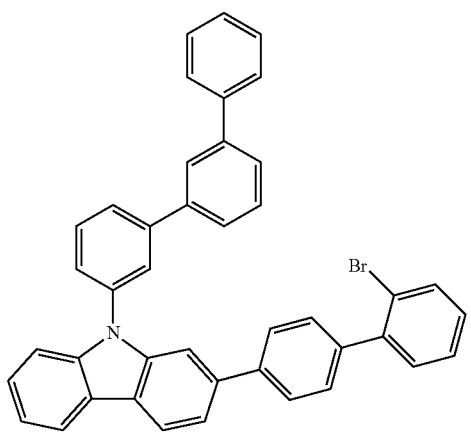
Sub 1-79
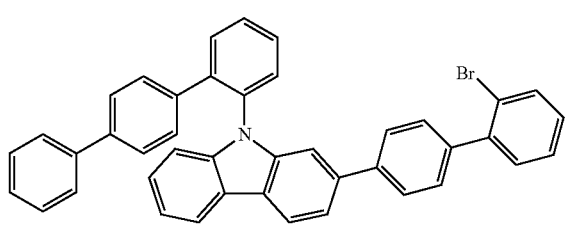
Sub 1-80
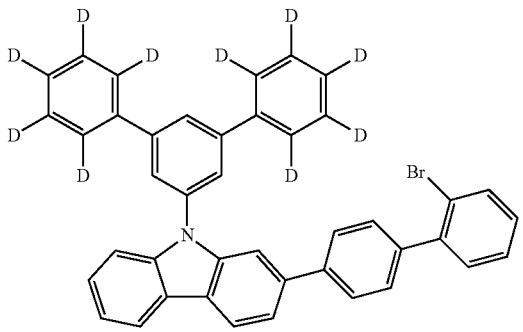
Sub 1-76
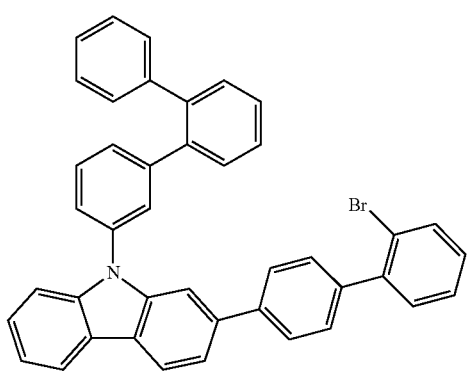
Sub 1-81
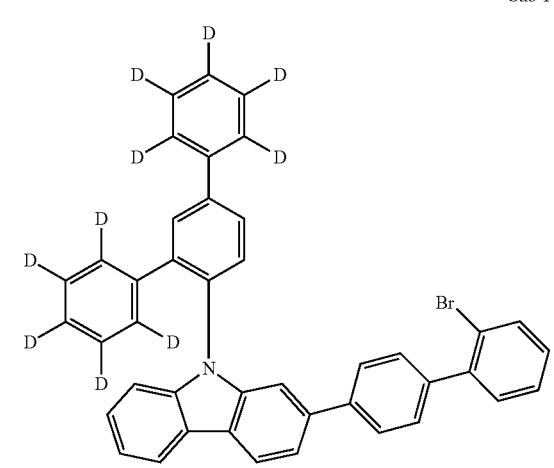
Sub 1-77
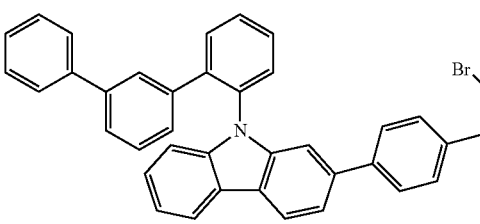

Sub 1-82
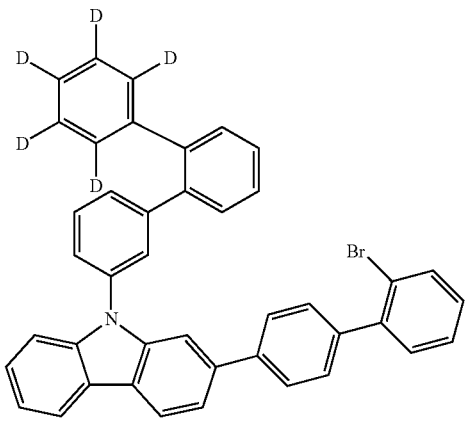
Sub 1-85
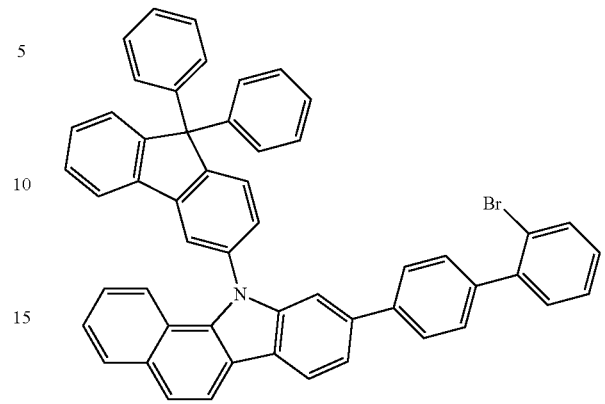
Sub 1-83
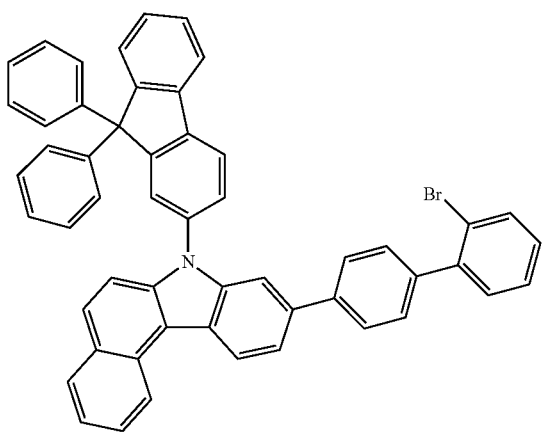
Sub 1-86
Sub 1-84
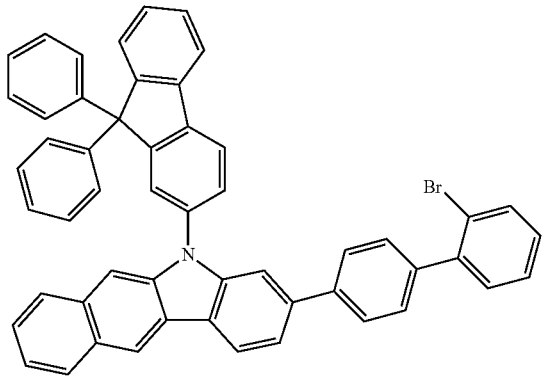
Sub 1-87
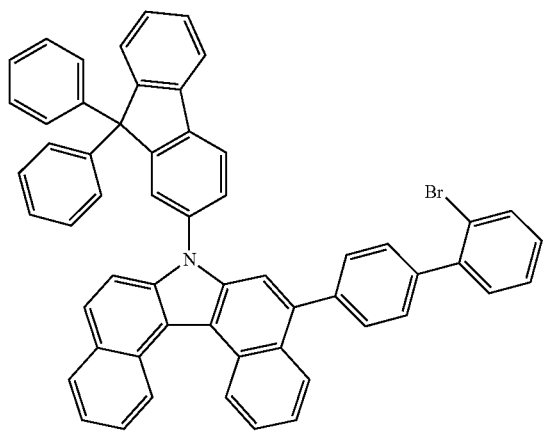

Sub 1-88
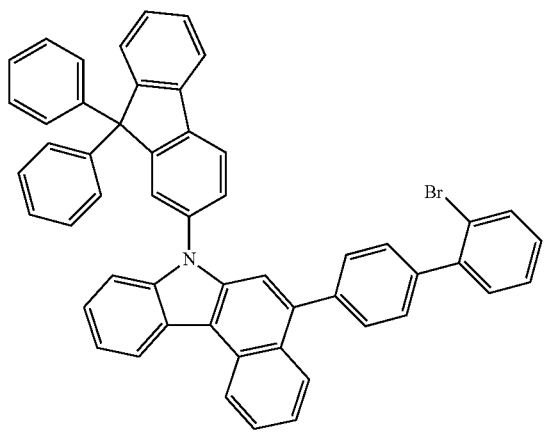
Sub 1-89
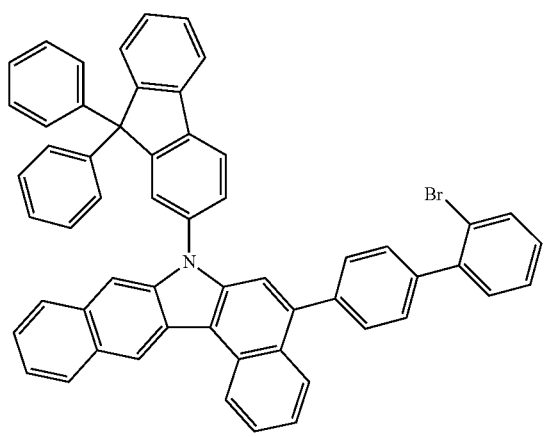
Sub 1-90
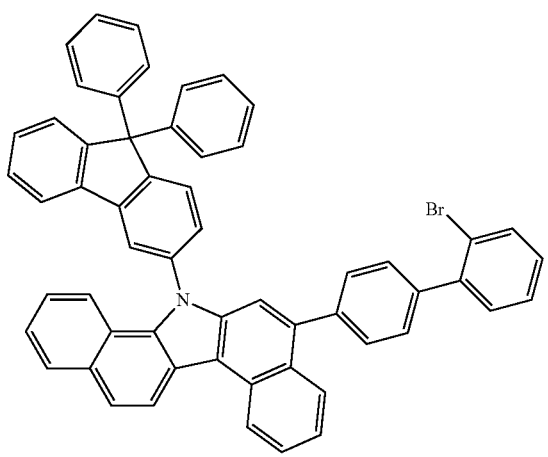
Sub 1-91
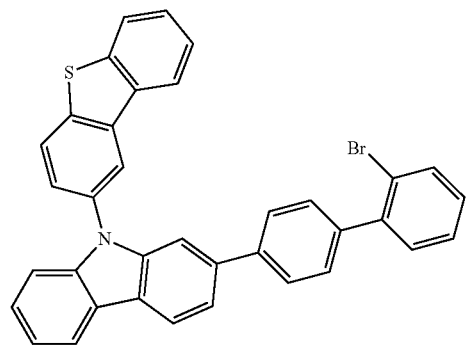
Sub 1-92
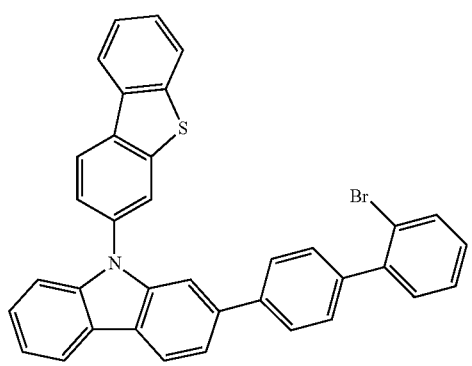
Sub 1-93
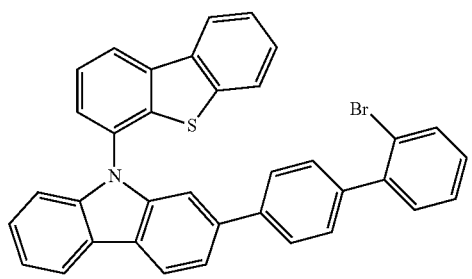
Sub 1-94
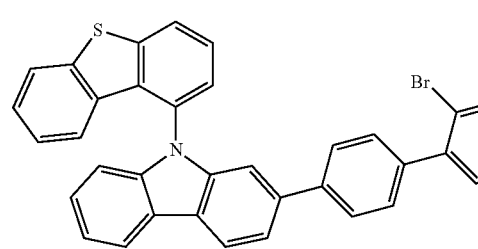
Sub 1-95
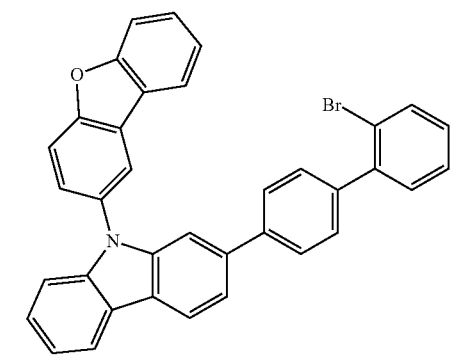

Sub 1-96
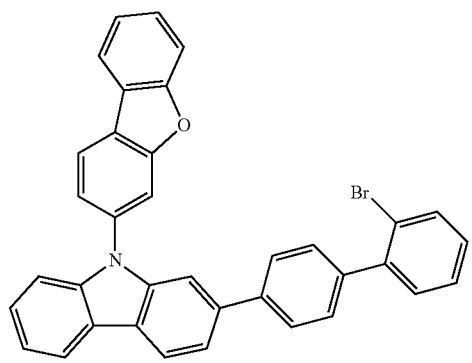
Sub 1-97
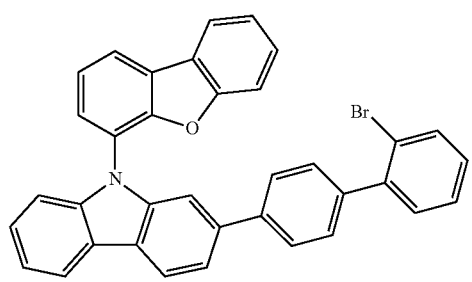
Sub 1-98
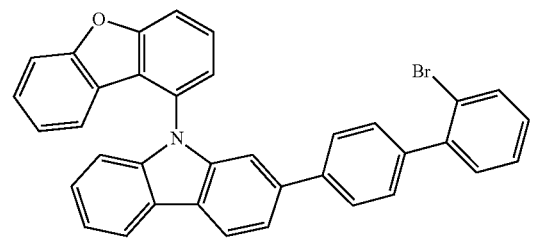
Sub 1-99
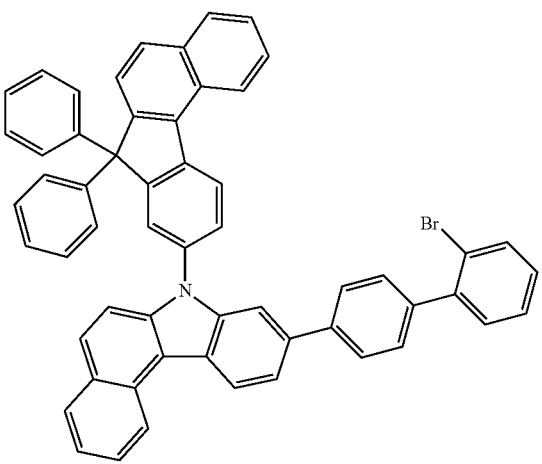
Sub 1-100
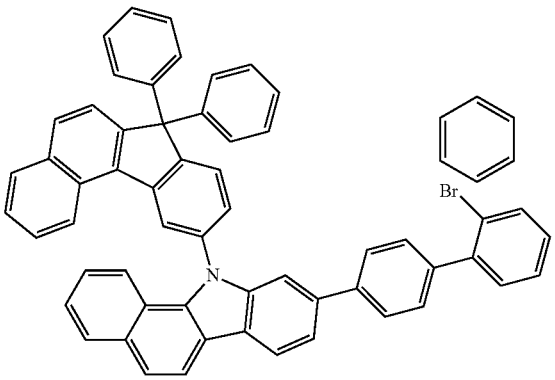
Sub 1-101
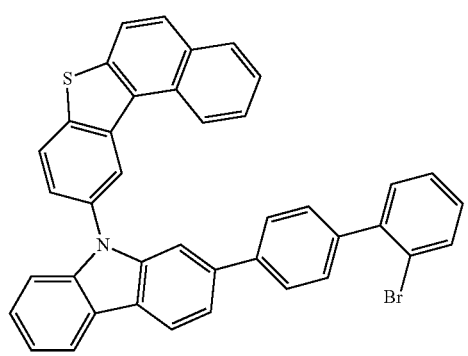
Sub 1-102
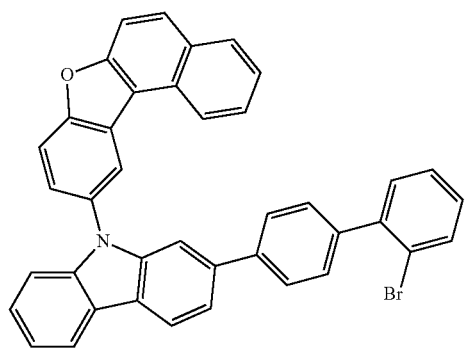
Sub 1-103
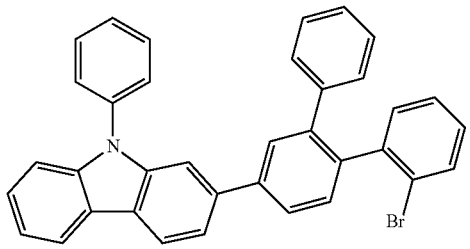
Sub 1-104
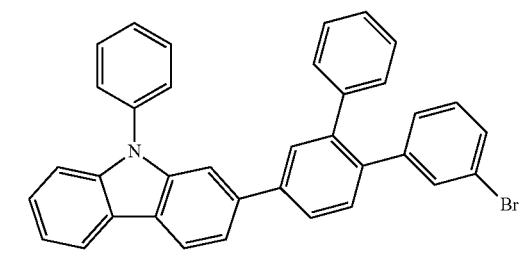

Sub 1-105
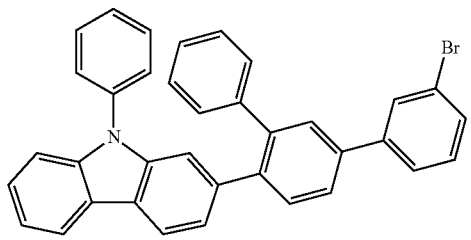
Sub 1-106
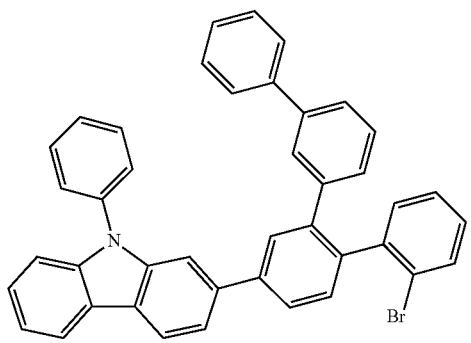
Sub 1-107
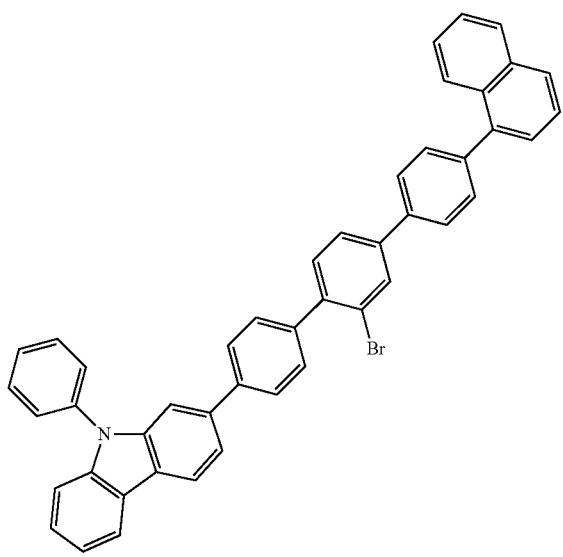
Sub 1-108
Sub 1-109
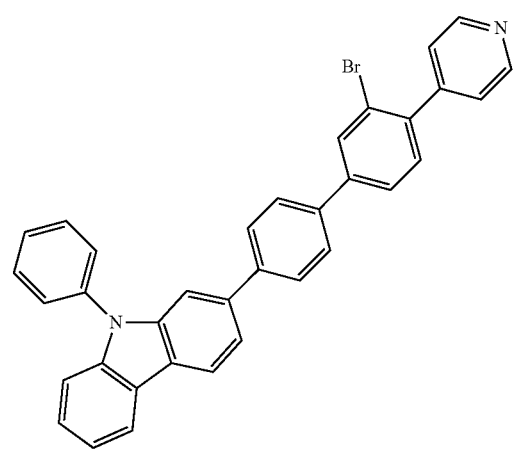
Sub 1-110
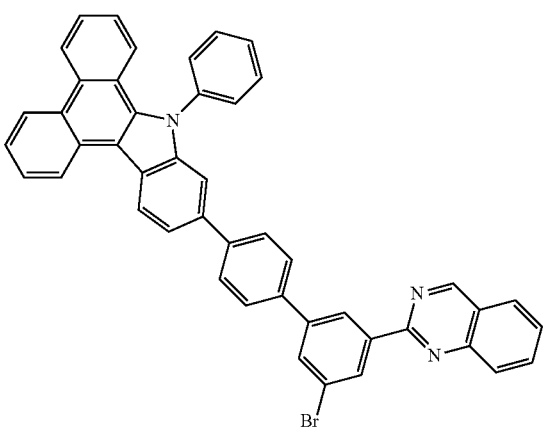

Sub 1-111

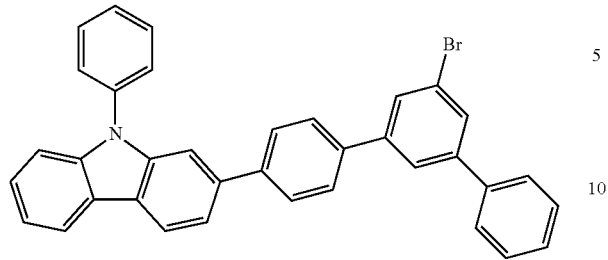

Sub 1-112

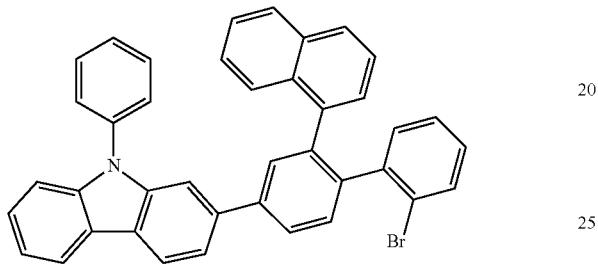

TABLE 1

| Compound | FD-MS | Compound | FD-MS |
| --- | --- | --- | --- |
| Sub 1-1 | m/z = 473.08($C_{30}H_{20}BrN$ = 474.39) | Sub 1-2 | m/z = 523.09($C_{34}H_{22}BrN$ = 524.45) |
| Sub 1-3 | m/z = 549.11($C_{36}H_{24}BrN$ = 550.49) | Sub 1-4 | m/z = 523.09($C_{34}H_{22}BrN$ = 524.45) |
| Sub 1-5 | m/z = 549.11($C_{36}H_{24}BrN$ = 550.49) | Sub 1-6 | m/z = 549.11($C_{36}H_{24}BrN$ = 550.49) |
| Sub 1-7 | m/z = 655.10($C_{42}H_{26}BrNS$ = 656.63) | Sub 1-8 | m/z = 552.09($C_{33}H_{21}BrN_4$ = 553.45) |
| Sub 1-A9 | m/z = 513.11($C_{33}H_{24}BrN$ = 514.45) | Sub 1-10 | m/z = 676.15($C_{45}H_{29}BrN_2$ = 677.63) |
| Sub 1-11 | m/z = 549.11($C_{36}H_{24}BrN$ = 550.49) | Sub 1-12 | m/z = 677.15($C_{44}H_{28}BrN_3$ = 678.62) |
| Sub 1-13 | m/z = 713.17($C_{49}H_{32}BrN$ = 714.69) | Sub 1-14 | m/z = 713.17($C_{49}H_{32}BrN$ = 714.69) |
| Sub 1-15 | m/z = 713.17($C_{49}H_{32}BrN$ = 714.69) | Sub 1-16 | m/z = 713.17($C_{49}H_{32}BrN$ = 714.69) |
| Sub 1-17 | m/z = 625.14 ($C_{42}H_{28}BrN$ = 626.58) | Sub 1-18 | m/z = 625.14($C_{42}H_{28}BrN$ = 626.58) |
| Sub 1-19 | m/z = 625.14 ($C_{42}H_{28}BrN$ = 626.58) | Sub 1-20 | m/z = 625.14 ($C_{42}H_{28}BrN$ = 626.58) |
| Sub 1-21 | m/z = 625.14 ($C_{42}H_{28}BrN$ = 626.58) | Sub 1-22 | m/z = 625.14 ($C_{42}H_{28}BrN$ = 626.58) |
| Sub 1-23 | m/z = 625.14 ($C_{42}H_{28}BrN$ = 626.58) | Sub 1-24 | m/z = 625.14 ($C_{42}H_{28}BrN$ = 626.58) |
| Sub 1-25 | m/z = 625.14 ($C_{42}H_{28}BrN$ = 626.58) | Sub 1-26 | m/z = 625.14 ($C_{42}H_{28}BrN$ = 626.58) |
| Sub 1-27 | m/z = 625.14 ($C_{42}H_{28}BrN$ = 626.58) | Sub 1-28 | m/z = 625.14 ($C_{42}H_{28}BrN$ = 626.58) |
| Sub 1-29 | m/z = 635.20($C_{42}H_{18}D_{10}BrN$ = 636.64) | Sub 1-30 | m/z = 635.20($C_{42}H_{18}D_{10}BrN$ = 636.64) |
| Sub 1-31 | m/z = 630.17($C_{42}H_{23}D_5BrN$ = 631.61) | Sub 1-32 | m/z = 763.19($C_{53}H_{34}BrN$ = 764.75) |
| Sub 1-33 | m/z = 763.19($C_{53}H_{34}BrN$ = 764.75) | Sub 1-34 | m/z = 763.19($C_{53}H_{34}BrN$ = 764.75) |
| Sub 1-35 | m/z = 813.20($C_{57}H_{36}BrN$ = 814.81) | Sub 1-36 | m/z = 813.20($C_{57}H_{36}BrN$ = 814.81) |
| Sub 1-37 | m/z = 763.19($C_{53}H_{34}BrN$ = 764.75) | Sub 1-38 | m/z = 813.20($C_{57}H_{36}BrN$ = 814.81) |
| Sub 1-39 | m/z = 813.20($C_{57}H_{36}BrN$ = 814.81) | Sub 1-40 | m/z = 579.07($C_{36}H_{22}BrNS$ = 580.54) |
| Sub 1-41 | m/z = 579.07($C_{36}H_{22}BrNS$ = 580.54) | Sub 1-42 | m/z = 579.07($C_{36}H_{22}BrNS$ = 580.54) |
| Sub 1-43 | m/z = 579.07($C_{36}H_{22}BrNS$ = 580.54) | Sub 1-44 | m/z = 563.09($C_{36}H_{22}BrNO$ = 564.47) |
| Sub 1-45 | m/z = 563.09($C_{36}H_{22}BrNO$ = 564.47) | Sub 1-46 | m/z = 563.09($C_{36}H_{22}BrNO$ = 564.47) |
| Sub 1-47 | m/z = 563.09($C_{36}H_{22}BrNO$ = 564.47) | Sub 1-48 | m/z = 813.20($C_{57}H_{36}BrN$ = 814.81) |
| Sub 1-49 | m/z = 813.20($C_{57}H_{36}BrN$ = 814.81) | Sub 1-50 | m/z = 629.08($C_{40}H_{24}BrNS$ = 630.59) |
| Sub 1-51 | m/z = 613.10($C_{40}H_{24}BrNO$ = 614.53) | Sub 1-52 | m/z = 473.08($C_{30}H_{20}BrN$ = 474.39) |
| Sub 1-53 | m/z = 523.09($C_{34}H_{22}BrN$ = 524.45) | Sub 1-54 | m/z = 549.11 ($C_{36}H_{24}BrN$ = 550.49) |
| Sub 1-55 | m/z = 523.09($C_{34}H_{22}BrN$ = 524.45) | Sub 1-56 | m/z = 549.11($C_{36}H_{24}BrN$ = 550.49) |
| Sub 1-57 | m/z = 549.11($C_{36}H_{24}BrN$ = 550.49) | Sub 1-58 | m/z = 655.10($C_{42}H_{26}BrNS$ = 656.63) |
| Sub 1-59 | m/z = 552.09($C_{33}H_{21}BrN_4$ = 553.45) | Sub 1-60 | m/z = 513.11($C_{33}H_{24}BrN$ = 514.45) |
| Sub 1-61 | m/z = 676.15($C_{45}H_{29}BrN_2$ = 677.63) | Sub 1-62 | m/z = 549.11($C_{36}H_{24}BrN$ = 550.49) |
| Sub 1-63 | m/z = 677.15($C_{44}H_{28}BrN_3$ = 678.62) | Sub 1-64 | m/z = 713.17($C_{49}H_{32}BrN$ = 714.69) |
| Sub 1-65 | m/z = 713.17($C_{49}H_{32}BrN$ = 714.69) | Sub 1-66 | m/z = 713.17($C_{49}H_{32}BrN$ = 714.69) |
| Sub 1-67 | m/z = 713.17($C_{49}H_{32}BrN$ = 714.69) | Sub 1-68 | m/z = 625.14($C_{42}H_{28}BrN$ = 626.58) |
| Sub 1-69 | m/z = 625.14($C_{42}H_{28}BrN$ = 626.58) | Sub 1-70 | m/z = 625.14($C_{42}H_{28}BrN$ = 626.58) |
| Sub 1-71 | m/z = 625.14($C_{42}H_{28}BrN$ = 626.58) | Sub 1-72 | m/z = 625.14($C_{42}H_{28}BrN$ = 626.58) |
| Sub 1-73 | m/z = 625.14($C_{42}H_{28}BrN$ = 626.58) | Sub 1-74 | m/z = 625.14($C_{42}H_{28}BrN$ = 626.58) |
| Sub 1-75 | m/z = 625.14($C_{42}H_{28}BrN$ = 626.58) | Sub 1-76 | m/z = 625.14($C_{42}H_{28}BrN$ = 626.58) |
| Sub 1-77 | m/z = 625.14($C_{42}H_{28}BrN$ = 626.58) | Sub 1-78 | m/z = 625.14($C_{42}H_{28}BrN$ = 626.58) |
| Sub 1-79 | m/z = 625.14($C_{42}H_{28}BrN$ = 626.58) | Sub 1-80 | m/z = 635.20($C_{42}H_{18}D_{10}BrN$ = 636.64) |
| Sub 1-81 | m/z = 635.20($C_{42}H_{18}D_{10}BrN$ = 636.64) | Sub 1-82 | m/z = 630.17($C_{42}H_{23}D_5BrN$ = 631.61) |
| Sub 1-83 | m/z = 763.19($C_{53}H_{34}BrN$ = 764.75) | Sub 1-84 | m/z = 763.19($C_{53}H_{34}BrN$ = 764.75) |

TABLE 1-continued

| Compound | FD-MS | Compound | FD-MS |
|---|---|---|---|
| Sub 1-85 | m/z = 763.19($C_{53}H_{34}BrN$ = 764.75) | Sub 1-86 | m/z = 813.20($C_{57}H_{36}BrN$ = 814.81) |
| Sub 1-87 | m/z = 813.20($C_{57}H_{36}BrN$ = 814.81) | Sub 1-88 | m/z = 763.19($C_{53}H_{34}BrN$ = 764.75) |
| Sub 1-89 | m/z = 813.20($C_{57}H_{36}BrN$ = 814.81) | Sub 1-90 | m/z = 813.20($C_{57}H_{36}BrN$ = 814.81) |
| Sub 1-91 | m/z = 579.07($C_{36}H_{22}BrNS$ = 580.54) | Sub 1-92 | m/z = 579.07($C_{36}H_{22}BrNS$ = 580.54) |
| Sub 1-93 | m/z = 579.07($C_{36}H_{22}BrNS$ = 580.54) | Sub 1-94 | m/z = 579.07($C_{36}H_{22}BrNS$ = 580.54) |
| Sub 1-95 | m/z = 563.09($C_{36}H_{22}BrNO$ = 564.47) | Sub 1-96 | m/z = 563.09($C_{36}H_{22}BrNO$ = 564.47) |
| Sub 1-97 | m/z = 563.09($C_{36}H_{22}BrNO$ = 564.47) | Sub 1-98 | m/z = 563.09($C_{36}H_{22}BrNO$ = 564.47) |
| Sub 1-99 | m/z = 813.20($C_{57}H_{36}BrN$ = 814.81) | Sub 1-100 | m/z = 813.20($C_{57}H_{36}BrN$ = 814.81) |
| Sub 1-101 | m/z = 629.08($C_{40}H_{24}BrNS$ = 630.59) | Sub 1-102 | m/z = 613.10($C_{40}H_{24}BrNO$ = 614.53) |
| Sub 1-103 | m/z = 549.11($C_{36}H_{24}BrN$ = 550.49) | Sub 1-104 | m/z = 549.11($C_{36}H_{24}BrN$ = 550.49) |
| Sub 1-105 | m/z = 549.11($C_{36}H_{24}BrN$ = 550.49) | Sub 1-106 | m/z = 625.14($C_{42}H_{28}BrN$ = 626.58) |
| Sub 1-107 | m/z = 675.16($C_{46}H_{30}BrN$ = 646.64) | Sub 1-108 | m/z = 675.16($C_{46}H_{30}BrN$ = 646.64) |
| Sub 1-109 | m/z = 550.10($C_{35}H_{23}BrN_2$ = 551.47) | Sub 1-110 | m/z = 701.15($C_{46}H_{28}BrN_3$ = 702.64) |
| Sub 1-111 | m/z = 549.11($C_{36}H_{24}BrN$ = 550.49) | Sub 1-112 | m/z = 599.12($C_{40}H_{26}BrN$ = 600.55) |

II. Synthesis Examples of Sub 2

Sub 2 of the Reaction Scheme 1 can be synthesized according to, but not limited to, the following Reaction Scheme 47.

1. Synthesis of Sub 2-1

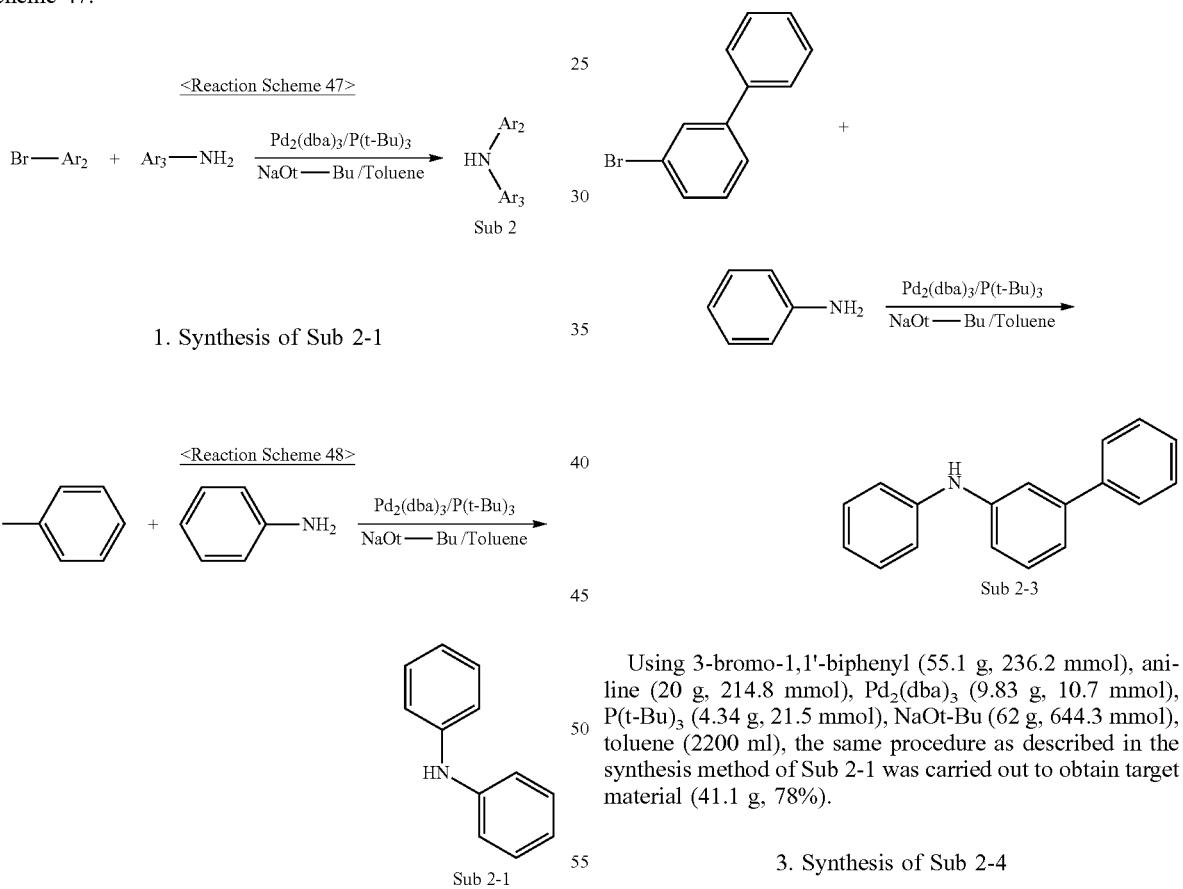

To a solution of bromobenzene (37.1 g, 236.2 mmol) in toluene (2200 ml) was added aniline (20 g, 214.8 mmol), Pd₂(dba)₃ (9.83 g, 10.7 mmol), P(t-Bu)₃ (4.34 g, 21.5 mmol), NaOt-Bu (62 g, 644.3 mmol) and stirred at 100° C. After completion of the reaction, the reactant was extracted with ether and water, and the organic layer was extracted over MgSO₄ and concentrated under pressure. The residue was separated by silica gel column and recrystallization to obtain target material (28 g, 77%).

2. Synthesis of Sub 2-3

Using 3-bromo-1,1'-biphenyl (55.1 g, 236.2 mmol), aniline (20 g, 214.8 mmol), Pd₂(dba)₃ (9.83 g, 10.7 mmol), P(t-Bu)₃ (4.34 g, 21.5 mmol), NaOt-Bu (62 g, 644.3 mmol), toluene (2200 ml), the same procedure as described in the synthesis method of Sub 2-1 was carried out to obtain target material (41.1 g, 78%).

3. Synthesis of Sub 2-4

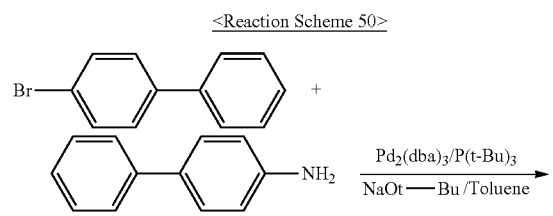

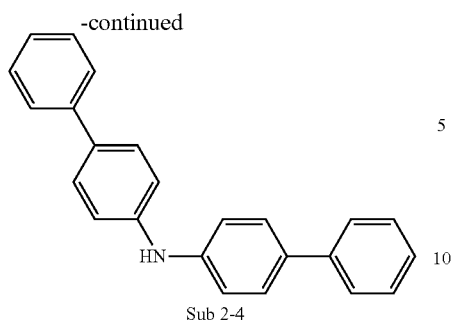

Sub 2-4

Using 4-bromo-1,1'-biphenyl (37.88 g, 162.5 mmol), [1,1'-biphenyl]-4-amine (25 g, 147.7 mmol), Pd$_2$(dba)$_3$ (6.76 g, 7.4 mmol), P(t-Bu)$_3$ (3 g, 14.8 mmol), NaOt-Bu (66.62 g, 693.2 mmol), toluene, the same procedure as described in the synthesis method of Sub 2-1 was carried out to obtain target material (35.6 g, 75%).

4. Synthesis of Sub 2-7

<Reaction Scheme 51>

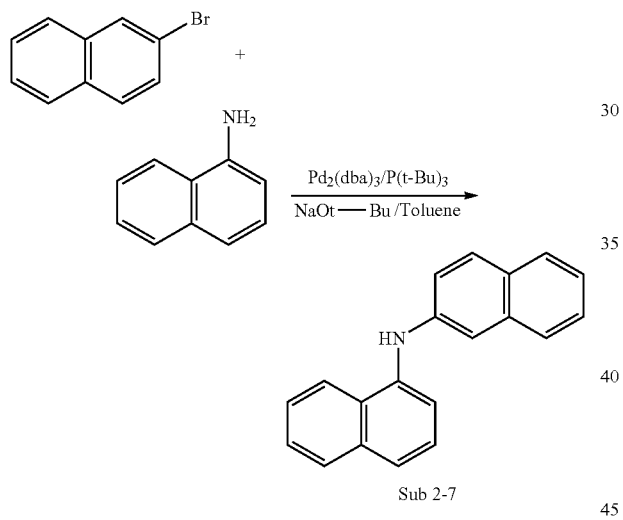

Sub 2-7

Using 2-bromonaphthalene (39.8 g, 192.1 mmol), naphthalen-1-amine (25 g, 174.6 mmol), Pd$_2$(dba)$_3$ (8.0 g, 8.73 mmol), P(t-Bu)$_3$ (3.53 g, 17.5 mmol), NaOt-Bu (50.3 g, 523.8 mmol), toluene (1800 ml), the same procedure as described in the synthesis method of Sub 2-1 was carried out to obtain target material (36.2 g, 77%).

5. Synthesis of Sub 2-9

<Reaction Scheme 52>

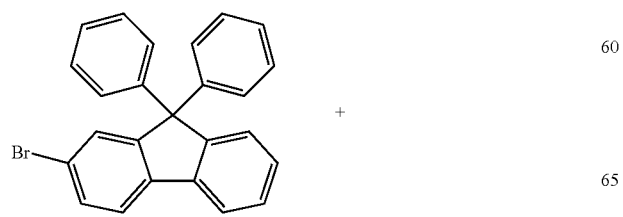

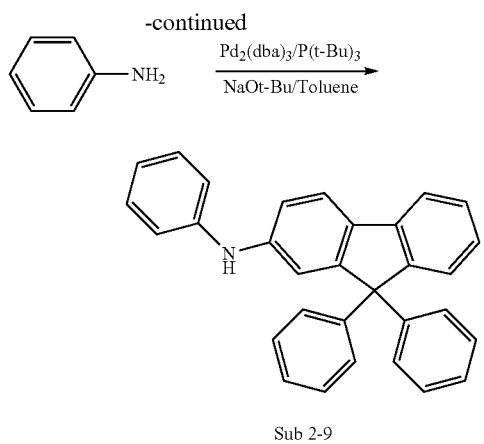

Sub 2-9

Using 2-bromo-9,9-diphenyl-9H-fluorene (93.9 g, 236.2 mmol), toluene (2250 ml), aniline (20 g, 214.8 mmol), Pd$_2$(dba)$_3$ (9.83 g, 10.7 mmol), P(t-Bu)$_3$ (4.34 g, 21.5 mmol), NaOt-Bu (62 g, 644.3 mmol), the same procedure as described in the synthesis method of Sub 2-1 was carried out to obtain target material (63.3 g, 72%).

6. Synthesis of Sub 2-12

<Reaction Scheme 53>

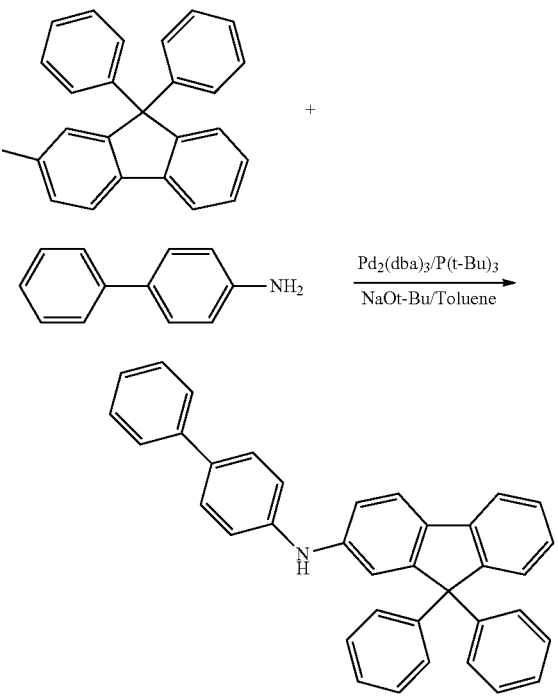

Sub 2-12

Using 2-bromo-9,9-diphenyl-9H-fluorene (64.6 g, 162.5 mmol), toluene (1550 ml), [1,1'-biphenyl]-4-amine (25 g, 147.7 mmol), Pd$_2$(dba)$_3$ (6.76 g, 162.5 mmol), P(t-Bu)$_3$ (3 g, 14.8 mmol), NaOt-Bu (42.6 g, 443.2 mmol), the same procedure as described in the synthesis method of Sub 2-1 was carried out to obtain target material (53.8 g, 75%).

7. Synthesis of Sub 2-13

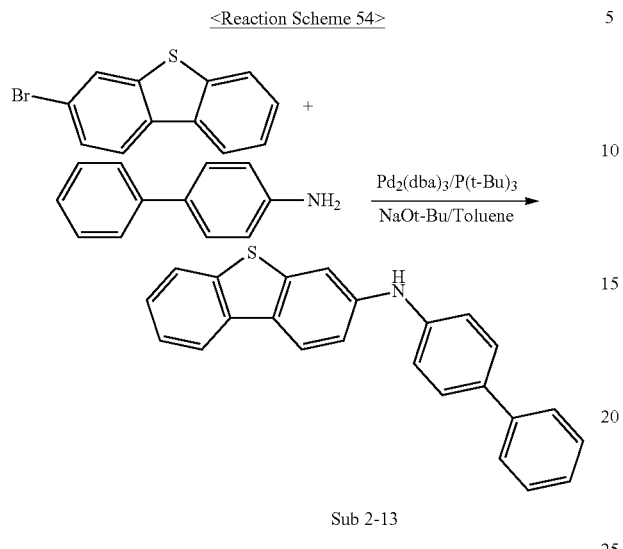

Sub 2-13

Using 3-bromodibenzo[b,d]thiophene (42.8 g, 162.5 mmol), toluene (1550 ml), [1,1'-biphenyl]-4-amine (25 g, 147.7 mmol), Pd$_2$(dba)$_3$ (6.76 g, 162.5 mmol), P(t-Bu)$_3$ (3 g, 14.8 mmol), NaOt-Bu (42.6 g, 443.2 mmol), the same procedure as described in the synthesis method of Sub 2-1 was carried out to obtain target material (37.9 g, 73%).

8. Synthesis of Sub 2-17

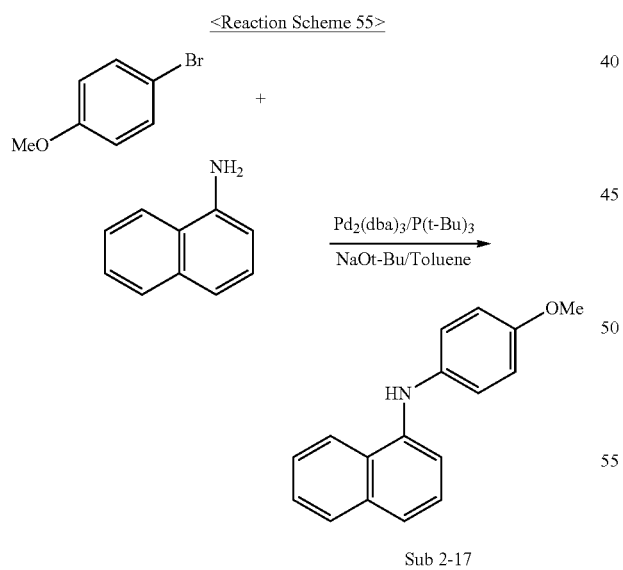

Sub 2-17

Using 1-bromo-4-methoxybenzene (36 g, 192.1 mmol), naphthalen-1-amine (25 g, 174.6 mmol), Pd$_2$(dba)$_3$ (8.0 g, 8.73 mmol), P(t-Bu)$_3$ (3.53 g, 17.5 mmol), NaOt-Bu (50.3 g, 523.8 mmol), toluene (1800 ml), the same procedure as described in the synthesis method of Sub 2-1 was carried out to obtain target material (32.2 g, 74%).

9. Synthesis of Sub 2-26

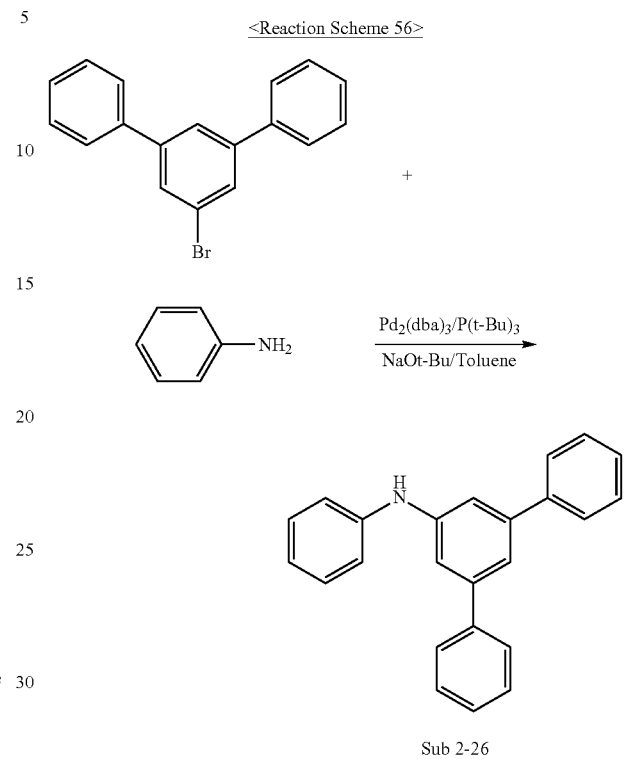

Sub 2-26

Using 5'-bromo-1,1':3',1''-terphenyl (73.04 g, 236.2 mmol), amine (20 g, 214.8 mmol), Pd$_2$(dba)$_3$ (9.83 g, 10.7 mmol), P(t-Bu)$_3$ (4.34 g, 21.5 mmol), NaOt-Bu (62 g, 644.3 mmol), toluene (2250 ml), the same procedure as described in the synthesis method of Sub 2-1 was carried out to obtain target material (49 g, 7%).

Examples of Sub 2 compounds include, but are not limited to, the following compounds, and FD-MS data of the compounds are given in Table 2 below.

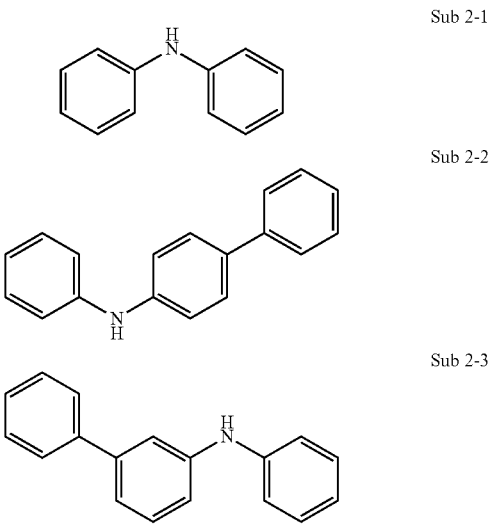

Sub 2-1

Sub 2-2

Sub 2-3

Sub 2-4
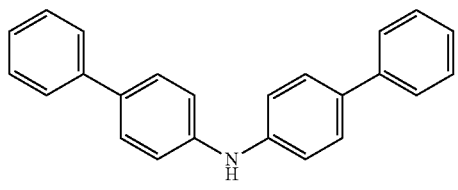
Sub 2-5
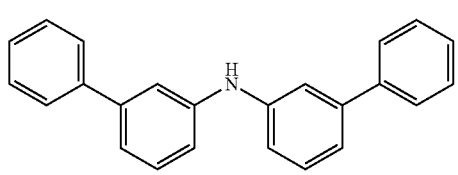
Sub 2-6
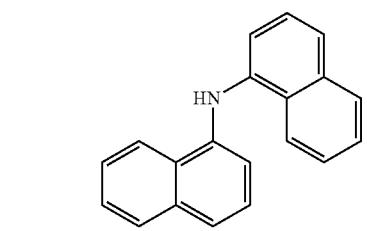
Sub 2-7
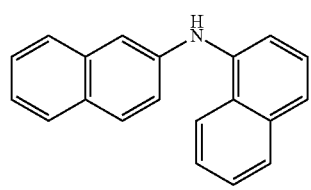
Sub 2-8
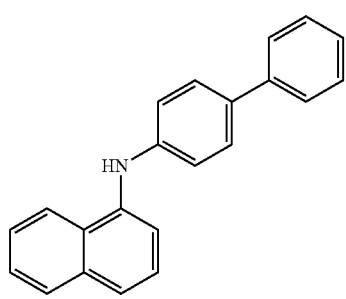
Sub 2-9
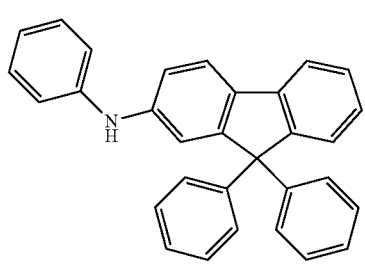
Sub 2-10
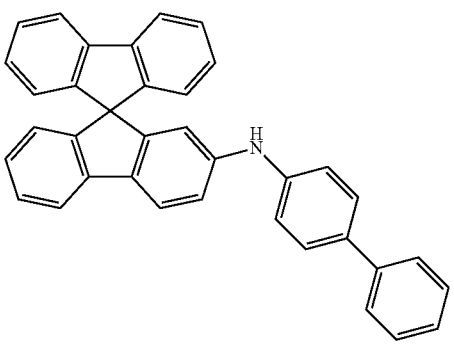
Sub 2-11
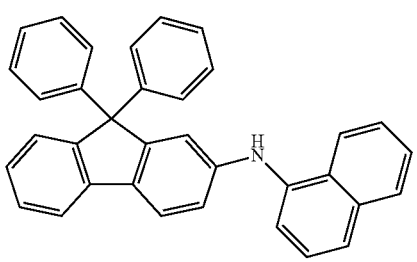
Sub 2-12
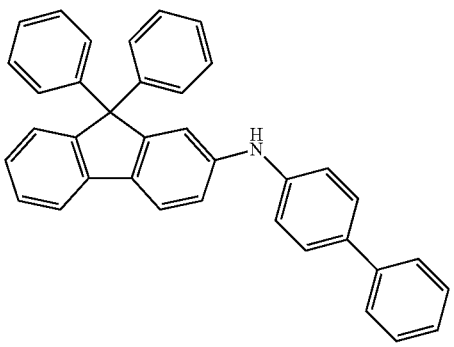
Sub 2-13
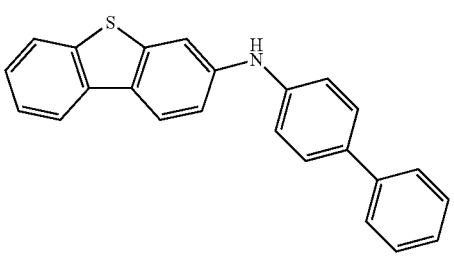
Sub 2-14
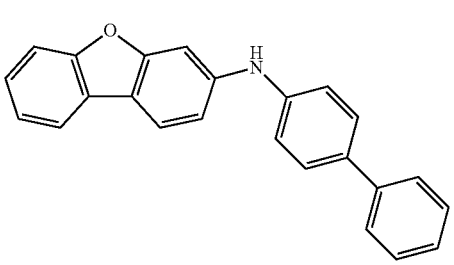

Sub 2-15
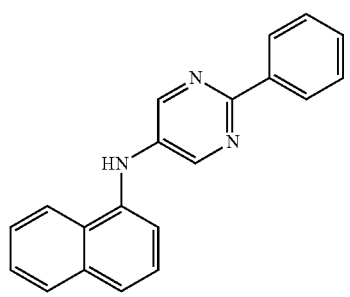
Sub 2-16
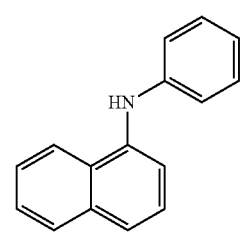
Sub 2-17
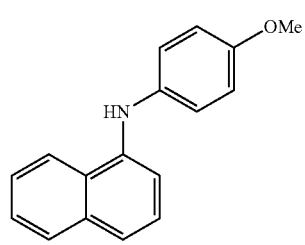
Sub 2-18
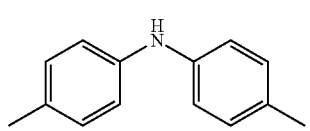
Sub 2-19
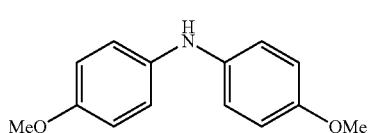
Sub 2-20
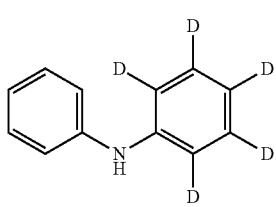
Sub 2-21
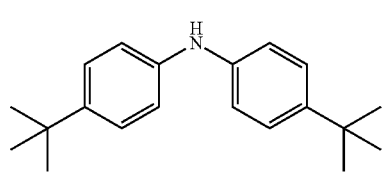
Sub 2-22
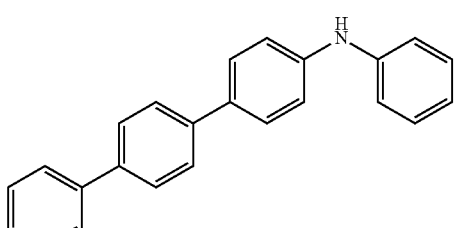
Sub 2-23
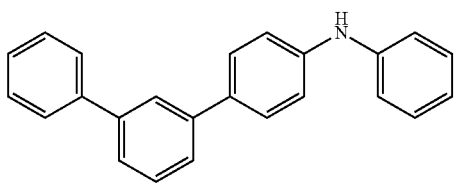
Sub 2-24
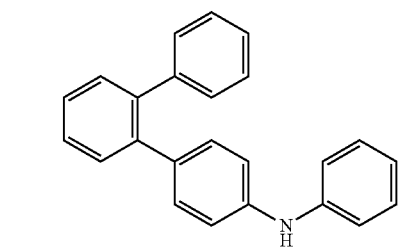
Sub 2-25
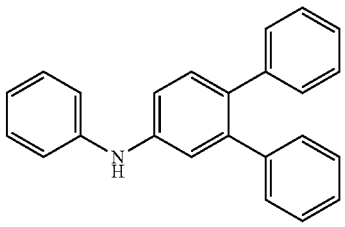
Sub 2-26
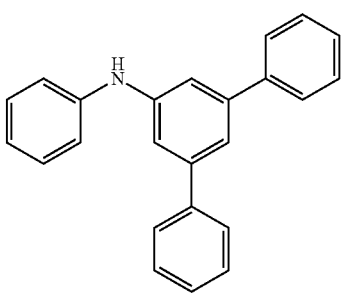
Sub 2-27
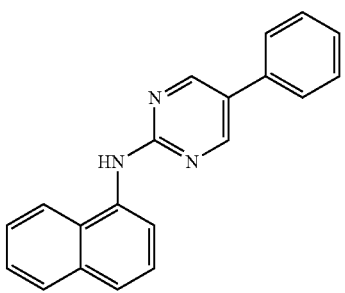

TABLE 2

| Compound | FD-MS | Compound | FD-MS |
|---|---|---|---|
| Sub 2-1 | m/z = 169.09($C_{12}H_{11}N$ = 169.22) | Sub 2-2 | m/z = 245.12($C_{18}H_{15}N$ = 245.32) |
| Sub 2-3 | m/z = 245.12($C_{18}H_{15}N$ = 245.32) | Sub 2-4 | m/z = 321.15($C_{24}H_{19}N$ = 321.41) |
| Sub 2-5 | m/z = 321.15 ($C_{24}H_{19}N$ = 321.41) | Sub 2-6 | m/z = 269.12($C_{20}H_{15}N$ = 269.34) |
| Sub 2-7 | m/z = 269.12($C_{20}H_{15}N$ = 269.34) | Sub 2-8 | m/z = 295.14($C_{22}H_{17}N$ = 295.38) |
| Sub 2-9 | m/z = 409.18($C_{31}H_{23}N$ = 409.52) | Sub 2-10 | m/z = 483.20($C_{37}H_{25}N$ = 483.60) |
| Sub 2-11 | m/z = 459.20($C_{35}H_{25}N$ = 459.58) | Sub 2-12 | m/z = 485.21($C_{37}H_{27}N$ = 485.62) |
| Sub 2-13 | m/z = 351.11($C_{34}H_{17}NS$ = 351.46) | Sub 2-14 | m/z = 335.13($C_{24}H_{17}NO$ = 335.40) |
| Sub 2-15 | m/z = 297.13($C_{20}H_{15}N_3$ = 297.35) | Sub 2-16 | m/z = 219.10($C_{16}H_{13}N$ = 219.28) |
| Sub 2-17 | m/z = 249.12($C_{17}H_{15}NO$ = 249.31) | Sub 2-18 | m/z = 197.12($C_{14}H_{15}N$ = 197.28) |
| Sub 2-19 | m/z = 229.11($C_{14}H_{15}NO_2$ = 229.27) | Sub 2-20 | m/z = 174.12($C_{12}H_6D_5N$ = 174.25) |
| Sub 2-21 | m/z = 281.21($C_{20}H_{27}N$ = 281.44) | Sub 2-22 | m/z = 321.15($C_{24}H_{19}N$ = 321.41) |
| Sub 2-23 | m/z = 321.15($C_{24}H_{19}N$ = 321.41) | Sub 2-24 | m/z = 321.15($C_{24}H_{19}N$ = 321.41) |
| Sub 2-25 | m/z = 321.15($C_{24}H_{19}N$ = 321.41) | Sub 2-26 | m/z = 321.15($C_{24}H_{19}N$ = 321.41) |
| Sub 2-27 | m/z = 297.13($C_{20}H_{15}N_3$ = 297.35) | | |

III. Synthesis Examples of Final Products

To a solution of Sub 2 (1 eq) in toluene was added Sub 1 (1.1 eq), Pd$_2$(dba)$_3$ (0.05 eq), P(t-Bu)$_3$ (0.1 eq), NaOt-Bu (3 eq), and stirred at 100° C. After completion of the reaction, the reactant was extracted with CH$_2$Cl$_2$ and water, dried over MgSO$_4$ and then concentrated under pressure. The residue was separated by silica gel column and recrystallization to obtain Final products.

1. Synthesis of Product P1-1

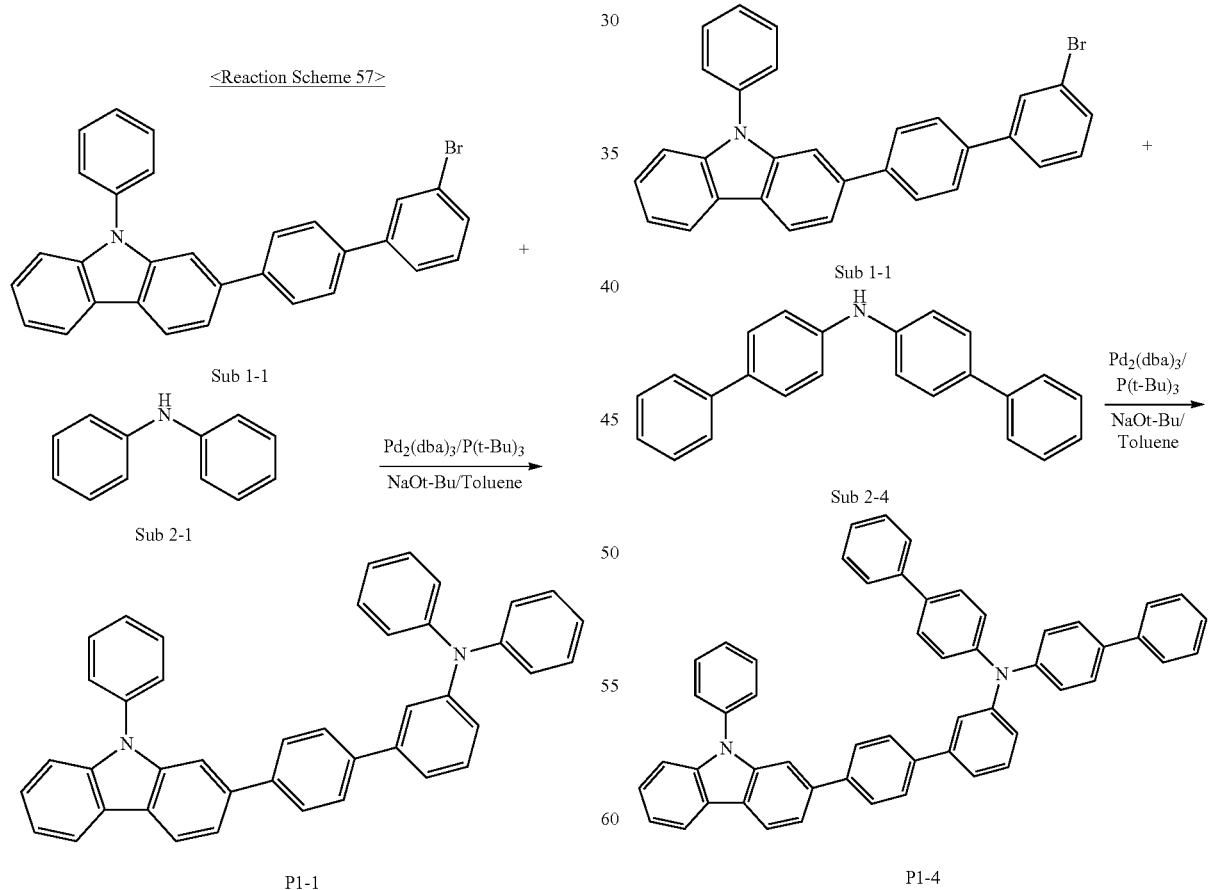

141.8 mmol) and stirred at 100° C. After completion of the reaction, the reactant was extracted with CH$_2$Cl$_2$ and water, dried over MgSO$_4$ and then concentrated under pressure. The residue was separated by silica gel column and recrystallization to obtain Final products (20.2 g, 76%).

2. Synthesis of Product P1-4

To a solution of Sub 2-1 (8 g, 47.3 mmol) in toluene (500 ml) was added Sub 1-1 (24.7 g, 52.0 mmol), Pd$_2$(dba)$_3$ (2.2 g, 2.4 mmol), P(t-Bu)$_3$ (1 g, 4.73 mmol), NaOt-Bu (13.6 g, Using Sub 2-4 (8 g, 24.9 mmol), Sub 1-1 (13 g, 27.4 mmol), Pd$_2$(dba)$_3$ (1.14 g, 1.24 mmol), P(t-Bu)$_3$ (0.5 g, 2.49 mmol), NaOt-Bu (7.17 g, 74.7 mmol), toluene (265 ml), the same procedure as described in the synthesis method of Product P1-1 was carried out to obtain target material (13 g, 73%).

3. Synthesis of Product P1-8

<Reaction Scheme 59>

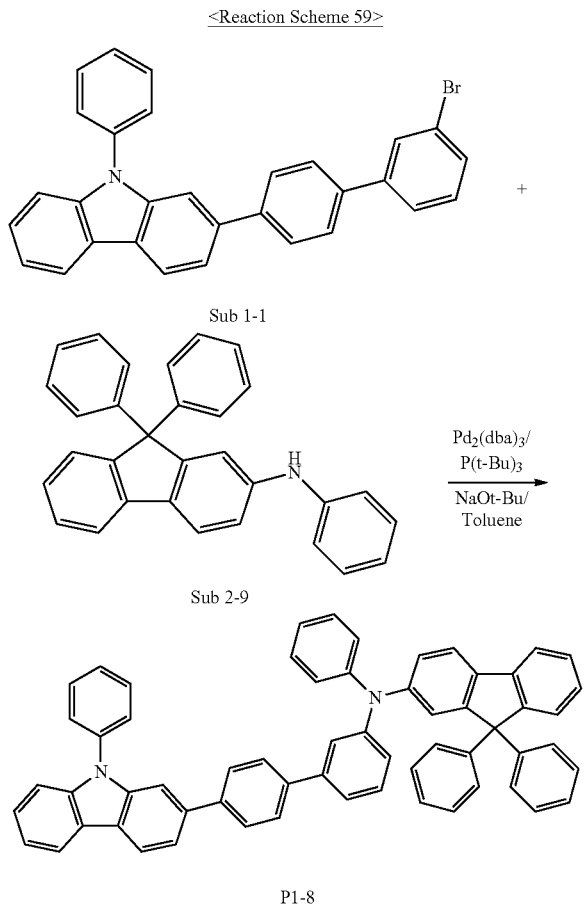

Using Sub 2-9 (10 g, 24.4 mmol), Sub 1-1 (12.7 g, 26.9 mmol), Pd₂(dba)₃ (1.12 g, 1.22 mmol), P(t-Bu)₃ (0.5 g, 2.44 mmol), NaOt-Bu (7.04 g, 73.3 mmol), toluene (260 ml), the same procedure as described in the synthesis method of Product P1-1 was carried out to obtain target material (15.1 g, 77%).

4. Synthesis of Product P1-17

<Reaction Scheme 60>

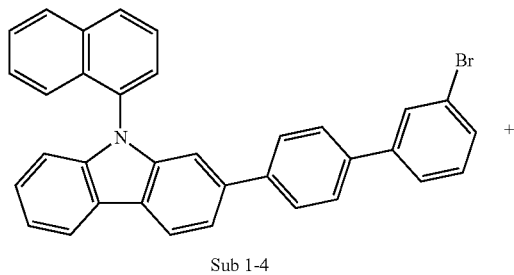

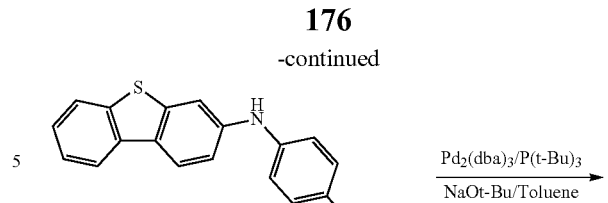

Sub 2-13

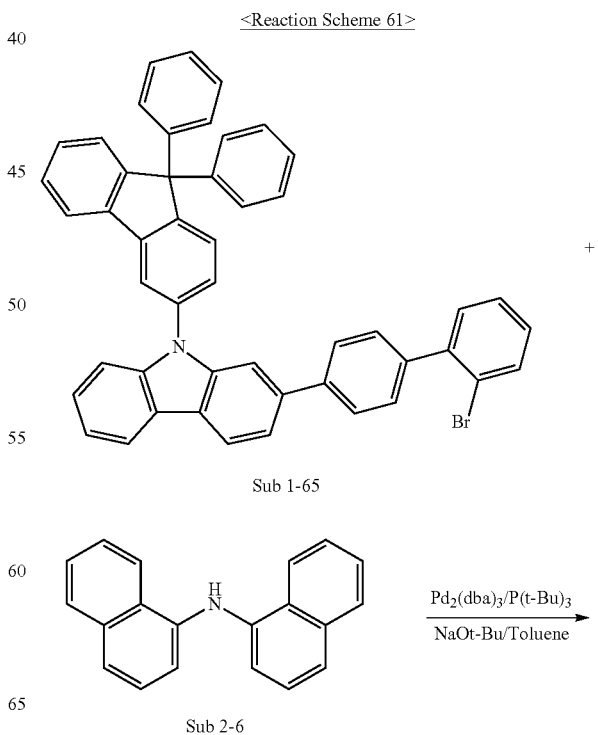

P1-17

Using Sub 2-13 (10 g, 28.5 mmol), Sub 1-4 (16.4 g, 31.3 mmol), Pd₂(dba)₃ (1.3 g, 1.42 mmol), P(t-Bu)₃ (0.6 g, 2.85 mmol), NaOt-Bu (8.2 g, 85.4 mmol), toluene (300 ml), the same procedure as described in the synthesis method of Product P1-1 was carried out to obtain target material (16.1 g, 71%).

5. Synthesis of Product P2-49

<Reaction Scheme 61>

-continued

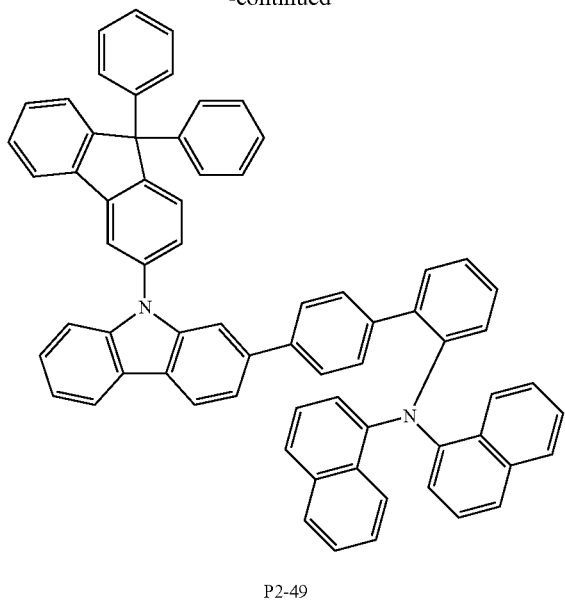

P2-49

Using Sub 2-6 (10 g, 37.13 mmol), Sub 1-65 (29.2 g, 40.84 mmol), Pd$_2$(dba)$_3$ (1.7 g, 1.9 mmol), P(t-Bu)$_3$ (0.8 g, 3.7 mmol), NaOt-Bu (10.7 g, 111.4 mmol), toluene (390 ml), the same procedure as described in the synthesis method of Product P1-1 was carried out to obtain target material (25.1 g, 75%).

6. Synthesis of Product P2-77

<Reaction Scheme 62>

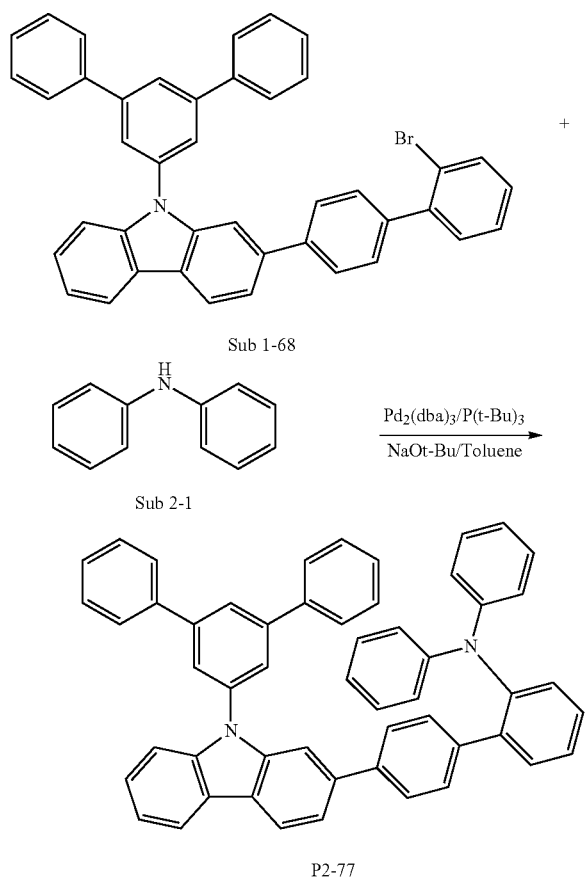

P2-77

Using Sub 2-1 (8 g, 47.3 mmol), Sub 1-68 (32.6 g, 52 mmol), Pd$_2$(dba)$_3$ (2.2 g, 2.4 mmol), P(t-Bu)$_3$ (1 g, 4.73 mmol), NaOt-Bu (13.6 g, 141.8 mmol), toluene (500 ml), the same procedure as described in the synthesis method of Product P1-1 was carried out to obtain target material (23.7 g, 70%).

7. Synthesis of Product P3-3

<Reaction Scheme 63>

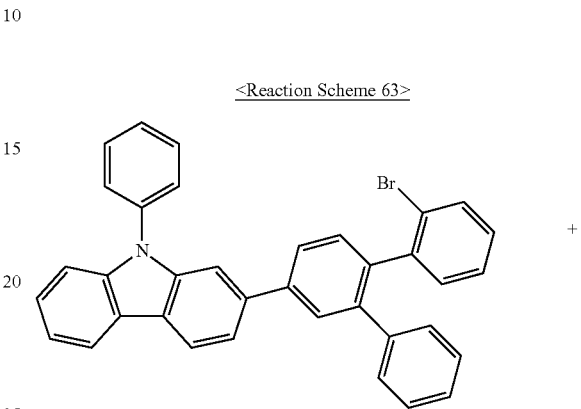

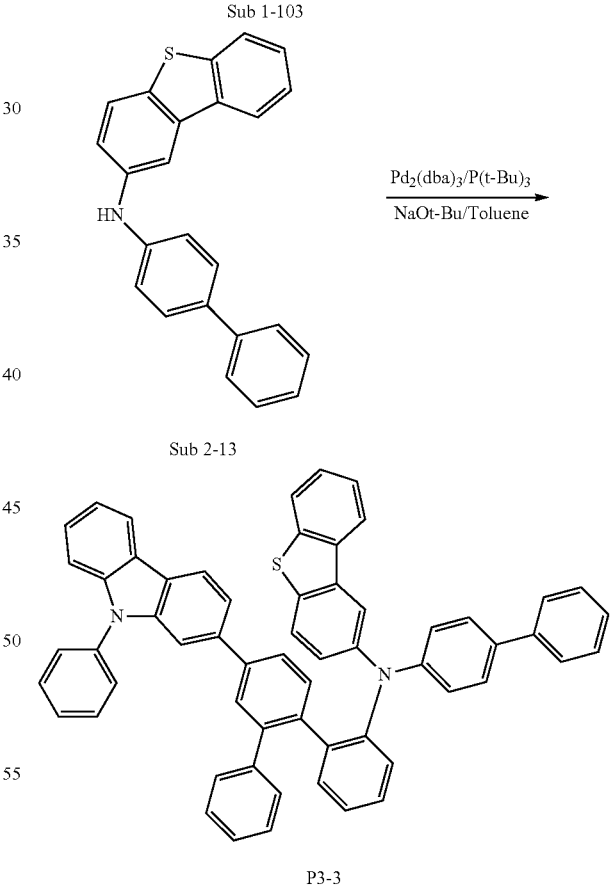

P3-3

Using Sub 1-103 (26.0 g, 47.3 mmol), Sub 2-13 (18.3 g, 52 mmol), Pd$_2$(dba)$_3$ (2.2 g, 2.4 mmol), P(t-Bu)$_3$ (1 g, 4.73 mmol), NaOt-Bu (13.6 g, 141.8 mmol), toluene (500 mL), the same procedure as described in the synthesis method of Product P1-1 was carried out to obtain target material (22.9 g, 59%).

8. Synthesis of Product P3-23

<Reaction Scheme 64>

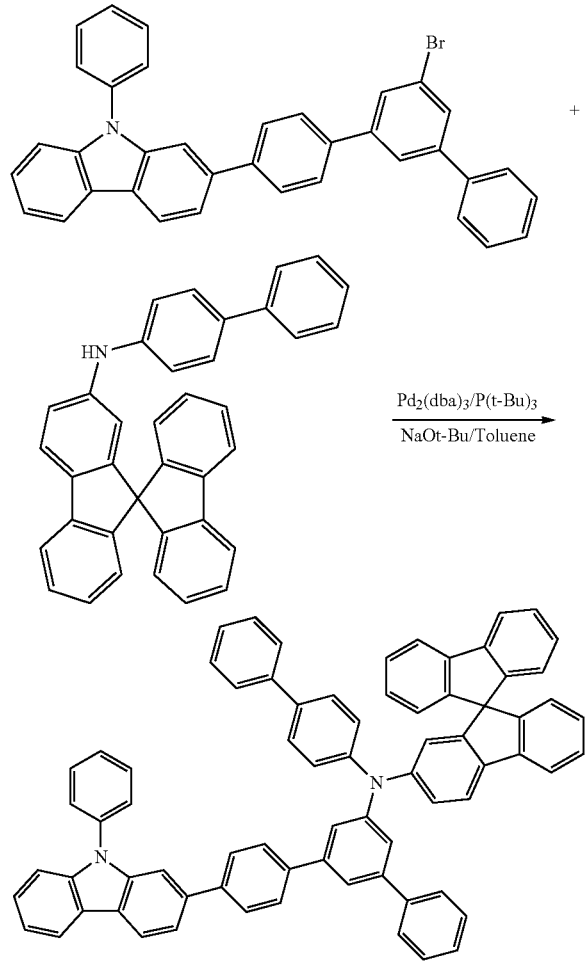

Using Sub 1-111 (26.0 g, 47.3 mmol), Sub 2-10 (25.1 g, 52 mmol), Pd$_2$(dba)$_3$ (2.2 g, 2.4 mmol), P(t-Bu)$_3$ (1 g, 4.73 mmol), NaOt-Bu (13.6 g, 141.8 mmol), toluene (500 mL), the same procedure as described in the synthesis method of Product P1-1 was carried out to obtain target material (29.3 g, 65%).

9. Synthesis of Product P3-17

<Reaction Scheme 65>

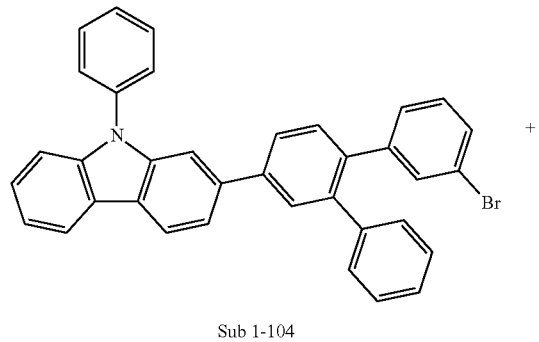

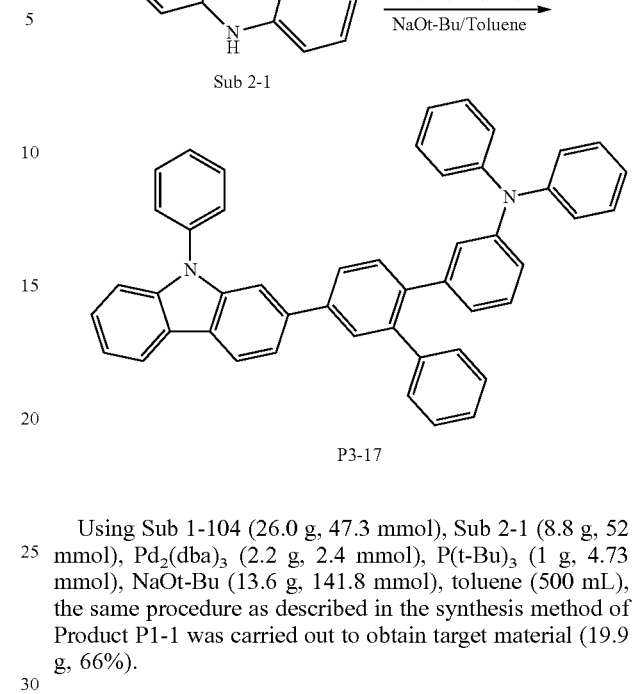

P3-17

Using Sub 1-104 (26.0 g, 47.3 mmol), Sub 2-1 (8.8 g, 52 mmol), Pd$_2$(dba)$_3$ (2.2 g, 2.4 mmol), P(t-Bu)$_3$ (1 g, 4.73 mmol), NaOt-Bu (13.6 g, 141.8 mmol), toluene (500 mL), the same procedure as described in the synthesis method of Product P1-1 was carried out to obtain target material (19.9 g, 66%).

10. Synthesis of Product P3-32

<Reaction Scheme 66>

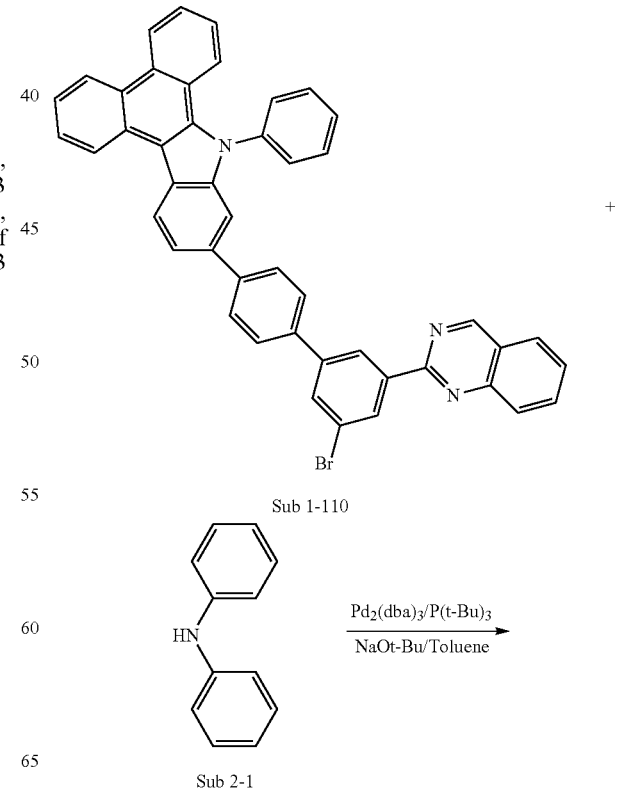

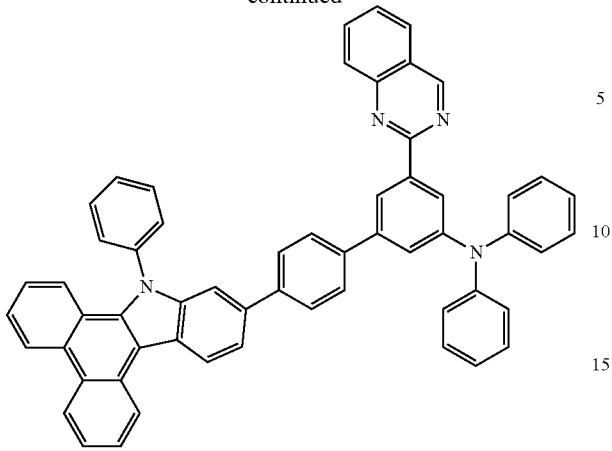

P3-32

Using Sub 1-110 (33.2 g, 47.3 mmol), Sub 2-1 (8.8 g, 52 mmol), Pd$_2$(dba)$_3$ (2.2 g, 2.4 mmol), P(t-Bu)$_3$ (1 g, 4.73 mmol), NaOt-Bu (13.6 g, 141.8 mmol), toluene (500 mL), the same procedure as described in the synthesis method of Product P1-1 was carried out to obtain target material (21.7 g, 58%).

FD-MS data of the final products are given in Table 3 below.

TABLE 3

| Compound | FD-MS | Compound | FD-MS |
| --- | --- | --- | --- |
| P1-1 | m/z = 562.24($C_{42}H_{30}N_2$ = 562.70) | P1-2 | m/z = 638.27($C_{48}H_{34}N_2$ = 638.80) |
| P1-3 | m/z = 638.27($C_{48}H_{34}N_2$ = 638.80) | P1-4 | m/z = 714.30($C_{48}H_{34}N_2$ = 714.89) |
| P1-5 | m/z = 662.27($C_{50}H_{34}N_2$ = 662.82) | P1-6 | m/z = 662.27($C_{50}H_{34}N_2$ = 662.82) |
| P1-7 | m/z = 688.29($C_{52}H_{36}N_2$ = 688.86) | P1-8 | m/z = 802.33($C_{52}H_{36}N_2$ = 803.00) |
| P1-9 | m/z = 714.30($C_{54}H_{38}N_2$ = 714.89) | P1-10 | m/z = 876.35($C_{67}H_{44}N_2$ = 877.08) |
| P1-11 | m/z = 612.26($C_{46}H_{32}N_2$ = 612.76) | P1-12 | m/z = 764.32($C_{58}H_{40}N_2$ = 764.95) |
| P1-13 | m/z = 928.38($C_{71}H_{48}N_2$ = 929.15) | P1-14 | m/z = 714.30($C_{54}H_{38}N_2$ = 714.89) |
| P1-15 | m/z = 764.32($C_{58}H_{40}N_2$ = 764.95) | P1-16 | m/z = 738.30($C_{56}H_{38}N_2$ = 738.91) |
| P1-17 | m/z = 794.28($C_{58}H_{38}N_2S$ = 795.00) | P1-18 | m/z = 778.30($C_{58}H_{38}N_2O$ = 778.94) |
| P1-19 | m/z = 740.29($C_{54}H_{36}N_4$ = 740.89) | P1-20 | m/z = 740.29($C_{54}H_{36}N_4$ = 740.89) |
| P1-21 | m/z = 638.27($C_{48}H_{34}N_2$ = 638.80) | P1-22 | m/z = 638.27($C_{48}H_{34}N_2$ = 638.80) |
| P1-23 | m/z = 856.39($C_{62}H_{52}N_2S$ = 857.15) | P1-24 | m/z = 741.29($C_{53}H_{35}N_5$ = 741.88) |
| P1-25 | m/z = 602.27($C_{45}H_{34}N_2$ = 602.76) | P1-26 | m/z = 815.33($C_{61}H_{41}N_3$ = 816.00) |
| P1-27 | m/z = 718.30($C_{53}H_{38}N_2O$ = 718.88) | P1-28 | m/z = 866.34($C_{64}H_{42}N_4$ = 867.05) |
| P1-29 | m/z = 802.33($C_{61}H_{42}N_2$ = 803.00) | P1-30 | m/z = 878.37($C_{67}H_{46}N_2$ = 879.10) |
| P1-31 | m/z = 878.37($C_{67}H_{46}N_2$ = 879.10) | P1-32 | m/z = 954.40($C_{73}H_{50}N_2$ = 955.19) |
| P1-33 | m/z = 902.37($C_{69}H_{46}N_2$ = 903.12) | P1-34 | m/z = 902.37($C_{69}H_{46}N_2$ = 903.12) |
| P1-35 | m/z = 928.38($C_{71}H_{48}N_2$ = 929.15) | P1-36 | m/z = 1092.44($C_{84}H_{56}N_2$ = 1093.36) |
| P1-37 | m/z = 954.40($C_{73}H_{50}N_2$ = 955.19) | P1-38 | m/z = 1116.44($C_{86}H_{56}N_2$ = 1117.38) |
| P1-39 | m/z = 852.35($C_{65}H_{44}N_2$ = 853.06) | P1-40 | m/z = 954.40($C_{73}H_{50}N_2$ = 955.19) |
| P1-41 | m/z = 954.40($C_{73}H_{50}N_2$ = 955.19) | P1-42 | m/z = 954.40($C_{73}H_{50}N_2$ = 955.19) |
| P1-43 | m/z = 954.40($C_{73}H_{50}N_2$ = 955.19) | P1-44 | m/z = 954.40($C_{73}H_{50}N_2$ = 955.19) |
| P1-45 | m/z = 802.33($C_{61}H_{42}N_2$ = 803.00) | P1-46 | m/z = 878.37($C_{67}H_{46}N_2$ = 879.10) |
| P1-47 | m/z = 878.37($C_{67}H_{46}N_2$ = 879.10) | P1-48 | m/z = 954.40($C_{73}H_{50}N_2$ = 955.19) |
| P1-49 | m/z = 902.37($C_{69}H_{46}N_2$ = 903.12) | P1-50 | m/z = 902.37($C_{69}H_{46}N_2$ = 903.12) |
| P1-51 | m/z = 928.38($C_{71}H_{48}N_2$ = 929.15) | P1-52 | m/z = 1092.44($C_{84}H_{56}N_2$ = 1093.36) |
| P1-53 | m/z = 954.40($C_{73}H_{50}N_2$ = 955.19) | P1-54 | m/z = 1116.44($C_{86}H_{56}N_2$ = 1117.38) |
| P1-55 | m/z = 852.35($C_{65}H_{44}N_2$ = 853.06) | P1-56 | m/z = 954.40($C_{73}H_{50}N_2$ = 955.19) |
| P1-57 | m/z = 954.40($C_{73}H_{50}N_2$ = 955.19) | P1-58 | m/z = 954.40($C_{73}H_{50}N_2$ = 955.19) |
| P1-59 | m/z = 954.40($C_{73}H_{50}N_2$ = 955.19) | P1-60 | m/z = 954.40($C_{73}H_{50}N_2$ = 955.19) |
| P1-61 | m/z = 802.33($C_{61}H_{42}N_2$ = 803.00) | P1-62 | m/z = 878.37($C_{67}H_{46}N_2$ = 879.10) |
| P1-63 | m/z = 878.37($C_{67}H_{46}N_2$ = 879.10) | P1-64 | m/z = 954.40($C_{73}H_{50}N_2$ = 955.19) |
| P1-65 | m/z = 902.37($C_{69}H_{46}N_2$ = 903.12) | P1-66 | m/z = 902.37($C_{69}H_{46}N_2$ = 903.12) |
| P1-67 | m/z = 928.38($C_{71}H_{48}N_2$ = 929.15) | P1-68 | m/z = 1092.44($C_{84}H_{56}N_2$ = 1093.36) |
| P1-69 | m/z = 954.40($C_{73}H_{50}N_2$ = 955.19) | P1-70 | m/z = 1116.44($C_{86}H_{56}N_2$ = 1117.38) |
| P1-71 | m/z = 852.35($C_{65}H_{44}N_2$ = 853.06) | P1-72 | m/z = 954.40($C_{73}H_{50}N_2$ = 955.19) |
| P1-73 | m/z = 954.40($C_{73}H_{50}N_2$ = 955.19) | P1-74 | m/z = 954.40($C_{73}H_{50}N_2$ = 955.19) |
| P1-75 | m/z = 954.40($C_{73}H_{50}N_2$ = 955.19) | P1-76 | m/z = 954.40($C_{73}H_{50}N_2$ = 955.19) |

TABLE 3-continued

| Compound | FD-MS | Compound | FD-MS |
| --- | --- | --- | --- |
| P1-77 | m/z = 714.30($C_{54}H_{38}N_2$ = 714.89) | P1-78 | m/z = 790.33($C_{60}H_{42}N_2$ = 790.99) |
| P1-79 | m/z = 790.33($C_{60}H_{42}N_2$ = 790.99) | P1-80 | m/z = 866.37($C_{66}H_{42}N_2$ = 867.08) |
| P1-81 | m/z = 814.33($C_{62}H_{42}N_2$ = 815.01) | P1-82 | m/z = 814.33($C_{62}H_{42}N_2$ = 815.01) |
| P1-83 | m/z = 840.35($C_{64}H_{44}N_2$ = 841.05) | P1-84 | m/z = 1004.41($C_{77}H_{52}N_2$ = 1005.25) |
| P1-85 | m/z = 866.37($C_{66}H_{46}N_2$ = 867.08) | P1-86 | m/z = 714.30($C_{54}H_{38}N_2$ = 714.89) |
| P1-87 | m/z = 714.30($C_{54}H_{38}N_2$ = 714.89) | P1-88 | m/z = 714.30($C_{54}H_{38}N_2$ = 714.89) |
| P1-89 | m/z = 724.37($C_{54}H_{28}D_{10}N_2$ = 724.95) | P1-90 | m/z = 800.40($C_{60}H_{32}D_{10}N_2$ = 801.05) |
| P1-91 | m/z = 871.40($C_{66}H_{41}D_5N_2$ = 872.12) | P1-92 | m/z = 719.33($C_{54}H_{33}D_5N_2$ = 719.92) |
| P1-93 | m/z = 852.35($C_{65}H_{44}N_2$ = 853.06) | P1-94 | m/z = 902.37($C_{69}H_{46}N_2$ = 903.12) |
| P1-95 | m/z = 852.35($C_{65}H_{44}N_2$ = 853.06) | P1-96 | m/z = 902.37($C_{69}H_{46}N_2$ = 903.12) |
| P1-97 | m/z = 930.40($C_{71}H_{50}N_2$ = 931.17) | P1-98 | m/z = 912.37($C_{67}H_{48}N_2O_2$ = 913.11) |
| P1-99 | m/z = 902.37($C_{69}H_{46}N_2$ = 903.12) | P1-100 | m/z = 902.37($C_{69}H_{46}N_2$ = 903.12) |
| P1-101 | m/z = 768.26($C_{56}H_{36}N_2S$ = 903.12) | P1-102 | m/z = 768.26($C_{56}H_{36}N_2S$ = 903.12) |
| P1-103 | m/z = 794.28($C_{58}H_{38}N_2S$ = 795.00) | P1-104 | m/z = 958.34($C_{71}H_{46}N_2S$ = 959.20) |
| P1-105 | m/z = 752.28($C_{56}H_{36}N_2O$ = 752.90) | P1-106 | m/z = 752.28($C_{56}H_{36}N_2O$ = 752.90) |
| P1-107 | m/z = 778.30($C_{58}H_{38}N_2O$ = 778.94) | P1-108 | m/z = 942.36($C_{71}H_{46}N_2O$ = 943.14) |
| P1-109 | m/z = 902.37($C_{69}H_{46}N_2$ = 903.12) | P1-110 | m/z = 902.37($C_{69}H_{46}N_2$ = 903.12) |
| P1-111 | m/z = 818.28($C_{60}H_{38}N_2$ = 819.02) | P1-112 | m/z = 802.30($C_{60}H_{38}N_2O$ = 802.96) |
| P2-1 | m/z = 562.24($C_{42}H_{30}N_2$ = 562.70) | P2-2 | m/z = 638.27($C_{48}H_{34}N_2$ = 638.80) |
| P2-3 | m/z = 638.27($C_{48}H_{34}N_2$ = 638.80) | P2-4 | m/z = 714.30($C_{48}H_{34}N_2$ = 714.89) |
| P2-5 | m/z = 662.27($C_{50}H_{34}N_2$ = 662.82) | P2-6 | m/z = 662.27($C_{50}H_{34}N_2$ = 662.82) |
| P2-7 | m/z = 688.29($C_{52}H_{36}N_2$ = 688.86) | P2-8 | m/z = 802.33($C_{52}H_{36}N_2$ = 803.00) |
| P2-9 | m/z = 714.30($C_{54}H_{38}N_2$ = 714.89) | P2-10 | m/z = 876.35($C_{67}H_{44}N_2$ = 877.08) |
| P2-11 | m/z = 612.26($C_{46}H_{32}N_2$ = 612.76) | P2-12 | m/z = 764.32($C_{58}H_{40}N_2$ = 764.95) |
| P2-13 | m/z = 928.38($C_{71}H_{48}N_2$ = 929.15) | P2-14 | m/z = 714.30($C_{54}H_{38}N_2$ = 714.89) |
| P2-15 | m/z = 764.32($C_{58}H_{40}N_2$ = 764.95) | P2-16 | m/z = 738.30($C_{56}H_{38}N_2$ = 738.91) |
| P2-17 | m/z = 794.28($C_{58}H_{38}N_2S$ = 795.00) | P2-18 | m/z = 778.30($C_{58}H_{38}N_2O$ = 778.94) |
| P2-19 | m/z = 740.29($C_{54}H_{36}N_4$ = 740.89) | P2-20 | m/z = 740.29($C_{54}H_{36}N_4$ = 740.89) |
| P2-21 | m/z = 638.27($C_{48}H_{34}N_2$ = 638.80) | P2-22 | m/z = 638.27($C_{48}H_{34}N_2$ = 638.80) |
| P2-23 | m/z = 856.39($C_{62}H_{52}N_2S$ = 857.15) | P2-24 | m/z = 741.29($C_{53}H_{35}N_5$ = 741.88) |
| P2-25 | m/z = 602.27($C_{45}H_{34}N_2$ = 602.76) | P2-26 | m/z = 815.33($C_{61}H_{41}N_3$ = 816.00) |
| P2-27 | m/z = 718.30($C_{53}H_{38}N_2O$ = 718.88) | P2-28 | m/z = 866.34($C_{64}H_{42}N_4$ = 867.05) |
| P2-29 | m/z = 802.33($C_{61}H_{42}N_2$ = 803.00) | P2-30 | m/z = 878.37($C_{67}H_{46}N_2$ = 879.10) |
| P2-31 | m/z = 878.37($C_{67}H_{46}N_2$ = 879.10) | P2-32 | m/z = 954.40($C_{73}H_{50}N_2$ = 955.19) |
| P2-33 | m/z = 902.37($C_{69}H_{46}N_2$ = 903.12) | P2-34 | m/z = 902.37($C_{69}H_{46}N_2$ = 903.12) |
| P2-35 | m/z = 928.38($C_{71}H_{48}N_2$ = 929.15) | P2-36 | m/z = 1092.44($C_{84}H_{56}N_2$ = 1093.36) |
| P2-37 | m/z = 954.40($C_{73}H_{50}N_2$ = 955.19) | P2-38 | m/z = 1116.44($C_{86}H_{56}N_2$ = 1117.38) |
| P2-39 | m/z = 852.35($C_{65}H_{44}N_2$ = 853.06) | P2-40 | m/z = 954.40($C_{73}H_{50}N_2$ = 955.19) |
| P2-41 | m/z = 954.40($C_{73}H_{50}N_2$ = 955.19) | P2-42 | m/z = 954.40($C_{73}H_{50}N_2$ = 955.19) |
| P2-43 | m/z = 954.40($C_{73}H_{50}N_2$ = 955.19) | P2-44 | m/z = 954.40($C_{73}H_{50}N_2$ = 955.19) |
| P2-45 | m/z = 802.33($C_{61}H_{42}N_2$ = 803.00) | P2-46 | m/z = 878.37($C_{67}H_{46}N_2$ = 879.10) |
| P2-47 | m/z = 878.37($C_{67}H_{46}N_2$ = 879.10) | P2-48 | m/z = 954.40($C_{73}H_{50}N_2$ = 955.19) |
| P2-49 | m/z = 902.37($C_{69}H_{46}N_2$ = 903.12) | P2-50 | m/z = 902.37($C_{69}H_{46}N_2$ = 903.12) |
| P2-51 | m/z = 928.38($C_{71}H_{48}N_2$ = 929.15) | P2-52 | m/z = 1092.44($C_{84}H_{56}N_2$ = 1093.36) |
| P2-53 | m/z = 954.40($C_{73}H_{50}N_2$ = 955.19) | P2-54 | m/z = 1116.44($C_{86}H_{56}N_2$ = 1117.38) |
| P2-55 | m/z = 852.35($C_{65}H_{44}N_2$ = 853.06) | P2-56 | m/z = 954.40($C_{73}H_{50}N_2$ = 955.19) |
| P2-57 | m/z = 954.40($C_{73}H_{50}N_2$ = 955.19) | P2-58 | m/z = 954.40($C_{73}H_{50}N_2$ = 955.19) |
| P2-59 | m/z = 954.40($C_{73}H_{50}N_2$ = 955.19) | P2-60 | m/z = 954.40($C_{73}H_{50}N_2$ = 955.19) |
| P2-61 | m/z = 802.33($C_{61}H_{42}N_2$ = 803.00) | P2-62 | m/z = 878.37($C_{67}H_{46}N_2$ = 879.10) |
| P2-63 | m/z = 878.37($C_{67}H_{46}N_2$ = 879.10) | P2-64 | m/z = 954.40($C_{73}H_{50}N_2$ = 955.19) |
| P2-65 | m/z = 902.37($C_{69}H_{46}N_2$ = 903.12) | P2-66 | m/z = 902.37($C_{69}H_{46}N_2$ = 903.12) |
| P2-67 | m/z = 928.38($C_{71}H_{48}N_2$ = 929.15) | P2-68 | m/z = 1092.44($C_{84}H_{56}N_2$ = 1093.36) |
| P2-69 | m/z = 954.40($C_{73}H_{50}N_2$ = 955.19) | P2-70 | m/z = 1116.44($C_{86}H_{56}N_2$ = 1117.38) |
| P2-71 | m/z = 852.35($C_{65}H_{44}N_2$ = 853.06) | P2-72 | m/z = 954.40($C_{73}H_{50}N_2$ = 955.19) |
| P2-73 | m/z = 954.40($C_{73}H_{50}N_2$ = 955.19) | P2-74 | m/z = 954.40($C_{73}H_{50}N_2$ = 955.19) |
| P2-75 | m/z = 954.40($C_{73}H_{50}N_2$ = 955.19) | P2-76 | m/z = 954.40($C_{73}H_{50}N_2$ = 955.19) |
| P2-77 | m/z = 714.30($C_{54}H_{38}N_2$ = 714.89) | P2-78 | m/z = 790.33($C_{60}H_{42}N_2$ = 790.99) |
| P2-79 | m/z = 790.33($C_{60}H_{42}N_2$ = 790.99) | P2-80 | m/z = 866.37($C_{66}H_{42}N_2$ = 867.08) |
| P2-81 | m/z = 814.33($C_{62}H_{42}N_2$ = 815.01) | P2-82 | m/z = 814.33($C_{62}H_{42}N_2$ = 815.01) |
| P2-83 | m/z = 840.35($C_{64}H_{44}N_2$ = 841.05) | P2-84 | m/z = 1004.41($C_{77}H_{52}N_2$ = 1005.25) |
| P2-85 | m/z = 866.37($C_{66}H_{46}N_2$ = 867.08) | P2-86 | m/z = 714.30($C_{54}H_{38}N_2$ = 714.89) |
| P2-87 | m/z = 714.30($C_{54}H_{38}N_2$ = 714.89) | P2-88 | m/z = 714.30($C_{54}H_{38}N_2$ = 714.89) |
| P2-89 | m/z = 724.37($C_{54}H_{28}D_{10}N_2$ = 724.95) | P2-90 | m/z = 800.40($C_{60}H_{32}D_{10}N_2$ = 801.05) |
| P2-91 | m/z = 871.40($C_{66}H_{41}D_5N_2$ = 872.12) | P2-92 | m/z = 719.33($C_{54}H_{33}D_5N_2$ = 719.92) |
| P2-93 | m/z = 852.35($C_{65}H_{44}N_2$ = 853.06) | P2-94 | m/z = 902.37($C_{69}H_{46}N_2$ = 903.12) |
| P2-95 | m/z = 852.35($C_{65}H_{44}N_2$ = 853.06) | P2-96 | m/z = 902.37($C_{69}H_{46}N_2$ = 903.12) |
| P2-97 | m/z = 930.40($C_{71}H_{50}N_2$ = 931.17) | P2-98 | m/z = 912.37($C_{67}H_{48}N_2O_2$ = 913.11) |
| P2-99 | m/z = 902.37($C_{69}H_{46}N_2$ = 903.12) | P2-100 | m/z = 902.37($C_{69}H_{46}N_2$ = 903.12) |
| P2-101 | m/z = 768.26($C_{56}H_{36}N_2S$ = 903.12) | P2-102 | m/z = 768.26($C_{56}H_{36}N_2S$ = 903.12) |
| P2-103 | m/z = 794.28($C_{58}H_{38}N_2S$ = 795.00) | P2-104 | m/z = 958.34($C_{71}H_{46}N_2S$ = 959.20) |
| P2-105 | m/z = 752.28($C_{56}H_{36}N_2O$ = 752.90) | P2-106 | m/z = 752.28($C_{56}H_{36}N_2O$ = 752.90) |
| P2-107 | m/z = 778.30($C_{58}H_{38}N_2O$ = 778.94) | P2-108 | m/z = 942.36($C_{71}H_{46}N_2O$ = 943.14) |
| P2-109 | m/z = 902.37($C_{69}H_{46}N_2$ = 903.12) | P2-110 | m/z = 902.37($C_{69}H_{46}N_2$ = 903.12) |
| P2-111 | m/z = 818.28($C_{60}H_{38}N_2$ = 819.02) | P2-112 | m/z = 802.30($C_{60}H_{38}N_2O$ = 802.96) |

TABLE 3-continued

| Compound | FD-MS | Compound | FD-MS |
|---|---|---|---|
| P3-1 | m/z = 638.27($C_{48}H_{34}N_2$ = 638.80) | P3-2 | m/z = 790.33($C_{60}H_{42}N_2$ = 790.99) |
| P3-3 | m/z = 820.29($C_{60}H_{40}N_2S$ = 821.04) | P3-4 | m/z = 804.31($C_{60}H_{40}N_2O$ = 804.97) |
| P3-5 | m/z = 830.37($C_{63}H_{46}N_2$ = 831.05) | P3-6 | m/z = 954.40($C_{43}H_{50}N_2$ = 955.19) |
| P3-7 | m/z = 952.38($C_{73}H_{48}N_2$ = 953.18) | P3-8 | m/z = 688.29($C_{52}H_{36}N_2$ = 688.86) |
| P3-9 | m/z = 688.29($C_{52}H_{36}N_2$ = 688.86) | P3-10 | m/z = 840.35($C_{64}H_{44}N_2$ = 841.05) |
| P3-11 | m/z = 896.32($C_{66}H_{44}N_2S$ = 897.13) | P3-12 | m/z = 880.35($C_{66}H_{44}N_2O$ = 881.07) |
| P3-13 | m/z = 956.41($C_{73}H_{52}N_2$ = 957.21) | P3-14 | m/z = 1080.44($C_{83}H_{56}N_2$ = 1081.35) |
| P3-15 | m/z = 953.38($C_{72}H_{47}N_3$ = 954.16) | P3-16 | m/z = 740.29($C_{54}H_{36}N_4$ = 740.89) |
| P3-17 | m/z = 638.27($C_{48}H_{34}N_2$ = 638.80) | P3-18 | m/z = 790.33($C_{60}H_{42}N_2$ = 790.99) |
| P3-19 | m/z = 820.29($C_{60}H_{40}N_2S$ = 821.04) | P3-20 | m/z = 804.31($C_{60}H_{40}N_2O$ = 804.97) |
| P3-21 | m/z = 830.37($C_{63}H_{46}N_2$ = 831.05) | P3-22 | m/z = 954.40($C_{43}H_{50}N_2$ = 955.19) |
| P3-23 | m/z = 952.38($C_{73}H_{48}N_2$ = 953.18) | P3-24 | m/z = 688.29($C_{52}H_{36}N_2$ = 688.86) |
| P3-25 | m/z = 688.29($C_{52}H_{36}N_2$ = 688.86) | P3-26 | m/z = 840.35($C_{64}H_{44}N_2$ = 841.05) |
| P3-27 | m/z = 896.32($C_{66}H_{44}N_2S$ = 897.13) | P3-28 | m/z = 880.35($C_{66}H_{44}N_2O$ = 881.07) |
| P3-29 | m/z = 956.41($C_{73}H_{52}N_2$ = 957.21) | P3-30 | m/z = 1080.44($C_{83}H_{56}N_2$ = 1081.35) |
| P3-31 | m/z = 953.38($C_{72}H_{47}N_3$ = 954.16) | P3-32 | m/z = 790.31($C_{58}H_{38}N_4$ = 790.95) |

Fabrication and Evaluation of Organic Electronic Element

[Example 1] A Hole Transport Layer (Green)

Organic light emitting diodes (OLEDs) were fabricated according to a conventional method by using a compound of the present invention as a hole transport layer material.

First, an ITO layer (anode) was formed on a glass substrate, and a film of 4,4',4"-Tris[2-naphthyl(phenyl)amino] triphenylamine ("2-TNATA") was vacuum-deposited on the ITO layer to form a hole injection layer with a thickness of 60 nm.

Subsequently, P1-1 of the present invention was vacuum-deposited with a thickness of 60 nm on the hole injection layer to form a hole transport layer.

Subsequently, a light emitting layer with a thickness of 30 nm was deposited on the hole transport layer by doping the hole transport layer with 4,4'-N,N'-dicarbazole-biphenyl ("CBP") as a host material and tris(2-phenylpyridine)-iridium ("Ir(ppy)$_3$") as a dopant material in a weight ratio of 90:10.

Next, a film of ((1,1'-bisphenyl)-4-olato)bis(2-methyl-8-quinolinolato)aluminum ("BAlq") was vacuum-deposited with a thickness of 10 nm on the light emitting layer to form a hole blocking layer, and a film of tris(8-quinolinolato) aluminum ("Alq$_3$") was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 256] A Hole Transport Layer (Green)

The OLEDs were manufactured in the same manner as described in Example 1, except that any one of the compounds P1-2 to P1-112, P2-1 to P2-112, and P3-1 and P3-32 of the present invention in the Table 4 below was used as the hole transport layer material of the light emitting layer, instead of the inventive compound P1-1.

Comparative Example 1

An OLED was manufactured in the same manner as described in Example 1, except that the following Comparative Compound A was used as the hole transport layer material, instead of the inventive compound P1-1.

<Comparative compound 1>

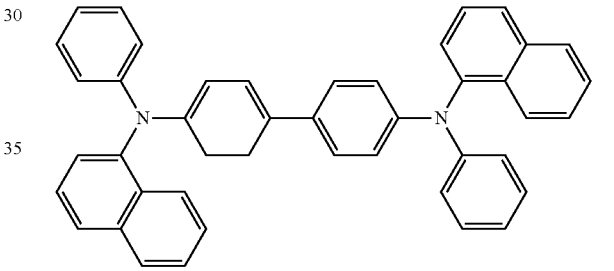

Comparative Example 2

An OLED was manufactured in the same manner as described in Example 1, except that the following Comparative Compound 2 was used as the hole transport layer material, instead of the inventive compound P1-1.

<Comparative compound 2>

Comparative Example 3

An OLED was manufactured in the same manner as described in Example 1, except that the following Comparative Compound 3 was used as the hole transport layer material, instead of the inventive compound P1-1.

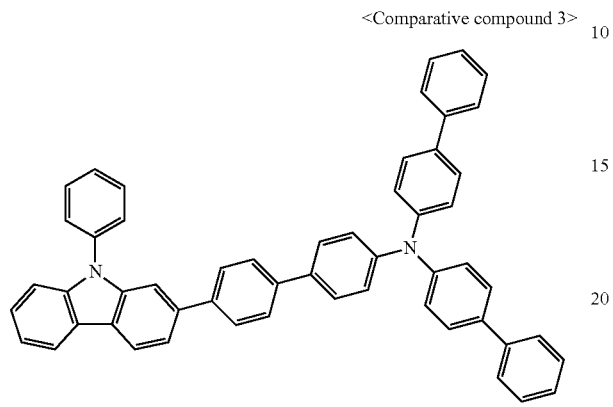

<Comparative compound 3>

Comparative Example 4

An OLED was manufactured in the same manner as described in Example 1, except that the following Comparative Compound 4 was used as the hole transport layer material, instead of the inventive compound P1-1.

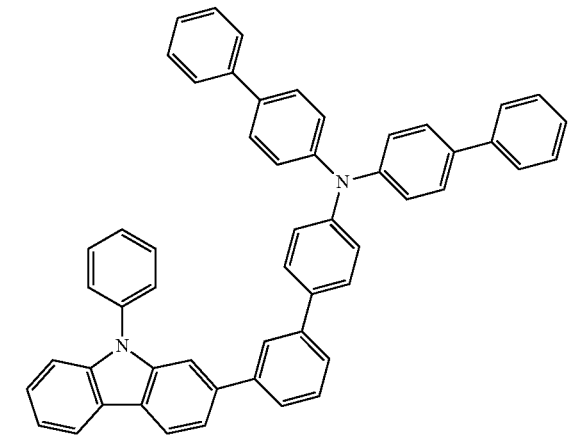

<Comparative compound 4>

A forward bias DC voltage was applied to each of the OLEDs manufactured through the Examples 1 to 224 and the Comparative Examples 1 to 4, and electro-luminescence (EL) characteristics of the OLED were measured by PR-650 (Photoresearch). Also, T90 life span was measured by life span measuring equipment (Mcscience) at the reference brightness of 5000 cd/m². Evaluation results are in the Table 4 below.

TABLE 4

|  | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Com. Ex (1) | Com. Com (1) | 5.6 | 17.9 | 5000 | 27.9 | 68.2 | 0.33 | 0.62 |
| Com. Ex (2) | Com. Com (2) | 5.3 | 16.0 | 5000 | 31.2 | 120.6 | 0.33 | 0.61 |
| Com. Ex (3) | Com. Com (3) | 5.4 | 14.5 | 5000 | 34.5 | 109.4 | 0.33 | 0.62 |
| Com. Ex (4) | Com. Com (4) | 5.6 | 13.5 | 5000 | 37.0 | 119.1 | 0.33 | 0.62 |
| Ex. (1) | P1-1 | 5.5 | 12.8 | 5000 | 39.0 | 124.3 | 0.33 | 0.62 |
| Ex. (2) | P1-2 | 5.4 | 13.6 | 5000 | 36.7 | 120.1 | 0.33 | 0.61 |
| Ex. (3) | P1-3 | 5.5 | 12.9 | 5000 | 38.7 | 121.1 | 0.33 | 0.61 |
| Ex. (4) | P1-4 | 5.4 | 12.8 | 5000 | 39.0 | 124.6 | 0.33 | 0.61 |
| Ex. (5) | P1-5 | 5.4 | 13.1 | 5000 | 38.3 | 124.1 | 0.33 | 0.62 |
| Ex. (6) | P1-6 | 5.4 | 13.0 | 5000 | 38.4 | 122.7 | 0.33 | 0.62 |
| Ex. (7) | P1-7 | 5.5 | 13.7 | 5000 | 36.4 | 120.4 | 0.33 | 0.61 |
| Ex. (8) | P1-8 | 5.4 | 12.9 | 5000 | 38.9 | 121.0 | 0.33 | 0.62 |
| Ex. (9) | P1-9 | 5.5 | 13.1 | 5000 | 38.3 | 121.7 | 0.33 | 0.61 |
| Ex. (10) | P1-10 | 5.5 | 13.8 | 5000 | 36.3 | 124.7 | 0.33 | 0.62 |
| Ex. (11) | P1-11 | 5.5 | 14.0 | 5000 | 35.7 | 121.7 | 0.33 | 0.61 |
| Ex. (12) | P1-12 | 5.6 | 12.7 | 5000 | 39.5 | 124.4 | 0.33 | 0.61 |
| Ex. (13) | P1-13 | 5.5 | 14.0 | 5000 | 35.8 | 120.3 | 0.33 | 0.61 |
| Ex. (14) | P1-14 | 5.4 | 13.1 | 5000 | 38.0 | 120.6 | 0.33 | 0.62 |
| Ex. (15) | P1-15 | 5.5 | 13.6 | 5000 | 36.7 | 124.7 | 0.33 | 0.61 |
| Ex. (16) | P1-16 | 5.6 | 13.6 | 5000 | 36.9 | 120.4 | 0.33 | 0.61 |
| Ex. (17) | P1-17 | 5.5 | 13.7 | 5000 | 36.5 | 123.8 | 0.33 | 0.62 |
| Ex. (18) | P1-18 | 5.6 | 13.5 | 5000 | 37.0 | 122.0 | 0.33 | 0.61 |
| Ex. (19) | P1-19 | 5.5 | 12.5 | 5000 | 40.0 | 121.5 | 0.33 | 0.62 |
| Ex. (20) | P1-20 | 5.5 | 13.4 | 5000 | 37.4 | 124.3 | 0.33 | 0.62 |
| Ex. (21) | P1-21 | 5.4 | 13.6 | 5000 | 36.9 | 123.1 | 0.33 | 0.61 |
| Ex. (22) | P1-22 | 5.5 | 13.1 | 5000 | 38.2 | 121.9 | 0.33 | 0.62 |
| Ex. (23) | P1-23 | 5.6 | 13.9 | 5000 | 35.9 | 123.7 | 0.33 | 0.62 |
| Ex. (24) | P1-24 | 5.5 | 12.9 | 5000 | 38.7 | 121.5 | 0.33 | 0.62 |
| Ex. (25) | P1-25 | 5.4 | 13.6 | 5000 | 36.7 | 122.9 | 0.33 | 0.62 |
| Ex. (26) | P1-26 | 5.5 | 13.6 | 5000 | 36.8 | 121.0 | 0.33 | 0.61 |
| Ex. (27) | P1-27 | 5.4 | 13.7 | 5000 | 36.4 | 123.3 | 0.33 | 0.61 |
| Ex. (28) | P1-28 | 5.5 | 13.9 | 5000 | 35.9 | 124.2 | 0.33 | 0.61 |
| Ex. (29) | P1-29 | 5.4 | 13.2 | 5000 | 37.9 | 124.0 | 0.33 | 0.62 |
| Ex. (30) | P1-30 | 5.5 | 14.0 | 5000 | 35.7 | 123.4 | 0.33 | 0.62 |

TABLE 4-continued

|  | Compound | Voltage (V) | Current Density (mA/cm$^2$) | Brightness (cd/m$^2$) | Efficiency (cd/A) | Lifetime T(95) | CIE x | y |
|---|---|---|---|---|---|---|---|---|
| Ex. (31) | P1-31 | 5.5 | 14.1 | 5000 | 35.5 | 122.6 | 0.33 | 0.62 |
| Ex. (32) | P1-32 | 5.5 | 12.6 | 5000 | 39.7 | 123.8 | 0.33 | 0.61 |
| Ex. (33) | P1-33 | 5.6 | 13.3 | 5000 | 37.5 | 123.9 | 0.33 | 0.61 |
| Ex. (34) | P1-34 | 5.5 | 14.2 | 5000 | 35.2 | 120.4 | 0.33 | 0.62 |
| Ex. (35) | P1-35 | 5.5 | 14.2 | 5000 | 35.3 | 124.9 | 0.33 | 0.62 |
| Ex. (36) | P1-36 | 5.5 | 14.1 | 5000 | 35.5 | 121.6 | 0.33 | 0.61 |
| Ex. (37) | P1-37 | 5.4 | 14.2 | 5000 | 35.2 | 120.1 | 0.33 | 0.62 |
| Ex. (38) | P1-38 | 5.4 | 13.3 | 5000 | 37.7 | 124.5 | 0.33 | 0.61 |
| Ex. (39) | P1-39 | 5.5 | 13.5 | 5000 | 37.0 | 121.0 | 0.33 | 0.62 |
| Ex. (40) | P1-40 | 5.4 | 13.3 | 5000 | 37.6 | 122.9 | 0.33 | 0.61 |
| Ex. (41) | P1-41 | 5.4 | 13.8 | 5000 | 36.3 | 124.7 | 0.33 | 0.62 |
| Ex. (42) | P1-42 | 5.5 | 13.1 | 5000 | 38.3 | 124.3 | 0.33 | 0.61 |
| Ex. (43) | P1-43 | 5.5 | 14.1 | 5000 | 35.4 | 121.2 | 0.33 | 0.62 |
| Ex. (44) | P1-44 | 5.5 | 12.7 | 5000 | 39.2 | 124.7 | 0.33 | 0.62 |
| Ex. (45) | P1-45 | 5.5 | 13.8 | 5000 | 36.1 | 120.2 | 0.33 | 0.62 |
| Ex. (46) | P1-46 | 5.6 | 13.6 | 5000 | 36.8 | 121.0 | 0.33 | 0.61 |
| Ex. (47) | P1-47 | 5.6 | 13.9 | 5000 | 36.0 | 124.5 | 0.33 | 0.62 |
| Ex. (48) | P1-48 | 5.6 | 14.2 | 5000 | 35.2 | 121.8 | 0.33 | 0.61 |
| Ex. (49) | P1-49 | 5.6 | 13.0 | 5000 | 38.4 | 124.4 | 0.33 | 0.61 |
| Ex. (50) | P1-50 | 5.5 | 12.8 | 5000 | 39.0 | 123.2 | 0.33 | 0.61 |
| Ex. (51) | P1-51 | 5.5 | 13.7 | 5000 | 36.4 | 120.4 | 0.33 | 0.61 |
| Ex. (52) | P1-52 | 5.6 | 13.9 | 5000 | 35.9 | 121.0 | 0.33 | 0.62 |
| Ex. (53) | P1-53 | 5.5 | 12.8 | 5000 | 38.9 | 121.8 | 0.33 | 0.61 |
| Ex. (54) | P1-54 | 5.5 | 13.1 | 5000 | 38.1 | 121.9 | 0.33 | 0.62 |
| Ex. (55) | P1-55 | 5.5 | 13.1 | 5000 | 38.1 | 121.5 | 0.33 | 0.61 |
| Ex. (56) | P1-56 | 5.5 | 14.2 | 5000 | 35.3 | 120.4 | 0.33 | 0.61 |
| Ex. (57) | P1-57 | 5.5 | 13.3 | 5000 | 37.5 | 123.0 | 0.33 | 0.62 |
| Ex. (58) | P1-58 | 5.5 | 13.0 | 5000 | 38.6 | 123.8 | 0.33 | 0.61 |
| Ex. (59) | P1-59 | 5.6 | 12.8 | 5000 | 39.0 | 124.6 | 0.33 | 0.61 |
| Ex. (60) | P1-60 | 5.6 | 14.0 | 5000 | 35.7 | 120.2 | 0.33 | 0.61 |
| Ex. (61) | P1-61 | 5.5 | 13.8 | 5000 | 36.3 | 124.0 | 0.33 | 0.62 |
| Ex. (62) | P1-62 | 5.6 | 13.1 | 5000 | 38.3 | 123.5 | 0.33 | 0.61 |
| Ex. (63) | P1-63 | 5.5 | 14.1 | 5000 | 35.4 | 122.2 | 0.33 | 0.62 |
| Ex. (64) | P1-64 | 5.6 | 12.8 | 5000 | 39.1 | 124.1 | 0.33 | 0.62 |
| Ex. (65) | P1-65 | 5.4 | 12.8 | 5000 | 39.0 | 124.3 | 0.33 | 0.61 |
| Ex. (66) | P1-66 | 5.4 | 13.0 | 5000 | 38.6 | 120.1 | 0.33 | 0.62 |
| Ex. (67) | P1-67 | 5.6 | 13.0 | 5000 | 38.6 | 123.7 | 0.33 | 0.61 |
| Ex. (68) | P1-68 | 5.5 | 13.6 | 5000 | 36.7 | 124.6 | 0.33 | 0.62 |
| Ex. (69) | P1-69 | 5.5 | 12.5 | 5000 | 40.0 | 123.2 | 0.33 | 0.62 |
| Ex. (70) | P1-70 | 5.6 | 14.2 | 5000 | 35.1 | 124.9 | 0.33 | 0.62 |
| Ex. (71) | P1-71 | 5.5 | 13.4 | 5000 | 37.3 | 124.4 | 0.33 | 0.61 |
| Ex. (72) | P1-72 | 5.4 | 13.0 | 5000 | 38.3 | 125.0 | 0.33 | 0.62 |
| Ex. (73) | P1-73 | 5.4 | 13.3 | 5000 | 37.7 | 120.7 | 0.33 | 0.61 |
| Ex. (74) | P1-74 | 5.4 | 13.2 | 5000 | 37.9 | 123.5 | 0.33 | 0.61 |
| Ex. (75) | P1-75 | 5.5 | 13.5 | 5000 | 37.0 | 123.2 | 0.33 | 0.61 |
| Ex. (76) | P1-76 | 5.5 | 14.1 | 5000 | 35.5 | 122.1 | 0.33 | 0.62 |
| Ex. (77) | P1-77 | 5.5 | 13.7 | 5000 | 36.4 | 123.7 | 0.33 | 0.62 |
| Ex. (78) | P1-78 | 5.5 | 13.9 | 5000 | 36.1 | 124.4 | 0.33 | 0.61 |
| Ex. (79) | P1-79 | 5.4 | 12.6 | 5000 | 39.7 | 120.7 | 0.33 | 0.62 |
| Ex. (80) | P1-80 | 5.5 | 12.8 | 5000 | 39.0 | 122.9 | 0.33 | 0.61 |
| Ex. (81) | P1-81 | 5.5 | 13.4 | 5000 | 37.3 | 121.9 | 0.33 | 0.61 |
| Ex. (82) | P1-82 | 5.5 | 14.3 | 5000 | 35.0 | 123.1 | 0.33 | 0.62 |
| Ex. (83) | P1-83 | 5.5 | 14.2 | 5000 | 35.3 | 123.2 | 0.33 | 0.61 |
| Ex. (84) | P1-84 | 5.6 | 14.1 | 5000 | 35.4 | 124.7 | 0.33 | 0.61 |
| Ex. (85) | P1-85 | 5.4 | 14.1 | 5000 | 35.4 | 120.7 | 0.33 | 0.61 |
| Ex. (86) | P1-86 | 5.4 | 12.7 | 5000 | 39.5 | 121.9 | 0.33 | 0.62 |
| Ex. (87) | P1-87 | 5.5 | 13.5 | 5000 | 36.9 | 122.3 | 0.33 | 0.61 |
| Ex. (88) | P1-88 | 5.5 | 14.0 | 5000 | 35.8 | 121.2 | 0.33 | 0.62 |
| Ex. (89) | P1-89 | 5.5 | 12.6 | 5000 | 39.8 | 124.6 | 0.33 | 0.62 |
| Ex. (90) | P1-90 | 5.5 | 13.9 | 5000 | 36.0 | 121.8 | 0.33 | 0.61 |
| Ex. (91) | P1-91 | 5.4 | 13.5 | 5000 | 37.0 | 120.7 | 0.33 | 0.62 |
| Ex. (92) | P1-92 | 5.6 | 12.9 | 5000 | 38.7 | 123.4 | 0.33 | 0.61 |
| Ex. (93) | P1-93 | 5.4 | 13.6 | 5000 | 36.9 | 122.7 | 0.33 | 0.62 |
| Ex. (94) | P1-94 | 5.5 | 13.3 | 5000 | 37.7 | 124.1 | 0.33 | 0.61 |
| Ex. (95) | P1-95 | 5.5 | 13.8 | 5000 | 36.2 | 124.3 | 0.33 | 0.61 |
| Ex. (96) | P1-96 | 5.6 | 12.9 | 5000 | 38.9 | 120.5 | 0.33 | 0.62 |
| Ex. (97) | P1-97 | 5.5 | 14.0 | 5000 | 35.7 | 121.8 | 0.33 | 0.61 |
| Ex. (98) | P1-98 | 5.4 | 13.1 | 5000 | 38.3 | 122.4 | 0.33 | 0.62 |
| Ex. (99) | P1-99 | 5.5 | 14.2 | 5000 | 35.1 | 123.0 | 0.33 | 0.62 |
| Ex. (100) | P1-100 | 5.4 | 13.3 | 5000 | 37.6 | 120.3 | 0.33 | 0.61 |

TABLE 4-continued

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (101) | P1-101 | 5.6 | 13.1 | 5000 | 38.1 | 120.2 | 0.33 | 0.61 |
| Ex. (102) | P1-102 | 5.4 | 13.2 | 5000 | 37.8 | 120.7 | 0.33 | 0.61 |
| Ex. (103) | P1-103 | 5.5 | 13.5 | 5000 | 37.2 | 122.0 | 0.33 | 0.62 |
| Ex. (104) | P1-104 | 5.6 | 13.4 | 5000 | 37.3 | 122.1 | 0.33 | 0.62 |
| Ex. (105) | P1-105 | 5.6 | 13.1 | 5000 | 38.3 | 123.0 | 0.33 | 0.62 |
| Ex. (106) | P1-106 | 5.5 | 12.9 | 5000 | 38.9 | 123.9 | 0.33 | 0.61 |
| Ex. (107) | P1-107 | 5.4 | 13.9 | 5000 | 35.8 | 124.8 | 0.33 | 0.61 |
| Ex. (108) | P1-108 | 5.5 | 14.0 | 5000 | 35.7 | 121.5 | 0.33 | 0.62 |
| Ex. (109) | P1-109 | 5.6 | 13.7 | 5000 | 36.5 | 121.3 | 0.33 | 0.62 |
| Ex. (110) | P1-110 | 5.5 | 13.6 | 5000 | 36.9 | 122.3 | 0.33 | 0.62 |
| Ex. (111) | P1-111 | 5.5 | 12.6 | 5000 | 39.8 | 121.6 | 0.33 | 0.61 |
| Ex. (112) | P1-112 | 5.6 | 13.5 | 5000 | 36.9 | 124.4 | 0.33 | 0.61 |
| Ex. (113) | P2-1 | 5.4 | 12.0 | 5000 | 41.5 | 125.5 | 0.33 | 0.61 |
| Ex. (114) | P2-2 | 5.5 | 12.5 | 5000 | 40.1 | 124.5 | 0.33 | 0.61 |
| Ex. (115) | P2-3 | 5.4 | 13.6 | 5000 | 36.9 | 122.8 | 0.33 | 0.61 |
| Ex. (116) | P2-4 | 5.6 | 11.7 | 5000 | 42.7 | 124.2 | 0.33 | 0.62 |
| Ex. (117) | P2-5 | 5.6 | 13.9 | 5000 | 36.0 | 124.9 | 0.33 | 0.61 |
| Ex. (118) | P2-6 | 5.5 | 12.2 | 5000 | 40.9 | 128.0 | 0.33 | 0.62 |
| Ex. (119) | P2-7 | 5.5 | 11.6 | 5000 | 43.1 | 125.2 | 0.33 | 0.61 |
| Ex. (120) | P2-8 | 5.5 | 13.5 | 5000 | 37.0 | 129.5 | 0.33 | 0.62 |
| Ex. (121) | P2-9 | 5.6 | 12.5 | 5000 | 39.9 | 124.2 | 0.33 | 0.61 |
| Ex. (122) | P2-10 | 5.5 | 11.3 | 5000 | 44.4 | 128.8 | 0.33 | 0.62 |
| Ex. (123) | P2-11 | 5.5 | 11.6 | 5000 | 43.2 | 122.3 | 0.33 | 0.61 |
| Ex. (124) | P2-12 | 5.5 | 13.1 | 5000 | 38.1 | 129.7 | 0.33 | 0.61 |
| Ex. (125) | P2-13 | 5.5 | 13.6 | 5000 | 36.9 | 124.2 | 0.33 | 0.61 |
| Ex. (126) | P2-14 | 5.4 | 12.8 | 5000 | 39.0 | 125.4 | 0.33 | 0.62 |
| Ex. (127) | P2-15 | 5.6 | 14.2 | 5000 | 35.1 | 126.6 | 0.33 | 0.61 |
| Ex. (128) | P2-16 | 5.5 | 11.9 | 5000 | 42.1 | 122.2 | 0.33 | 0.62 |
| Ex. (129) | P2-17 | 5.5 | 11.6 | 5000 | 43.0 | 124.7 | 0.33 | 0.62 |
| Ex. (130) | P2-18 | 5.5 | 12.1 | 5000 | 41.5 | 129.7 | 0.33 | 0.62 |
| Ex. (131) | P2-19 | 5.4 | 13.2 | 5000 | 37.9 | 125.8 | 0.33 | 0.61 |
| Ex. (132) | P2-20 | 5.6 | 12.0 | 5000 | 41.5 | 128.8 | 0.33 | 0.62 |
| Ex. (133) | P2-21 | 5.5 | 11.3 | 5000 | 44.4 | 129.6 | 0.33 | 0.62 |
| Ex. (134) | P2-22 | 5.6 | 13.0 | 5000 | 38.5 | 129.5 | 0.33 | 0.61 |
| Ex. (135) | P2-23 | 5.5 | 14.2 | 5000 | 35.2 | 125.7 | 0.33 | 0.62 |
| Ex. (136) | P2-24 | 5.4 | 12.1 | 5000 | 41.2 | 128.9 | 0.33 | 0.61 |
| Ex. (137) | P2-25 | 5.4 | 13.7 | 5000 | 36.5 | 126.7 | 0.33 | 0.61 |
| Ex. (138) | P2-26 | 5.6 | 13.4 | 5000 | 37.3 | 129.0 | 0.33 | 0.61 |
| Ex. (139) | P2-27 | 5.5 | 12.6 | 5000 | 39.8 | 128.5 | 0.33 | 0.61 |
| Ex. (140) | P2-28 | 5.4 | 12.4 | 5000 | 40.4 | 123.4 | 0.33 | 0.61 |
| Ex. (141) | P2-29 | 5.5 | 11.3 | 5000 | 44.3 | 128.9 | 0.33 | 0.62 |
| Ex. (142) | P2-30 | 5.4 | 12.2 | 5000 | 40.9 | 122.6 | 0.33 | 0.62 |
| Ex. (143) | P2-31 | 5.6 | 13.7 | 5000 | 36.4 | 123.0 | 0.33 | 0.62 |
| Ex. (144) | P2-32 | 5.5 | 13.2 | 5000 | 38.0 | 125.0 | 0.33 | 0.61 |
| Ex. (145) | P2-33 | 5.6 | 11.2 | 5000 | 44.8 | 126.7 | 0.33 | 0.61 |
| Ex. (146) | P2-34 | 5.5 | 12.5 | 5000 | 39.8 | 122.6 | 0.33 | 0.62 |
| Ex. (147) | P2-35 | 5.5 | 12.5 | 5000 | 39.9 | 126.7 | 0.33 | 0.62 |
| Ex. (148) | P2-36 | 5.6 | 12.1 | 5000 | 41.4 | 124.1 | 0.33 | 0.62 |
| Ex. (149) | P2-37 | 5.5 | 14.1 | 5000 | 35.4 | 123.1 | 0.33 | 0.62 |
| Ex. (150) | P2-38 | 5.4 | 13.5 | 5000 | 37.0 | 129.8 | 0.33 | 0.62 |
| Ex. (151) | P2-39 | 5.6 | 12.8 | 5000 | 39.1 | 124.4 | 0.33 | 0.61 |
| Ex. (152) | P2-40 | 5.4 | 13.9 | 5000 | 35.9 | 128.7 | 0.33 | 0.61 |
| Ex. (153) | P2-41 | 5.6 | 11.5 | 5000 | 43.5 | 124.6 | 0.33 | 0.62 |
| Ex. (154) | P2-42 | 5.4 | 14.0 | 5000 | 35.6 | 124.2 | 0.33 | 0.62 |
| Ex. (155) | P2-43 | 5.4 | 11.4 | 5000 | 43.7 | 125.1 | 0.33 | 0.62 |
| Ex. (156) | P2-44 | 5.5 | 12.5 | 5000 | 40.0 | 123.5 | 0.33 | 0.61 |
| Ex. (157) | P2-45 | 5.5 | 13.0 | 5000 | 38.3 | 128.8 | 0.33 | 0.61 |
| Ex. (158) | P2-46 | 5.5 | 11.8 | 5000 | 42.4 | 122.5 | 0.33 | 0.61 |
| Ex. (159) | P2-47 | 5.5 | 14.1 | 5000 | 35.4 | 128.1 | 0.33 | 0.61 |
| Ex. (160) | P2-48 | 5.5 | 12.7 | 5000 | 39.3 | 128.5 | 0.33 | 0.62 |
| Ex. (161) | P2-49 | 5.5 | 11.6 | 5000 | 43.0 | 123.5 | 0.33 | 0.62 |
| Ex. (162) | P2-50 | 5.5 | 13.7 | 5000 | 36.5 | 123.8 | 0.33 | 0.62 |
| Ex. (163) | P2-51 | 5.5 | 14.2 | 5000 | 35.2 | 127.3 | 0.33 | 0.62 |
| Ex. (164) | P2-52 | 5.5 | 13.0 | 5000 | 38.4 | 123.1 | 0.33 | 0.62 |
| Ex. (165) | P2-53 | 5.5 | 12.7 | 5000 | 39.2 | 128.9 | 0.33 | 0.62 |
| Ex. (166) | P2-54 | 5.5 | 13.6 | 5000 | 36.8 | 129.5 | 0.33 | 0.62 |
| Ex. (167) | P2-55 | 5.5 | 11.5 | 5000 | 43.6 | 128.8 | 0.33 | 0.62 |
| Ex. (168) | P2-56 | 5.5 | 13.8 | 5000 | 36.2 | 129.2 | 0.33 | 0.61 |
| Ex. (169) | P2-57 | 5.5 | 11.4 | 5000 | 43.7 | 127.6 | 0.33 | 0.61 |
| Ex. (170) | P2-58 | 5.6 | 12.4 | 5000 | 40.5 | 126.5 | 0.33 | 0.62 |
| Ex. (171) | P2-59 | 5.6 | 13.0 | 5000 | 38.4 | 126.5 | 0.33 | 0.61 |
| Ex. (172) | P2-60 | 5.4 | 11.4 | 5000 | 43.8 | 128.6 | 0.33 | 0.62 |
| Ex. (173) | P2-61 | 5.6 | 12.3 | 5000 | 40.6 | 129.3 | 0.33 | 0.62 |
| Ex. (174) | P2-62 | 5.5 | 13.2 | 5000 | 37.8 | 127.8 | 0.33 | 0.61 |
| Ex. (175) | P2-63 | 5.5 | 11.2 | 5000 | 44.7 | 126.2 | 0.33 | 0.62 |

TABLE 4-continued

| | Compound | Voltage (V) | Current Density (mA/cm$^2$) | Brightness (cd/m$^2$) | Efficiency (cd/A) | Lifetime T(95) | CIE x | y |
|---|---|---|---|---|---|---|---|---|
| Ex. (176) | P2-64 | 5.4 | 14.2 | 5000 | 35.1 | 122.6 | 0.33 | 0.61 |
| Ex. (177) | P2-65 | 5.5 | 13.1 | 5000 | 38.1 | 126.8 | 0.33 | 0.61 |
| Ex. (178) | P2-66 | 5.5 | 13.4 | 5000 | 37.3 | 122.4 | 0.33 | 0.62 |
| Ex. (179) | P2-67 | 5.5 | 11.4 | 5000 | 43.8 | 128.9 | 0.33 | 0.62 |
| Ex. (180) | P2-68 | 5.5 | 12.5 | 5000 | 39.9 | 122.5 | 0.33 | 0.61 |
| Ex. (181) | P2-69 | 5.6 | 12.3 | 5000 | 40.8 | 127.8 | 0.33 | 0.62 |
| Ex. (182) | P2-70 | 5.5 | 14.2 | 5000 | 35.3 | 128.0 | 0.33 | 0.62 |
| Ex. (183) | P2-71 | 5.5 | 12.9 | 5000 | 38.7 | 127.9 | 0.33 | 0.61 |
| Ex. (184) | P2-72 | 5.5 | 13.1 | 5000 | 38.1 | 126.0 | 0.33 | 0.62 |
| Ex. (185) | P2-73 | 5.5 | 11.8 | 5000 | 42.5 | 127.2 | 0.33 | 0.61 |
| Ex. (186) | P2-74 | 5.4 | 14.1 | 5000 | 35.5 | 127.2 | 0.33 | 0.62 |
| Ex. (187) | P2-75 | 5.5 | 13.0 | 5000 | 38.4 | 124.3 | 0.33 | 0.62 |
| Ex. (188) | P2-76 | 5.5 | 11.7 | 5000 | 42.9 | 123.6 | 0.33 | 0.61 |
| Ex. (189) | P2-77 | 5.4 | 13.9 | 5000 | 35.9 | 126.8 | 0.33 | 0.61 |
| Ex. (190) | P2-78 | 5.5 | 13.2 | 5000 | 37.9 | 126.0 | 0.33 | 0.62 |
| Ex. (191) | P2-79 | 5.6 | 11.3 | 5000 | 44.4 | 123.2 | 0.33 | 0.61 |
| Ex. (192) | P2-80 | 5.6 | 11.4 | 5000 | 44.0 | 123.5 | 0.33 | 0.61 |
| Ex. (193) | P2-81 | 5.5 | 13.6 | 5000 | 36.7 | 128.6 | 0.33 | 0.62 |
| Ex. (194) | P2-82 | 5.4 | 11.6 | 5000 | 43.1 | 122.2 | 0.33 | 0.61 |
| Ex. (195) | P2-83 | 5.5 | 13.5 | 5000 | 37.1 | 128.4 | 0.33 | 0.61 |
| Ex. (196) | P2-84 | 5.4 | 11.3 | 5000 | 44.1 | 127.1 | 0.33 | 0.61 |
| Ex. (197) | P2-85 | 5.5 | 12.8 | 5000 | 39.1 | 129.9 | 0.33 | 0.61 |
| Ex. (198) | P2-86 | 5.6 | 12.7 | 5000 | 39.3 | 125.1 | 0.33 | 0.62 |
| Ex. (199) | P2-87 | 5.4 | 11.3 | 5000 | 44.1 | 122.5 | 0.33 | 0.62 |
| Ex. (200) | P2-88 | 5.5 | 11.2 | 5000 | 44.8 | 124.7 | 0.33 | 0.61 |
| Ex. (201) | P2-89 | 5.5 | 14.0 | 5000 | 35.6 | 124.6 | 0.33 | 0.61 |
| Ex. (202) | P2-90 | 5.6 | 12.1 | 5000 | 41.3 | 123.6 | 0.33 | 0.62 |
| Ex. (203) | P2-91 | 5.5 | 12.9 | 5000 | 38.6 | 124.9 | 0.33 | 0.62 |
| Ex. (204) | P2-92 | 5.5 | 12.1 | 5000 | 41.4 | 123.5 | 0.33 | 0.62 |
| Ex. (205) | P2-93 | 5.6 | 13.9 | 5000 | 36.1 | 125.3 | 0.33 | 0.62 |
| Ex. (206) | P2-94 | 5.6 | 12.0 | 5000 | 41.7 | 129.7 | 0.33 | 0.61 |
| Ex. (207) | P2-95 | 5.6 | 12.2 | 5000 | 40.9 | 127.7 | 0.33 | 0.61 |
| Ex. (208) | P2-96 | 5.4 | 12.3 | 5000 | 40.6 | 129.2 | 0.33 | 0.61 |
| Ex. (209) | P2-97 | 5.5 | 13.3 | 5000 | 37.5 | 123.6 | 0.33 | 0.62 |
| Ex. (210) | P2-98 | 5.5 | 12.3 | 5000 | 40.8 | 125.7 | 0.33 | 0.62 |
| Ex. (211) | P2-99 | 5.5 | 13.8 | 5000 | 36.4 | 127.0 | 0.33 | 0.62 |
| Ex. (212) | P2-100 | 5.5 | 11.3 | 5000 | 44.2 | 122.1 | 0.33 | 0.61 |
| Ex. (213) | P2-101 | 5.5 | 11.9 | 5000 | 42.2 | 123.2 | 0.33 | 0.61 |
| Ex. (214) | P2-102 | 5.5 | 13.8 | 5000 | 36.3 | 123.6 | 0.33 | 0.61 |
| Ex. (215) | P2-103 | 5.6 | 12.0 | 5000 | 41.7 | 127.1 | 0.33 | 0.62 |
| Ex. (216) | P2-104 | 5.5 | 14.2 | 5000 | 35.2 | 128.9 | 0.33 | 0.61 |
| Ex. (217) | P2-105 | 5.5 | 11.2 | 5000 | 44.5 | 123.7 | 0.33 | 0.62 |
| Ex. (218) | P2-106 | 5.5 | 12.3 | 5000 | 40.7 | 123.1 | 0.33 | 0.62 |
| Ex. (219) | P2-107 | 5.6 | 13.0 | 5000 | 38.4 | 126.8 | 0.33 | 0.61 |
| Ex. (220) | P2-108 | 5.5 | 12.2 | 5000 | 40.9 | 123.5 | 0.33 | 0.62 |
| Ex. (221) | P2-109 | 5.4 | 11.8 | 5000 | 42.2 | 127.2 | 0.33 | 0.62 |
| Ex. (222) | P2-110 | 5.4 | 11.2 | 5000 | 44.8 | 129.2 | 0.33 | 0.61 |
| Ex. (223) | P2-111 | 5.5 | 12.0 | 5000 | 41.6 | 126.7 | 0.33 | 0.61 |
| Ex. (224) | P2-112 | 5.6 | 13.8 | 5000 | 36.2 | 128.8 | 0.33 | 0.61 |
| Ex. (225) | P3-1 | 5.3 | 12.3 | 5000.0 | 40.6 | 122.4 | 0.33 | 0.62 |
| Ex. (226) | P3-2 | 5.3 | 12.3 | 5000.0 | 40.7 | 121.4 | 0.33 | 0.61 |
| Ex. (227) | P3-3 | 5.5 | 12.3 | 5000.0 | 40.7 | 125.4 | 0.33 | 0.61 |
| Ex. (228) | P3-4 | 5.5 | 12.0 | 5000.0 | 41.6 | 120.2 | 0.33 | 0.61 |
| Ex. (229) | P3-5 | 5.5 | 12.3 | 5000.0 | 40.6 | 128.0 | 0.33 | 0.62 |
| Ex. (230) | P3-6 | 5.4 | 11.6 | 5000.0 | 43.0 | 127.6 | 0.33 | 0.62 |
| Ex. (231) | P3-7 | 5.4 | 11.8 | 5000.0 | 42.4 | 121.7 | 0.33 | 0.61 |
| Ex. (232) | P3-8 | 5.5 | 12.3 | 5000.0 | 40.5 | 120.2 | 0.33 | 0.62 |
| Ex. (233) | P3-9 | 5.3 | 12.1 | 5000.0 | 41.4 | 120.7 | 0.33 | 0.61 |
| Ex. (234) | P3-10 | 5.4 | 12.3 | 5000.0 | 40.7 | 120.4 | 0.33 | 0.62 |
| Ex. (235) | P3-11 | 5.5 | 11.7 | 5000.0 | 42.9 | 122.2 | 0.33 | 0.61 |
| Ex. (236) | P3-12 | 5.4 | 12.3 | 5000.0 | 40.8 | 122.1 | 0.33 | 0.61 |
| Ex. (237) | P3-13 | 5.4 | 12.4 | 5000.0 | 40.2 | 129.2 | 0.33 | 0.61 |
| Ex. (238) | P3-14 | 5.4 | 11.8 | 5000.0 | 42.5 | 120.0 | 0.33 | 0.62 |
| Ex. (239) | P3-15 | 5.4 | 12.0 | 5000.0 | 41.7 | 127.8 | 0.33 | 0.61 |
| Ex. (240) | P3-16 | 5.4 | 12.3 | 5000.0 | 40.5 | 128.2 | 0.33 | 0.61 |
| Ex. (241) | P3-17 | 5.4 | 12.5 | 5000.0 | 39.9 | 129.1 | 0.33 | 0.62 |
| Ex. (242) | P3-18 | 5.5 | 12.4 | 5000.0 | 40.3 | 129.0 | 0.33 | 0.61 |
| Ex. (243) | P3-19 | 5.3 | 12.4 | 5000.0 | 40.4 | 125.8 | 0.33 | 0.62 |
| Ex. (244) | P3-20 | 5.5 | 12.5 | 5000.0 | 40.0 | 124.4 | 0.33 | 0.62 |
| Ex. (245) | P3-21 | 5.3 | 12.6 | 5000.0 | 39.8 | 126.3 | 0.33 | 0.61 |
| Ex. (246) | P3-22 | 5.3 | 12.4 | 5000.0 | 40.5 | 121.9 | 0.33 | 0.62 |
| Ex. (247) | P3-23 | 5.4 | 12.4 | 5000.0 | 40.4 | 127.9 | 0.33 | 0.62 |
| Ex. (248) | P3-24 | 5.3 | 12.3 | 5000.0 | 40.6 | 126.8 | 0.33 | 0.62 |
| Ex. (249) | P3-25 | 5.4 | 12.9 | 5000.0 | 38.8 | 123.4 | 0.33 | 0.62 |
| Ex. (250) | P3-26 | 5.3 | 12.5 | 5000.0 | 39.9 | 124.8 | 0.33 | 0.61 |

TABLE 4-continued

|  | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (251) | P3-27 | 5.4 | 12.7 | 5000.0 | 39.2 | 124.7 | 0.33 | 0.61 |
| Ex. (252) | P3-28 | 5.4 | 13.1 | 5000.0 | 38.3 | 120.6 | 0.33 | 0.61 |
| Ex. (253) | P3-29 | 5.4 | 12.9 | 5000.0 | 38.7 | 121.0 | 0.33 | 0.62 |
| Ex. (254) | P3-30 | 5.5 | 12.6 | 5000.0 | 39.7 | 122.2 | 0.33 | 0.62 |
| Ex. (255) | P3-31 | 5.3 | 13.1 | 5000.0 | 38.1 | 127.3 | 0.33 | 0.62 |
| Ex. (256) | P3-32 | 5.3 | 12.9 | 5000.0 | 38.8 | 129.0 | 0.33 | 0.61 |

It can be seen from the results in Table 4 above, that the OLEDs employing the inventive compounds as hole transport layer materials showed predominantly improved efficiency and lifespan, compared to the OLEDs employing comparative compound 1 as a hole transport layer material.

Also, in the OLEDs using comparative compounds 2 to 4 as hole transport layer materials, the compounds having carbazole as core as the structure in the present invention, the organic element having a compound where a linker is linked to 3-position of the carbazole core ('Com. Ex(2)') showed decreased efficiency yet increased life span, compared to the organic element having a compound where a linker is linked to 2-position of the carbazole moiety ('Com. Ex(3) and 'Com. Ex(4)'). Also, the organic element of Com. Ex(4) having a non-linear linker showed increased efficiency, compared to the organic element of Com. Ex(3) having a linear linker to 2-position of the carbazole moiety.

From the result in Table 4, it is seen that the organic element using as a hole transport layer material, the compound of the present invention wherein the linker biphenyl is linked linear to the carbazole derivative and an amine group is linked on meta- or ortho-position of the biphenyl, showed high efficiency, compared to the organic element of Com. Ex (4) wherein the amine groups are linked to biphenyl on para-position and the linker is linked non-linear.

In addition, the compounds of the present invention in P2 type (P2-1 to P2-112; the type where the amine group is linked on ortho position of the linker biphenyl) have high efficiency and long life span as compared to the compounds of the present invention in P1 type (P1-1 to P1-112; the type where the amine group is linked on meta position of the linker biphenyl).

These results are believed to come from that in a compound where the linker is linked on 2-position of the carbazole core, the conjugation length gets shorter than in a compound where the linker is linked on 3-position of the carbazole core, and the band gap gets widened and the HOMO value gets deepen. Also, where an amine group is linked on meta- or ortho-position of the linker, the bonding angle gets decreased than in a case where it is linked on para-position, and the T1 values get higher to improve the electron blocking abilities, and as a result the exciton is more easily produced to improve efficiency and lengthen lifespan.

Considering the characteristics (deep HOMO energy level, high T1 value, heat-stability) described above together, it can be seen that the band gap and electrical properties, as well as the surface properties can change much depending on the linking position of the carbazole core and the amine, which can be main factors in improving performance of the organic electric elements.

Furthermore, properties from the hole transport layer should be considered in relation with the light emitting layer (host), and one skilled in the art, even using a similar core compound, would have difficulty in inferring the characteristics shown by the hole transport layer using the compound of the present invention.

[Example 257] An Emission-Auxiliary Layer (Red)

Organic light emitting diodes (OLEDs) were fabricated according to a conventional method by using a compound of the present invention as an emission-auxiliary layer material.

First, an ITO layer (anode) was formed on a glass substrate, and a film of 2-TNATA was vacuum-deposited on the ITO layer to form a hole injection layer with a thickness of 60 nm. Subsequently, N,N'-Bis(1-naphthalenyl)-N,N'-bis-phenyl-(1,1'-biphenyl)-4,4'-diamine ("NPD") was vacuum-deposited with a thickness of 60 nm on the hole injection layer to form a hole transport layer.

Subsequently, a film of the compound P1-1 of the present invention was vacuum-deposited on the hole transport layer to form a emission-auxiliary layer with a thickness of 20 nm.

A light emitting layer with a thickness of 30 nm was deposited on the emission-auxiliary layer by using the CBP as a host material and bis-(1-phenylisoquinolyl)iridium(III) acetylacetonate ("(piq)$_2$Ir(acac)") as a dopant material in a weight ratio of 95:5.

Next, a film of BAlq was vacuum-deposited with a thickness of 10 nm on the light emitting layer to form a hole blocking layer, and a film of Alq$_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 258] to [Example 346] An Emission-Auxiliary Layer (Red)

The OLED was manufactured in the same manner as described in Test Example 257, except that any one of the compounds P1-2 to P1-16, P1-63, P1-64, P1-101 to P1-108, P2-1 to P2-20, P2-45 to P2-52, P2-61 to P2-64, P3-1 to P3-32 of the present invention in the Table 5 below was used as the emission-auxiliary layer material, instead of the inventive compound P1-1.

Comparative Example 5

An OLED was manufactured in the same manner as described in Test Example 257, except that Comparative Compound 2 above was used as the emission-auxiliary layer material, instead of the inventive compound P1-1.

Comparative Example 6

An OLED was manufactured in the same manner as described in Test Example 257, except that Comparative Compound 3 above was used as the emission-auxiliary layer material, instead of the inventive compound P1-1.

Comparative Example 7

An OLED was manufactured in the same manner as described in Test Example 257, except that Comparative Compound 4 above was used as the emission-auxiliary layer material, instead of the inventive compound P1-1.

Comparative Example 8

An OLED was manufactured in the same manner as described in Test Example 257, except not to form the emission-auxiliary layer.

A forward bias DC voltage was applied to each of the OLEDs manufactured through Test Examples 257 to 346 and Comparative Example 5 to 8, and electro-luminescence (EL) characteristics of the OLED were measured by PR-650 (Photoresearch). Also, T95 life span was measured by life span measuring equipment (Mcscience) at a reference brightness of 2500 cd/m². Table 5 below shows evaluation results of OLEDs manufactured Test Examples and Comparative Examples.

TABLE 5

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Com. Ex (5) | Com.Com (2) | 5.9 | 29.0 | 2500.0 | 8.6 | 102.0 | 0.65 | 0.31 |
| Com. Ex (6) | Com.Com (3) | 6.0 | 28.1 | 2500.0 | 8.9 | 111.2 | 0.64 | 0.34 |
| Com. Ex (7) | Com.Com (4) | 6.1 | 27.5 | 2500.0 | 9.1 | 116.0 | 0.66 | 0.33 |
| Com. Ex (8) | — | 5.7 | 34.2 | 2500.0 | 7.3 | 51.5 | 0.64 | 0.31 |
| Ex. (257) | P1-1 | 5.8 | 23.8 | 2500.0 | 10.5 | 134.4 | 0.64 | 0.32 |
| Ex. (258) | P1-2 | 5.8 | 20.2 | 2500.0 | 12.4 | 132.9 | 0.65 | 0.31 |
| Ex. (259) | P1-3 | 5.8 | 23.7 | 2500.0 | 10.6 | 125.8 | 0.66 | 0.32 |
| Ex. (260) | P1-4 | 5.9 | 22.7 | 2500.0 | 11.0 | 130.5 | 0.66 | 0.30 |
| Ex. (261) | P1-5 | 6.1 | 20.2 | 2500.0 | 12.4 | 126.8 | 0.66 | 0.32 |
| Ex. (262) | P1-6 | 6.0 | 24.5 | 2500.0 | 10.2 | 128.8 | 0.64 | 0.30 |
| Ex. (263) | P1-7 | 6.0 | 22.4 | 2500.0 | 11.2 | 132.6 | 0.66 | 0.33 |
| Ex. (264) | P1-8 | 6.0 | 24.8 | 2500.0 | 10.1 | 127.4 | 0.65 | 0.30 |
| Ex. (265) | P1-9 | 5.9 | 20.0 | 2500.0 | 12.5 | 131.9 | 0.65 | 0.31 |
| Ex. (266) | P1-10 | 6.0 | 21.7 | 2500.0 | 11.5 | 128.6 | 0.66 | 0.33 |
| Ex. (267) | P1-11 | 5.9 | 23.9 | 2500.0 | 10.5 | 134.5 | 0.65 | 0.32 |
| Ex. (268) | P1-12 | 6.2 | 21.4 | 2500.0 | 11.7 | 130.6 | 0.65 | 0.30 |
| Ex. (269) | P1-13 | 6.0 | 19.6 | 2500.0 | 12.8 | 129.4 | 0.65 | 0.34 |
| Ex. (270) | P1-14 | 5.9 | 19.7 | 2500.0 | 12.7 | 130.7 | 0.64 | 0.34 |
| Ex. (271) | P1-15 | 6.0 | 19.3 | 2500.0 | 13.0 | 128.9 | 0.64 | 0.31 |
| Ex. (272) | P1-16 | 6.0 | 22.3 | 2500.0 | 11.2 | 129.2 | 0.65 | 0.32 |
| Ex. (273) | P1-63 | 6.2 | 23.3 | 2500.0 | 10.7 | 127.7 | 0.65 | 0.30 |
| Ex. (274) | P1-64 | 6.2 | 21.4 | 2500.0 | 11.7 | 129.9 | 0.66 | 0.32 |
| Ex. (275) | P1-101 | 5.9 | 23.6 | 2500.0 | 10.6 | 131.2 | 0.64 | 0.31 |
| Ex. (276) | P1-102 | 6.1 | 20.9 | 2500.0 | 11.9 | 131.9 | 0.66 | 0.31 |
| Ex. (277) | P1-103 | 6.2 | 19.7 | 2500.0 | 12.7 | 128.7 | 0.65 | 0.30 |
| Ex. (278) | P1-104 | 6.1 | 19.6 | 2500.0 | 12.7 | 133.2 | 0.64 | 0.31 |
| Ex. (279) | P1-105 | 5.8 | 21.3 | 2500.0 | 11.7 | 132.5 | 0.64 | 0.31 |
| Ex. (280) | P1-106 | 5.9 | 21.8 | 2500.0 | 11.5 | 126.6 | 0.65 | 0.33 |
| Ex. (281) | P1-107 | 6.1 | 23.0 | 2500.0 | 10.9 | 132.3 | 0.65 | 0.34 |
| Ex. (282) | P1-108 | 5.9 | 21.9 | 2500.0 | 11.4 | 129.2 | 0.64 | 0.31 |
| Ex. (283) | P2-1 | 5.8 | 15.5 | 2500.0 | 16.1 | 145.2 | 0.65 | 0.31 |
| Ex. (284) | P2-2 | 6.1 | 16.3 | 2500.0 | 15.3 | 140.7 | 0.65 | 0.31 |
| Ex. (285) | P2-3 | 5.8 | 15.0 | 2500.0 | 16.7 | 145.2 | 0.65 | 0.33 |
| Ex. (286) | P2-4 | 6.2 | 16.0 | 2500.0 | 15.6 | 135.3 | 0.66 | 0.31 |
| Ex. (287) | P2-5 | 6.0 | 17.7 | 2500.0 | 14.2 | 130.8 | 0.64 | 0.33 |
| Ex. (288) | P2-6 | 5.9 | 17.1 | 2500.0 | 14.6 | 137.4 | 0.64 | 0.31 |
| Ex. (289) | P2-7 | 6.1 | 15.7 | 2500.0 | 15.9 | 146.9 | 0.64 | 0.31 |
| Ex. (290) | P2-8 | 6.0 | 16.3 | 2500.0 | 15.4 | 141.0 | 0.65 | 0.30 |
| Ex. (291) | P2-9 | 5.8 | 17.5 | 2500.0 | 14.3 | 134.0 | 0.65 | 0.34 |
| Ex. (292) | P2-10 | 6.1 | 15.7 | 2500.0 | 16.0 | 141.1 | 0.66 | 0.33 |
| Ex. (293) | P2-11 | 6.0 | 15.0 | 2500.0 | 16.7 | 148.1 | 0.66 | 0.31 |
| Ex. (294) | P2-12 | 5.9 | 14.8 | 2500.0 | 16.9 | 137.9 | 0.65 | 0.31 |
| Ex. (295) | P2-13 | 6.0 | 15.6 | 2500.0 | 16.1 | 139.2 | 0.66 | 0.32 |
| Ex. (296) | P2-14 | 6.1 | 17.6 | 2500.0 | 14.2 | 143.1 | 0.65 | 0.33 |
| Ex. (297) | P2-15 | 6.2 | 15.6 | 2500.0 | 16.0 | 138.7 | 0.65 | 0.33 |
| Ex. (298) | P2-16 | 5.8 | 16.5 | 2500.0 | 15.2 | 133.5 | 0.65 | 0.32 |
| Ex. (299) | P2-17 | 6.1 | 17.2 | 2500.0 | 14.5 | 148.7 | 0.65 | 0.31 |
| Ex. (300) | P2-18 | 6.2 | 17.5 | 2500.0 | 14.3 | 148.3 | 0.64 | 0.30 |
| Ex. (301) | P2-19 | 6.1 | 15.8 | 2500.0 | 15.9 | 146.7 | 0.65 | 0.33 |
| Ex. (302) | P2-20 | 5.9 | 14.8 | 2500.0 | 16.9 | 135.8 | 0.66 | 0.31 |
| Ex. (303) | P2-45 | 5.9 | 15.4 | 2500.0 | 16.2 | 140.8 | 0.64 | 0.31 |
| Ex. (304) | P2-46 | 5.9 | 17.3 | 2500.0 | 14.4 | 149.0 | 0.66 | 0.30 |

TABLE 5-continued

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex. (305) | P2-47 | 6.0 | 15.7 | 2500.0 | 15.9 | 136.9 | 0.65 | 0.31 |
| Ex. (306) | P2-48 | 6.1 | 17.3 | 2500.0 | 14.4 | 133.7 | 0.66 | 0.30 |
| Ex. (307) | P2-49 | 6.1 | 16.1 | 2500.0 | 15.5 | 131.9 | 0.65 | 0.33 |
| Ex. (308) | P2-50 | 6.0 | 15.6 | 2500.0 | 16.1 | 138.8 | 0.66 | 0.34 |
| Ex. (309) | P2-51 | 6.2 | 16.7 | 2500.0 | 15.0 | 146.9 | 0.66 | 0.31 |
| Ex. (310) | P2-52 | 6.2 | 16.3 | 2500.0 | 15.3 | 130.8 | 0.65 | 0.34 |
| Ex. (311) | P2-61 | 6.1 | 17.6 | 2500.0 | 14.2 | 148.1 | 0.65 | 0.32 |
| Ex. (312) | P2-62 | 5.9 | 15.6 | 2500.0 | 16.1 | 137.0 | 0.65 | 0.32 |
| Ex. (313) | P2-63 | 6.2 | 17.7 | 2500.0 | 14.1 | 141.9 | 0.64 | 0.30 |
| Ex. (314) | P2-64 | 6.2 | 15.1 | 2500.0 | 16.6 | 139.1 | 0.66 | 0.32 |
| Ex. (315) | P3-1 | 5.6 | 13.2 | 2500.0 | 19.0 | 150.9 | 0.64 | 0.32 |
| Ex. (316) | P3-2 | 5.6 | 13.0 | 2500.0 | 19.2 | 150.7 | 0.65 | 0.31 |
| Ex. (317) | P3-3 | 5.6 | 13.1 | 2500.0 | 19.0 | 153.0 | 0.66 | 0.32 |
| Ex. (318) | P3-4 | 5.6 | 12.5 | 2500.0 | 19.9 | 151.4 | 0.66 | 0.30 |
| Ex. (319) | P3-5 | 5.6 | 12.8 | 2500.0 | 19.6 | 150.2 | 0.66 | 0.32 |
| Ex. (320) | P3-6 | 5.6 | 12.8 | 2500.0 | 19.6 | 152.9 | 0.64 | 0.30 |
| Ex. (321) | P3-7 | 5.5 | 14.1 | 2500.0 | 17.8 | 152.0 | 0.66 | 0.33 |
| Ex. (322) | P3-8 | 5.7 | 13.3 | 2500.0 | 18.8 | 151.1 | 0.65 | 0.30 |
| Ex. (323) | P3-9 | 5.7 | 12.7 | 2500.0 | 19.6 | 150.8 | 0.65 | 0.31 |
| Ex. (324) | P3-10 | 5.7 | 13.8 | 2500.0 | 18.1 | 150.2 | 0.66 | 0.33 |
| Ex. (325) | P3-11 | 5.5 | 13.1 | 2500.0 | 19.1 | 151.4 | 0.65 | 0.32 |
| Ex. (326) | P3-12 | 5.7 | 14.4 | 2500.0 | 17.4 | 150.7 | 0.65 | 0.30 |
| Ex. (327) | P3-13 | 5.5 | 13.5 | 2500.0 | 18.6 | 151.6 | 0.65 | 0.34 |
| Ex. (328) | P3-14 | 5.7 | 14.0 | 2500.0 | 17.9 | 152.3 | 0.64 | 0.34 |
| Ex. (329) | P3-15 | 5.6 | 13.4 | 2500.0 | 18.7 | 150.6 | 0.64 | 0.31 |
| Ex. (330) | P3-16 | 5.6 | 12.8 | 2500.0 | 19.5 | 152.0 | 0.65 | 0.32 |
| Ex. (331) | P3-17 | 5.7 | 13.1 | 2500.0 | 19.1 | 152.4 | 0.65 | 0.30 |
| Ex. (332) | P3-18 | 5.6 | 13.2 | 2500.0 | 19.0 | 150.2 | 0.66 | 0.32 |
| Ex. (333) | P3-19 | 5.6 | 13.0 | 2500.0 | 19.3 | 150.3 | 0.64 | 0.31 |
| Ex. (334) | P3-20 | 5.5 | 12.9 | 2500.0 | 19.4 | 150.0 | 0.66 | 0.31 |
| Ex. (335) | P3-21 | 5.5 | 14.2 | 2500.0 | 17.6 | 150.0 | 0.65 | 0.30 |
| Ex. (336) | P3-22 | 5.6 | 13.1 | 2500.0 | 19.0 | 152.6 | 0.64 | 0.31 |
| Ex. (337) | P3-23 | 5.7 | 13.6 | 2500.0 | 18.3 | 151.0 | 0.64 | 0.31 |
| Ex. (338) | P3-24 | 5.6 | 13.6 | 2500.0 | 18.4 | 151.6 | 0.65 | 0.33 |
| Ex. (339) | P3-25 | 5.6 | 13.3 | 2500.0 | 18.8 | 151.1 | 0.65 | 0.34 |
| Ex. (340) | P3-26 | 5.6 | 13.9 | 2500.0 | 18.0 | 152.9 | 0.64 | 0.31 |
| Ex. (341) | P3-27 | 5.7 | 13.3 | 2500.0 | 18.9 | 150.7 | 0.65 | 0.31 |
| Ex. (342) | P3-28 | 5.5 | 12.7 | 2500.0 | 19.7 | 152.6 | 0.65 | 0.31 |
| Ex. (343) | P3-29 | 5.5 | 13.8 | 2500.0 | 18.2 | 152.2 | 0.65 | 0.33 |
| Ex. (344) | P3-30 | 5.7 | 14.4 | 2500.0 | 17.4 | 151.9 | 0.66 | 0.31 |
| Ex. (345) | P3-31 | 5.7 | 12.7 | 2500.0 | 19.6 | 150.9 | 0.64 | 0.33 |
| Ex. (346) | P3-32 | 5.6 | 12.5 | 2500.0 | 20.0 | 152.9 | 0.64 | 0.31 |
| Ex. (347) | P3-33 | 5.5 | 12.9 | 2500.0 | 19.4 | 151.1 | 0.64 | 0.31 |
| Ex. (348) | P3-34 | 5.6 | 13.7 | 2500.0 | 18.2 | 152.6 | 0.65 | 0.30 |
| Ex. (349) | P3-35 | 5.5 | 13.4 | 2500.0 | 18.7 | 152.7 | 0.65 | 0.34 |
| Ex. (350) | P3-36 | 5.7 | 13.6 | 2500.0 | 18.4 | 152.1 | 0.66 | 0.33 |

[Example 351] An Emission-Auxiliary Layer (Green)

Organic light emitting diodes (OLEDs) were fabricated according to a conventional method by using a compound of the present invention as an emission-auxiliary layer material First, an ITO layer (anode) was formed on a glass substrate, and a film of 2-TNATA was vacuum-deposited on the ITO layer to form a hole injection layer with a thickness of 60 nm. Subsequently, NPD was vacuum-deposited with a thickness of 60 nm on the hole injection layer to form a hole transport layer.

Subsequently, a film of the compound P1-21 of the present invention was vacuum-deposited on the hole transport layer to form a emission-auxiliary layer with a thickness of 20 nm. A light emitting layer with a thickness of 30 nm was deposited on the emission-auxiliary layer by using the CBP as a host material and Ir(ppy)$_3$ as a dopant material in a weight ratio of 95:5.

Next, a film of BAlq was vacuum-deposited with a thickness of 10 nm on the light emitting layer to form a hole blocking layer, and a film of Alq$_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 352] to [Example 390] An Emission-Auxiliary Layer (Green)

The OLED was manufactured in the same manner as described in Test Example 351, except that any one of the compounds P1-22 to P1-38, P3-1 to P3-10, and P3-17 to P3-28 of the present invention in the Table 6 below was used as the emission-auxiliary layer material, instead of the inventive compound P1-21.

Comparative Example 9

An OLED was manufactured in the same manner as described in Test Example 351, except that Comparative Compound 2 above was used as the emission-auxiliary layer material, instead of the inventive compound P1-21.

Comparative Example 10

An OLED was manufactured in the same manner as described in Test Example 351, except that Comparative Compound 3 above was used as the emission-auxiliary layer material, instead of the inventive compound P1-21.

Comparative Example 11

An OLED was manufactured in the same manner as described in Test Example 351, except that Comparative Compound 4 above was used as the emission-auxiliary layer material, instead of the inventive compound P1-21.

Comparative Example 12

An OLED was manufactured in the same manner as described in Test Example 351, except not to form the emission-auxiliary layer.

A forward bias DC voltage was applied to each of the OLEDs manufactured through Test Examples 351 to 390 and Comparative Example 9 to 12, and electro-luminescence (EL) characteristics of the OLED were measured by PR-650 (Photoresearch). Also, T95 life span was measured by life span measuring equipment (Mcscience) at a reference brightness of 5000 cd/m$^2$. Table 6 below shows evaluation results of OLEDs manufactured Test Examples and Comparative Examples.

TABLE 6

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Com. Ex (9) | Com. Com (2) | 5.9 | 13.6 | 5000.0 | 36.8 | 116.9 | 0.33 | 0.61 |
| Com. Ex (10) | Com. Com (3) | 6.0 | 12.3 | 5000.0 | 40.5 | 118.7 | 0.33 | 0.61 |
| Com. Ex (11) | Com. Com (4) | 6.3 | 11.6 | 5000.0 | 43.2 | 124.5 | 0.33 | 0.61 |
| Com. Ex (12) | — | 5.8 | 17.9 | 5000.0 | 27.9 | 68.2 | 0.33 | 0.62 |
| Ex. (351) | P1-21 | 5.8 | 11.2 | 5000 | 44.8 | 136.1 | 0.33 | 0.62 |
| Ex. (352) | P1-22 | 5.6 | 10.9 | 5000 | 45.7 | 133.7 | 0.33 | 0.62 |
| Ex. (353) | P1-23 | 5.9 | 11.0 | 5000 | 45.3 | 137.4 | 0.33 | 0.61 |
| Ex. (354) | P1-24 | 5.9 | 11.5 | 5000 | 43.5 | 142.6 | 0.33 | 0.61 |
| Ex. (355) | P1-25 | 6.0 | 11.0 | 5000 | 45.6 | 133.8 | 0.33 | 0.62 |
| Ex. (356) | P1-26 | 5.7 | 11.2 | 5000 | 44.5 | 137.2 | 0.33 | 0.61 |
| Ex. (357) | P1-27 | 5.7 | 10.7 | 5000 | 46.7 | 133.7 | 0.33 | 0.62 |
| Ex. (358) | P1-28 | 5.9 | 11.4 | 5000 | 43.8 | 134.5 | 0.33 | 0.62 |
| Ex. (359) | P1-29 | 5.8 | 10.2 | 5000 | 49.0 | 133.9 | 0.33 | 0.62 |
| Ex. (360) | P1-30 | 5.8 | 11.2 | 5000 | 44.7 | 137.7 | 0.33 | 0.61 |
| Ex. (361) | P1-31 | 5.8 | 11.3 | 5000 | 44.1 | 136.3 | 0.33 | 0.62 |
| Ex. (362) | P1-32 | 5.7 | 11.2 | 5000 | 44.7 | 137.7 | 0.33 | 0.61 |
| Ex. (363) | P1-33 | 5.7 | 11.1 | 5000 | 45.2 | 134.6 | 0.33 | 0.62 |
| Ex. (364) | P1-34 | 5.7 | 11.2 | 5000 | 44.5 | 144.1 | 0.33 | 0.61 |
| Ex. (365) | P1-35 | 5.8 | 10.0 | 5000 | 49.8 | 141.4 | 0.33 | 0.61 |
| Ex. (366) | P1-36 | 6.0 | 10.7 | 5000 | 46.8 | 142.9 | 0.33 | 0.62 |
| Ex. (367) | P1-37 | 5.9 | 11.2 | 5000 | 44.8 | 133.9 | 0.33 | 0.61 |
| Ex. (368) | P1-38 | 6.0 | 11.6 | 5000 | 43.3 | 133.5 | 0.33 | 0.61 |
| Ex. (369) | P1-39 | 5.7 | 11.4 | 5000 | 43.8 | 142.1 | 0.33 | 0.62 |
| Ex. (370) | P1-40 | 5.6 | 10.1 | 5000 | 49.4 | 144.1 | 0.33 | 0.61 |
| Ex. (371) | P1-41 | 5.7 | 10.8 | 5000 | 46.4 | 134.9 | 0.33 | 0.61 |
| Ex. (372) | P1-42 | 5.8 | 10.7 | 5000 | 46.7 | 143.7 | 0.33 | 0.62 |
| Ex. (373) | P1-43 | 5.9 | 11.4 | 5000 | 43.9 | 133.6 | 0.33 | 0.61 |
| Ex. (374) | P1-44 | 5.8 | 10.8 | 5000 | 46.2 | 137.7 | 0.33 | 0.62 |
| Ex. (375) | P1-77 | 5.7 | 10.2 | 5000 | 48.9 | 133.1 | 0.33 | 0.62 |
| Ex. (376) | P1-78 | 5.9 | 10.9 | 5000 | 45.9 | 144.6 | 0.33 | 0.61 |
| Ex. (377) | P1-79 | 5.8 | 10.3 | 5000 | 48.6 | 140.3 | 0.33 | 0.61 |
| Ex. (378) | P1-80 | 5.6 | 10.4 | 5000 | 47.9 | 143.2 | 0.33 | 0.61 |
| Ex. (379) | P1-81 | 5.9 | 10.7 | 5000 | 46.7 | 142.3 | 0.33 | 0.62 |
| Ex. (380) | P1-82 | 5.8 | 10.2 | 5000 | 49.1 | 134.4 | 0.33 | 0.62 |
| Ex. (381) | P1-83 | 5.7 | 11.1 | 5000 | 45.0 | 139.9 | 0.33 | 0.61 |
| Ex. (382) | P1-84 | 5.9 | 11.4 | 5000 | 43.9 | 142.2 | 0.33 | 0.62 |
| Ex. (383) | P1-85 | 5.7 | 10.9 | 5000 | 45.7 | 144.2 | 0.33 | 0.61 |
| Ex. (384) | P1-86 | 5.8 | 10.0 | 5000 | 49.8 | 135.5 | 0.33 | 0.61 |
| Ex. (385) | P1-87 | 5.9 | 11.3 | 5000 | 44.4 | 133.6 | 0.33 | 0.61 |
| Ex. (386) | P1-88 | 5.9 | 11.0 | 5000 | 45.4 | 133.9 | 0.33 | 0.62 |
| Ex. (387) | P1-89 | 5.8 | 10.6 | 5000 | 47.1 | 133.8 | 0.33 | 0.62 |
| Ex. (388) | P1-90 | 5.8 | 10.2 | 5000 | 48.8 | 135.4 | 0.33 | 0.61 |
| Ex. (389) | P1-91 | 6.0 | 11.1 | 5000 | 44.9 | 136.8 | 0.33 | 0.61 |
| Ex. (390) | P1-92 | 5.8 | 10.5 | 5000 | 47.4 | 142.9 | 0.33 | 0.61 |
| Ex. (384) | P1-93 | 5.9 | 10.3 | 5000 | 48.6 | 134.4 | 0.33 | 0.62 |
| Ex. (385) | P1-94 | 5.7 | 10.0 | 5000 | 49.8 | 135.4 | 0.33 | 0.62 |
| Ex. (386) | P1-95 | 5.8 | 10.9 | 5000 | 46.0 | 135.1 | 0.33 | 0.62 |
| Ex. (387) | P1-96 | 5.8 | 10.4 | 5000 | 48.2 | 140.3 | 0.33 | 0.62 |
| Ex. (388) | P1-97 | 5.7 | 10.3 | 5000 | 48.5 | 138.2 | 0.33 | 0.62 |
| Ex. (389) | P1-98 | 5.9 | 11.3 | 5000 | 44.4 | 143.0 | 0.33 | 0.62 |
| Ex. (390) | P1-99 | 5.7 | 11.5 | 5000 | 43.6 | 135.3 | 0.33 | 0.62 |
| Ex. (391) | P1-100 | 5.8 | 10.6 | 5000 | 47.1 | 144.9 | 0.33 | 0.61 |
| Ex. (392) | P1-101 | 5.8 | 11.0 | 5000 | 45.5 | 136.8 | 0.33 | 0.62 |
| Ex. (393) | P1-102 | 5.7 | 10.2 | 5000 | 49.1 | 135.2 | 0.33 | 0.62 |

TABLE 6-continued

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex. (394) | P1-103 | 5.9 | 10.2 | 5000 | 48.9 | 140.2 | 0.33 | 0.61 |
| Ex. (395) | P1-104 | 5.8 | 10.7 | 5000 | 46.9 | 139.3 | 0.33 | 0.62 |
| Ex. (396) | P1-105 | 5.7 | 10.7 | 5000 | 46.7 | 144.1 | 0.33 | 0.62 |
| Ex. (397) | P1-106 | 5.8 | 10.7 | 5000 | 46.8 | 143.3 | 0.33 | 0.61 |
| Ex. (398) | P1-107 | 5.6 | 10.7 | 5000 | 46.7 | 139.6 | 0.33 | 0.62 |
| Ex. (399) | P1-108 | 5.7 | 10.1 | 5000 | 49.3 | 143.3 | 0.33 | 0.62 |
| Ex. (400) | P1-109 | 5.9 | 10.3 | 5000 | 48.5 | 143.3 | 0.33 | 0.62 |
| Ex. (401) | P1-110 | 5.8 | 11.6 | 5000 | 43.3 | 134.3 | 0.33 | 0.61 |
| Ex. (402) | P1-111 | 5.9 | 10.5 | 5000 | 47.7 | 133.3 | 0.33 | 0.61 |
| Ex. (403) | P1-112 | 5.9 | 10.9 | 5000 | 45.7 | 133.0 | 0.33 | 0.62 |
| Ex. (404) | P2-21 | 5.7 | 10.1 | 5000 | 49.7 | 147.5 | 0.33 | 0.61 |
| Ex. (405) | P2-22 | 5.6 | 9.9 | 5000 | 50.3 | 140.3 | 0.33 | 0.61 |
| Ex. (406) | P2-23 | 5.8 | 9.3 | 5000 | 53.7 | 141.1 | 0.33 | 0.61 |
| Ex. (407) | P2-24 | 5.7 | 9.8 | 5000 | 51.3 | 150.1 | 0.33 | 0.61 |
| Ex. (408) | P2-25 | 5.8 | 10.1 | 5000 | 49.6 | 143.2 | 0.33 | 0.62 |
| Ex. (409) | P2-26 | 5.8 | 9.8 | 5000 | 51.0 | 140.5 | 0.33 | 0.61 |
| Ex. (410) | P2-27 | 5.7 | 10.4 | 5000 | 48.0 | 145.1 | 0.33 | 0.61 |
| Ex. (411) | P2-28 | 5.9 | 9.7 | 5000 | 51.6 | 149.3 | 0.33 | 0.61 |
| Ex. (412) | P2-29 | 5.9 | 10.0 | 5000 | 49.8 | 142.1 | 0.33 | 0.61 |
| Ex. (413) | P2-30 | 5.9 | 10.1 | 5000 | 49.7 | 150.7 | 0.33 | 0.61 |
| Ex. (414) | P2-31 | 5.6 | 9.3 | 5000 | 53.9 | 141.7 | 0.33 | 0.61 |
| Ex. (415) | P2-32 | 5.6 | 9.7 | 5000 | 51.6 | 144.8 | 0.33 | 0.62 |
| Ex. (416) | P2-33 | 5.8 | 10.3 | 5000 | 48.3 | 148.0 | 0.33 | 0.62 |
| Ex. (417) | P2-34 | 5.9 | 10.1 | 5000 | 49.5 | 139.8 | 0.33 | 0.62 |
| Ex. (418) | P2-35 | 5.9 | 9.4 | 5000 | 53.5 | 143.7 | 0.33 | 0.62 |
| Ex. (419) | P2-36 | 5.7 | 9.9 | 5000 | 50.6 | 140.7 | 0.33 | 0.61 |
| Ex. (420) | P2-37 | 5.8 | 9.9 | 5000 | 50.4 | 148.8 | 0.33 | 0.61 |
| Ex. (421) | P2-38 | 6.0 | 10.2 | 5000 | 49.1 | 150.7 | 0.33 | 0.61 |
| Ex. (422) | P2-39 | 5.7 | 9.4 | 5000 | 53.3 | 147.1 | 0.33 | 0.62 |
| Ex. (423) | P2-40 | 5.8 | 10.3 | 5000 | 48.5 | 138.0 | 0.33 | 0.61 |
| Ex. (424) | P2-41 | 6.0 | 10.3 | 5000 | 48.4 | 145.3 | 0.33 | 0.61 |
| Ex. (425) | P2-42 | 5.7 | 9.6 | 5000 | 51.9 | 151.6 | 0.33 | 0.62 |
| Ex. (426) | P2-43 | 6.0 | 9.6 | 5000 | 52.0 | 143.0 | 0.33 | 0.61 |
| Ex. (427) | P2-44 | 5.9 | 9.7 | 5000 | 51.3 | 149.6 | 0.33 | 0.62 |
| Ex. (428) | P2-77 | 5.7 | 9.1 | 5000 | 55.0 | 146.8 | 0.33 | 0.62 |
| Ex. (429) | P2-78 | 5.6 | 9.6 | 5000 | 52.1 | 140.6 | 0.33 | 0.61 |
| Ex. (430) | P2-79 | 6.0 | 9.7 | 5000 | 51.5 | 148.6 | 0.33 | 0.62 |
| Ex. (431) | P2-80 | 5.7 | 9.7 | 5000 | 51.7 | 142.3 | 0.33 | 0.62 |
| Ex. (432) | P2-81 | 5.8 | 9.6 | 5000 | 52.2 | 144.4 | 0.33 | 0.61 |
| Ex. (433) | P2-82 | 5.7 | 9.9 | 5000 | 50.6 | 143.5 | 0.33 | 0.61 |
| Ex. (434) | P2-83 | 5.8 | 9.5 | 5000 | 52.6 | 144.9 | 0.33 | 0.61 |
| Ex. (435) | P2-84 | 5.9 | 10.0 | 5000 | 50.1 | 149.2 | 0.33 | 0.61 |
| Ex. (436) | P2-85 | 5.9 | 10.2 | 5000 | 49.2 | 148.9 | 0.33 | 0.61 |
| Ex. (437) | P2-86 | 5.8 | 10.0 | 5000 | 50.2 | 147.1 | 0.33 | 0.62 |
| Ex. (438) | P2-87 | 5.7 | 9.5 | 5000 | 52.4 | 144.8 | 0.33 | 0.61 |
| Ex. (439) | P2-88 | 5.7 | 9.9 | 5000 | 50.5 | 143.3 | 0.33 | 0.62 |
| Ex. (440) | P2-89 | 5.6 | 9.3 | 5000 | 54.0 | 151.9 | 0.33 | 0.62 |
| Ex. (441) | P2-90 | 5.6 | 9.6 | 5000 | 51.9 | 148.4 | 0.33 | 0.62 |
| Ex. (442) | P2-91 | 5.7 | 10.0 | 5000 | 49.9 | 147.2 | 0.33 | 0.62 |
| Ex. (443) | P2-92 | 6.0 | 9.7 | 5000 | 51.6 | 151.0 | 0.33 | 0.61 |
| Ex. (444) | P2-93 | 5.7 | 10.3 | 5000 | 48.6 | 150.8 | 0.33 | 0.62 |
| Ex. (445) | P2-94 | 5.9 | 10.3 | 5000 | 48.4 | 144.2 | 0.33 | 0.62 |
| Ex. (446) | P2-95 | 5.9 | 9.9 | 5000 | 50.4 | 142.0 | 0.33 | 0.62 |
| Ex. (447) | P2-96 | 5.9 | 10.1 | 5000 | 49.7 | 142.2 | 0.33 | 0.62 |
| Ex. (448) | P2-97 | 5.9 | 10.2 | 5000 | 49.1 | 148.6 | 0.33 | 0.62 |
| Ex. (449) | P2-98 | 6.0 | 9.3 | 5000 | 53.7 | 146.9 | 0.33 | 0.62 |
| Ex. (450) | P2-99 | 5.9 | 9.9 | 5000 | 50.4 | 139.0 | 0.33 | 0.62 |
| Ex. (451) | P2-100 | 5.7 | 10.4 | 5000 | 48.1 | 138.0 | 0.33 | 0.61 |
| Ex. (452) | P2-101 | 5.9 | 9.3 | 5000 | 53.6 | 140.0 | 0.33 | 0.62 |
| Ex. (453) | P2-102 | 5.7 | 9.3 | 5000 | 54.0 | 143.1 | 0.33 | 0.61 |
| Ex. (454) | P2-103 | 5.7 | 9.7 | 5000 | 51.5 | 143.5 | 0.33 | 0.62 |
| Ex. (455) | P2-104 | 5.7 | 10.4 | 5000 | 48.1 | 144.8 | 0.33 | 0.61 |
| Ex. (456) | P2-105 | 6.0 | 9.2 | 5000 | 54.1 | 150.3 | 0.33 | 0.61 |
| Ex. (457) | P2-106 | 5.7 | 9.6 | 5000 | 52.2 | 149.0 | 0.33 | 0.62 |
| Ex. (458) | P2-107 | 5.8 | 9.8 | 5000 | 50.9 | 143.8 | 0.33 | 0.62 |
| Ex. (459) | P2-108 | 5.6 | 10.3 | 5000 | 48.8 | 147.9 | 0.33 | 0.61 |
| Ex. (460) | P2-109 | 5.9 | 9.3 | 5000 | 53.6 | 151.5 | 0.33 | 0.62 |
| Ex. (461) | P2-110 | 5.9 | 10.1 | 5000 | 49.6 | 148.2 | 0.33 | 0.62 |
| Ex. (462) | P2-111 | 5.6 | 9.9 | 5000 | 50.4 | 146.4 | 0.33 | 0.62 |
| Ex. (463) | P2-112 | 5.9 | 10.3 | 5000 | 48.3 | 138.2 | 0.33 | 0.62 |
| Ex. (464) | P3-1 | 5.7 | 10.2 | 5000.0 | 48.8 | 145.9 | 0.33 | 0.62 |
| Ex. (465) | P3-2 | 5.6 | 9.8 | 5000.0 | 51.0 | 146.0 | 0.33 | 0.61 |
| Ex. (466) | P3-3 | 5.5 | 10.0 | 5000.0 | 49.9 | 149.1 | 0.33 | 0.61 |
| Ex. (467) | P3-4 | 5.7 | 10.0 | 5000.0 | 50.1 | 148.2 | 0.33 | 0.62 |
| Ex. (468) | P3-5 | 5.5 | 10.0 | 5000.0 | 50.2 | 148.5 | 0.33 | 0.61 |

TABLE 6-continued

| Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|
| Ex. (469) P3-6 | 5.6 | 10.0 | 5000.0 | 50.0 | 148.7 | 0.33 | 0.62 |
| Ex. (470) P3-7 | 5.7 | 9.8 | 5000.0 | 51.0 | 148.5 | 0.33 | 0.62 |
| Ex. (471) P3-8 | 5.7 | 9.7 | 5000.0 | 51.5 | 149.8 | 0.33 | 0.61 |
| Ex. (472) P3-9 | 5.7 | 10.0 | 5000.0 | 50.2 | 148.5 | 0.33 | 0.61 |
| Ex. (473) P3-10 | 5.7 | 10.1 | 5000.0 | 49.4 | 147.3 | 0.33 | 0.61 |
| Ex. (474) P3-17 | 5.6 | 10.2 | 5000.0 | 49.0 | 141.4 | 0.33 | 0.62 |
| Ex. (475) P3-18 | 5.5 | 10.3 | 5000.0 | 48.3 | 142.6 | 0.33 | 0.62 |
| Ex. (476) P3-19 | 5.7 | 10.3 | 5000.0 | 48.7 | 140.1 | 0.33 | 0.61 |
| Ex. (477) P3-20 | 5.5 | 10.4 | 5000.0 | 48.2 | 144.5 | 0.33 | 0.62 |
| Ex. (478) P3-21 | 5.7 | 10.3 | 5000.0 | 48.5 | 144.3 | 0.33 | 0.61 |
| Ex. (479) P3-22 | 5.6 | 10.3 | 5000.0 | 48.5 | 141.4 | 0.33 | 0.61 |
| Ex. (480) P3-23 | 5.6 | 10.2 | 5000.0 | 48.8 | 142.7 | 0.33 | 0.61 |
| Ex. (481) P3-24 | 5.5 | 10.1 | 5000.0 | 49.4 | 144.8 | 0.33 | 0.62 |
| Ex. (482) P3-25 | 5.7 | 10.2 | 5000.0 | 49.0 | 144.8 | 0.33 | 0.62 |
| Ex. (483) P3-26 | 5.6 | 10.1 | 5000.0 | 49.3 | 140.1 | 0.33 | 0.61 |
| Ex. (484) P3-27 | 5.6 | 10.2 | 5000.0 | 48.8 | 140.5 | 0.33 | 0.61 |
| Ex. (485) P3-28 | 5.6 | 10.4 | 5000.0 | 48.0 | 142.7 | 0.33 | 0.61 |

It can be seen from the results in Table 5 and 6 above, that the OLEDs using the inventive compounds as the auxiliary emission layer material showed predominantly improved efficiency and lifespan, compared to the OLEDs using comparative compounds 2 to 4 as the auxiliary emission layer material and the OLEDs not having the auxiliary emission layer. Especially, the OLEDs using the present invention compounds showed predominantly improved efficiency and long life span, compared to the OLEDs not forming the auxiliary emission layer (Com. Ex (12)).

Also, significant difference in life span was shown between the compounds having a linker equally linked to the same 2-position of the carbazole cores yet the substituent amine group is linked on a different position of the linker. This is believed because different bonding angle occurs depending on to which position of the linker the amine group is linked, so does the different T1 values, which causes different electron blocking abilities.

In addition, referring to the result in Table 5 and 6, it can be seen that although efficiency is similar or slightly increased driving voltage and life span are improved where the compounds (P3-1 to P3-32) of the present invention having R$^3$ or R$^4$ substituted with a substituent other than hydrogen is used as a red or green auxiliary emission layer, compared to the compounds having R$^3$ or R$^4$ substituted with hydrogen.

As described above, it was shown that the linking position of the amine groups or linker is important factor because the performance ability of the organic elements changes depending on the compounds having different linking position between the carbazole core and the linker, and between the linker and the amine group substituted thereto.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula 1:

[Formula 1]

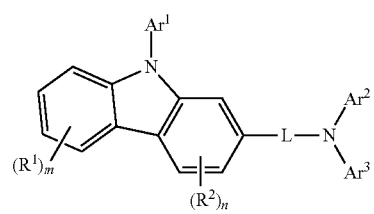

wherein,
L is

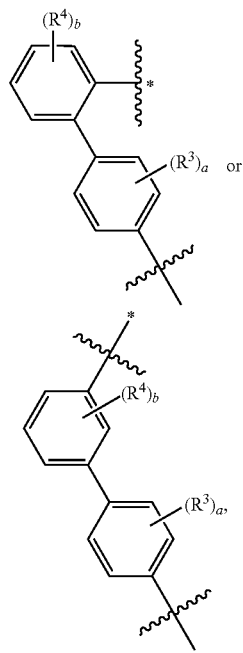

wherein * indicates the position to which the nitrogen atom (N) of the amine group in Formula 1 is linked,
Ar$^1$ to Ar$^3$ are each independently selected from the group consisting of a C$_6$-C$_{60}$ aryl group; a fluorenylene group; a C$_2$-C$_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and combinations thereof, a, b and m are each an integer of 0 to 4, and n is an integer of 0 to 3, $R^1$ to $R^4$ are each independently selected from the group consisting of i) deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; -L'-N($R^a$)($R^b$); and combinations thereof, or ii) at least one of any two adjacent groups may be linked to form a ring and the group(s) of R' to $R^4$ not forming a ring are the same as defined in i) above, L' is selected from the group consisting of a single bond; a $C_6$-$C_{60}$ arylene group; a fluorenylene group; a fused ring formed by a $C_3$-$C_{60}$ aliphatic ring and a $C_6$-$C_{60}$ aromatic ring; a $C_2$-$C_{60}$ heterocyclic group containing at least one heteroatom selected from the group consisting of O, N, S, Si, and P, $R^a$ and $R^b$ are each independently selected from the group consisting of a $C_6$-$C_{60}$ aryl group; a fluorenyl group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si, and P, each of the above aryl group, fluorenyl group, heterocyclic group, fused ring group, alkyl group, alkenyl group, alkynyl group, alkoxy group, aryloxy group, arylene group and fluorenylene group may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si, and P; a $C_3$-$C_{20}$ cycloalkyl group; a $C_7$-$C_{20}$ arylalkyl group; and a $C_8$-$C_{20}$ arylalkenyl group.

2. The compound of claim 1, wherein a and b are each 0 (zero), or $R^3$ and $R^4$ are each independently selected from the following structures:

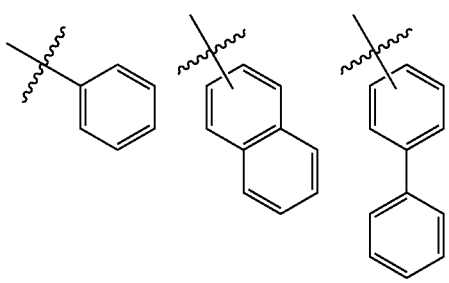

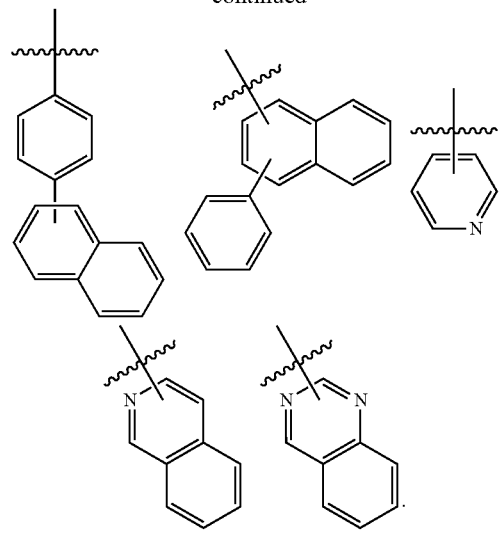

3. The compound of claim 1, wherein at least one of $R^1$ or $R^2$ is linked to form at least one ring between any two adjacent groups.

4. The compound of claim 3 represented by one of Formulas below:

[Formula 2]

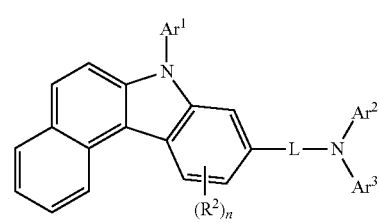

[Formula 3]

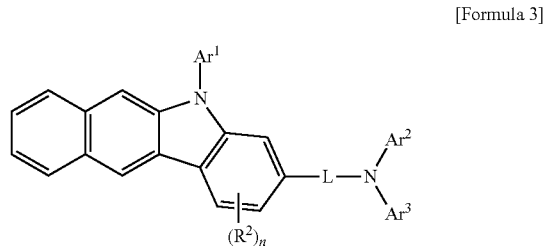

[Formula 4]

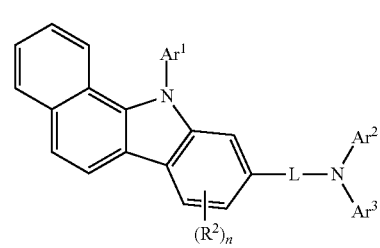

[Formula 5]

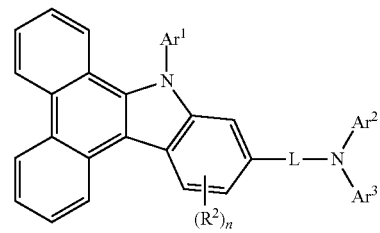

[Formula 6]

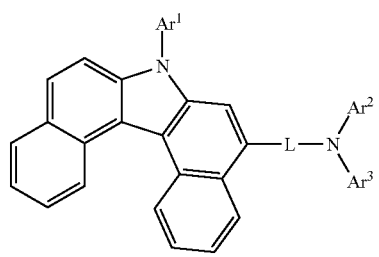

[Formula 7]

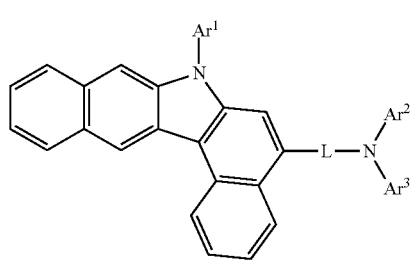

[Formula 8]

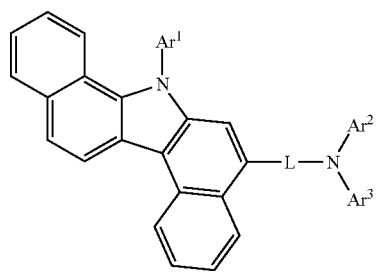

[Formula 9]

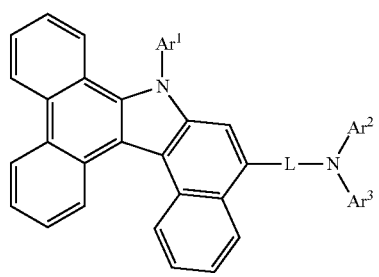

[Formula 10]

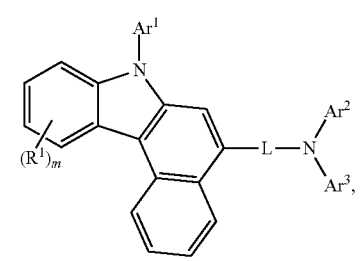

wherein $Ar^1$ to $Ar^3$, L, $R^1$, $R^2$, m and n are the same as defined in claim 1.

5. The compound of claim 1, wherein $Ar^1$ is selected from the following structures:

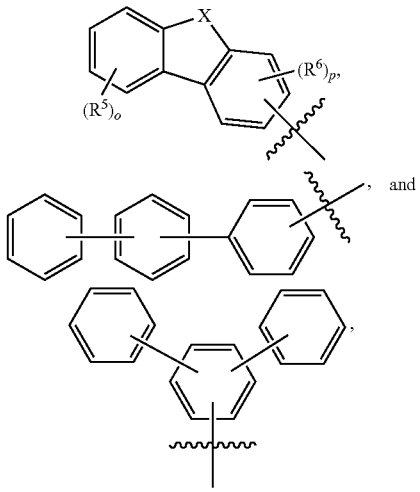

wherein X is O, S or C(R')(R''),

R' and R'' are each independently selected from the group consisting of hydrogen; deuterium; tritium; a $C_6$-$C_{20}$ aryl group; a $C_1$-$C_{20}$ alkyl group; and a $C_2$-$C_{20}$ alkenyl group; or R' and R'' may be linked together to form a spiro compound with the carbon to which they are attached, o is an integer of 0 to 4, p is an integer of 0 to 3, $R^5$ and $R^6$ are each independently selected from the group consisting of i) deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and combinations thereof, or ii) any two adjacent groups may be independently linked together to form at least one fused ring, and the other group(s) of $R^5$ to $R^6$ not forming a ring are the same as defined in i) above.

6. The compound of claim 5,
wherein $Ar^1$ is

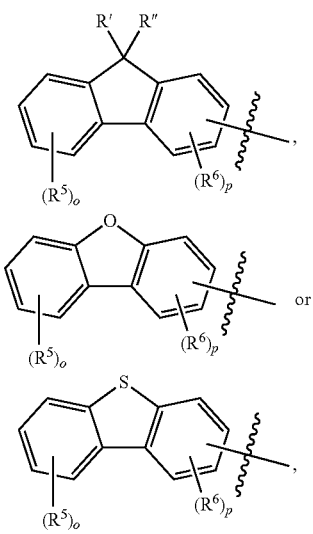

and wherein Formula 1 is represented by one of Formulas 11 to 20 below:

[Formula 11]
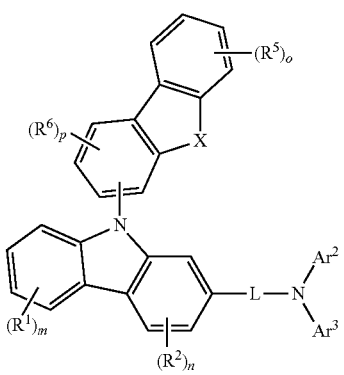
[Formula 12]
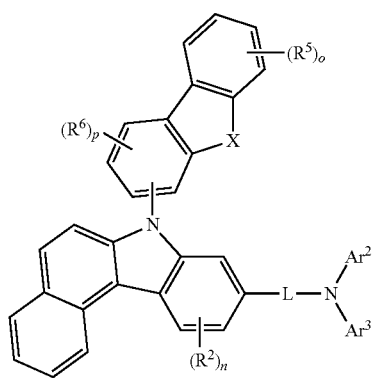
[Formula 13]
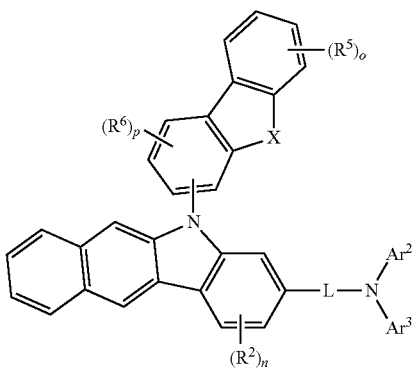
[Formula 14]
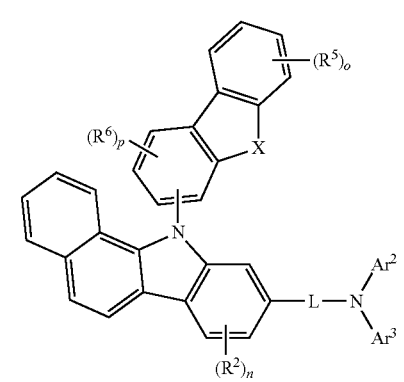
[Formula 15]
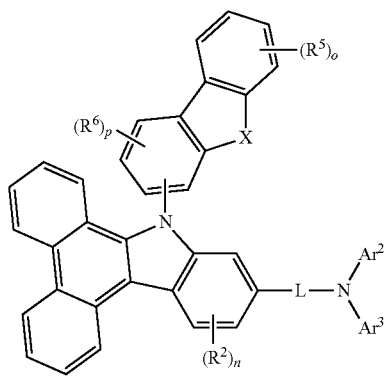
[Formula 16]
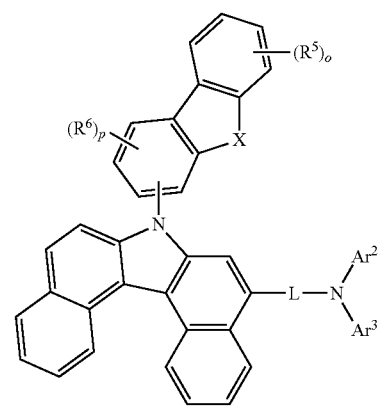
[Formula 17]
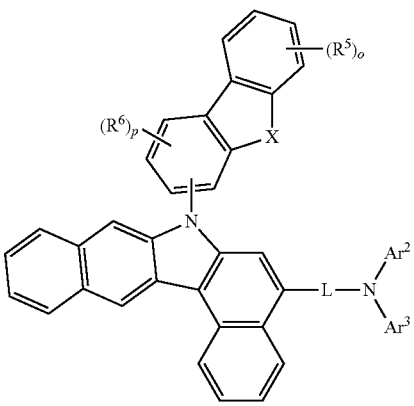
[Formula 18]
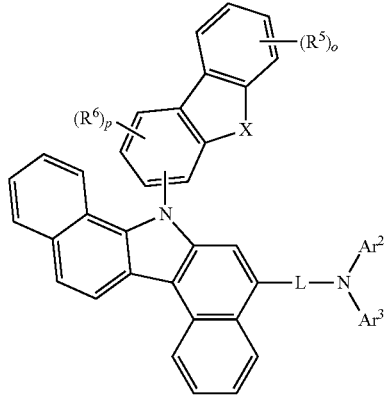

-continued
[Formula 18]
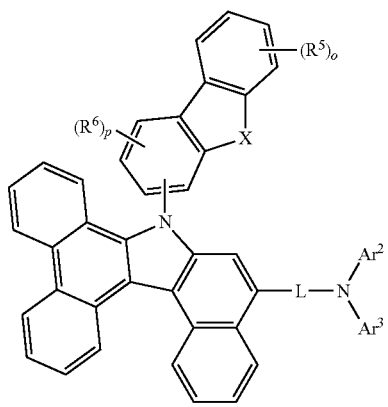
[Formula 20]
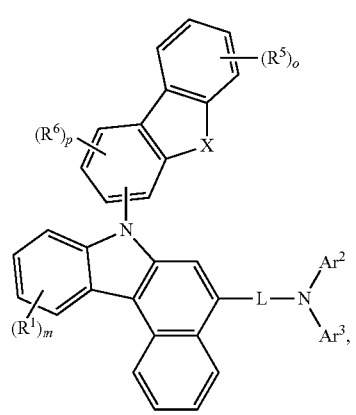
in Formula 11 to Formula 20, $Ar^2$, $Ar^3$, L, $R^1$, $R^2$, m and n are the same as defined in claim 1, and X, $R^5$, $R^6$, o and p are the same as defined in claim 5.
7. The compound of claim 1, wherein $Ar^2$ and $Ar^3$ are each independently selected from the following structures:
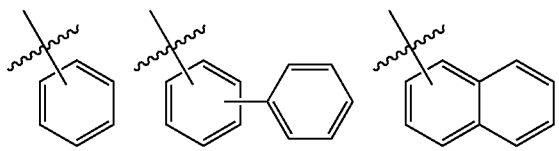
-continued
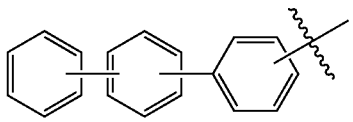
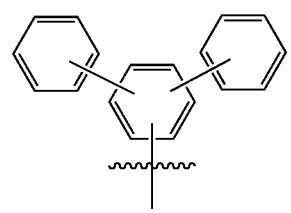
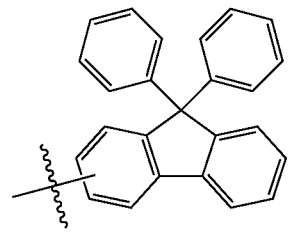
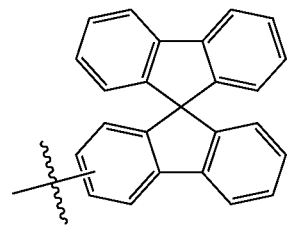
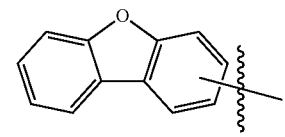
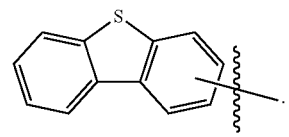
8. The compound of claim 1, wherein Formula 1 is any one of the compounds below:
P1-1
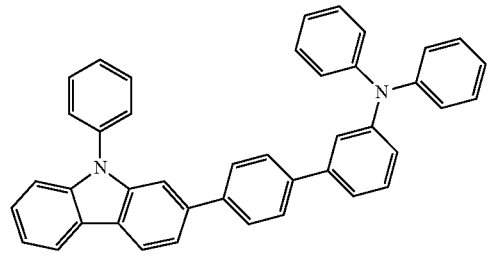
P1-2
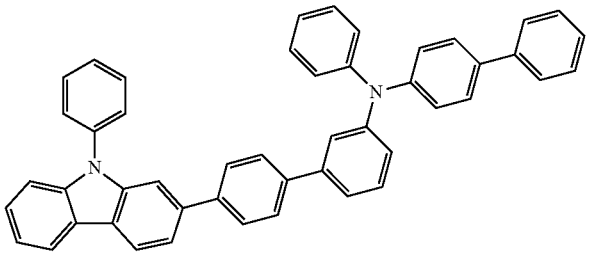

-continued
P1-3
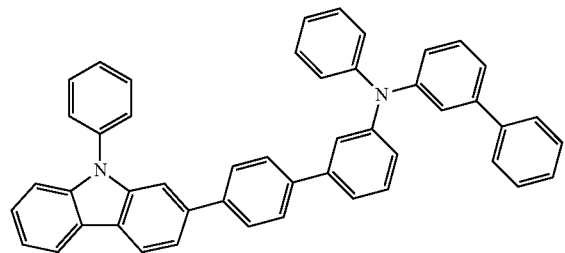
P1-4
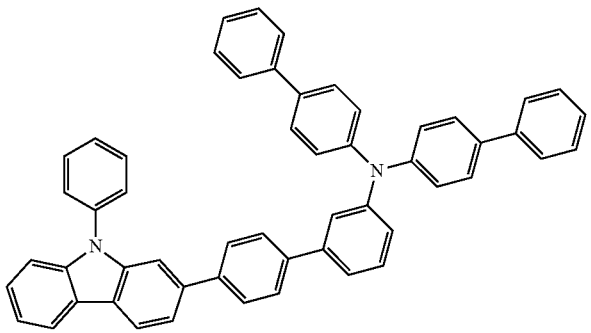
P1-5
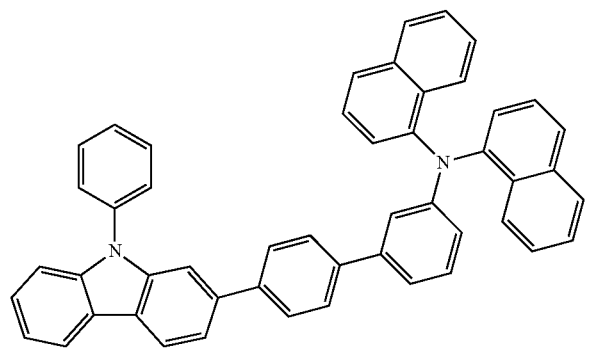
P1-6
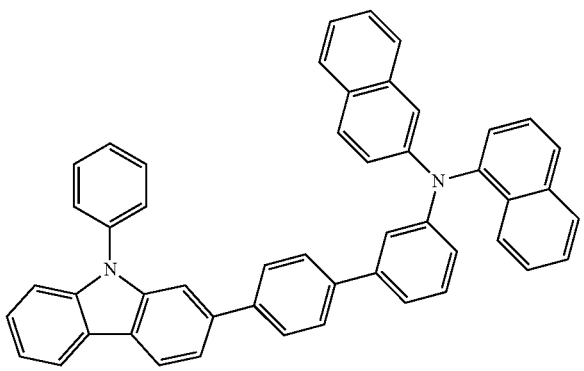
P1-7
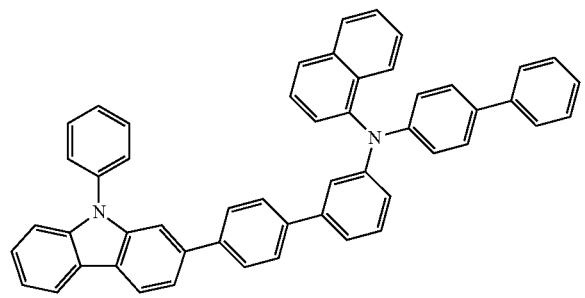
P1-8
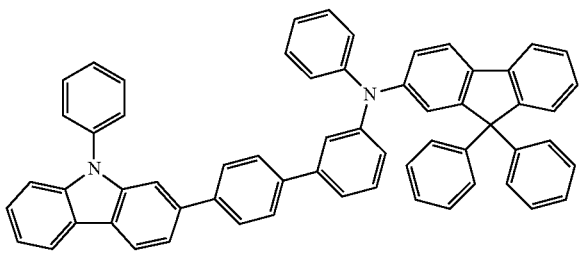
P1-9
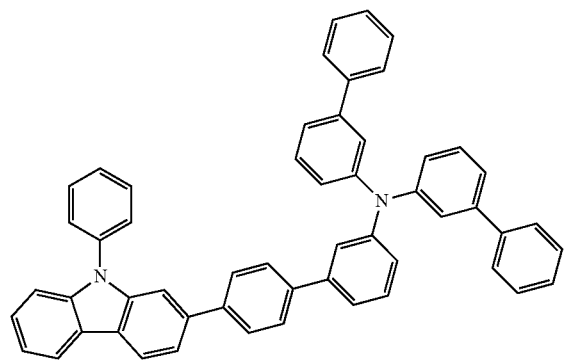
P1-10
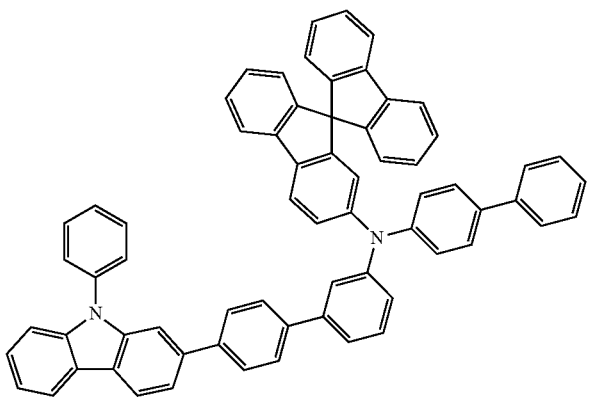

-continued
P1-11
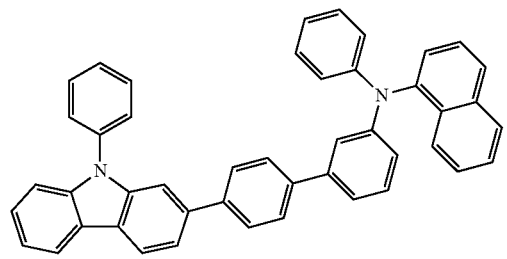
P1-12
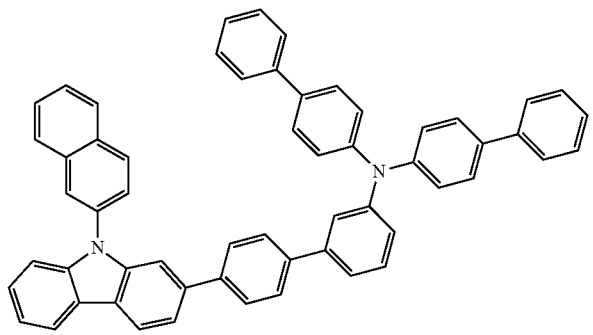
P1-13
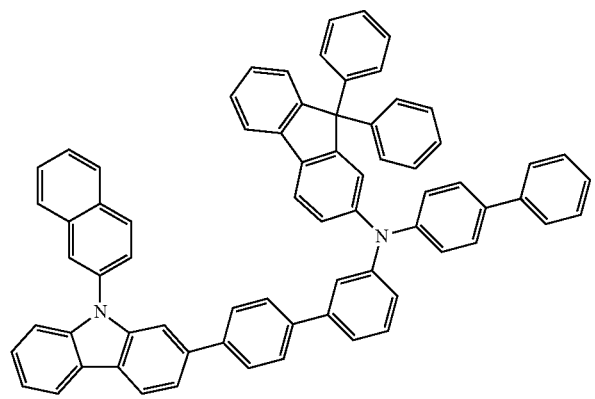
P1-14
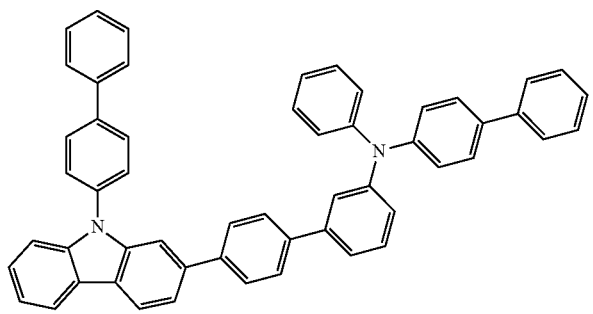
P1-15
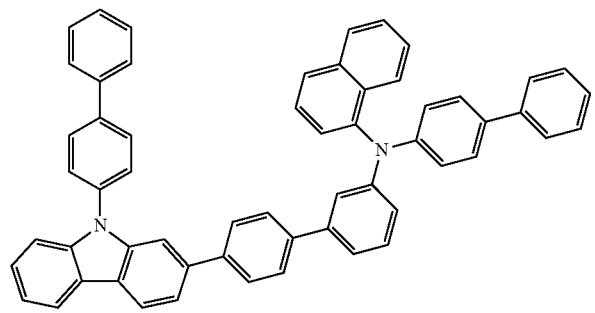
P1-16
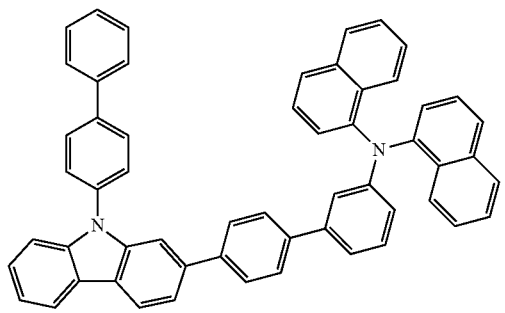
P1-17
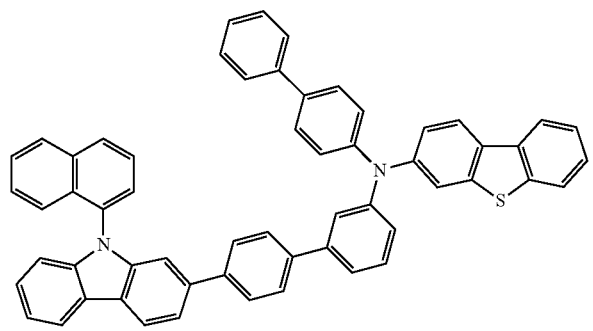
P1-18
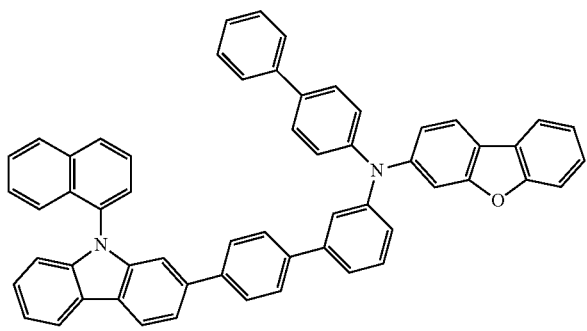

-continued
P1-19
P1-20
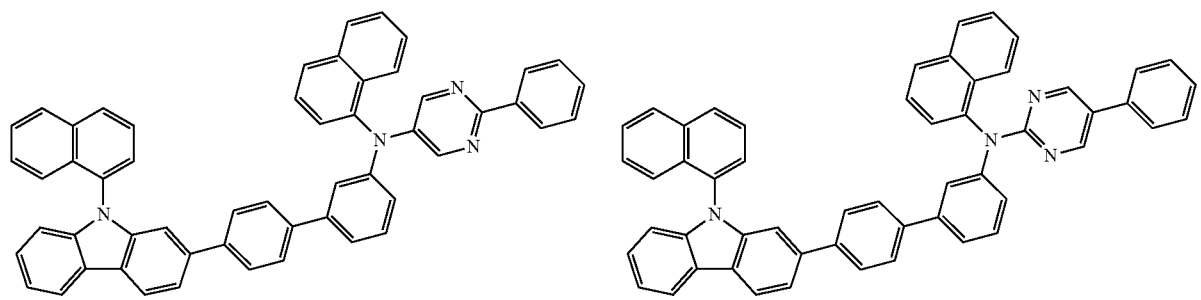
P1-21
P1-22
P1-23
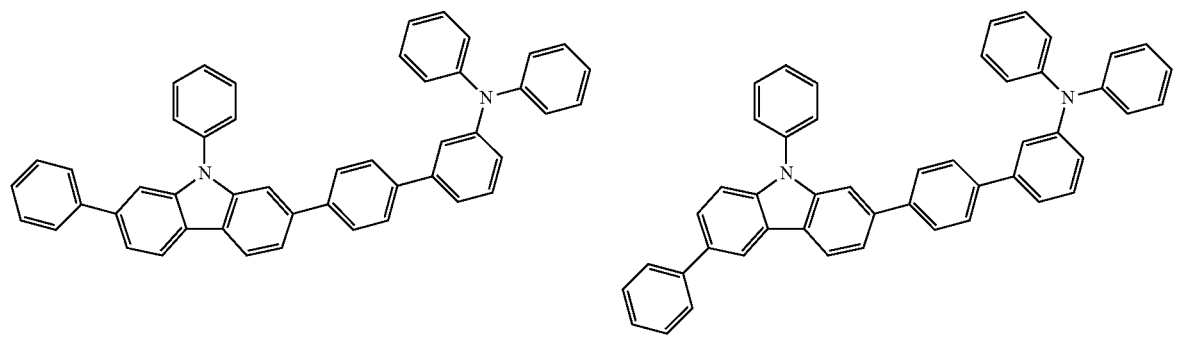
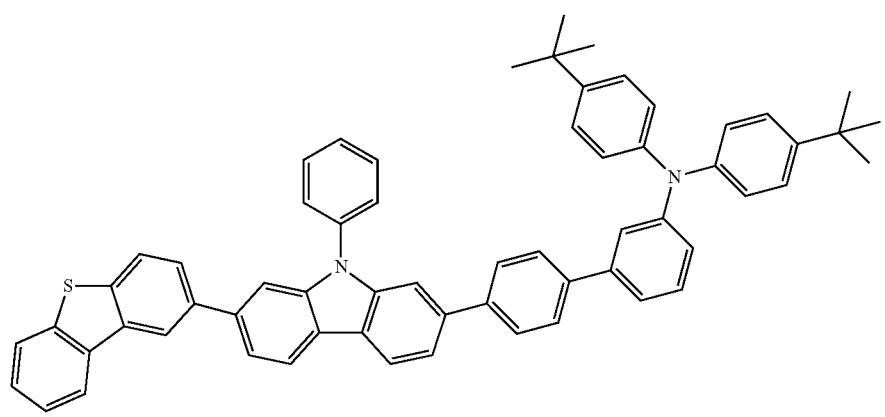
P1-24
P1-25
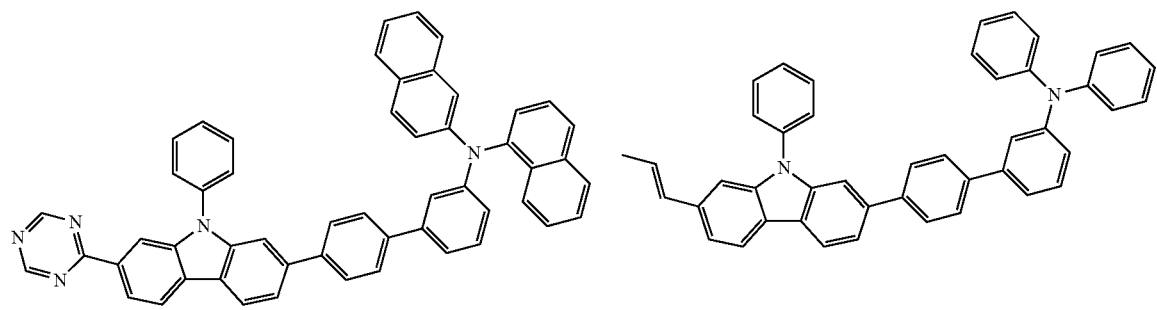

P1-26
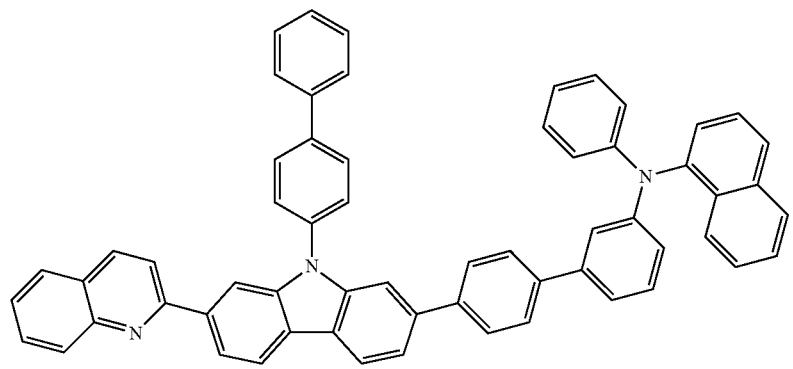
P1-27
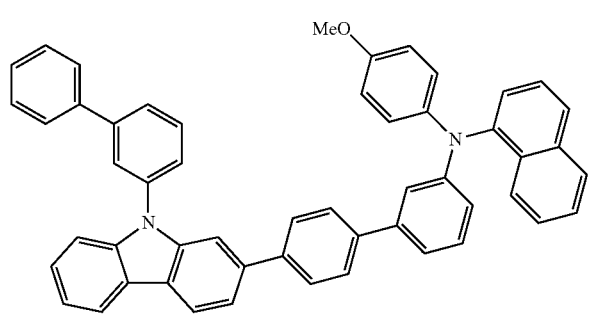
P1-28
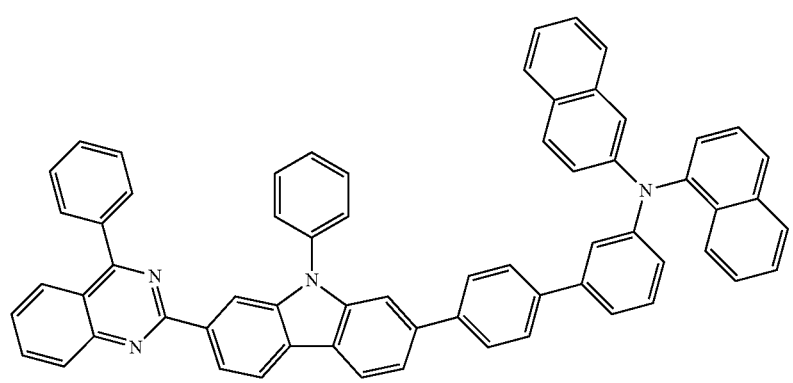
P1-29
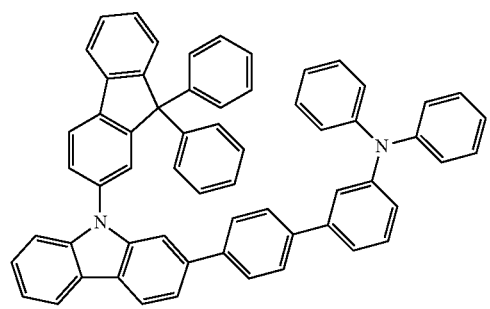
P1-30
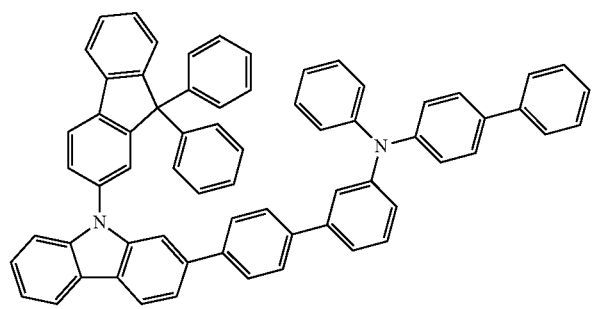

-continued
P1-31
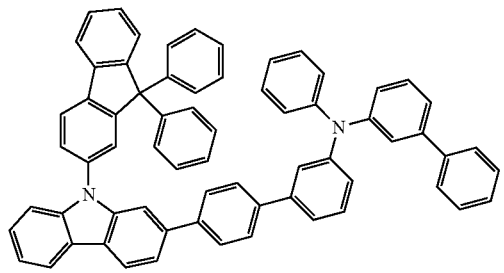
P1-32
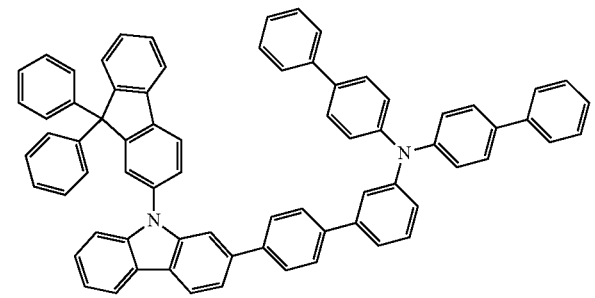
P1-33
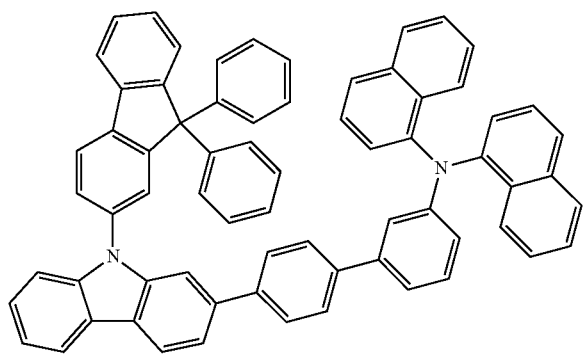
P1-34
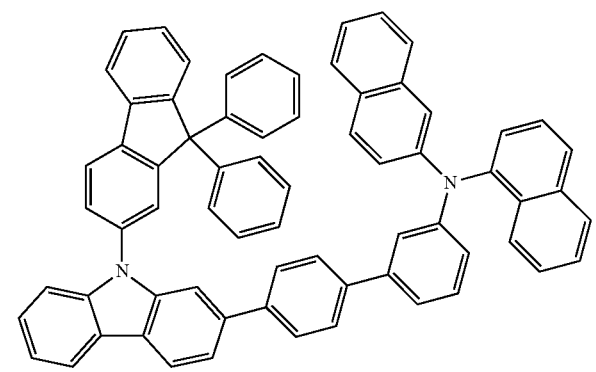
P1-35
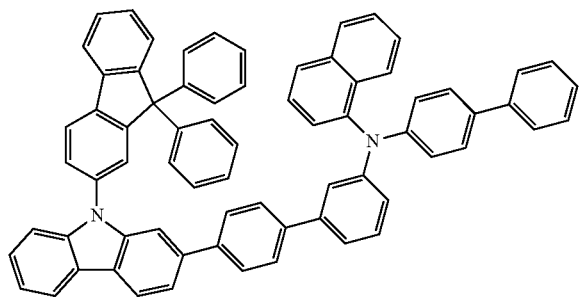
P1-36
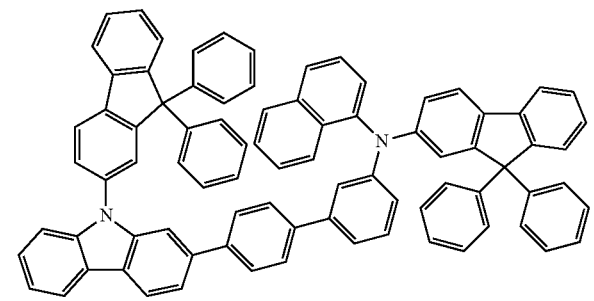
P1-37
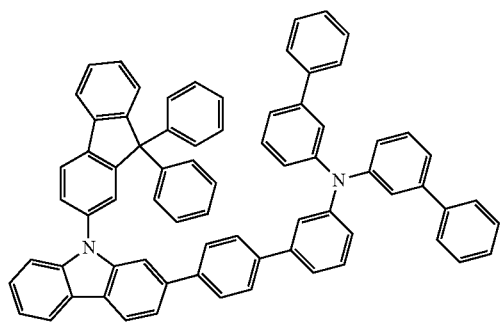
P1-38
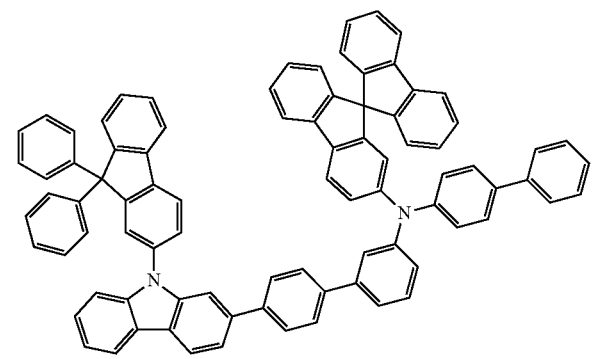

-continued
P1-39
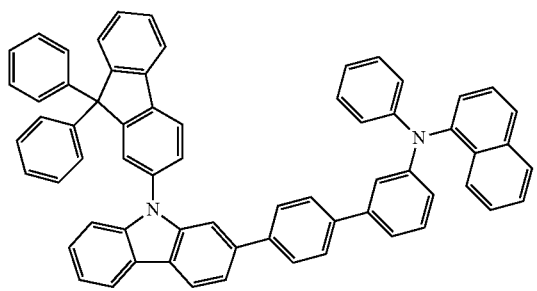
P1-40
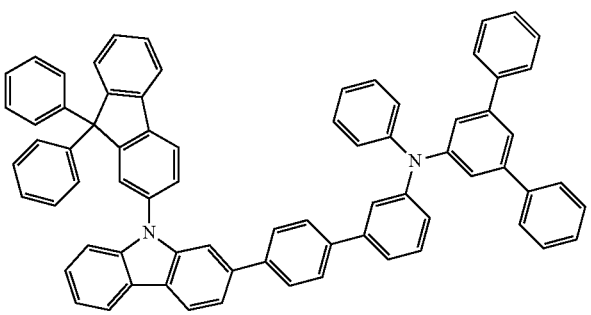
P1-41
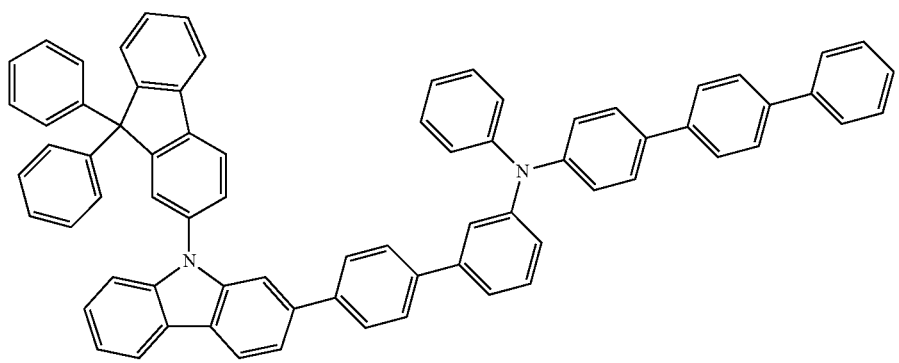
P1-42
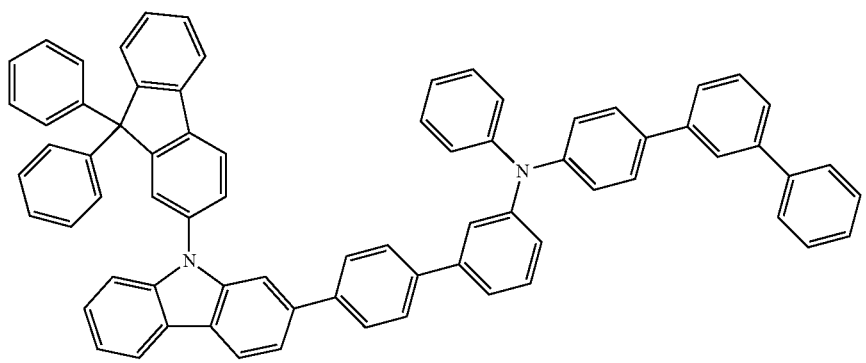
P1-43
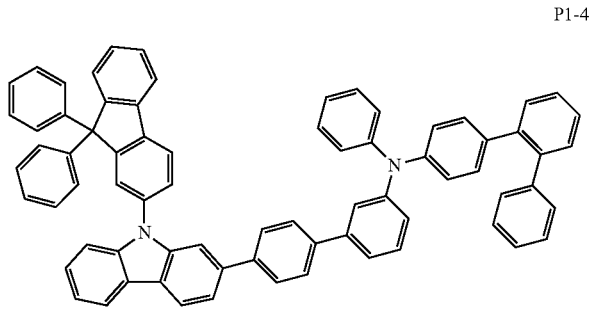
P1-44
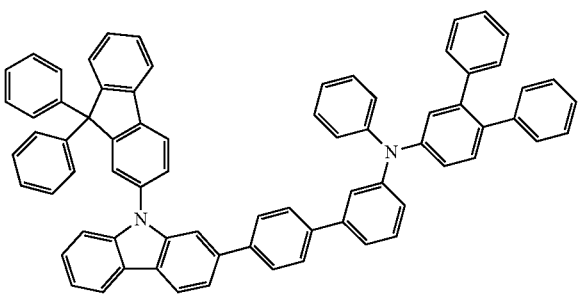

-continued
P1-45
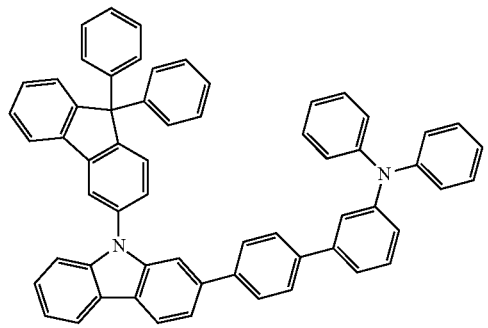
P1-46
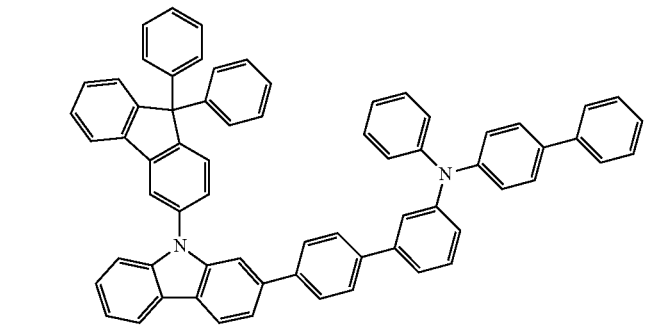
P1-47
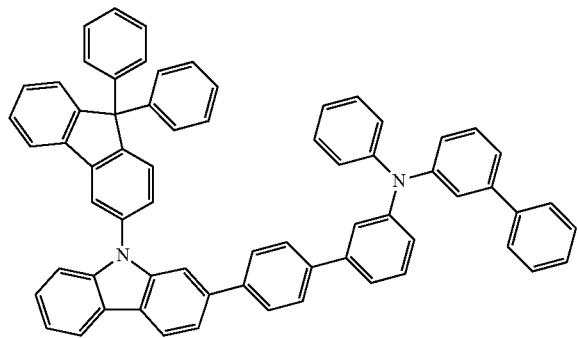
P1-48
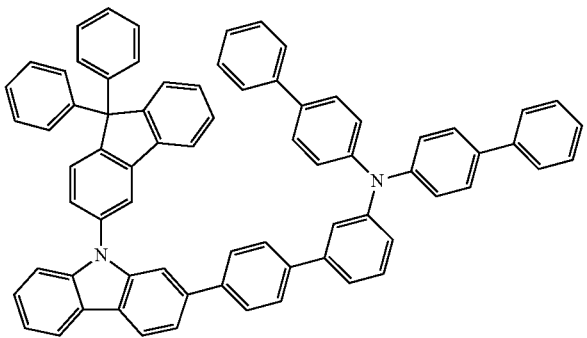
P1-49
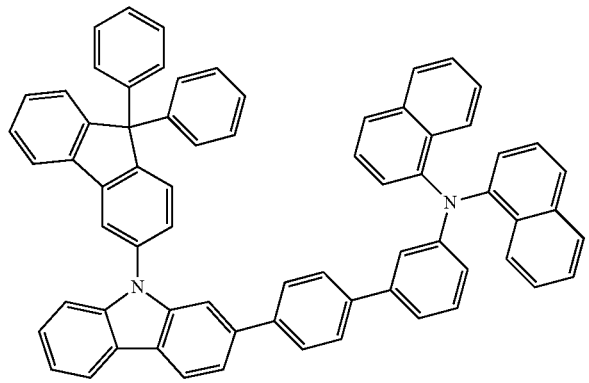
P1-50
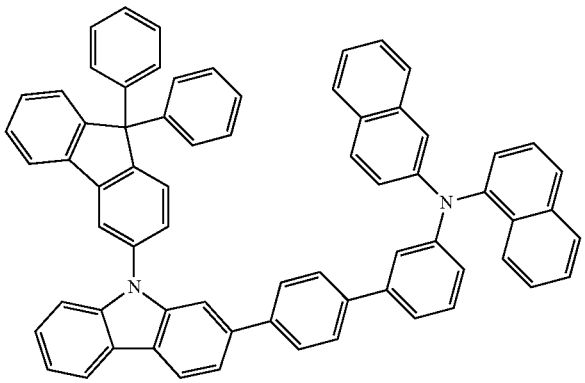
P1-51
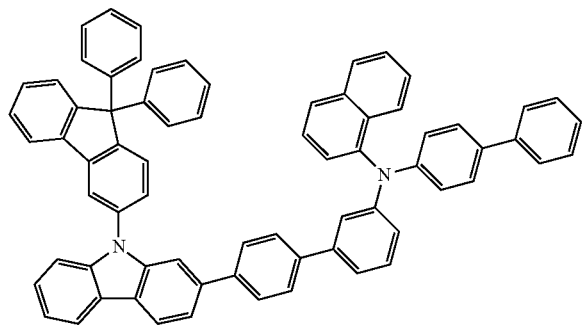
P1-52
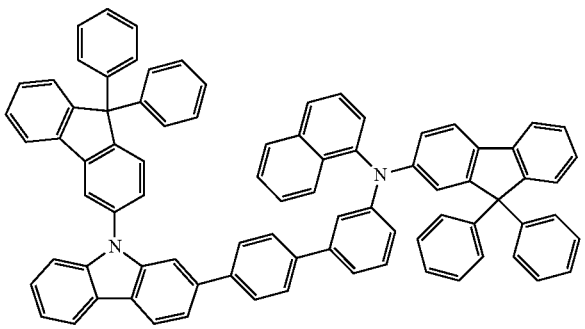

-continued
P1-53
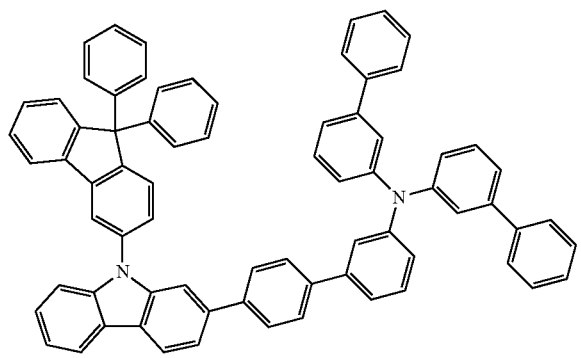
P1-54
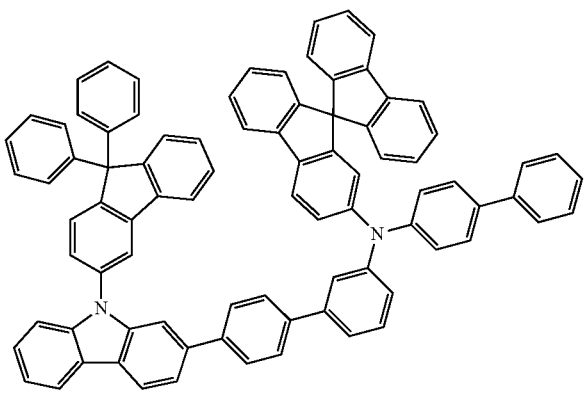
P1-55
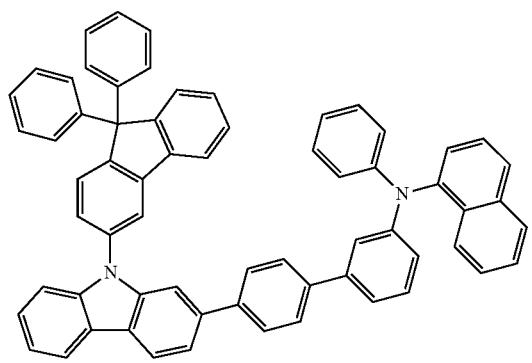
P1-56
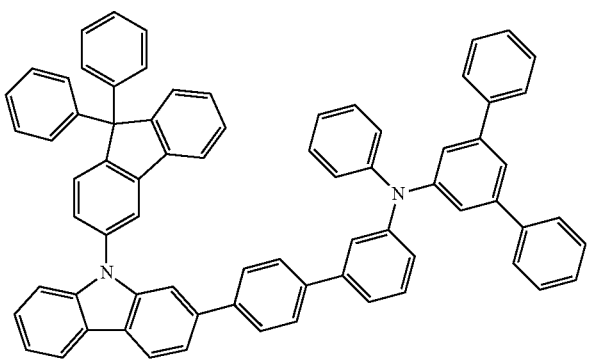
P1-57
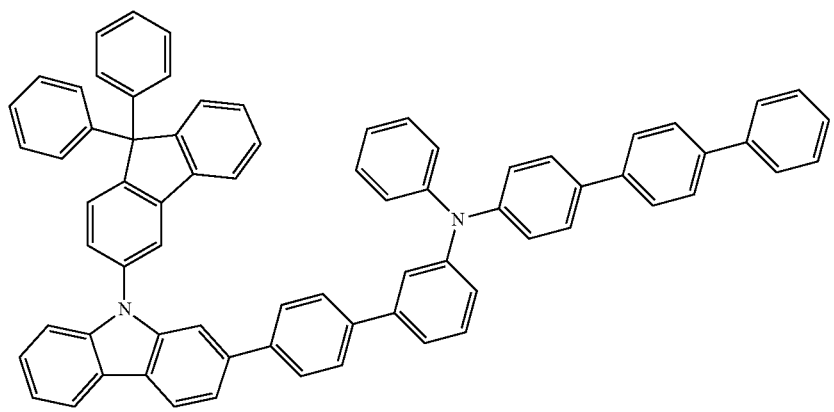
P1-58
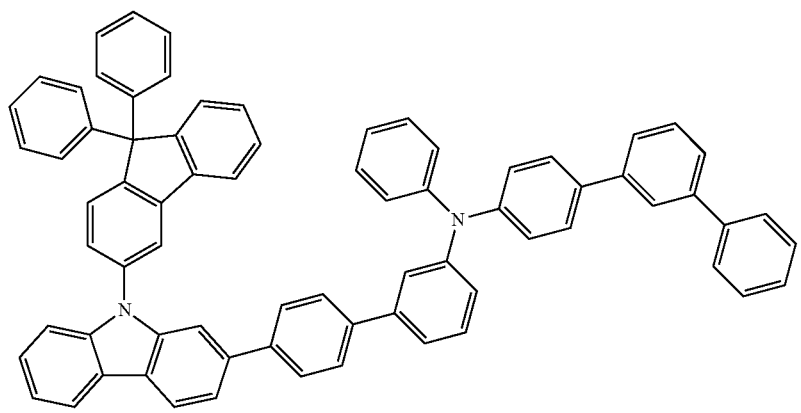

-continued
P1-59
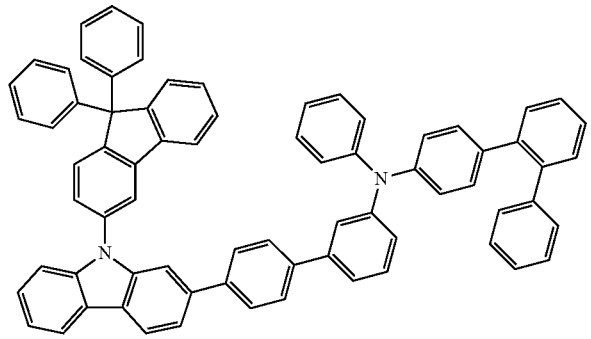
P1-60
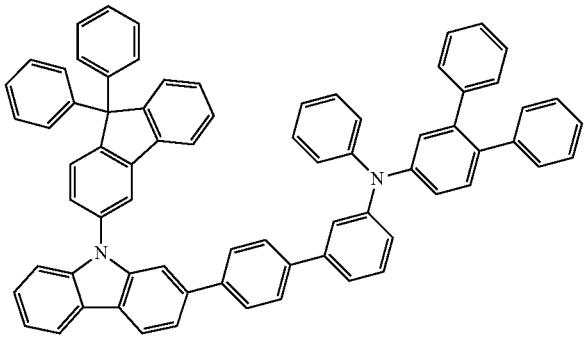
P1-61
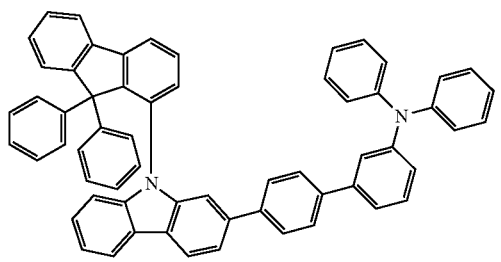
P1-62
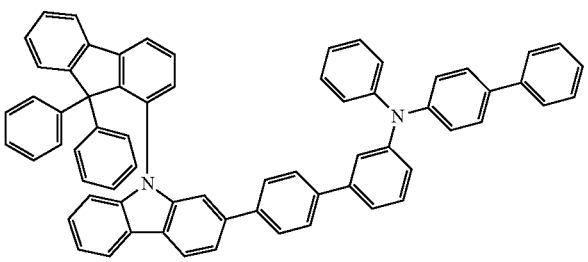
P1-63
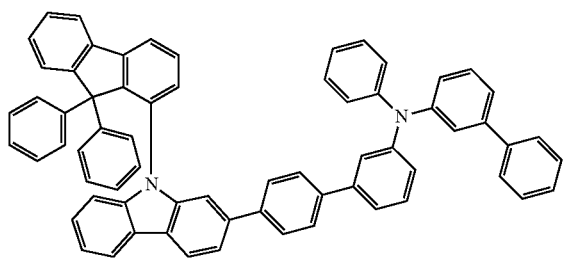
P1-64
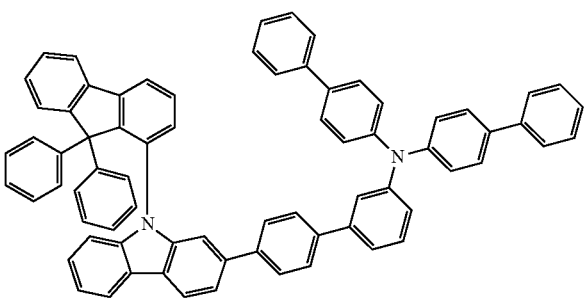
P1-65
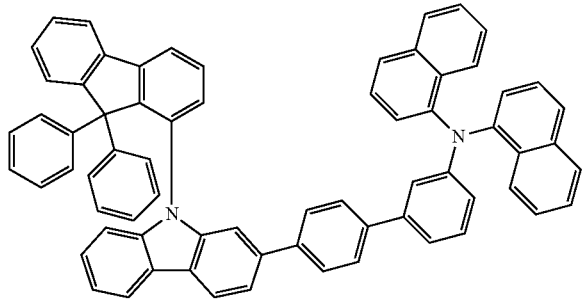
P1-66
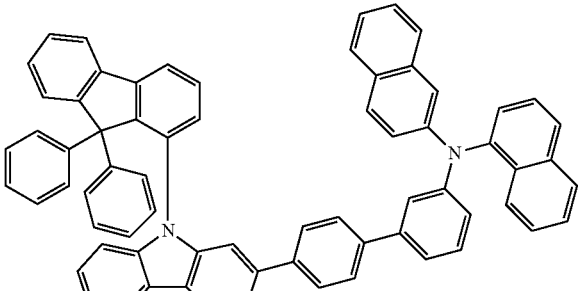
P1-67
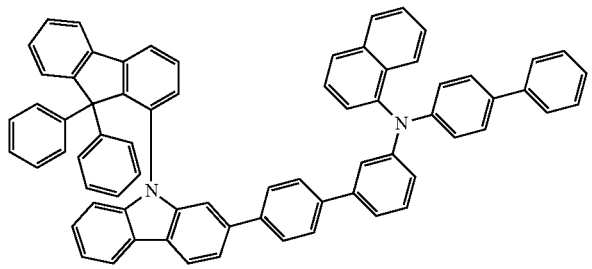
P1-68
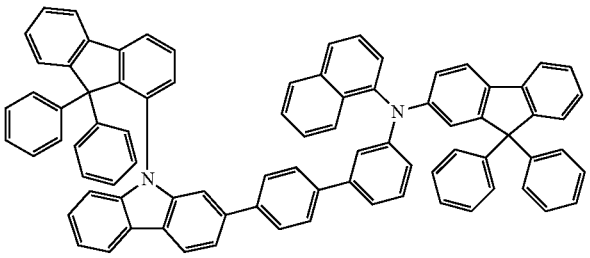

-continued
P1-69
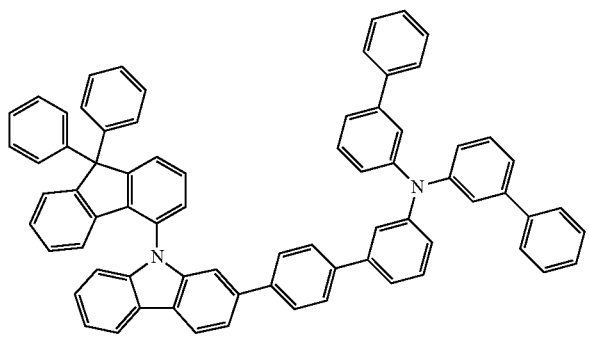
P1-70
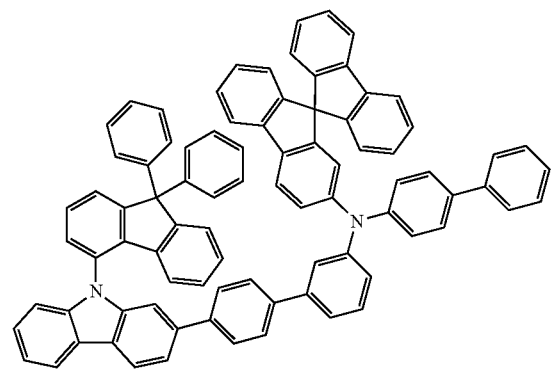
P1-71
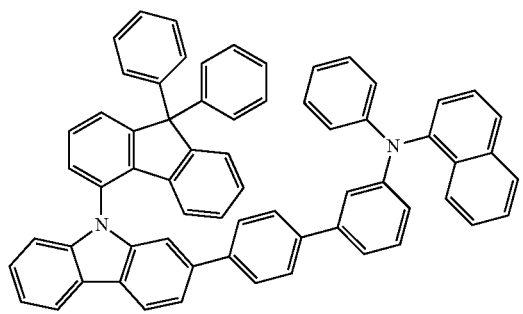
P1-72
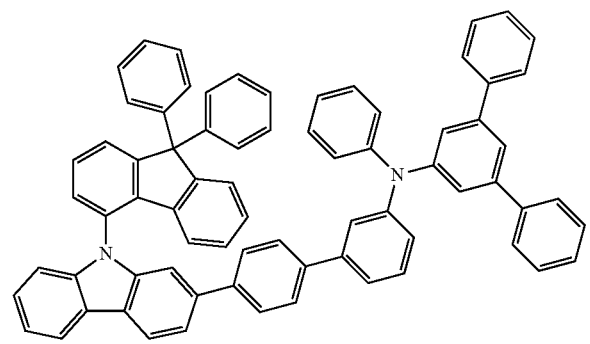
P1-73
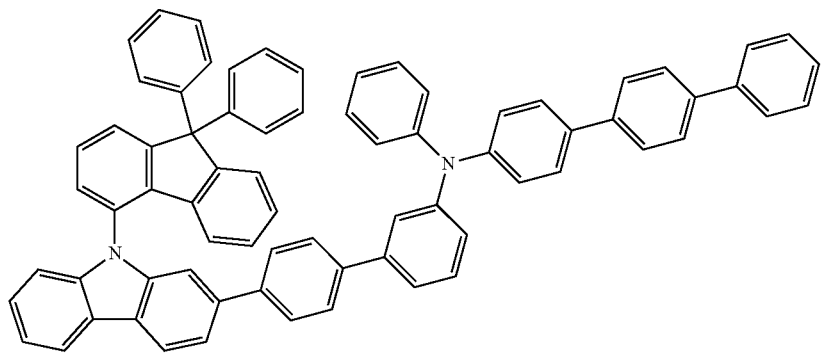
P1-74
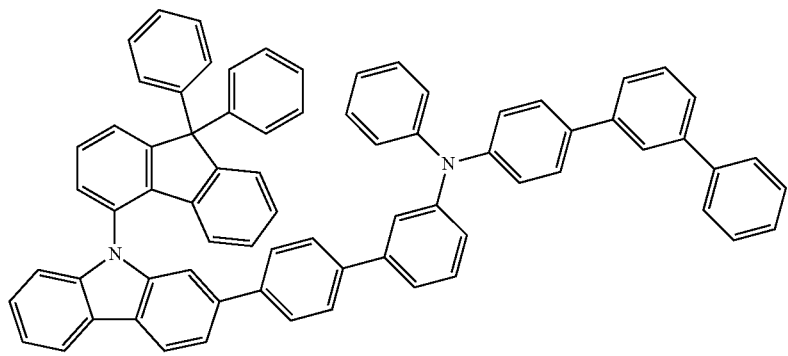

-continued
P1-75
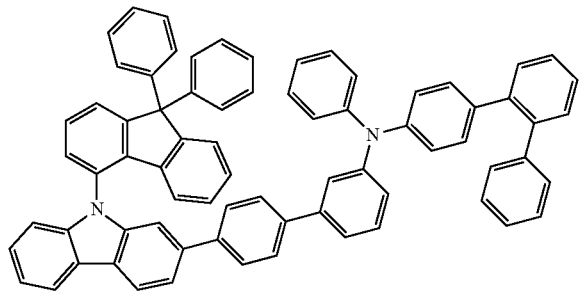
P1-76
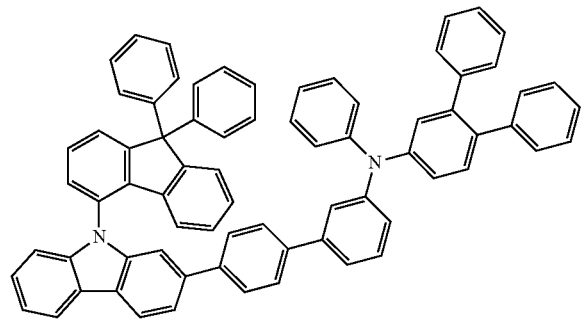
P1-77
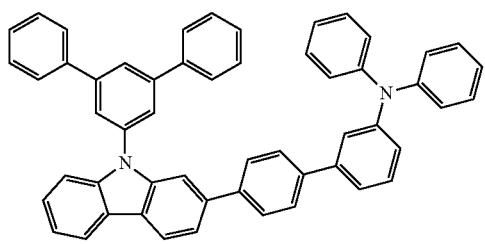
P1-78
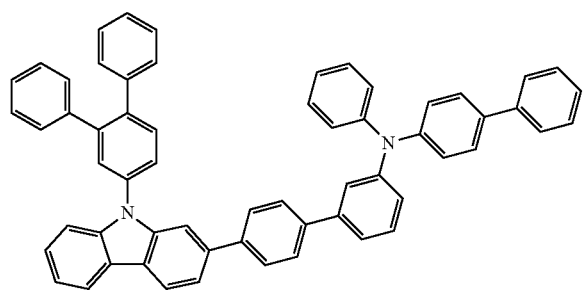
P1-79
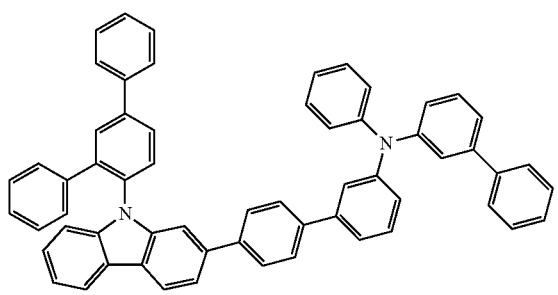
P1-80
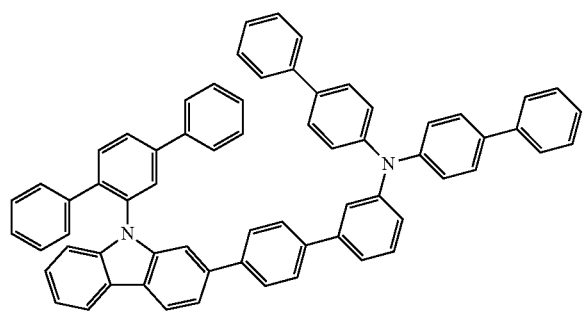
P1-81
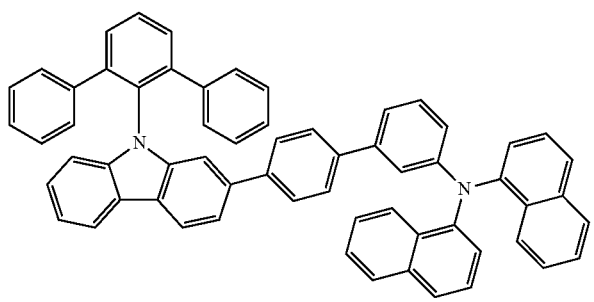
P1-82
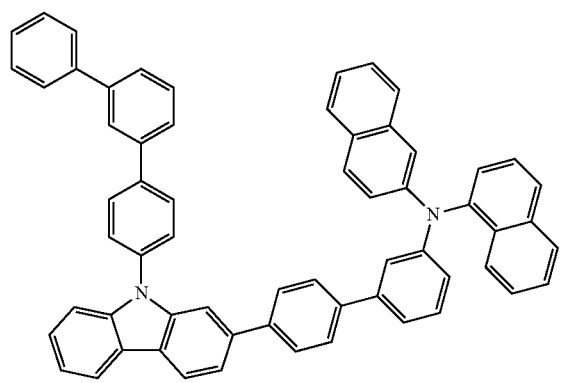

-continued
P1-83
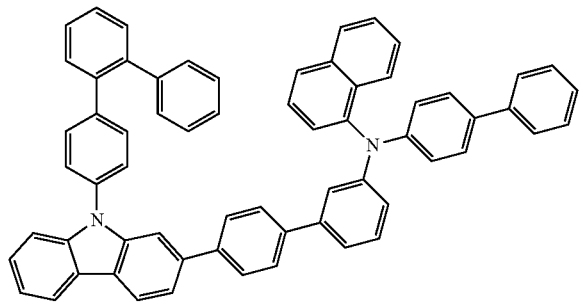
P1-84
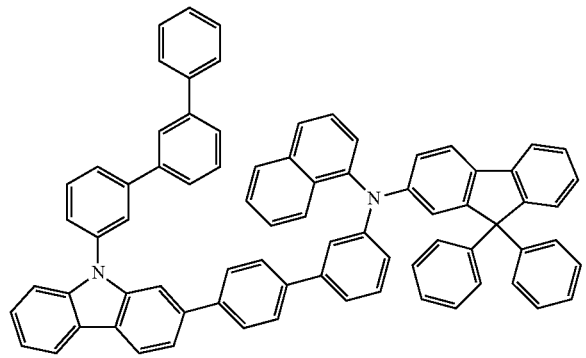
P1-85
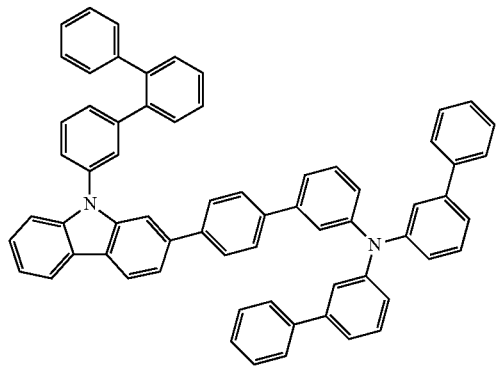
P1-86
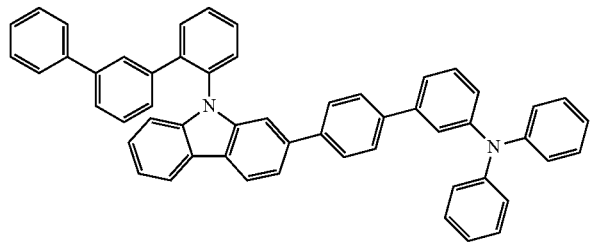
P1-87
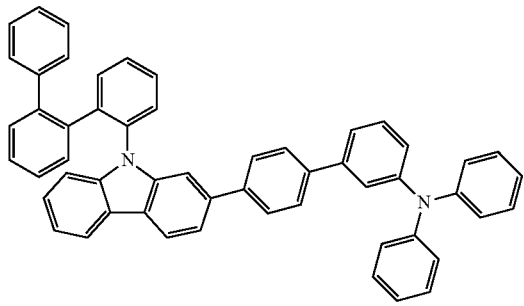
P1-88
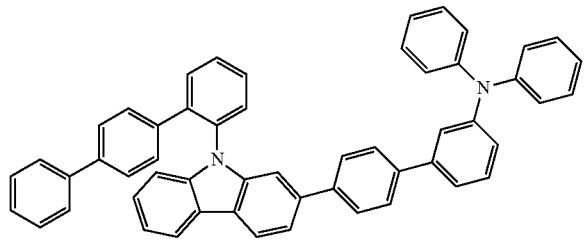
P1-89
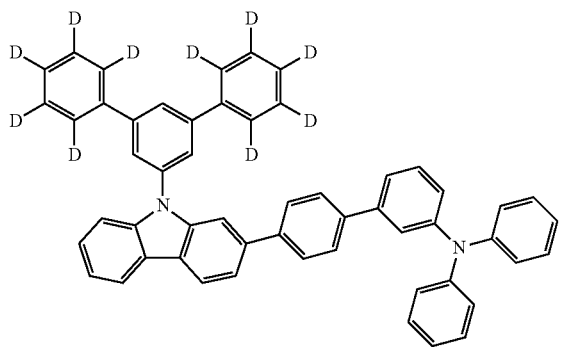
P1-90
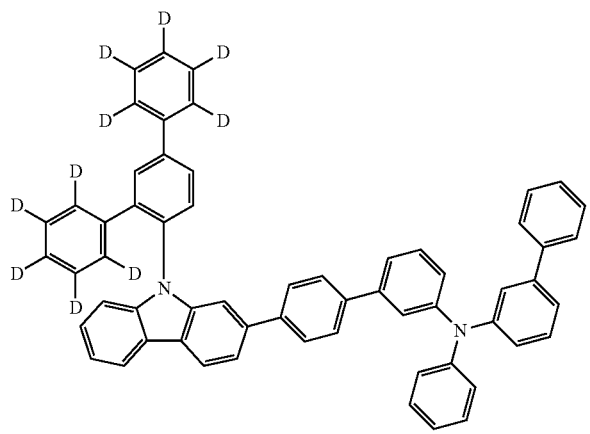

-continued
P1-91
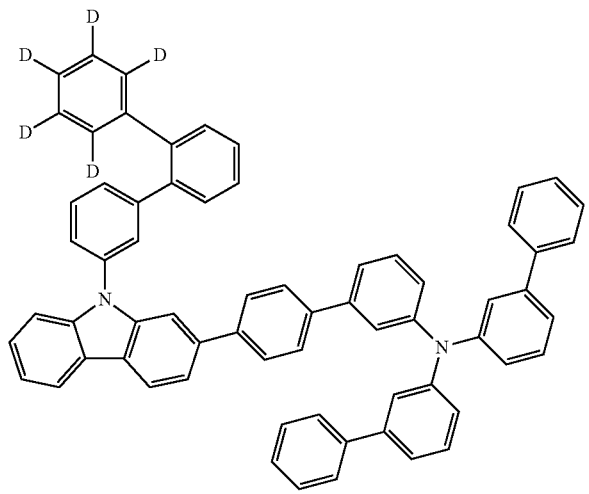
P1-92
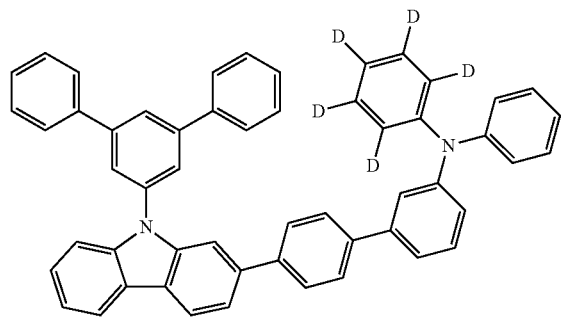
P1-93
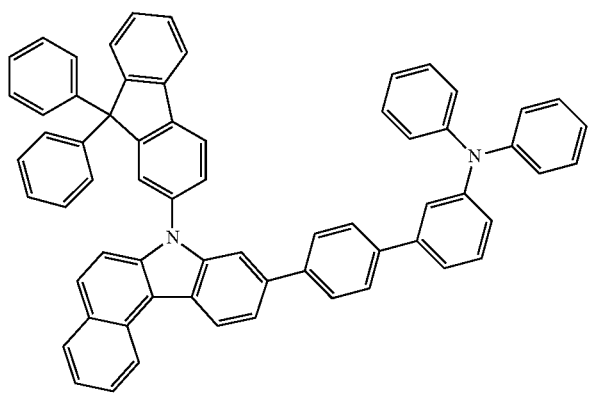
P1-94
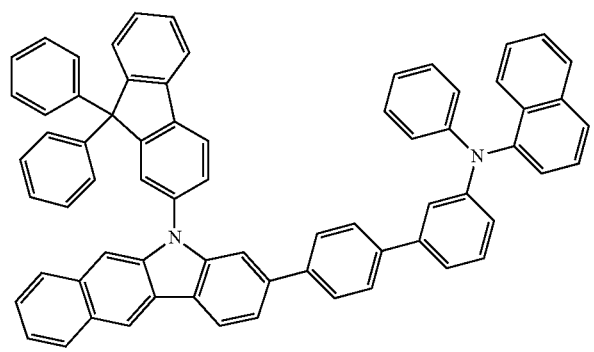
P1-95
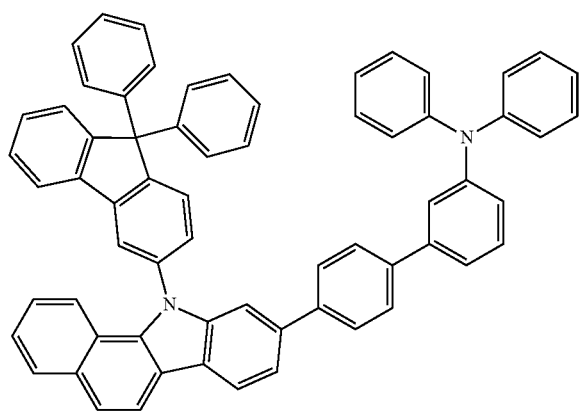
P1-96
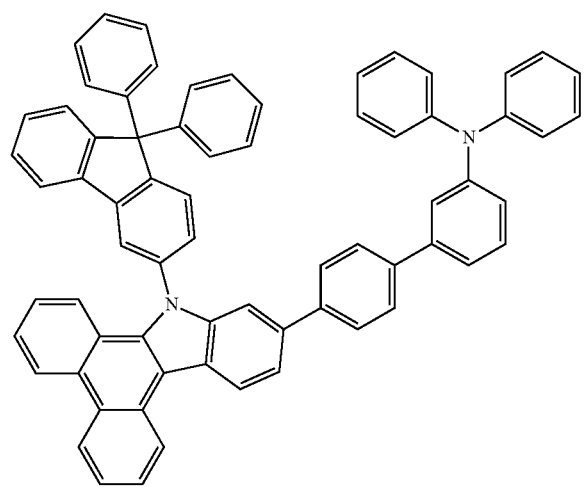

-continued
P1-97
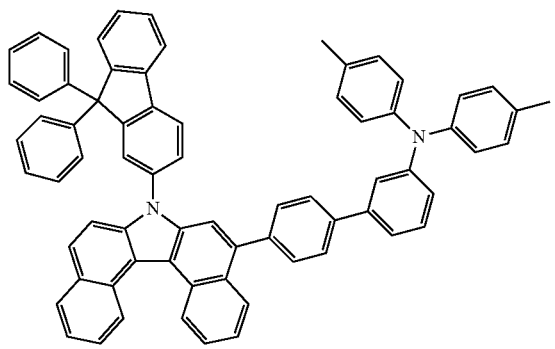
P1-98
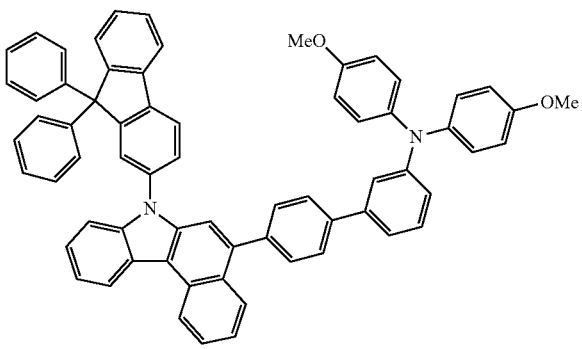
P1-99
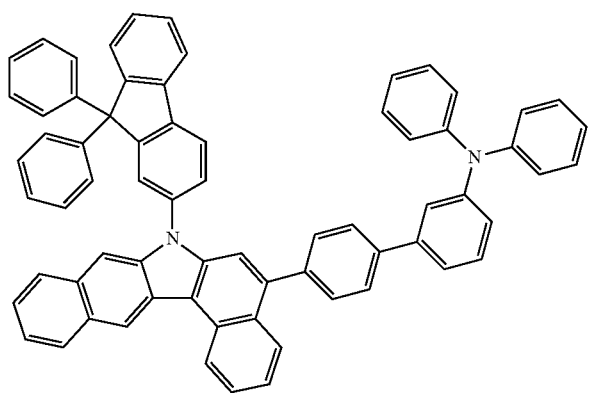
P1-100
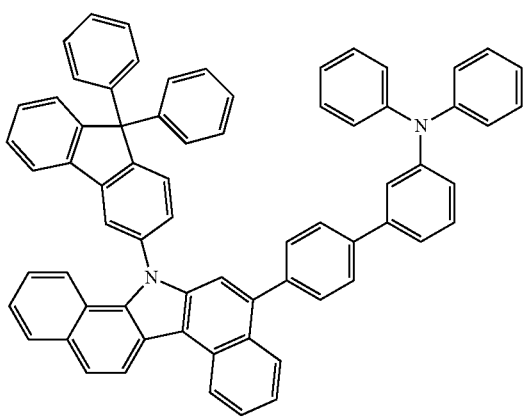
P1-101
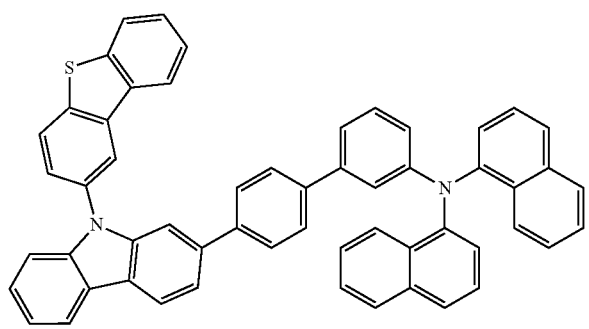
P1-102
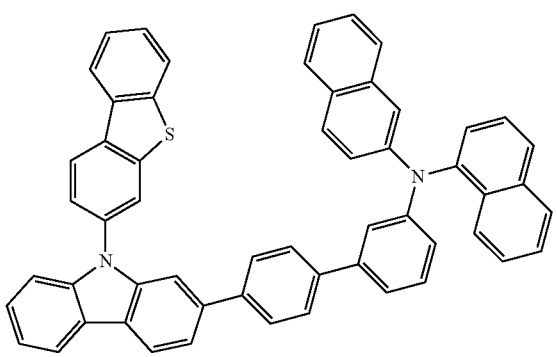
P1-103
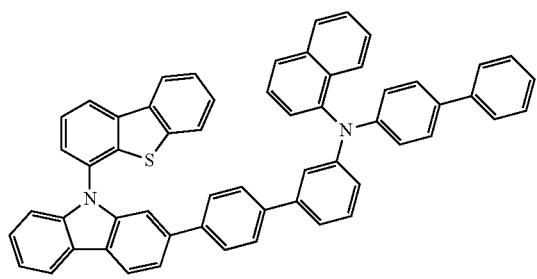
P1-104
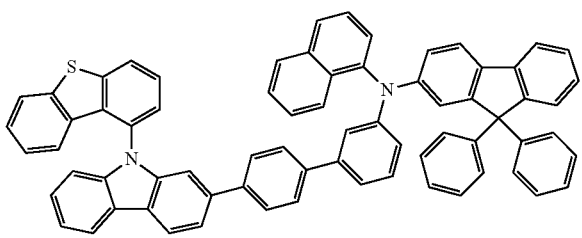

-continued
P1-105
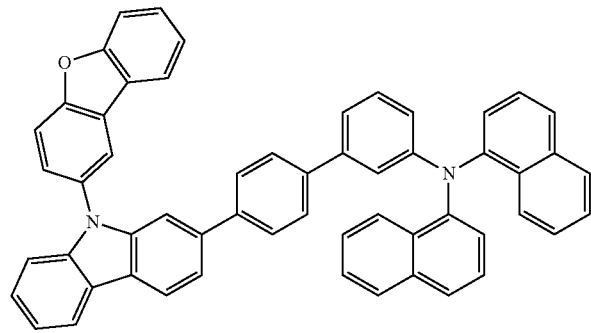
P1-106
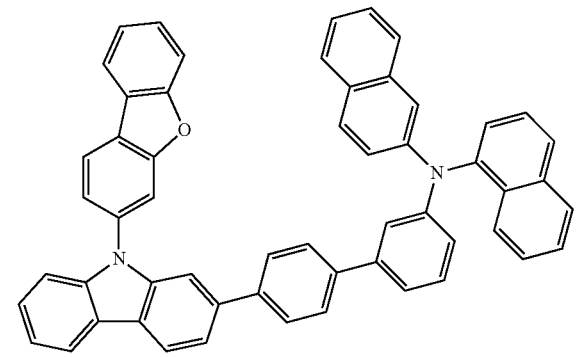
P1-107
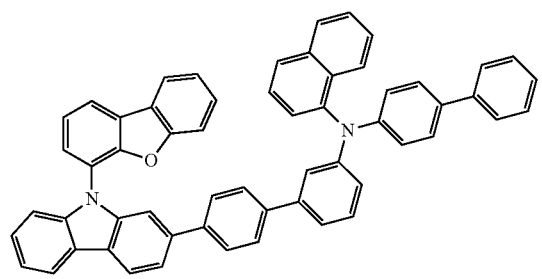
P1-108
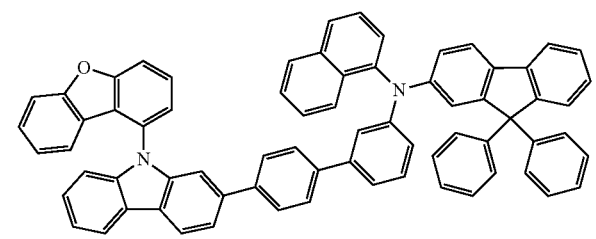
P1-109
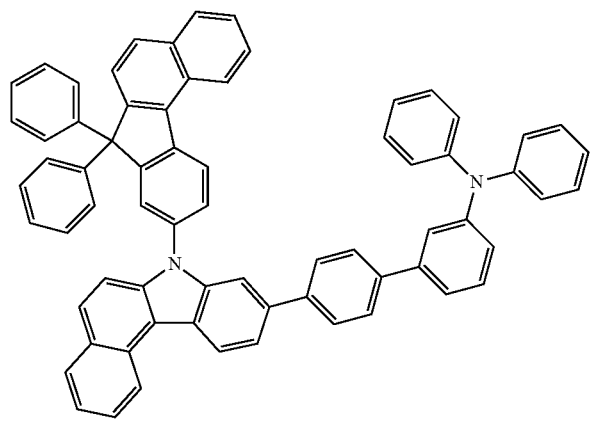
P1-110
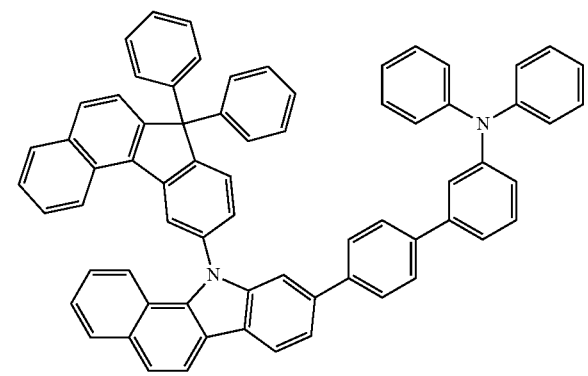
P1-111
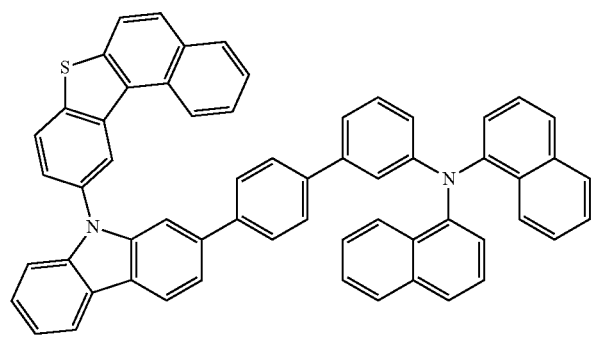
P1-112
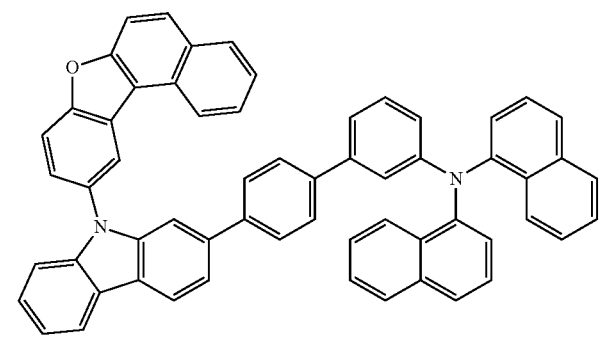

-continued
P2-1
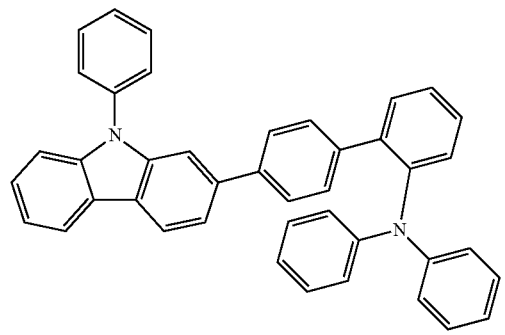
P2-2
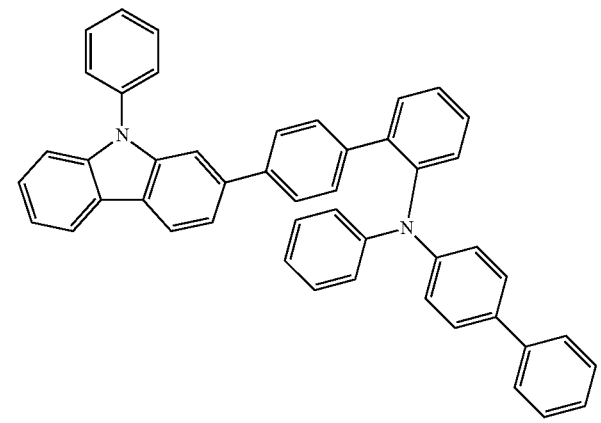
P2-3
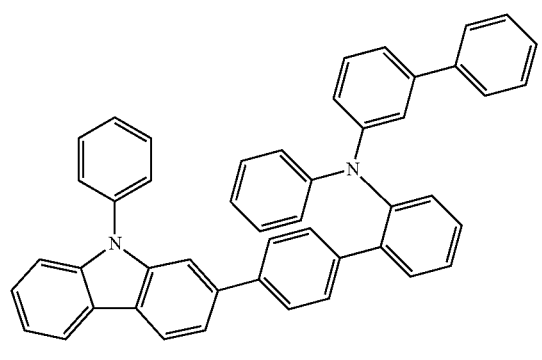
P2-4
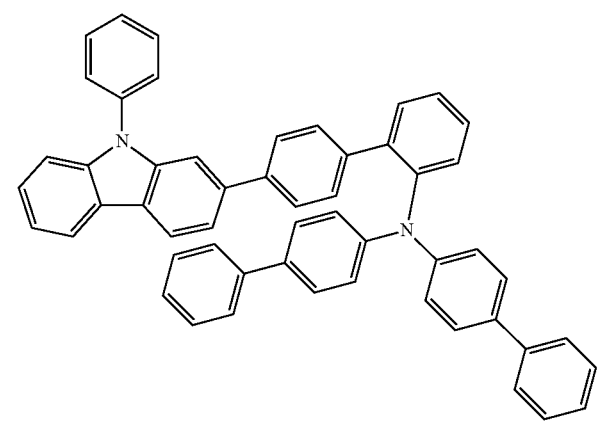
P2-5
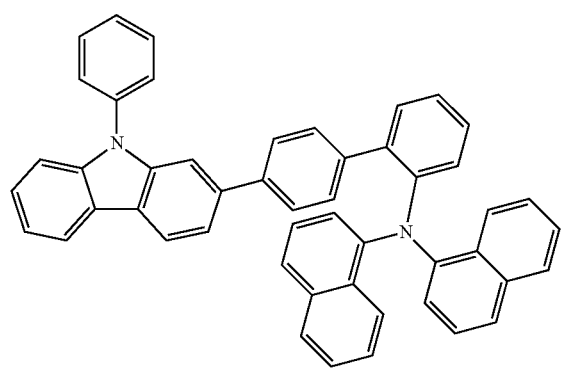
P2-6
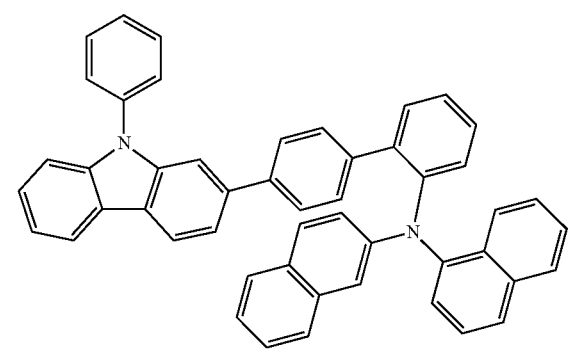

-continued
P2-7
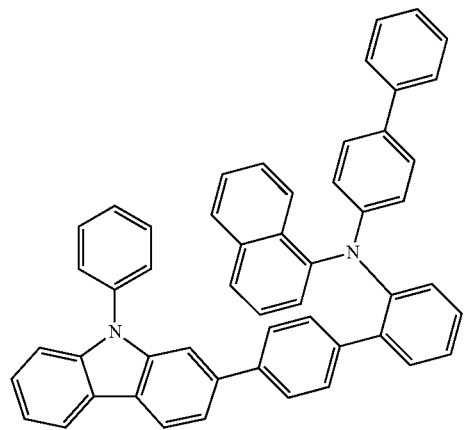
P2-8
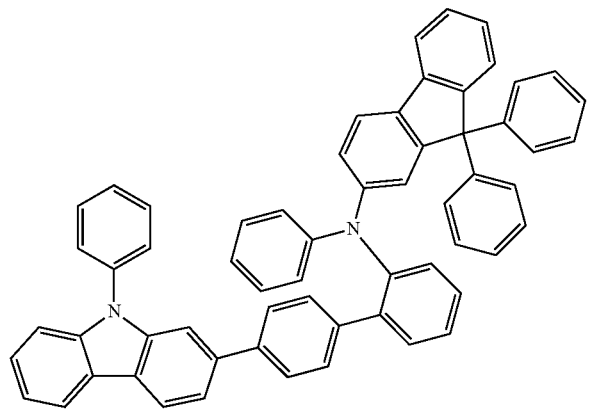
P2-9
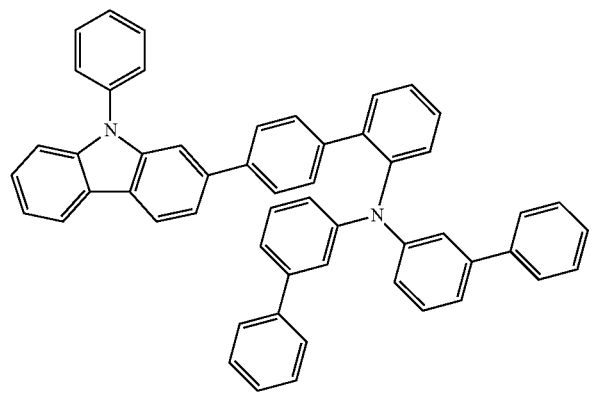
P2-10
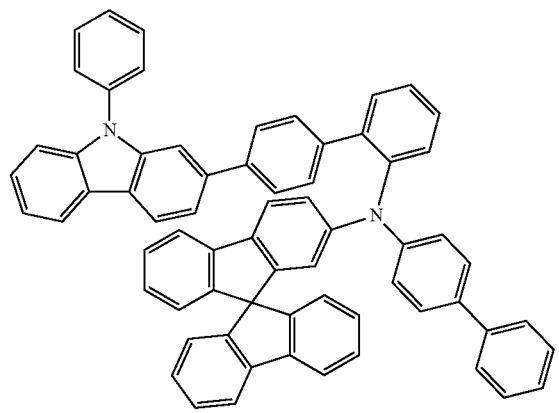
P2-11
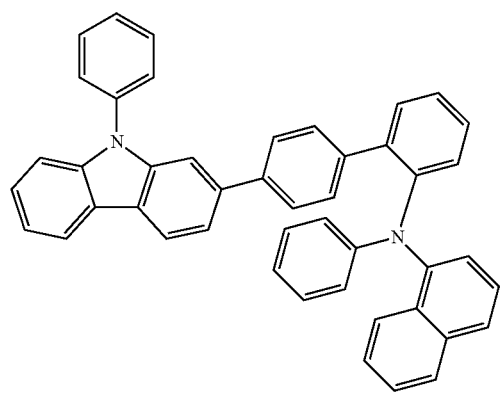
P2-12
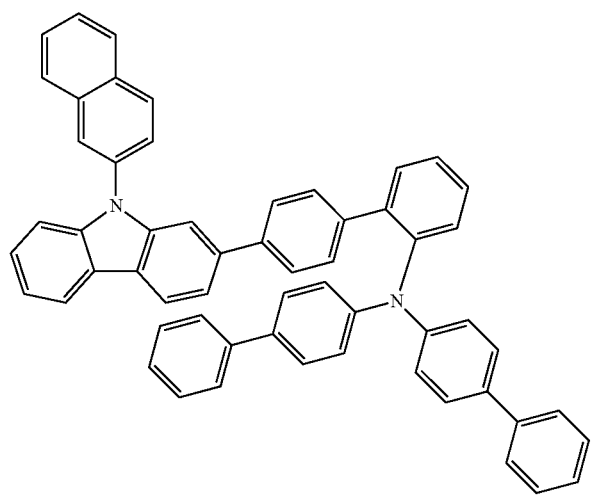

-continued
P2-13
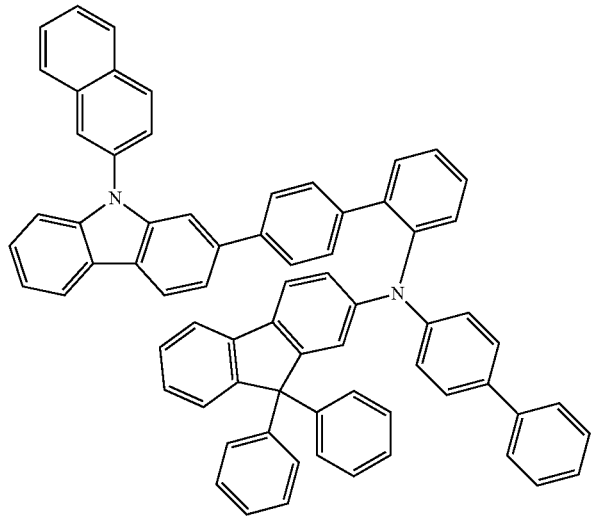
P2-14
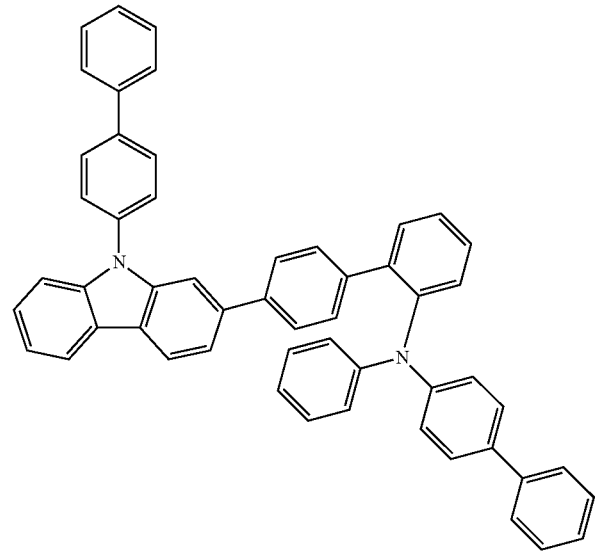
P2-15
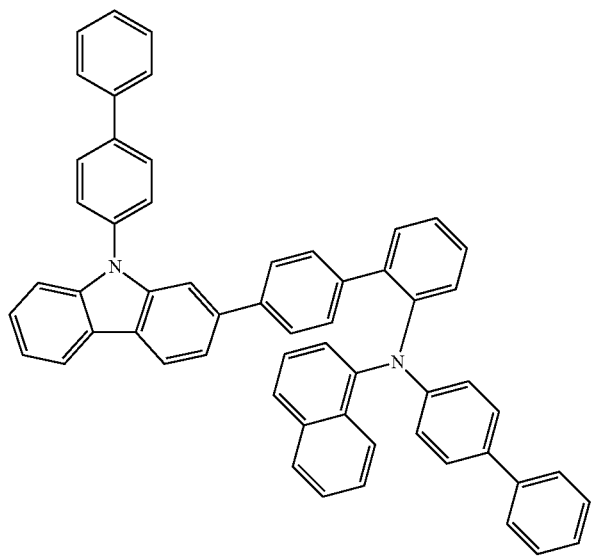
P2-16
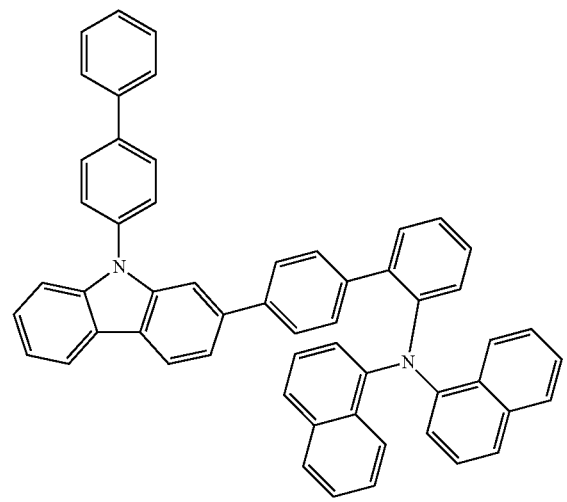
P2-17
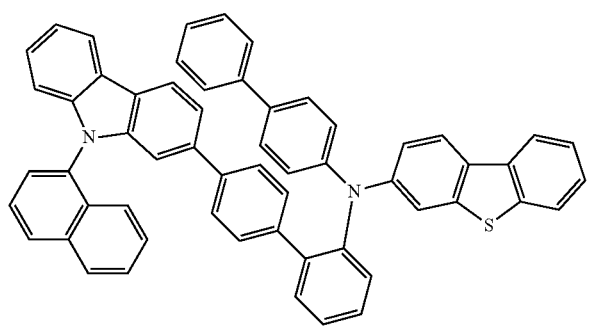
P2-18
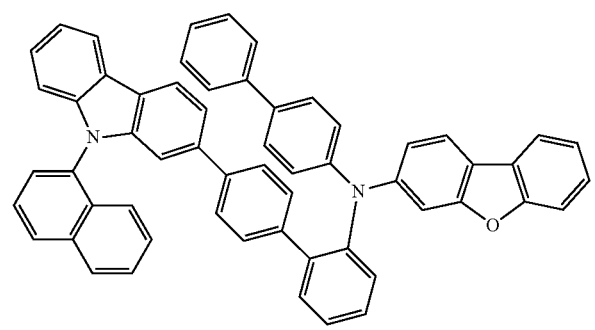

-continued
P2-19
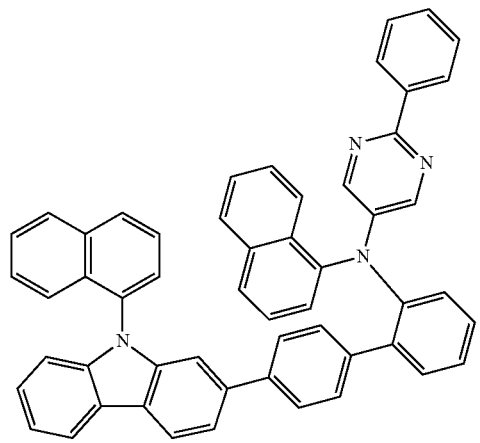
P2-20
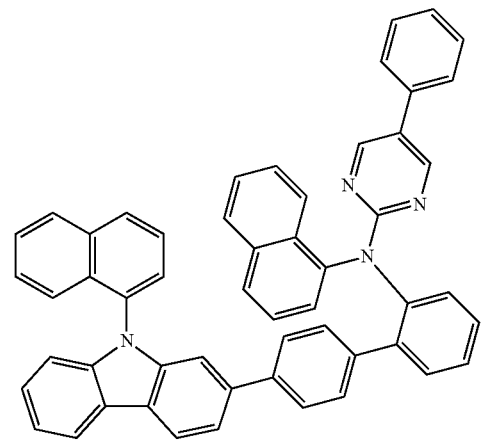
P2-21
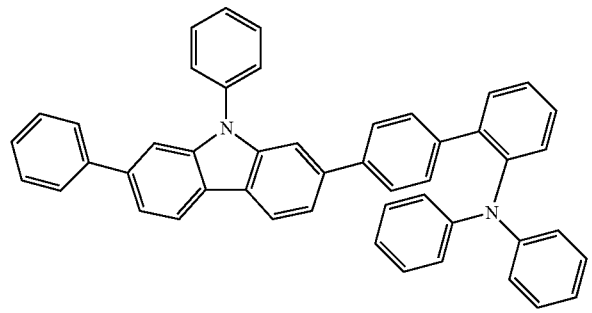
P2-22
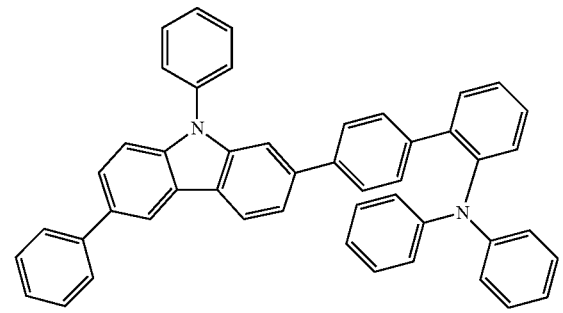
P2-23
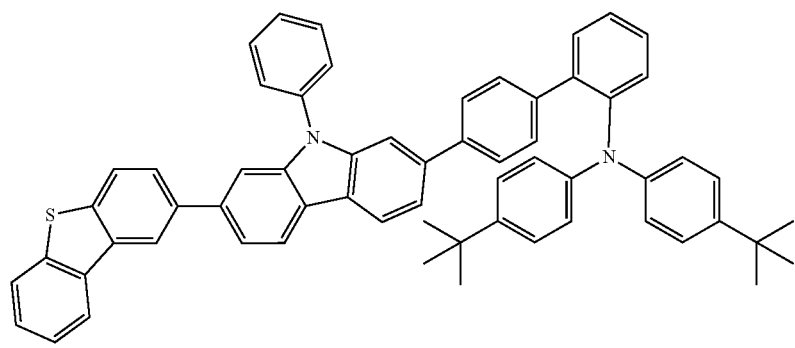
P2-24
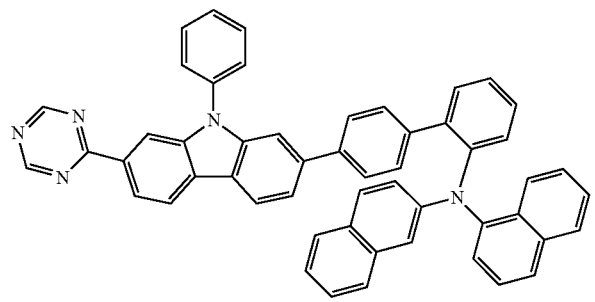
P2-25
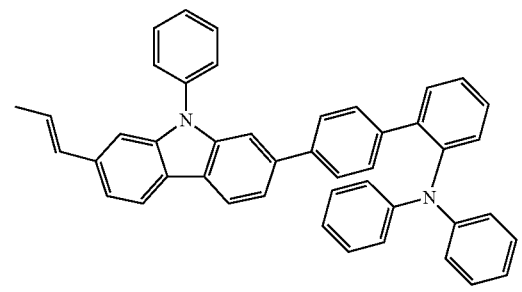

-continued
P2-26
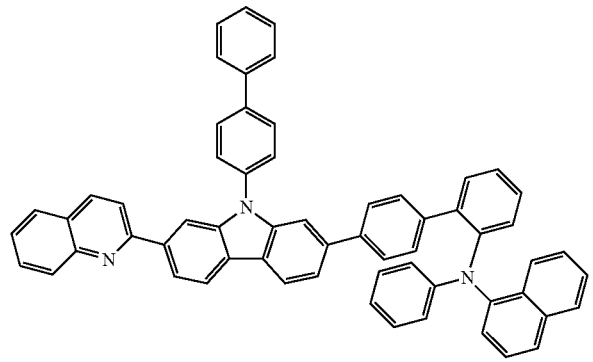
P2-27
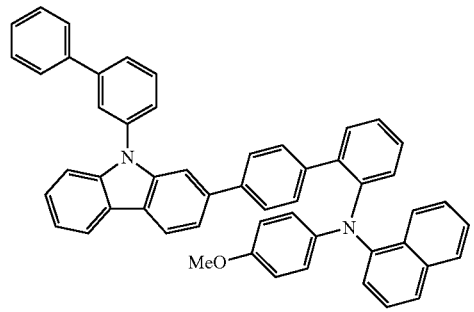
P2-28
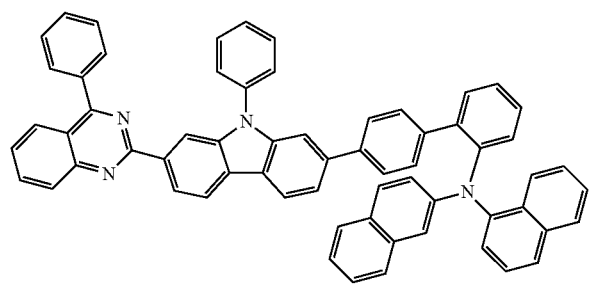
P2-29
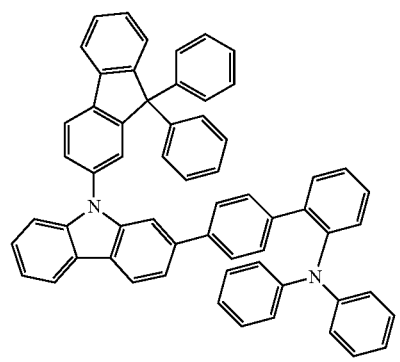
P2-30
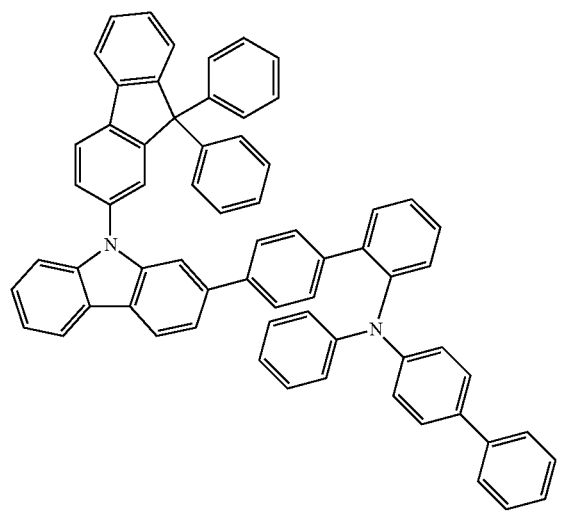
P2-31
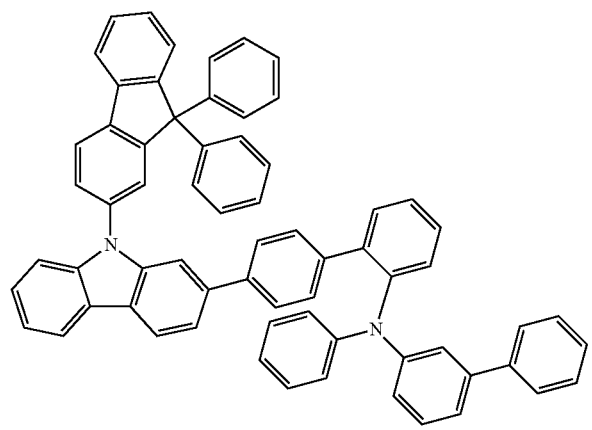

-continued
P2-32
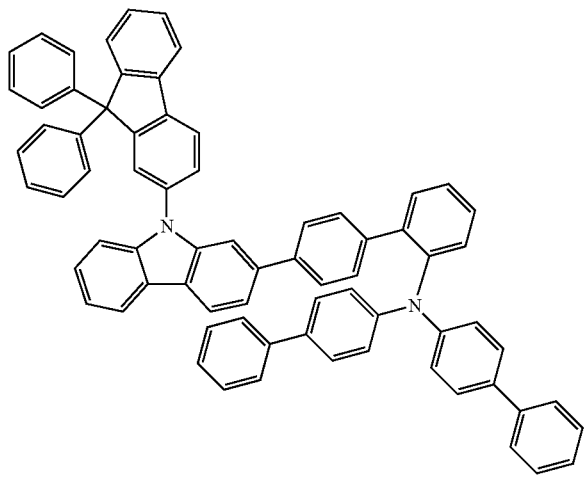
P2-33
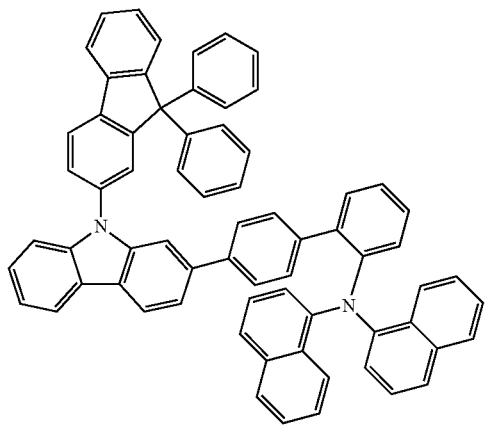
P2-34
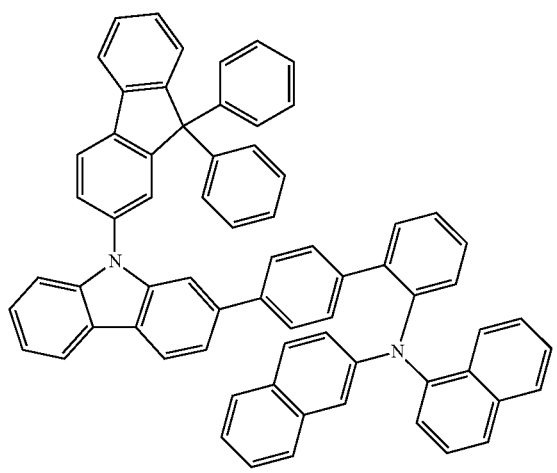
P2-35
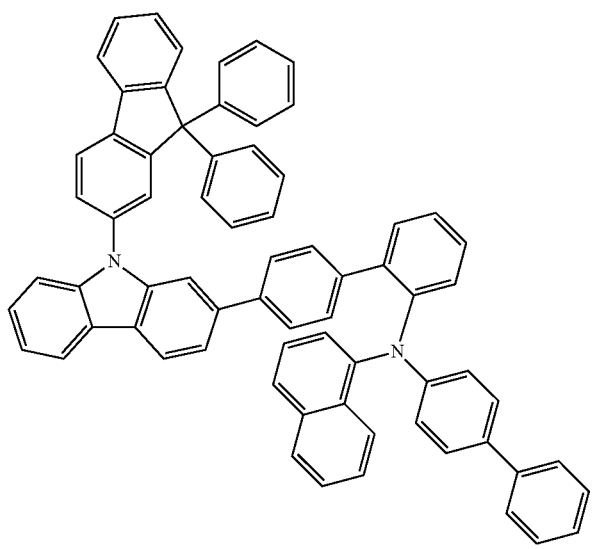
P2-36
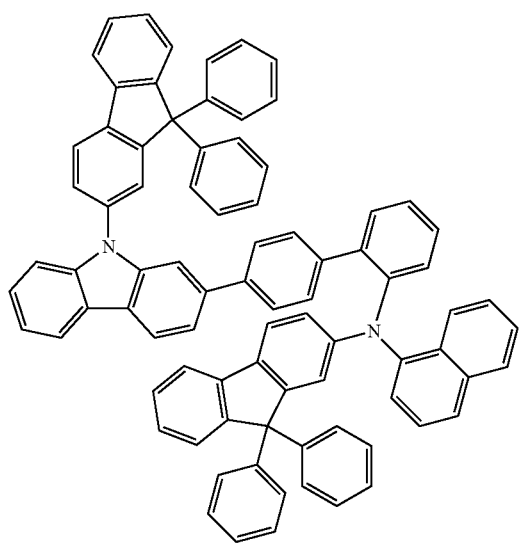
P2-37
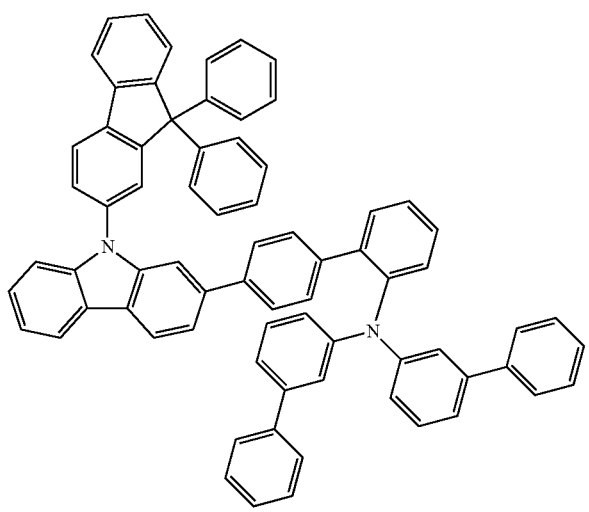

-continued
P2-38
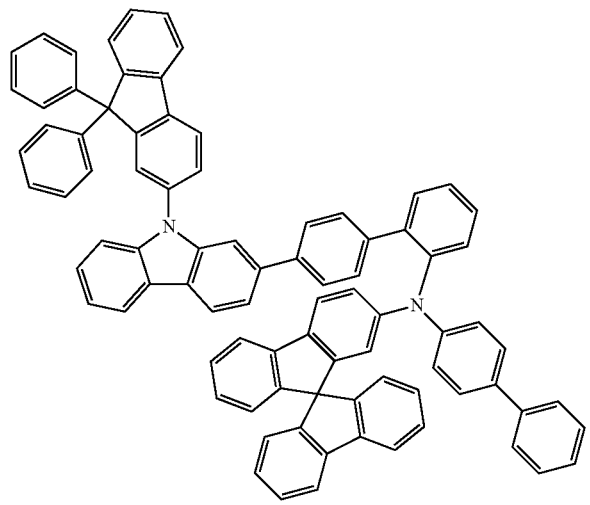
P2-39
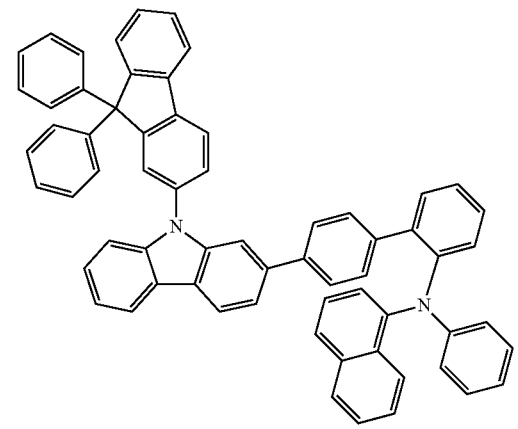
P2-40
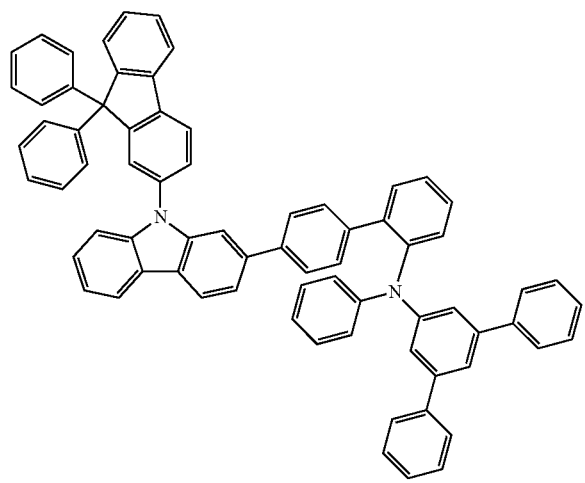
P2-41
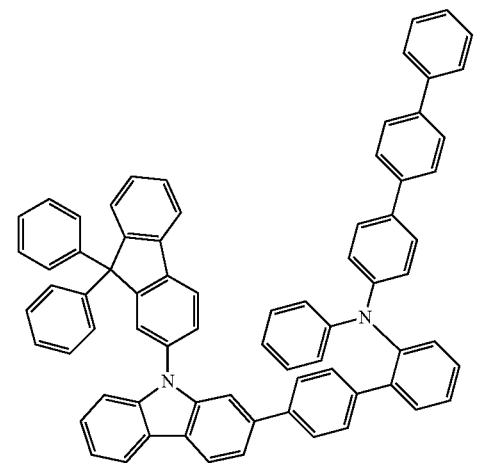
P2-42
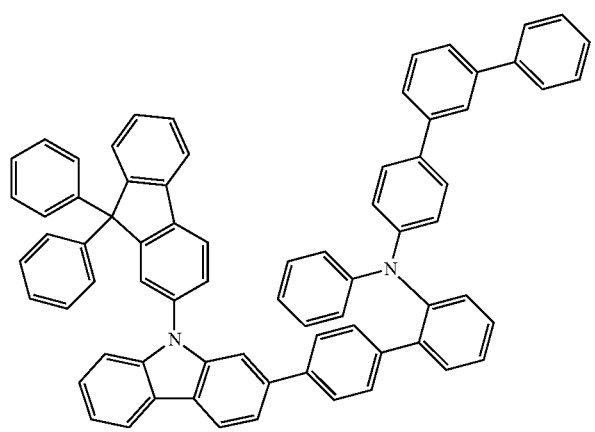
P2-43
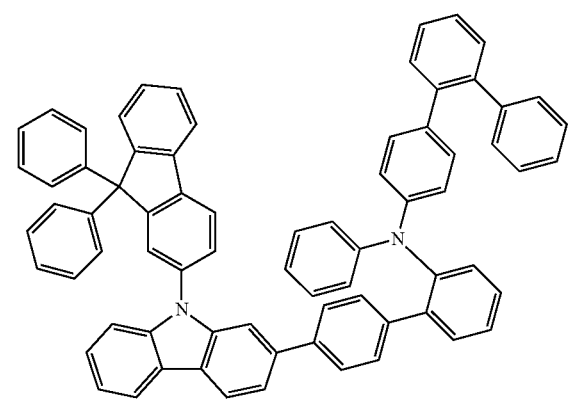

-continued
P2-44
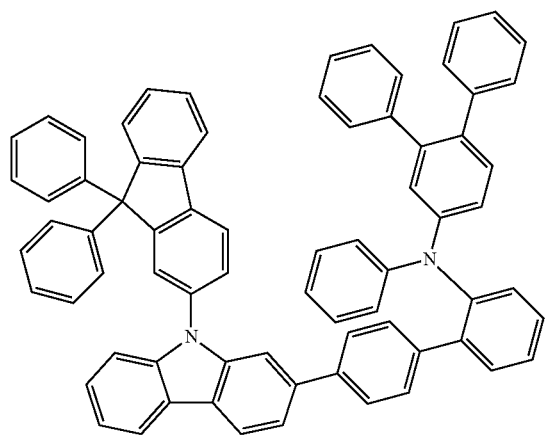
P2-45
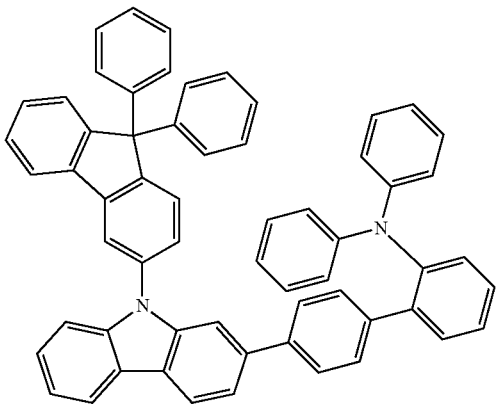
P2-46
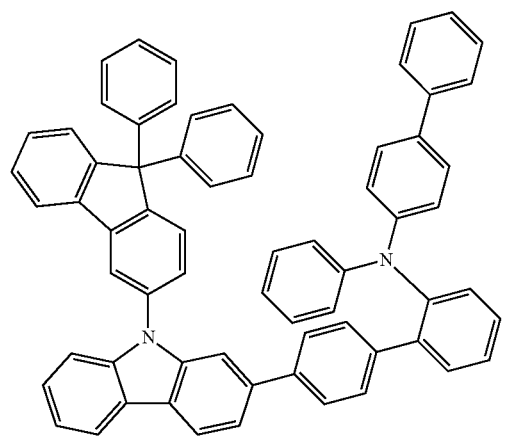
P2-47
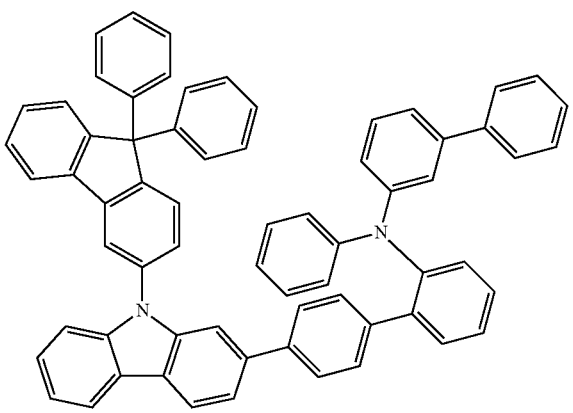
P2-48
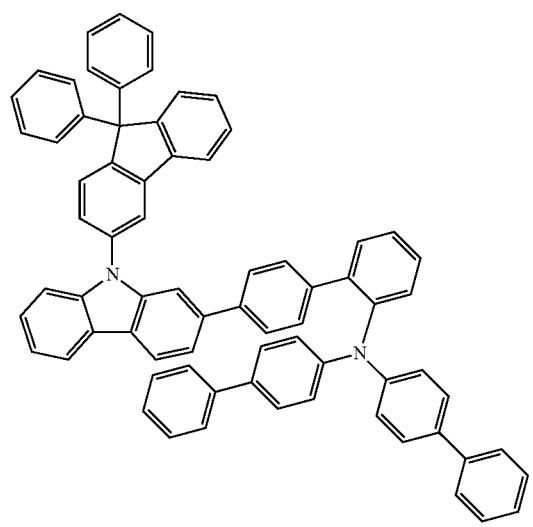
P2-49
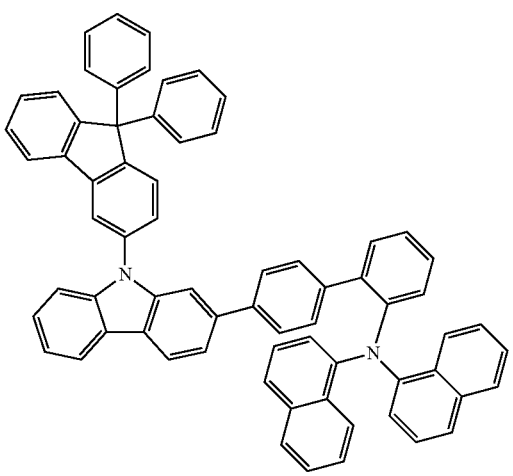

-continued
P2-50
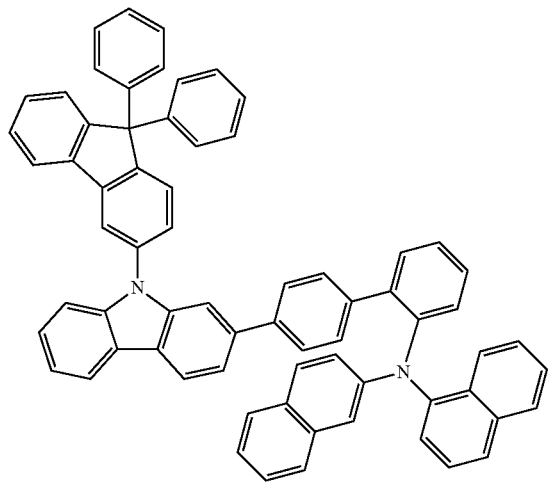
P2-51
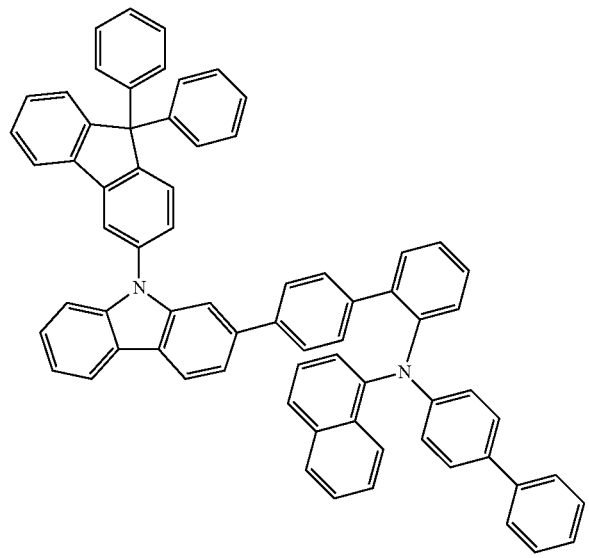
P2-52
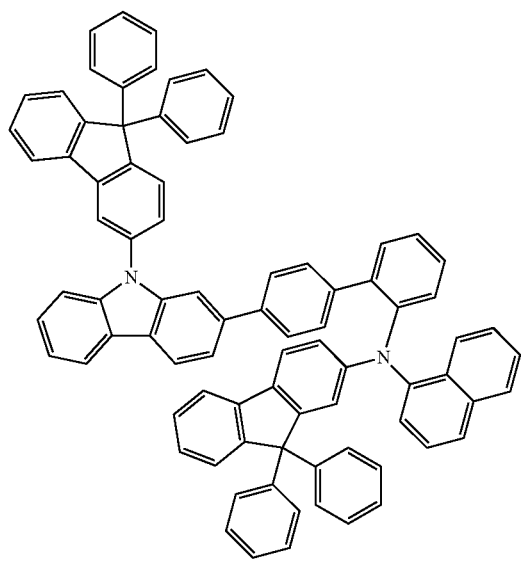
P2-53
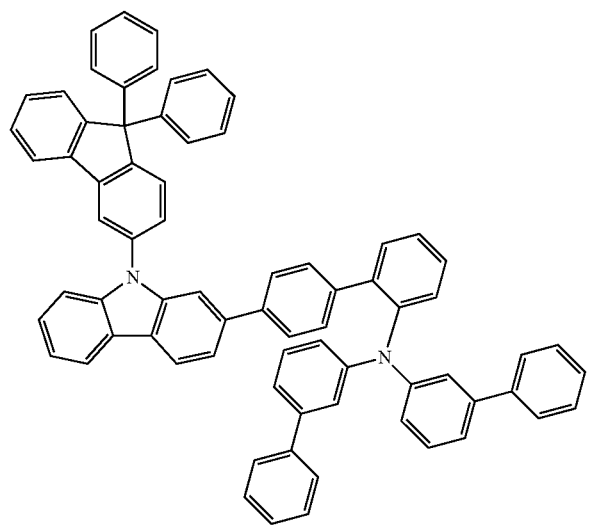

P2-54
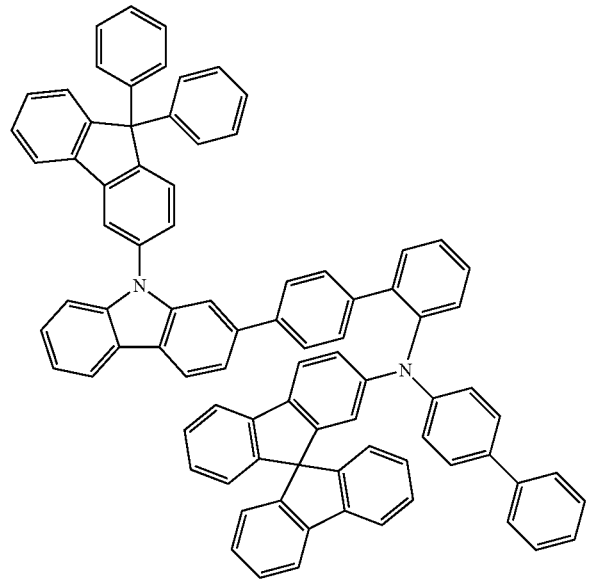
P2-55
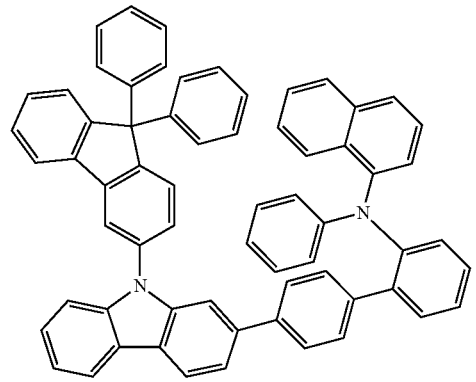
P2-56
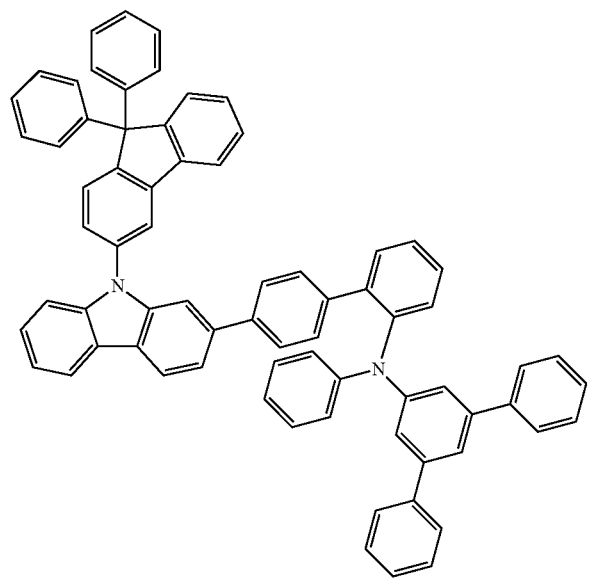
P2-57
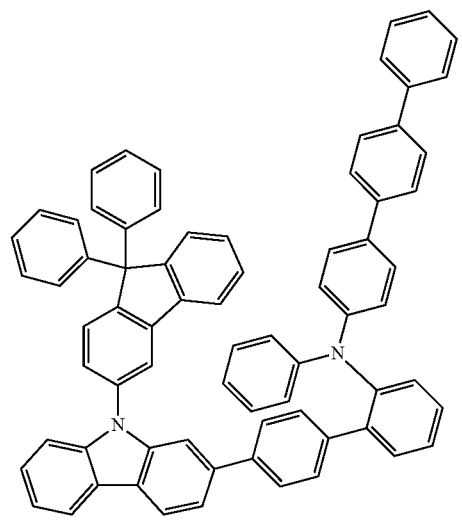

-continued
P2-58
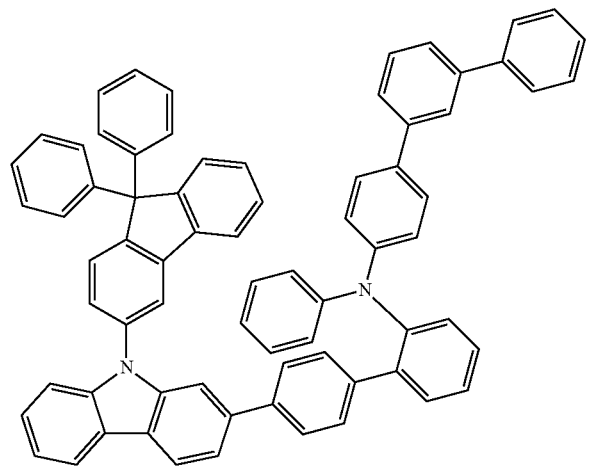
P2-59
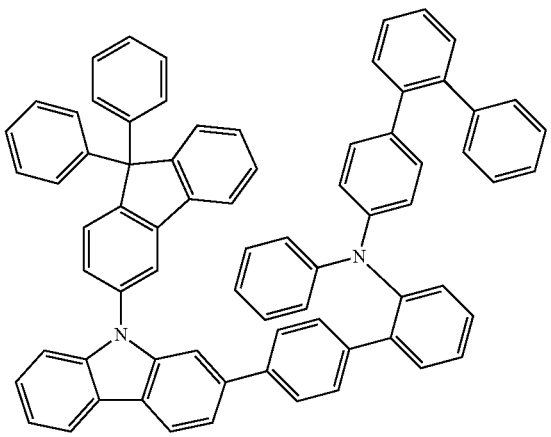
P2-60
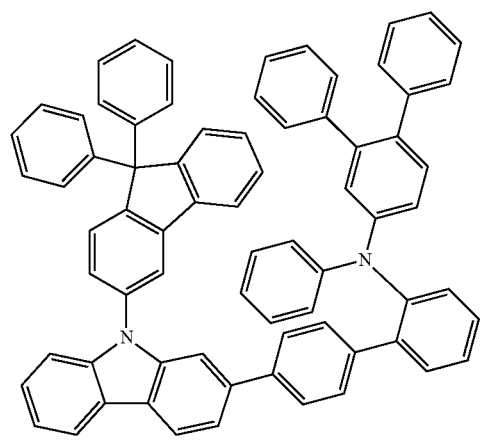
P2-61
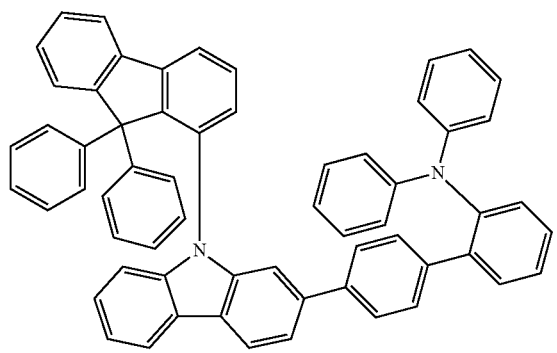
P2-62
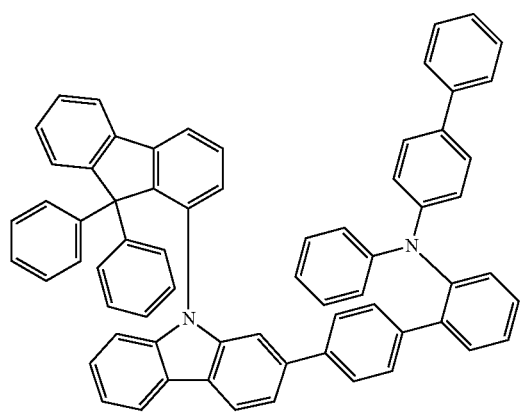
P2-63
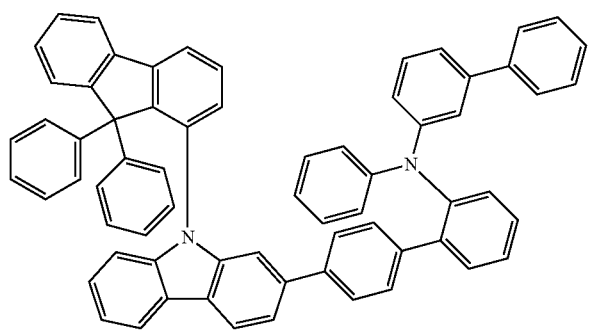

-continued
P2-64
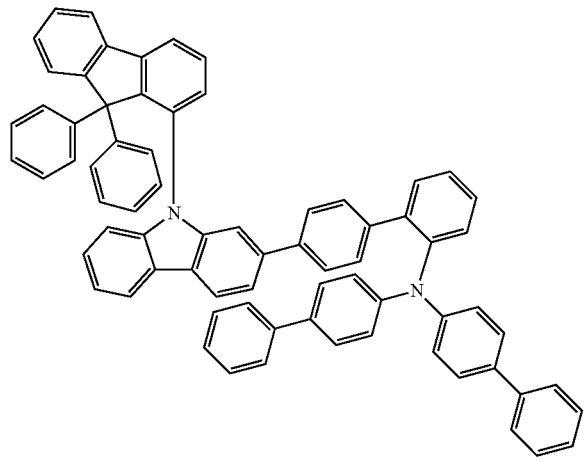
P2-65
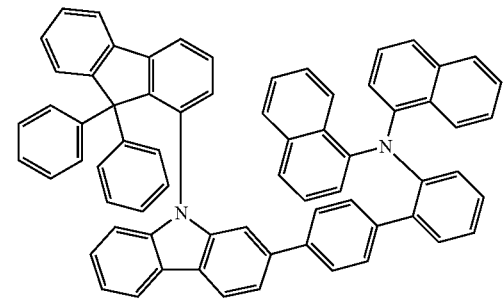
P2-66
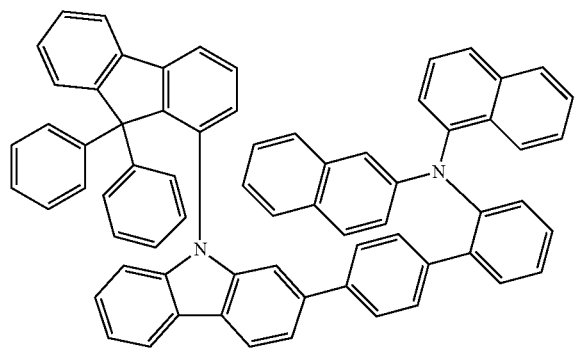
P2-67
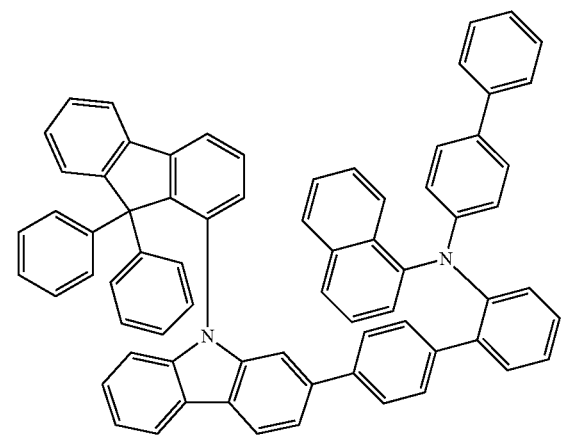
P2-68
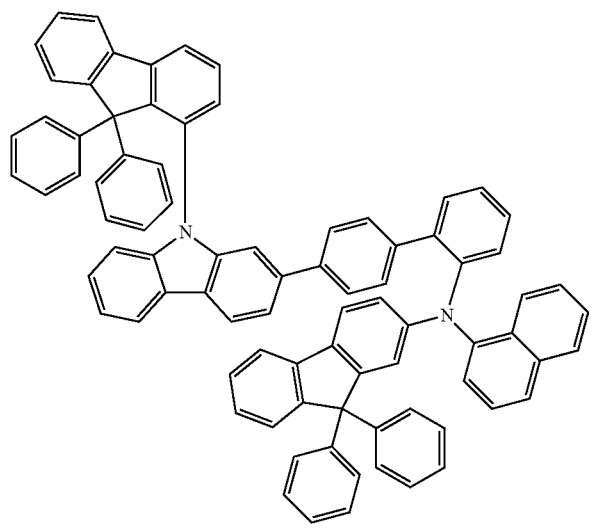
P2-69
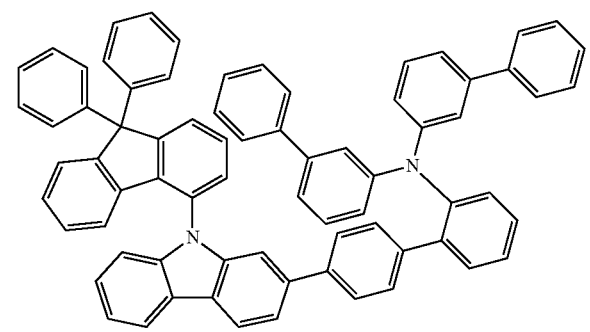

-continued
P2-70
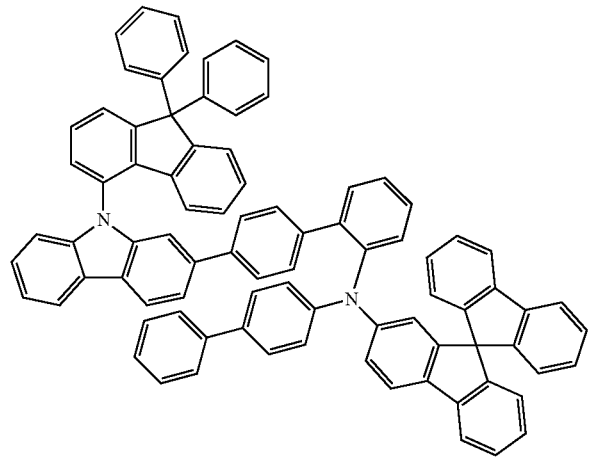
P2-71
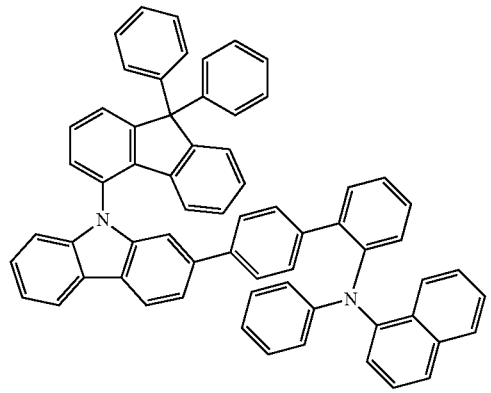
P2-72
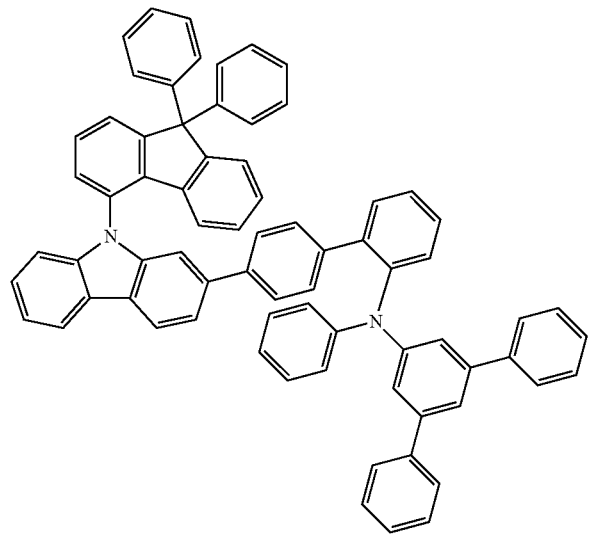
P2-73
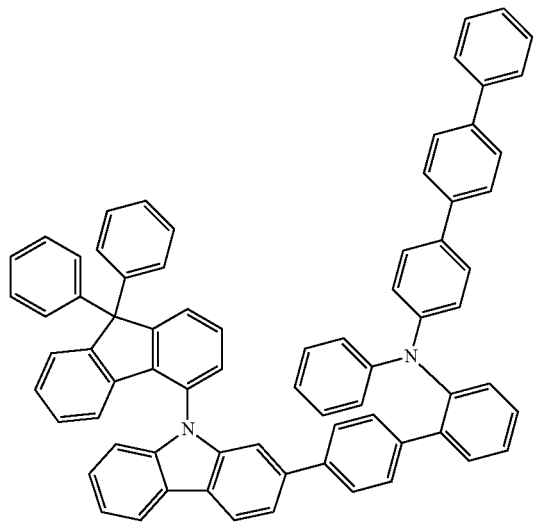
P2-74
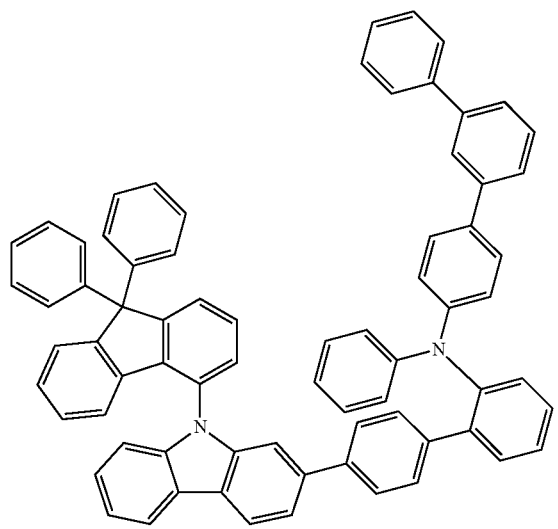
P2-75
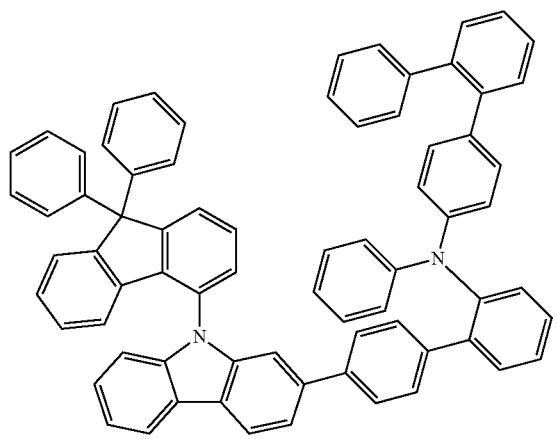

-continued
P2-76
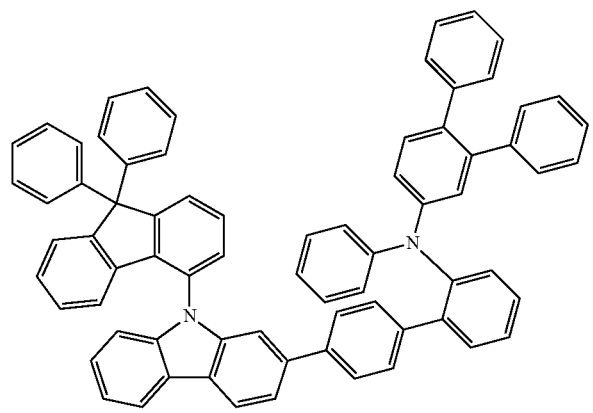
P2-77
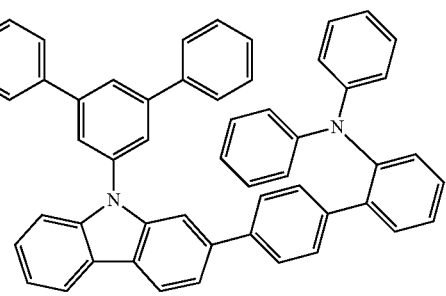
P2-78
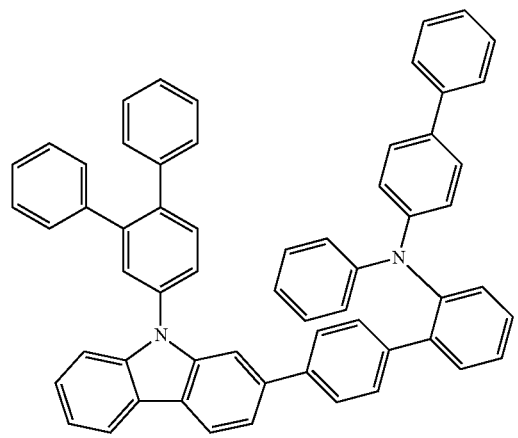
P2-79
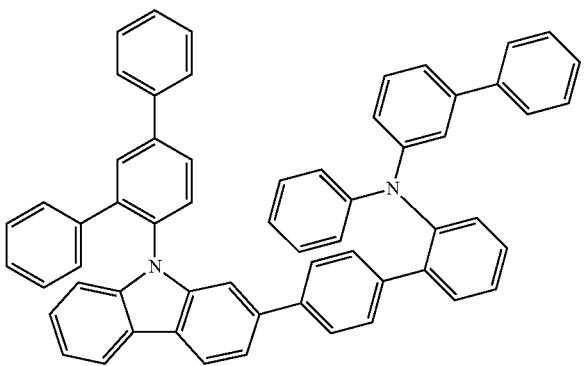
P2-80
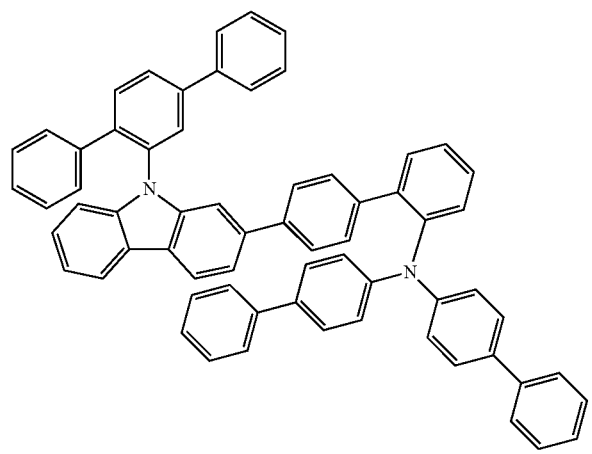
P2-81
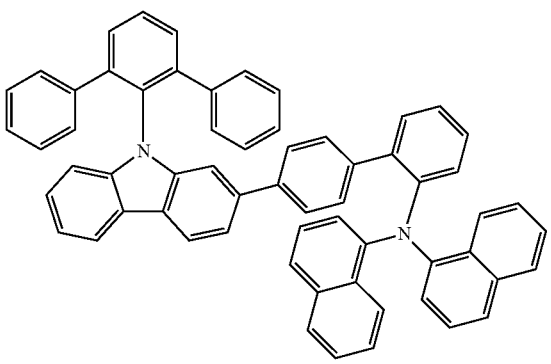

-continued
P2-82
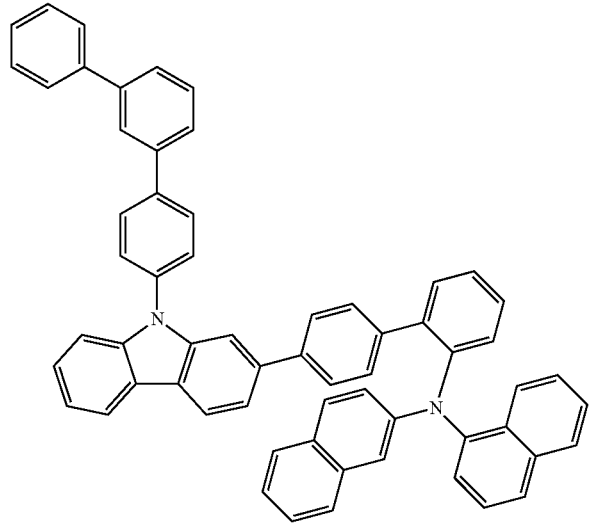
P2-83
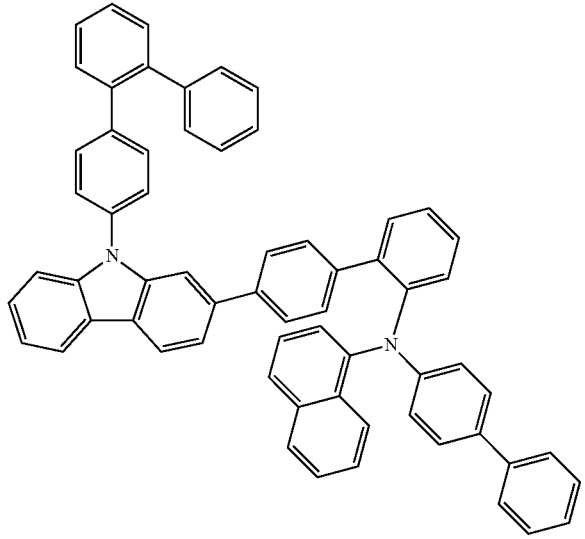
P2-84
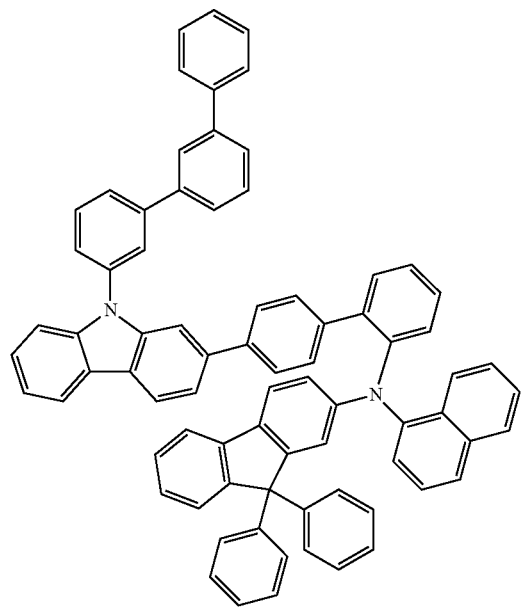
P2-85
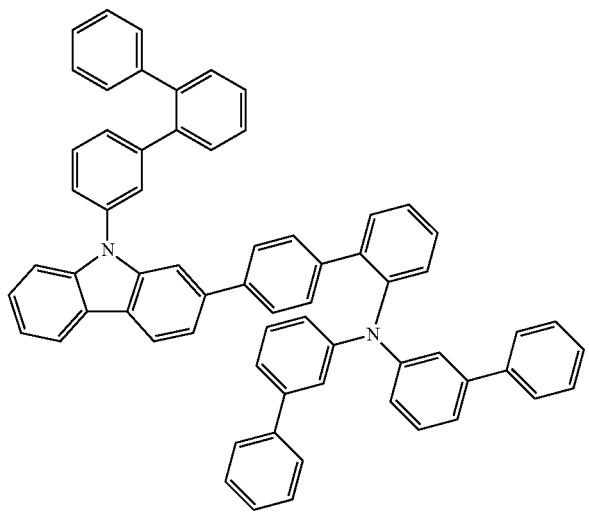
P2-86
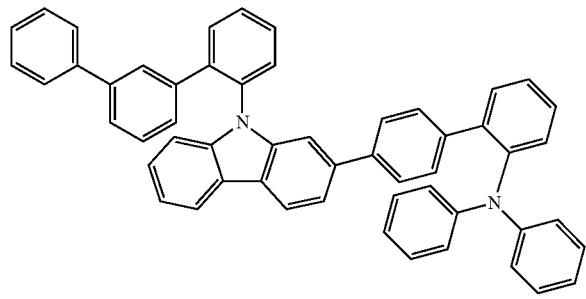
P2-87
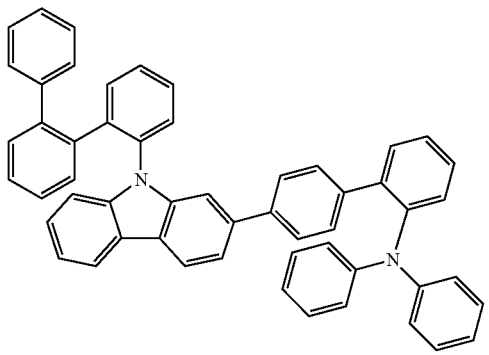

-continued
P2-88
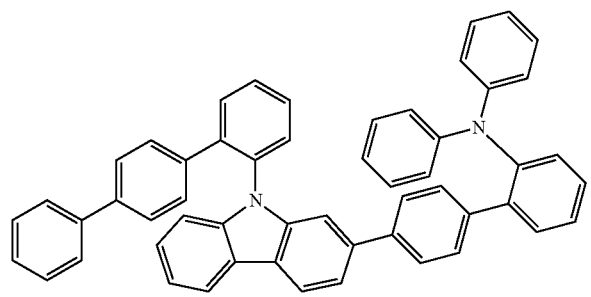
P2-89
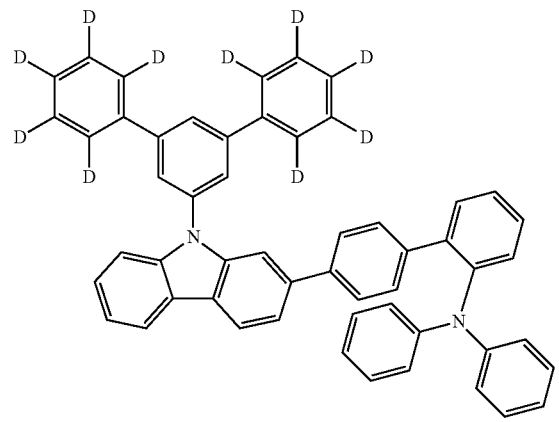
P2-90
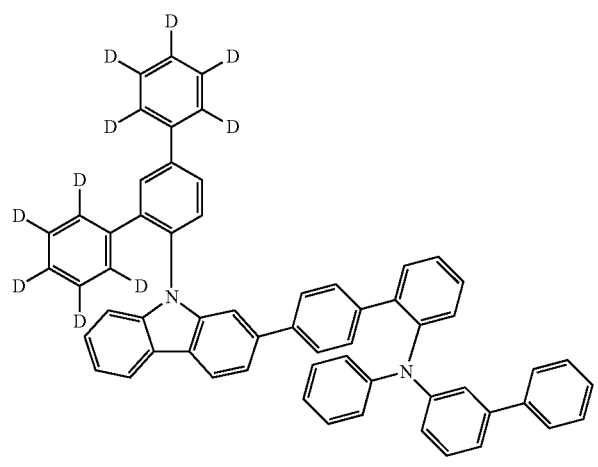
P2-91
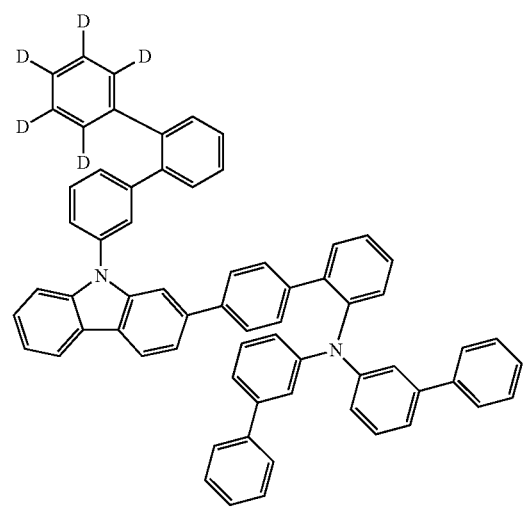
P2-92
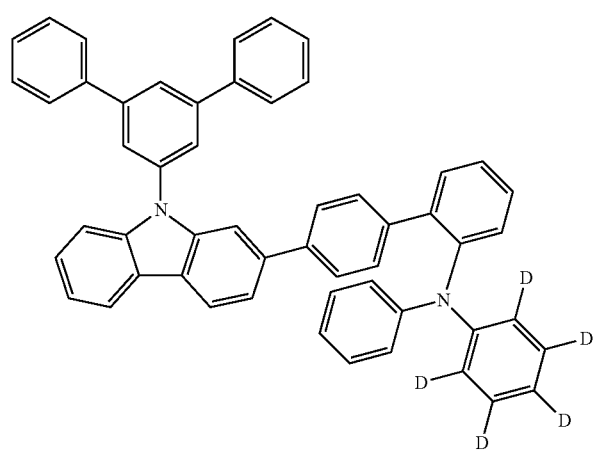
P2-93
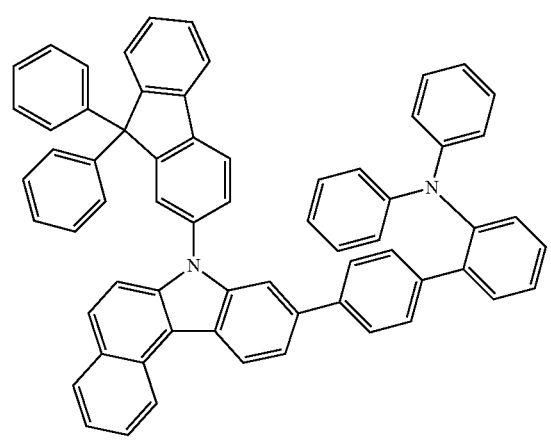

-continued
P2-94
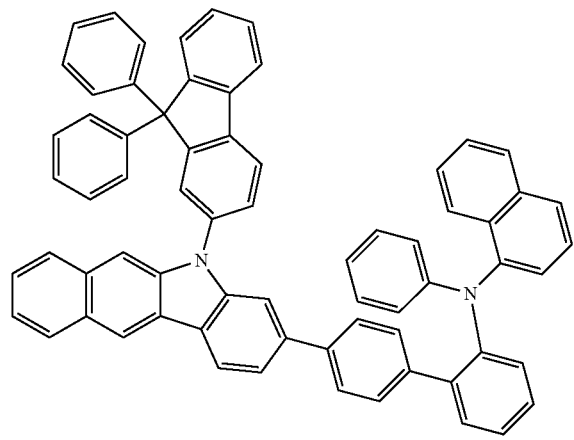
P2-95
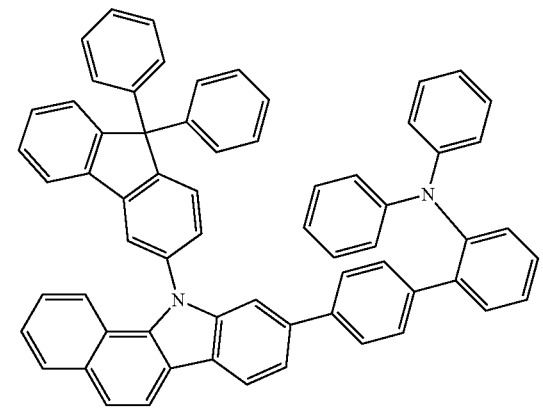
P2-96
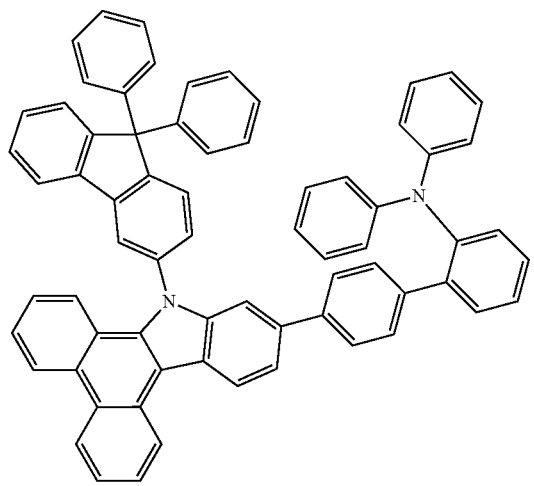
P2-97
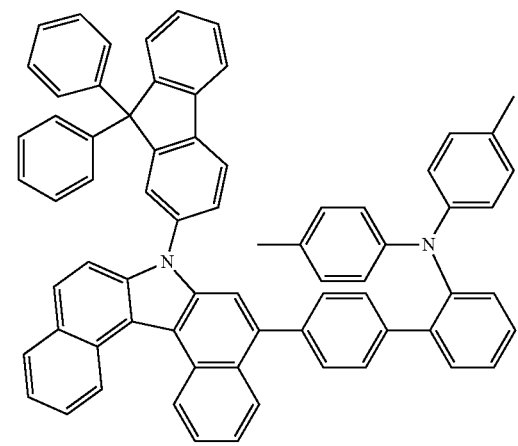
P2-98
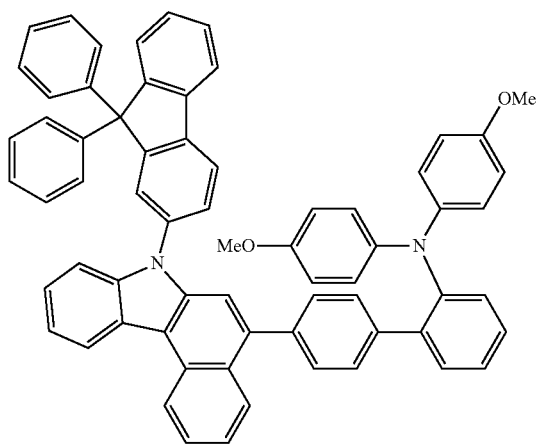
P2-99
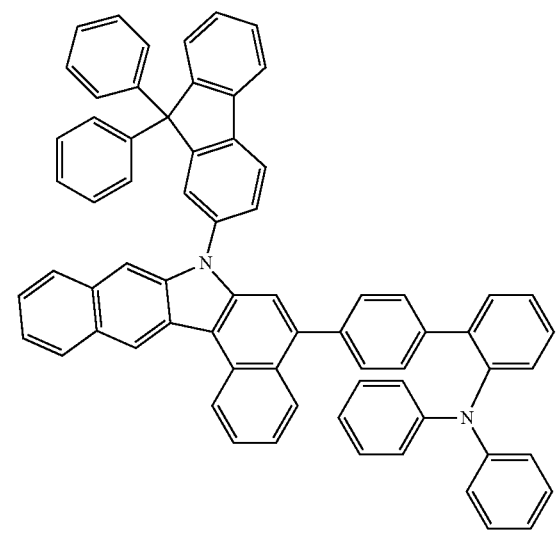

-continued
P2-100
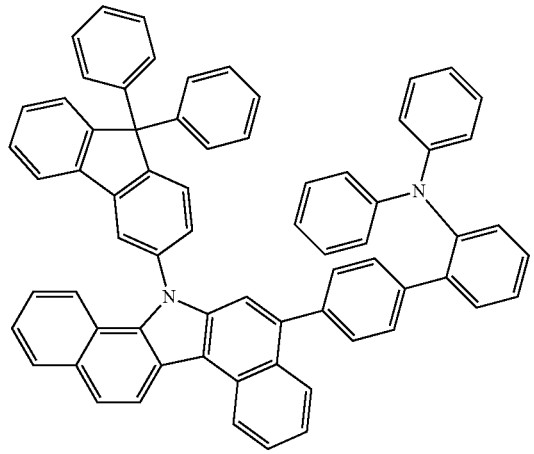
P2-101
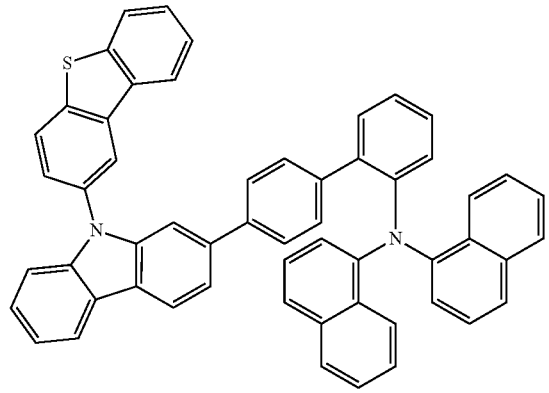
P2-102
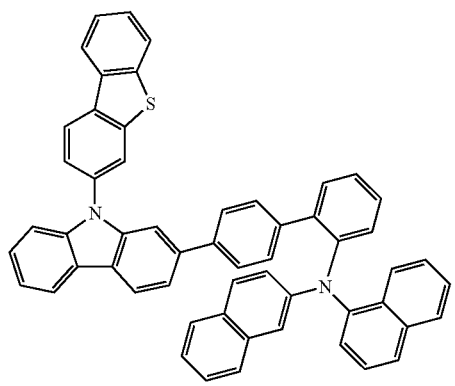
P2-103
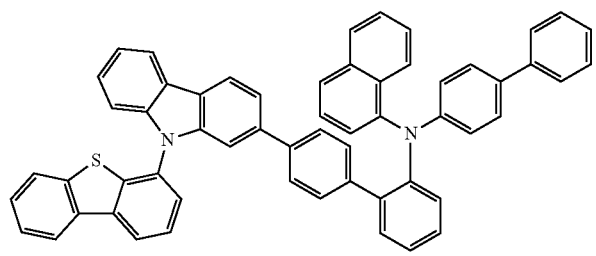
P2-104
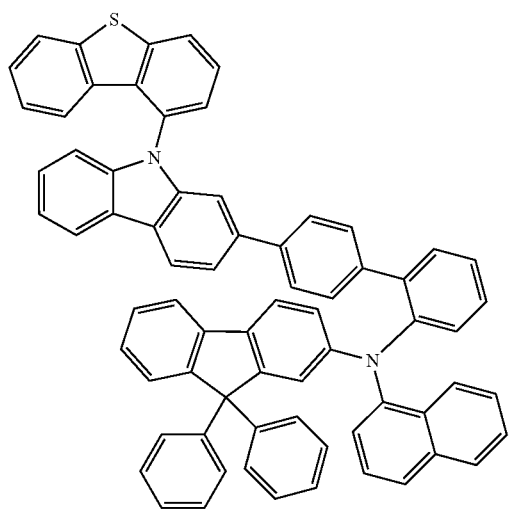
P2-105
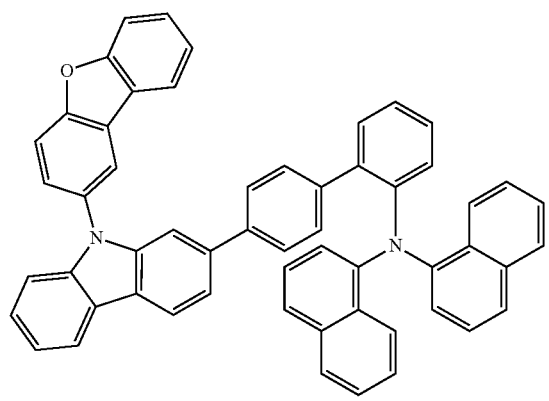

-continued
P2-106
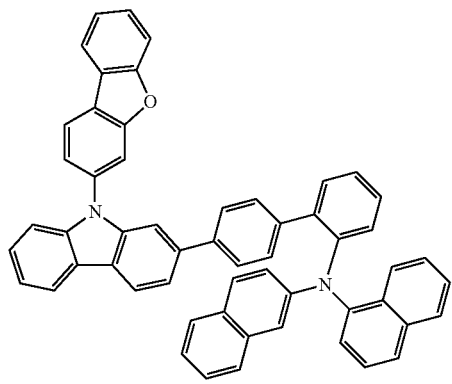
P2-107
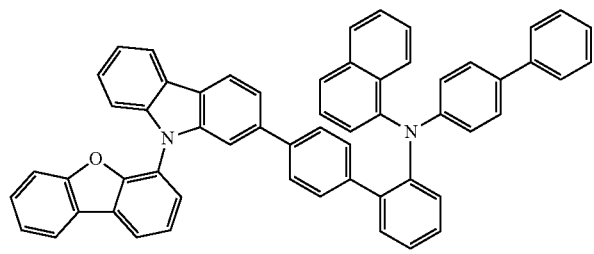
P2-108
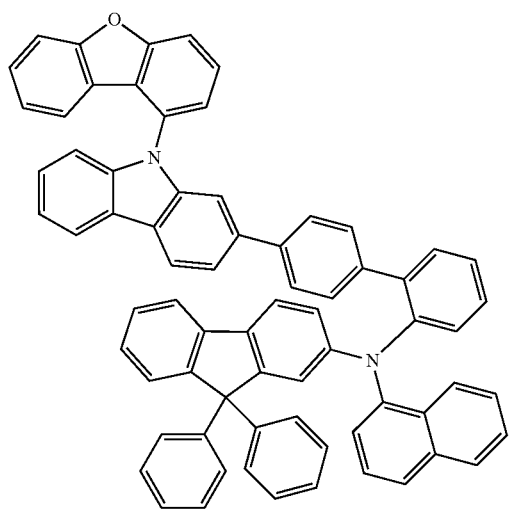
P2-109
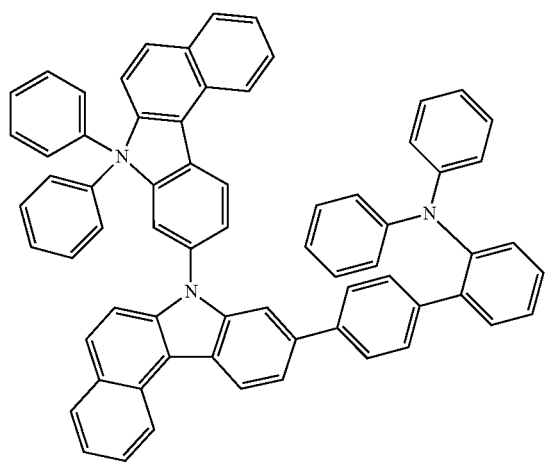
P2-110
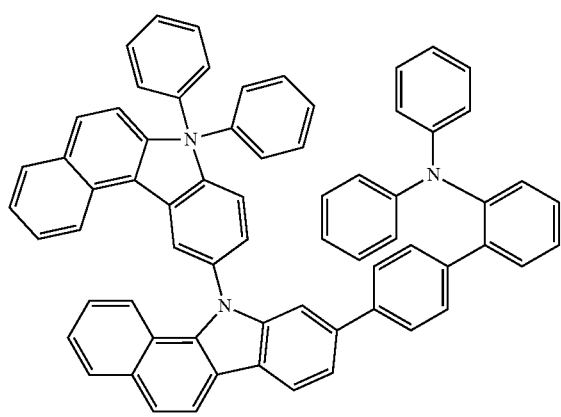
P2-111
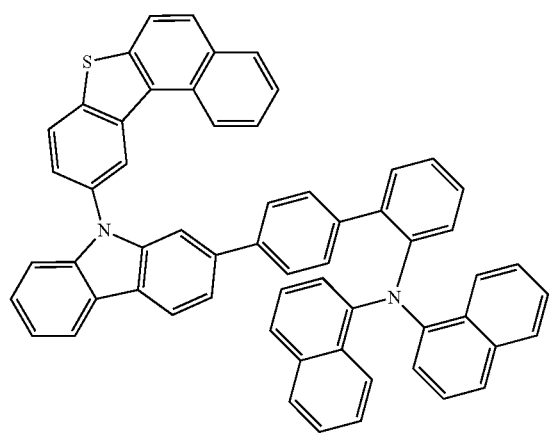

-continued
P2-112
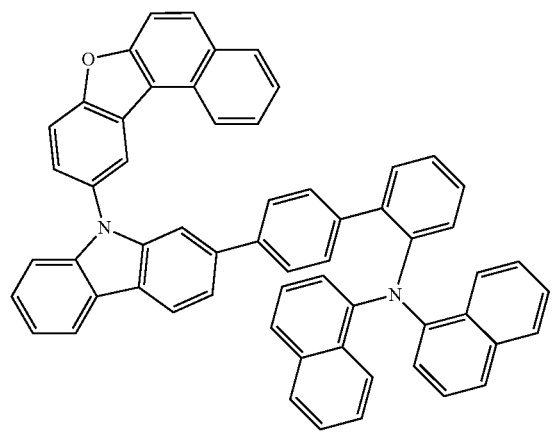
P3-1
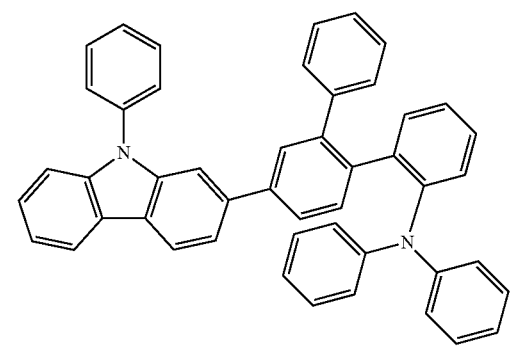
P3-2
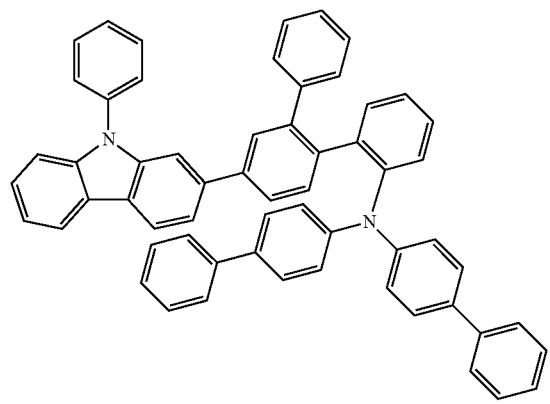
P3-3
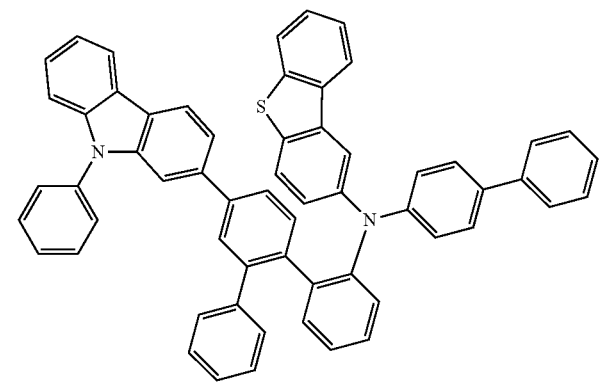
P3-4
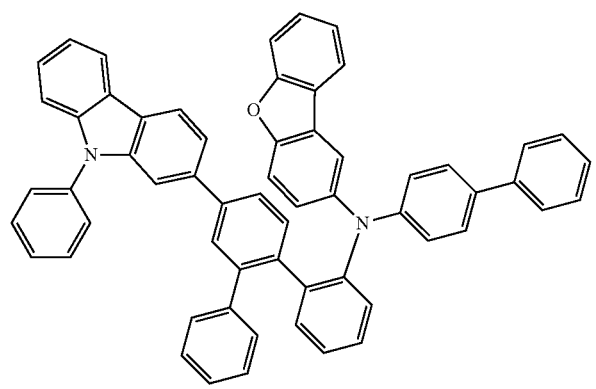
P3-5
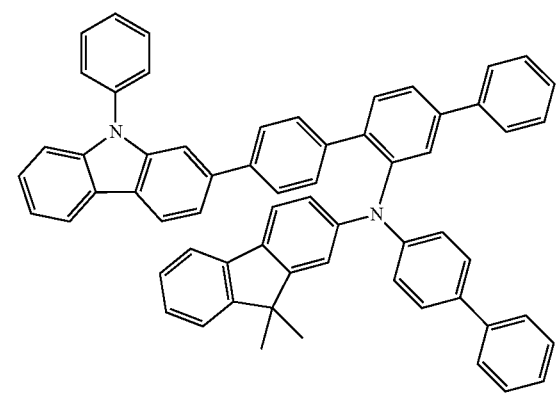

-continued
P3-6
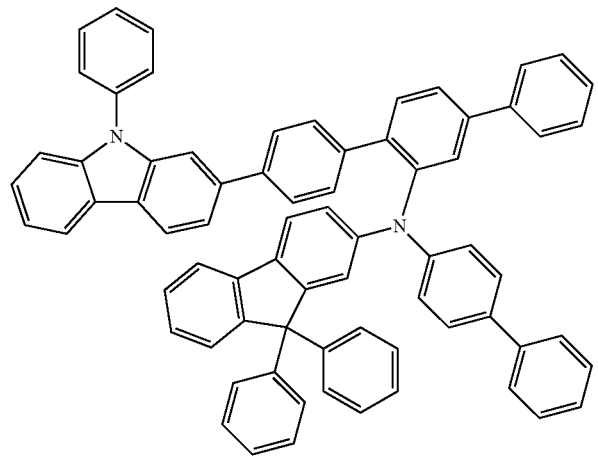
P3-7
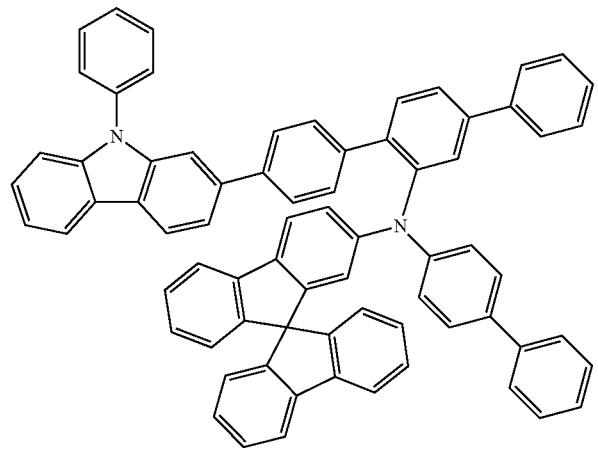
P3-8
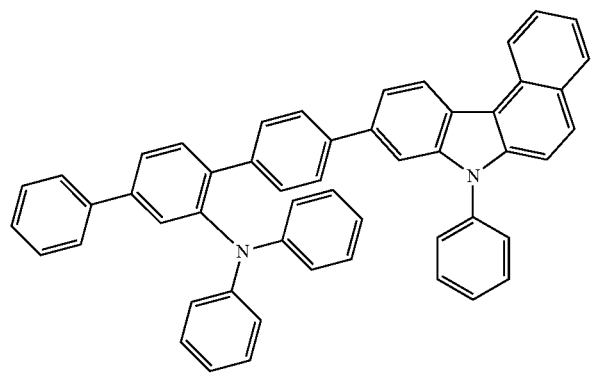
P3-9
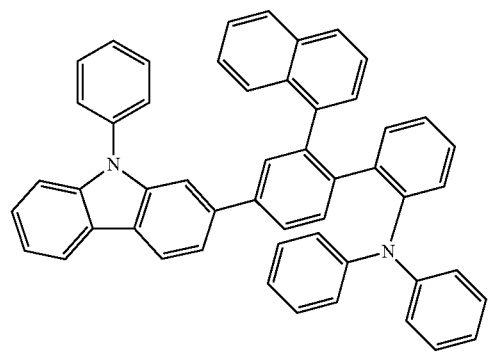
P3-10
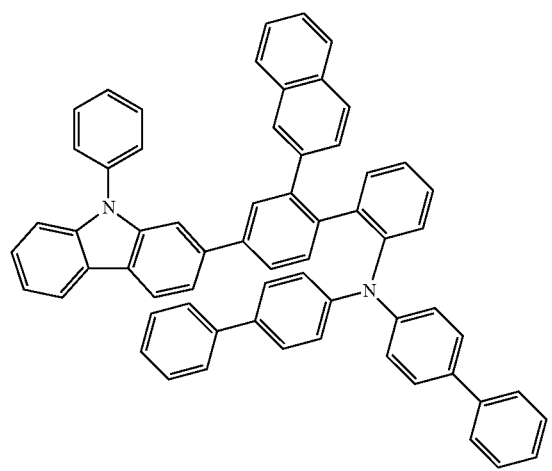
P3-11
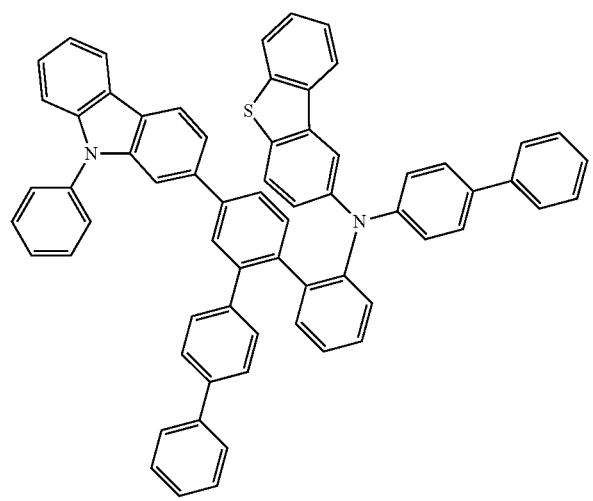

-continued
P3-12
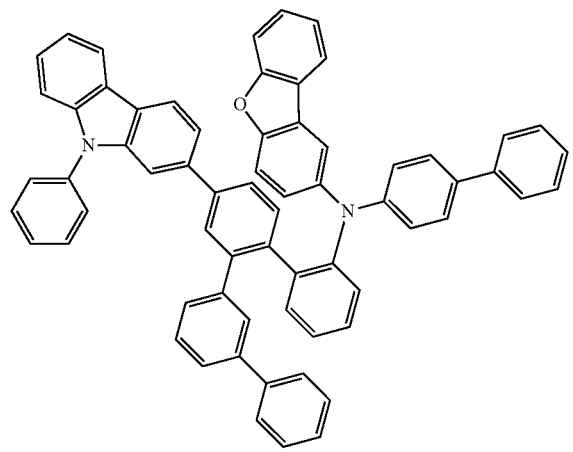
P3-13
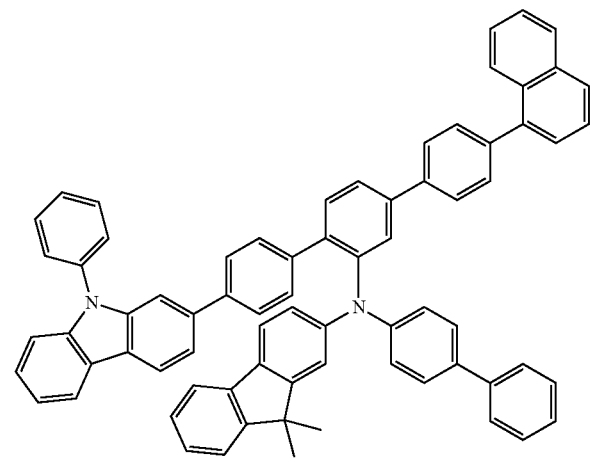
P3-14
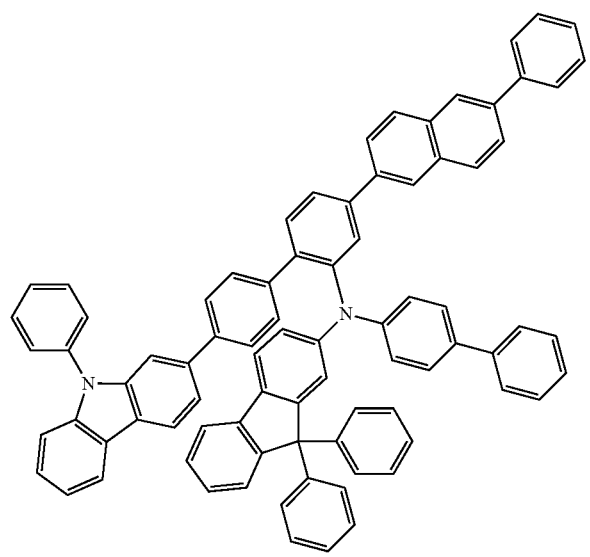
P3-15
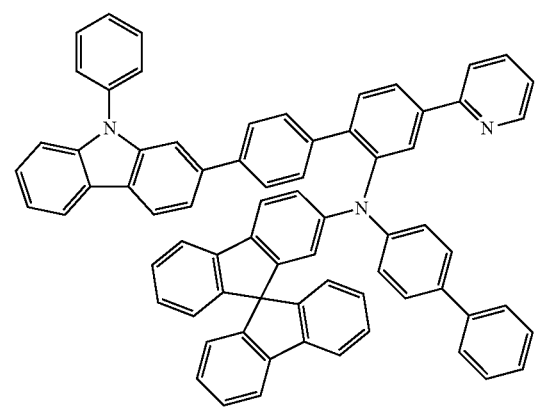
P3-16
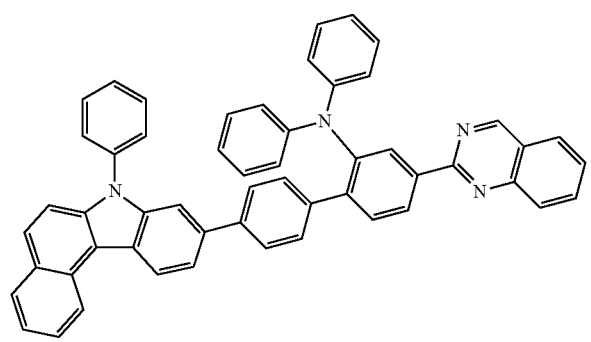
P3-17
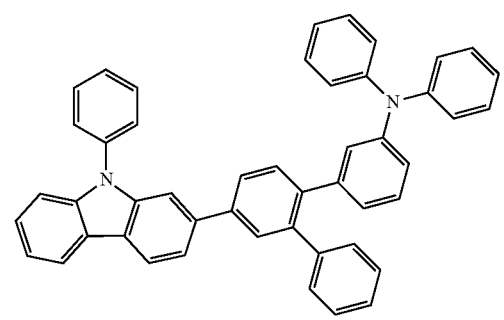

-continued
P3-18
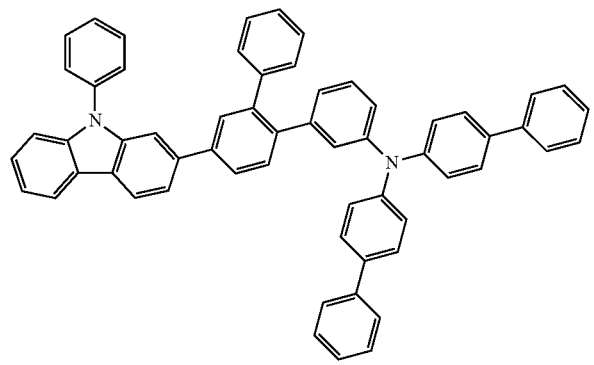
P3-19
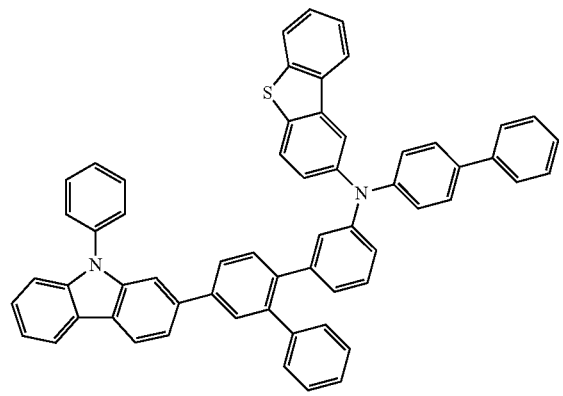
P3-20
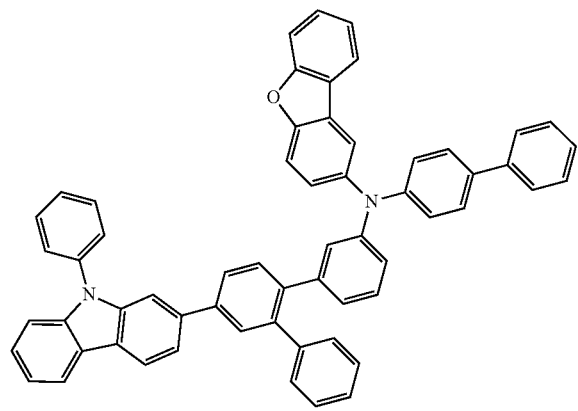
P3-21
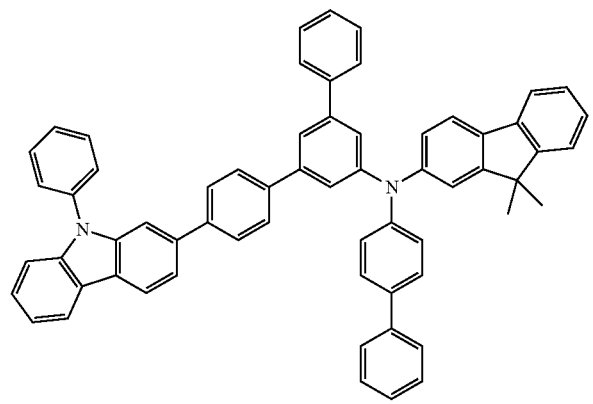
P3-22
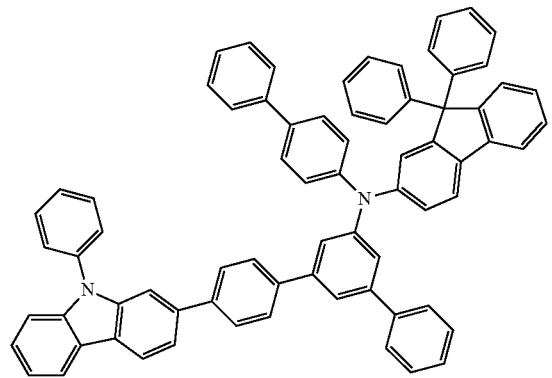
P3-23
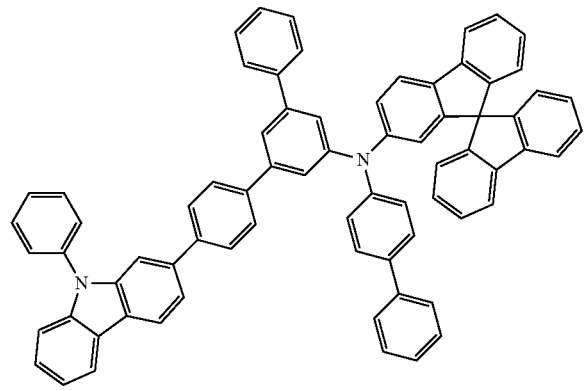

-continued
P3-24
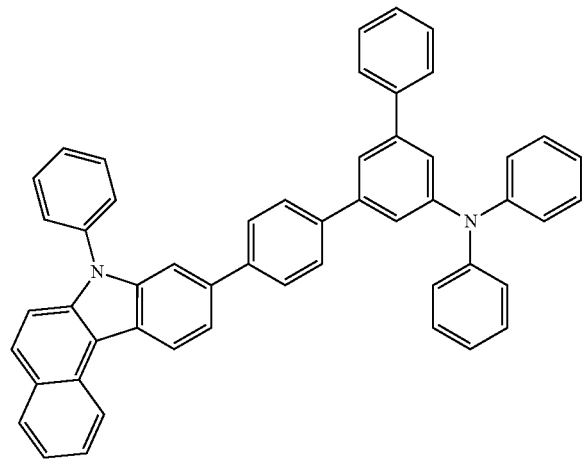
P3-25
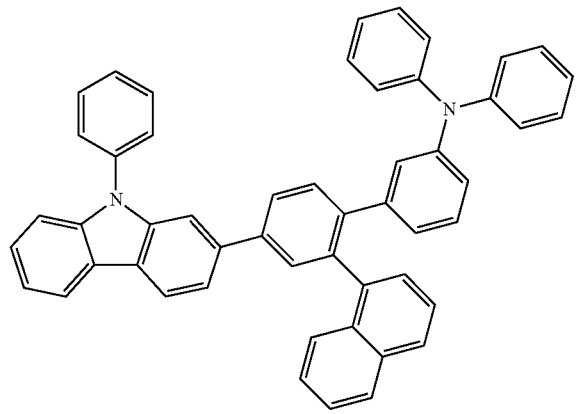
P3-26
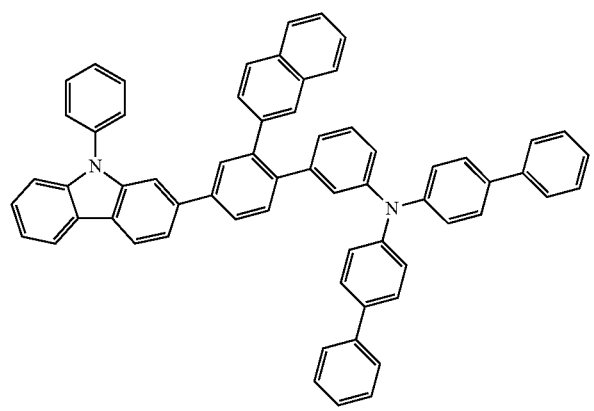
P3-27
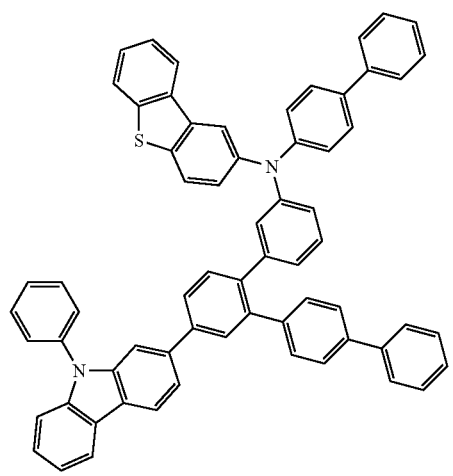
P3-28
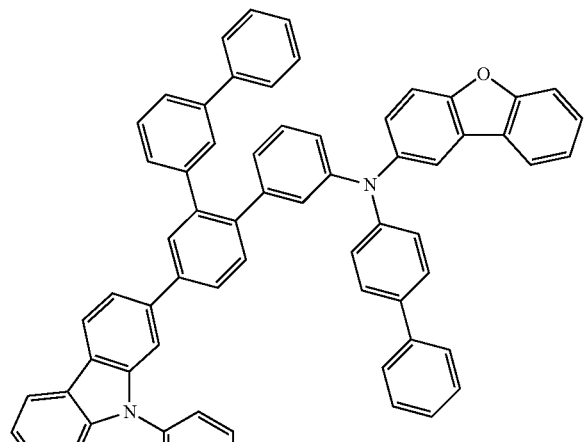
P3-29
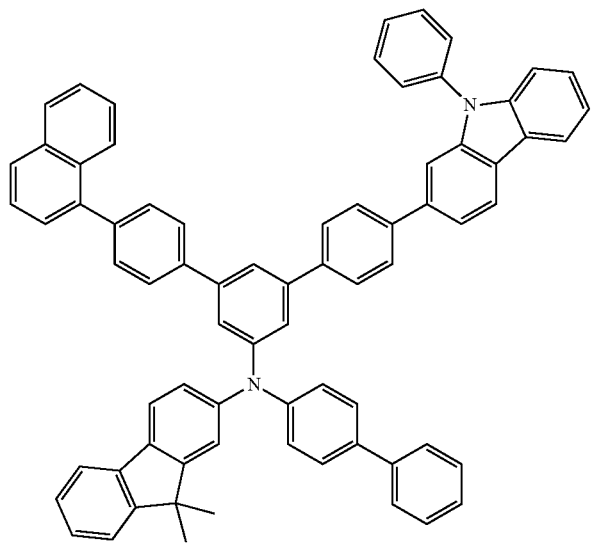

-continued

P3-30
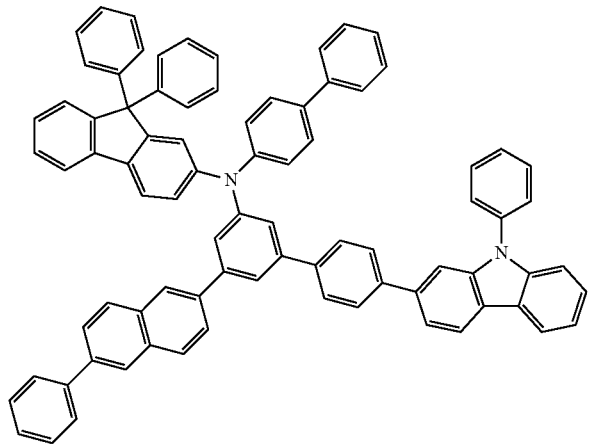

P3-31
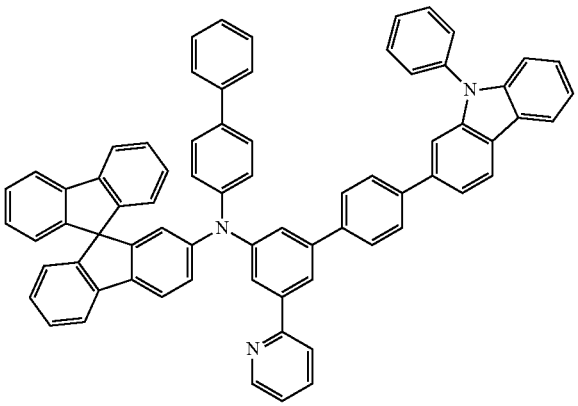

P3-32
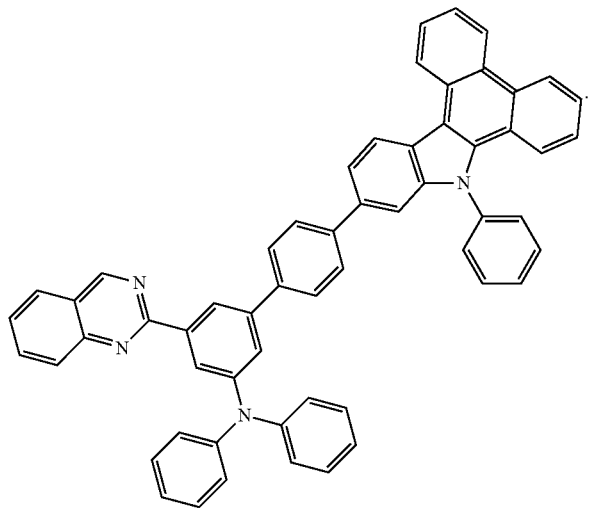

9. An organic electric element comprising a first electrode, a second electrode, and an organic material layer disposed between the first electrode and the second electrode, wherein the organic material layer comprises the compound of claim 1.

10. The organic electric element of claim 9, wherein the organic material layer comprises at least one of a hole injection layer, a hole transport layer, an emission-auxiliary layer and an emitting layer, and at least one of the layers comprises the compound in the same kind or two or more different kinds.

11. The organic electric element of claim 9, wherein the organic electric element further comprises at least one layer to improve luminous efficiency, formed on at least one of the sides of the first and second electrodes opposite to the organic material layer.

12. The organic electric element of claim 9, wherein the organic material layer is formed by any one of the processes of spin coating, nozzle printing, inkjet printing, slot coating, dip coating and roll-to-roll.

13. An electronic device comprising a display device, which comprises the organic electric element of claim 9, and a control unit for driving the display device.

14. The electronic device of claim 13, wherein the organic electric element comprises at least one of an organic light emitting diode (OLED), an organic solar cell, an organic photo conductor (OPC), an organic transistor (organic TFT), and an element for monochromatic or white illumination.

* * * * *